(12) United States Patent
Metcalf et al.

(10) Patent No.: US 9,981,939 B2
(45) Date of Patent: *May 29, 2018

(54) COMPOUNDS AND USES THEREOF FOR THE MODULATION OF HEMOGLOBIN

(71) Applicant: Global Blood Therapeutics, Inc., South San Francisco, CA (US)

(72) Inventors: Brian W. Metcalf, South San Francisco, CA (US); Zhe Li, South San Francisco, CA (US); Qing Xu, South San Francisco, CA (US); Stephen L. Gwaltney, II, South San Francisco, CA (US); Jason R. Harris, South San Francisco, CA (US); Calvin W. Yee, South San Francisco, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/776,603

(22) PCT Filed: Mar. 10, 2014

(86) PCT No.: PCT/US2014/022789
§ 371 (c)(1),
(2) Date: Sep. 14, 2015

(87) PCT Pub. No.: WO2014/150276
PCT Pub. Date: Sep. 25, 2014

(65) Prior Publication Data
US 2016/0046613 A1 Feb. 18, 2016

Related U.S. Application Data

(63) Continuation-in-part of application No. 13/815,770, filed on Mar. 15, 2013, now Pat. No. 9,422,279.

(60) Provisional application No. 61/905,803, filed on Nov. 18, 2013, provisional application No. 61/905,802, filed on Nov. 18, 2013.

(51) Int. Cl.
| | |
|---|---|
| *C07D 401/04* | (2006.01) |
| *C07D 471/04* | (2006.01) |
| *C07D 213/30* | (2006.01) |
| *C07D 227/08* | (2006.01) |
| *C07D 257/04* | (2006.01) |
| *C07D 401/12* | (2006.01) |
| *A61K 31/5375* | (2006.01) |
| *A61K 31/445* | (2006.01) |
| *A61K 8/49* | (2006.01) |
| *C07D 211/70* | (2006.01) |
| *C07D 213/69* | (2006.01) |
| *C07D 401/14* | (2006.01) |
| *C07D 405/04* | (2006.01) |
| *C07D 405/14* | (2006.01) |

(52) U.S. Cl.
CPC .......... *C07D 401/04* (2013.01); *A61K 8/4913* (2013.01); *A61K 31/445* (2013.01); *A61K 31/5375* (2013.01); *C07D 211/70* (2013.01); *C07D 213/30* (2013.01); *C07D 213/69* (2013.01); *C07D 227/08* (2013.01); *C07D 257/04* (2013.01); *C07D 401/12* (2013.01); *C07D 401/14* (2013.01); *C07D 405/04* (2013.01); *C07D 405/14* (2013.01); *C07D 471/04* (2013.01)

(58) Field of Classification Search
None
See application file for complete search history.

(56) References Cited

U.S. PATENT DOCUMENTS

| | | |
|---|---|---|
| 3,236,893 A | 2/1966 | Blout et al. |
| 4,062,858 A | 12/1977 | Hoehn et al. |
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Baiani |
| 5,290,941 A | 3/1994 | Voiante et al. |
| 5,403,816 A | 4/1995 | Takabe et al. |
| 5,679,678 A | 10/1997 | Binder et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |

(Continued)

FOREIGN PATENT DOCUMENTS

| | | |
|---|---|---|
| CA | 2720096 | 10/2009 |
| CN | 101113148 | 1/2008 |

(Continued)

OTHER PUBLICATIONS

U.S. Appl. No. 13/815,735, filed Mar. 15, 2013, Xu.

(Continued)

*Primary Examiner* — Jeffrey S Lundgren
*Assistant Examiner* — Stephanie K Springer
(74) *Attorney, Agent, or Firm* — Sheppard Mullin Richter & Hampton LLP

(57) ABSTRACT

Provide herein are compounds and pharmaceutical compositions suitable as modulators of hemoglobin, methods and intermediates for their preparation, and methods for their use in treating disorders mediated by hemoglobin and disorders that would benefit from tissue and/or cellular oxygenation.

7 Claims, No Drawings

(56) References Cited

U.S. PATENT DOCUMENTS

| | | | |
|---|---|---|---|
| 6,127,355 | A | 10/2000 | Greenwald et al. |
| 6,153,655 | A | 10/2000 | Martinez et al. |
| 6,194,580 | B1 | 2/2001 | Greenwald et al. |
| 6,214,817 | B1 | 4/2001 | Riley et al. |
| 6,232,320 | B1 | 5/2001 | Stewart et al. |
| 6,239,176 | B1 | 5/2001 | Nudelman et al. |
| 6,242,644 | B1 | 6/2001 | Ackermann et al. |
| 6,355,661 | B1 | 3/2002 | Lai et al. |
| 6,395,266 | B1 | 5/2002 | Martinez et al. |
| 6,593,472 | B2 | 7/2003 | Hoffmann et al. |
| 6,608,076 | B1 | 8/2003 | Greenwald et al. |
| 6,627,646 | B2 | 9/2003 | Bakale |
| 6,630,496 | B1 | 10/2003 | Seehra et al. |
| 7,160,910 | B2 | 1/2007 | Safo et al. |
| 7,411,083 | B2 | 8/2008 | Gapalasamy et al. |
| 8,952,171 | B2 | 2/2015 | Xu et al. |
| 9,012,450 | B2 | 4/2015 | Metcalf et al. |
| 9,018,210 | B2 | 4/2015 | Metcalf et al. |
| 9,248,199 | B2 | 2/2016 | Metcalf et al. |
| 9,422,279 | B2 | 8/2016 | Metcalf et al. |
| 9,447,071 | B2 | 9/2016 | Li et al. |
| 9,458,139 | B2 | 10/2016 | Xu et al. |
| 9,604,999 | B2 | 3/2017 | Harris et al. |
| 9,776,960 | B2 | 10/2017 | Xu et al. |
| 2001/0046997 | A1 | 11/2001 | Abraham et al. |
| 2002/0095035 | A1 | 7/2002 | Warshawsky et al. |
| 2002/0142995 | A1 | 10/2002 | Nicolau et al. |
| 2002/0147138 | A1 | 10/2002 | Firestone et al. |
| 2003/0022923 | A1 | 1/2003 | Lai et al. |
| 2003/0060425 | A1 | 3/2003 | Ahlem et al. |
| 2003/0073712 | A1 | 4/2003 | Wang et al. |
| 2003/0165714 | A1 | 9/2003 | Lee et al. |
| 2003/0187026 | A1 | 10/2003 | Li et al. |
| 2003/0190333 | A1 | 10/2003 | Mossman et al. |
| 2003/0199511 | A1 | 10/2003 | Li et al. |
| 2004/0072796 | A1 | 4/2004 | Embury et al. |
| 2004/0186077 | A1 | 9/2004 | Diakur et al. |
| 2004/0209921 | A1 | 10/2004 | Bridger et al. |
| 2005/0085484 | A1 | 4/2005 | Mitchell et al. |
| 2005/0096337 | A1 | 5/2005 | Ackermann et al. |
| 2005/0143420 | A1 | 6/2005 | Moutouh-de Parseval et al. |
| 2005/0159605 | A1 | 7/2005 | Tarur et al. |
| 2006/0094761 | A1 | 5/2006 | Hague et al. |
| 2007/0213323 | A1 | 9/2007 | Imogai et al. |
| 2007/0293698 | A1 | 12/2007 | Quick et al. |
| 2008/0114167 | A1 | 5/2008 | Castro et al. |
| 2009/0023709 | A1 | 1/2009 | Gillespie et al. |
| 2009/0143371 | A1 | 6/2009 | Buettelmann et al. |
| 2009/0163512 | A1 | 6/2009 | Chen et al. |
| 2009/0312315 | A1 | 12/2009 | Yamaguchi et al. |
| 2010/0204235 | A1 | 8/2010 | Lizos et al. |
| 2010/0210651 | A1 | 8/2010 | Hernandez et al. |
| 2010/0311748 | A1 | 12/2010 | Dakin et al. |
| 2012/0220569 | A1 | 8/2012 | Ohashi et al. |
| 2012/0245344 | A1 | 9/2012 | Endo et al. |
| 2013/0045251 | A1 | 2/2013 | Cen et al. |
| 2013/0072472 | A1 | 3/2013 | Gless et al. |
| 2013/0190315 | A1 | 7/2013 | Metcalf et al. |
| 2013/0190316 | A1 | 7/2013 | Metcalf et al. |
| 2013/0190375 | A1 | 7/2013 | Dunkel et al. |
| 2014/0271591 | A1 | 9/2014 | Sinha et al. |
| 2014/0274961 | A1 | 9/2014 | Metcalf et al. |
| 2014/0275152 | A1 | 9/2014 | Metcalf et al. |
| 2014/0275176 | A1 | 9/2014 | Xu et al. |
| 2014/0275181 | A1 | 9/2014 | Harris et al. |
| 2015/0057251 | A1 | 2/2015 | Harris |
| 2015/0133430 | A1 | 5/2015 | Xu et al. |
| 2015/0141465 | A1 | 5/2015 | Yee et al. |
| 2015/0259296 | A1 | 9/2015 | Li et al. |
| 2015/0344472 | A1 | 12/2015 | Metcalf et al. |
| 2015/0344483 | A1 | 12/2015 | Metcalf et al. |
| 2016/0024127 | A1 | 1/2016 | Harris et al. |
| 2016/0031865 | A1 | 2/2016 | Li et al. |
| 2016/0031904 | A1 | 2/2016 | Li et al. |
| 2016/0038474 | A1 | 2/2016 | Sinha et al. |
| 2016/0039801 | A1 | 2/2016 | Metcalf et al. |
| 2016/0083343 | A1 | 3/2016 | Xu et al. |
| 2016/0303099 | A1 | 3/2016 | Dufu et al. |
| 2016/0152602 | A1 | 6/2016 | Xu et al. |
| 2016/0206604 | A1 | 7/2016 | Metcalf et al. |
| 2016/0206614 | A1 | 7/2016 | Metcalf et al. |
| 2016/0207904 | A1 | 7/2016 | Li et al. |
| 2016/0332984 | A1 | 11/2016 | Metcalf et al. |
| 2016/0346263 | A1 | 12/2016 | Li et al. |
| 2017/0107199 | A1 | 4/2017 | Metcalf et al. |
| 2017/0157101 | A1 | 6/2017 | Ramos et al. |
| 2017/0174654 | A1 | 6/2017 | Metcalf et al. |

FOREIGN PATENT DOCUMENTS

| | | |
|---|---|---|
| CN | 102116772 | 7/2011 |
| DE | 2238734 | 2/1973 |
| DE | 2238628 | 3/1973 |
| DE | 2853765 | 8/1980 |
| DE | 2904829 | 8/1980 |
| DE | 226590 | 8/1985 |
| DE | 3503435 | 8/1985 |
| DE | 3431004 | 3/1986 |
| DE | 3704223 | 8/1987 |
| DE | 258226 | 7/1988 |
| DE | 276479 | 2/1990 |
| DE | 276480 | 2/1990 |
| DE | 3931954 | 3/1990 |
| DE | 4318550 | 12/1994 |
| DE | 4442050 | 5/1996 |
| EP | 10063 | 4/1980 |
| EP | 0054924 | 6/1982 |
| EP | 236140 | 9/1987 |
| EP | 0 268 989 | 6/1988 |
| EP | 0 637 586 | 6/1988 |
| EP | 278686 | 8/1988 |
| EP | 291916 | 11/1988 |
| EP | 303465 | 2/1989 |
| EP | 336369 | 10/1989 |
| EP | 0348155 | 12/1989 |
| EP | 0365328 | 4/1990 |
| EP | 0401517 | 12/1990 |
| EP | 453210 | 10/1991 |
| EP | 462800 | 12/1991 |
| EP | 481802 | 4/1992 |
| EP | 498380 | 8/1992 |
| EP | 0528337 | 2/1993 |
| EP | 0542372 | 5/1993 |
| EP | 567133 | 10/1993 |
| EP | 0632036 | 1/1995 |
| EP | 0640609 | 3/1995 |
| EP | 0747393 | 12/1996 |
| EP | 2123637 | 11/2009 |
| EP | 2149545 | 3/2010 |
| EP | 2305625 | 6/2011 |
| FR | 2 217 016 | 9/1974 |
| FR | 2909379 | 6/2008 |
| GB | 1409865 | 10/1975 |
| GB | 1593417 | 7/1981 |
| IL | 64573 | 4/1985 |
| JP | 57-145844 | 9/1982 |
| JP | 59029667 | 2/1984 |
| JP | 61040236 | 2/1986 |
| JP | 63230687 | 9/1988 |
| JP | S 63258463 | 10/1988 |
| JP | 01190688 | 7/1989 |
| JP | 06041118 | 2/1994 |
| JP | 07025882 | 1/1995 |
| JP | 2002-523469 | 7/2002 |
| JP | 2002-528537 | 9/2002 |
| JP | 2003-075970 | 3/2003 |
| JP | 2003-513060 | 4/2003 |
| JP | 2006342115 | 12/2006 |
| JP | 2009203230 | 9/2009 |
| WO | WO 199119697 | 12/1991 |
| WO | WO 199202503 | 2/1992 |
| WO | WO 199317013 | 9/1993 |
| WO | WO 199401406 | 1/1994 |
| WO | WO 199514015 | 5/1995 |

(56) References Cited

FOREIGN PATENT DOCUMENTS

| | | |
|---|---|---|
| WO | WO 199521854 | 8/1995 |
| WO | WO 199611902 | 4/1996 |
| WO | WO 199744306 | 11/1997 |
| WO | WO 199808818 | 3/1998 |
| WO | WO 199821199 | 5/1998 |
| WO | WO-99/29694 | 6/1999 |
| WO | WO-99/48490 | 9/1999 |
| WO | WO 199943672 | 9/1999 |
| WO | WO 199947529 | 9/1999 |
| WO | WO 199959978 | 11/1999 |
| WO | WO 199962908 | 12/1999 |
| WO | WO 00/12121 | 3/2000 |
| WO | WO 00/26202 | 5/2000 |
| WO | WO 2000035858 | 6/2000 |
| WO | WO 2000040564 | 7/2000 |
| WO | WO 200071123 A1 | 11/2000 |
| WO | WO 2000075145 | 12/2000 |
| WO | WO 2001000612 | 1/2001 |
| WO | WO 2001019823 | 3/2001 |
| WO | WO 2001023383 | 4/2001 |
| WO | WO 01/32596 | 5/2001 |
| WO | WO 2001036375 | 5/2001 |
| WO | WO 2001057006 | 8/2001 |
| WO | WO 2001057044 | 8/2001 |
| WO | WO 2001062705 | 8/2001 |
| WO | WO 2001070663 | 9/2001 |
| WO | WO 2002000622 | 1/2002 |
| WO | WO 2002012235 | 2/2002 |
| WO | WO 2002024635 | 3/2002 |
| WO | WO 2002024679 | 3/2002 |
| WO | WO 2002051849 | 7/2002 |
| WO | WO 2002053547 | 7/2002 |
| WO | WO 2003051366 | 6/2003 |
| WO | WO 2003053368 | 7/2003 |
| WO | WO 2003101959 | 12/2003 |
| WO | WO 2004014899 | 2/2004 |
| WO | WO 2004018430 | 3/2004 |
| WO | WO 2004024705 | 3/2004 |
| WO | WO 2004050030 | 6/2004 |
| WO | WO 2004056727 | 7/2004 |
| WO | WO 2004058790 | 7/2004 |
| WO | WO-2004/087075 | 10/2004 |
| WO | WO 2004/111031 | 12/2004 |
| WO | WO 2005047249 | 5/2005 |
| WO | WO 2005074513 | 8/2005 |
| WO | WO 2005077932 | 8/2005 |
| WO | WO 2005/086951 | 9/2005 |
| WO | WO 2005087766 | 9/2005 |
| WO | WO 2005/096337 | 10/2005 |
| WO | WO 2006011469 | 2/2006 |
| WO | WO 2006/065204 | 6/2006 |
| WO | WO 2006088173 | 8/2006 |
| WO | WO 2006103463 | 10/2006 |
| WO | WO 2006106711 | 10/2006 |
| WO | WO 2006116764 | 11/2006 |
| WO | WO 2006/003923 | 12/2006 |
| WO | WO 2007003962 | 1/2007 |
| WO | WO 2007009389 | 1/2007 |
| WO | WO 2007017267 | 2/2007 |
| WO | WO 2007047204 | 4/2007 |
| WO | WO 2007049675 | 5/2007 |
| WO | WO 2007061923 | 5/2007 |
| WO | WO-2007/084914 | 7/2007 |
| WO | WO 2007117180 | 10/2007 |
| WO | WO 2008013414 | 1/2008 |
| WO | WO 2008016132 | 2/2008 |
| WO | WO-2008/029200 | 3/2008 |
| WO | WO 2008041118 | 4/2008 |
| WO | WO 2008051532 | 5/2008 |
| WO | WO 2008080391 | 5/2008 |
| WO | WO 2008/066145 | 6/2008 |
| WO | WO 2008081096 | 7/2008 |
| WO | WO 2008101682 | 8/2008 |
| WO | WO 2008116620 | 10/2008 |
| WO | WO 2009001214 | 12/2008 |
| WO | WO 2009050183 | 4/2009 |
| WO | WO 2009/128537 | 10/2009 |
| WO | WO 2009125606 | 10/2009 |
| WO | WO 2009130560 | 10/2009 |
| WO | WO 2009136889 | 11/2009 |
| WO | WO 2009146555 | 12/2009 |
| WO | WO 2010031589 | 3/2010 |
| WO | WO 2010056631 | 5/2010 |
| WO | WO 2010129055 | 11/2010 |
| WO | WO 2011033045 | 3/2011 |
| WO | WO 2011136459 | 11/2011 |
| WO | WO 2012138981 | 10/2012 |
| WO | WO 2012141228 | 10/2012 |
| WO | WO 2013/052803 | 4/2013 |
| WO | WO 2013/102145 | 7/2013 |
| WO | WO-2013/102145 | 7/2013 |
| WO | WO 2013102142 | 7/2013 |
| WO | WO 2013102145 | 7/2013 |
| WO | WO-2014/150256 | 9/2014 |
| WO | WO-2014/150258 | 9/2014 |
| WO | WO-2014/150261 | 9/2014 |
| WO | WO-2014/150268 | 9/2014 |
| WO | WO-2014/150276 | 9/2014 |
| WO | WO-2014/150289 | 9/2014 |
| WO | WO-2015/031284 | 3/2015 |
| WO | WO-2015/031285 | 3/2015 |

OTHER PUBLICATIONS

U.S. Appl. No. 13/815,776, filed Mar. 15, 2103, Xu.
U.S. Appl. No. 13/815,810, filed Mar. 15, 2013, Metcalf.
U.S. Appl. No. 13/815,872, filed Mar. 15, 2013, Metcalf.
U.S. Appl. No. 13/815,874, filed Mar. 15, 2013, Harris.
U.S. Appl. No. 13/815,810, filed Mar. 15, 2013, Metcalf et al.
U.S. Appl. No. 14/010,455, filed Aug. 26, 2013, Harris.
U.S. Appl. No. 14/207,289, filed Mar. 12, 2014, Li.
U.S. Appl. No. 61/581,053, filed Dec. 28, 2011, Metcalf et al.
U.S. Appl. No. 61/661,320, filed Jun. 18, 2012, Metcalf et al.
Abdulmalik et al., "Crystallographic analysis of human hemoglobin elucidates the structural basis of the potent and dual antisickling activity of pyridyl derivatives of vanillin," Acta Crystallographica Section D. Biol Crystallogr., 67(11):920-928 (2011).
Abdulmalik et al., "Sickle cell disease: current therapeutic approaches," Expert Opinion Ther. Patents, 15(11):1497-1506 (2005).
Abraham et al., "Vanillin, a potential agent for the treatment of sickle cell anemia," Blood, 77(6): 1334-1341 (1991).
Adhikary et al., "A new antisickling agent: In vitro studies of its effect on S/S erythrocytes and on hemoglobin S," Experientia, 34(6):804-806 (1978).
Bacsa et al., "Novel products from Baylis-Hillman reactions of salicylaldehydes," South African Journal of Chemistry, 51(1): 47-54 (1998).
Ballerini et al., High pressure Diels-Alder approach to hydroxy-substituted 6a-cyano-tetrahydro-6H-benzo[c]chromen-6-ones: A route to Δ6-Cis-Cannabidiol., J. Org. Chem., 74(11):4511-4317 (2009).
Ballet et al., "Novel selective human melanocortin-3 receptor ligands: Use of the 4-amino-1,2,4,5-tetrahydro-2-benzazepin-3-one (Aba) scaffold," Bioorganic & Medicinal Chemistry Letters, 17(9): 2492-2498 (2007).
Baxter et al., "Reductive aminations of carbonyl compounds with borohydride and borane reducing agents," Organic Reactions (Hoboken, NJ, United States), 59, including pp. 1-57 and 660-727, 125 pages (2002).
Beddell, "Substituted benzaldehydes designed to increase the oxygen affinity of human haemoglobin and inhibit the sickling of sickle erythrocytes," Br. J. Pharmac., 82:397-407 (1984).
Beena et al., "Synthesis and antibacterial activity evaluation of metronidazole-triazole conjugates," Bioorg Med Chem Lett., 19(5):1396-1398 (2009).
Berge et al., "Pharmaceutical Salts," Journal of Pharmaceutical Science, 66:1-19 (1977).

(56) References Cited

OTHER PUBLICATIONS

Bode et al., "Novel synthesis and x-ray crystal structure of a coumarin derivative," South African Journal of Chemistry, 45(1):25-27 (1992).
Britton et al., "Structure-activity relationships of a series of benzothiophene-derived NPY Y1 antagonists: optimization of the C-2 side chain," Bioorganic & Medicinal Chemistry Letters 9(3):475-480 (1999).
Brown et al., "1,2-Dihydroisoquinolines—III. Dimerization," Tetrahedron, 22(8):2437-2443 (1966).
Chemical Abstract Registry No. 1142191-55-6, Indexed in the Registry File on STN CAS Online May 4, 2009, 1 page (2009).
Cherian et al., "Structure-activity relationships of antitubercula nitroimidazoles 3, exploration of the linker and lipophilic tail of ((S)-2-nitro-6,7-dihydro-5H-imidazol[2, 1b] [1,3]oxazin-6-y1)-(4-trifluoromethoxy-benzyl)amine (6-Amino PA-824)," J. Med. Chem, 54(16):5639-5659 (2011).
Ciganek, "The catalyzed alpha-hydroxyalkylation and alpha-aminoalkylation of activated olefins (the Morita-Baylis-Hillman reaction," Organic Reactions (Hoboken, NJ, United States), 51:201-267 and 342-350, 76 pages (1997).
Cos et al., "Structure-activity relationship and classification of flavonoids as inhibitors of xanthineoxidease and superoxide scavengers," J. Nat. Prod., 61:71-76 (1998).
Database Espacenet, Bibliographic data: CN102952062 (A), Li et al., "Substituted-benzoheterocycle derivatives, preparation, and application for preparation of antiviral or antineoplastic drugs," XP002726578 retrieved from STN Database accession No. 2013:366779 (English language abstract); RN:1427163-92-5 & CN 102 952 062A, (1 page) Mar. 6, 2013.
Ding et al., "Crystal structure of bis(µ3-oxo)-bis[µ2-2-(2-formylphenoxy)acetato-O,O']-bis[µ2-2-(2-formylphenoxy)acetato-O,O']-octakis(n-butyl)tetratin(IV), Sn4O2(C9H7O4)4(C4H9)8," Zeitschrift fuer Kristallographie—New Crystal Structures, 226(1):31-32 (2011).
Elwahy, "Synthesis of new benzo-substituted macrocyclic ligands containing quinoxaline subunits," Tetrahedron, 56(6): 897-907 (2000).
Gadaginamath et al., "Synthesis and antibacterial activity of novel 1-butyl-2-phenoxy/2-phenylthio/2-aminomethy1-5-methoxyindole derivatives," Polish Journal of Chemistry, 71(7):923-928 (1997).
Gao et al., "A novel one-pot three-step synthesis of 2-(1-benzofuran-2-yl)quinoline-3-carboxylic acid derivatives," Journal of the Brazilian Chemical Society, 21(5):806-812 (2010).
Ghate et al., "Synthesis of vanillin ethers from 4-(bromomethyl) coumarins as anti-inflammatory agents," European Journal of Medicinal Chemistry, 38(3):297-302 (2003).
Grashey, "The nitro group as a 1,3-dipole in cycloadditions," Angewandte Chemie, 74:155 (1962).
Gunter et al., "Structural control of co-receptor binding in porphyrin-bipyridinium supramolecular assemblies," Journal of the Chemical Society, Perkin Transactions 1: Organic and Bio-Organic Chemistry, (12):1945-1958 (1998).
Hanmantgad et al., "Synthesis and pharmacological properties of some 4-(2'-benzo[b]furanyl)coumarins," Indian Journal of Chemistry, Section B: Organic Chemistry Including Medicinal Chemistry, 25B(7):779-781 (1986).
He et al., "Prodrugs of phosphonates, phosphinates, and phosphates", Prodrugs: Challenges and Rewards, Part 2, edited by Stella et al., pp. 223-264 (2007).
Heimbach et al., "2.2.1: Over-coming poor aqueous solubility of drugs for oral delivery," from Prodrugs: Challenges and Rewards, Part I, New York NY, Singer: AAPS Press, pp. 157-215 (2007).
Heimbach et al., "Enzyme-mediated precipitation of parent drugs from their phosphate prodrugs," International Journal of Pharmaceutics. 261:81-92 (2002).
Ito et at, "A medium-term rat liver bioassay for rapid in vivo detection of carcinogenic potential of chemicals," Cancer Science, 94(1):3-8 (2003).
Jarvest et al., "Discovery and optimisation of potent, selective, ethanolamine inhibitors of bacterial phenylalanyl tRNA synthetase," Bioorganic & Medicinal Chemistry Letters, 15(9):2305-2309 (2005).
Karche et al., "Electronic effects in migratory groups. [1,4]- versus [1,2]-rearrangement in rhodium carbenoid generated bicyclic oxonium ylides," Journal of Organic Chemistry, 66(19):6323-6332 (2001).
Katritzky et al., "Synthesis of 3-hydroxymethyl-2,3-dihydrobenzofurans and 3-hydroxymethylbenzofurans," ARKIVOC (Gainesville, FL, United States), (6):49-61 (2003).
Kaye et al. "DABCO-catalyzed reactions of salicylaldehydes with acrylate derivatives," Synthetic Communications: An International Journal for Rapid Communication of Synthetic Organic Chemistry, 26(11):2085-97 (1996).
Kaye et al., "Does the DABCO-catalysed reaction of 2-hydroxybenzaldehydes with methyl acrylate follow a Baylis-Hillman pathway?," Organic & Biomolecular Chemistry, 1(7):1133-1138 (2003).
Kessar et al., "An interesting application of photocyclisation in aporhoeadane alkaloid synthesis", Tetrahedron Letters, 28(44):5323-5326 (1987).
Kessar et al., "Synthesis of isoindolobenzazepines via photocyclization of N-(2-formylphenethyl)phthalimide derivatives," Indian Journal of Chemistry, 30B(11):999-1005 (1991).
Kise et al., "Electroreductive intramolecular coupling of phthalimides with aromatic aldehydes: application to the synthesis of lennoxamine," Journal of Organic Chemistry, 76(23):9856-9860 (2011).
Krow, Grant R., "Chapter 3, The Baeyer-Villiger oxidation of ketones and aldehydes," Organic Reactions, 43:251-353 and 775-808 (1993).
Lakkannavar et al., "4-[2'-Benzylideneanilino aryloxymethyl] coumarins E and Z isomers," Indian Journal of Heterocyclic Chemistry, 4(4):303-304 (1995).
Liu et al., "Synthesis of Double-Armed Benzo-15-crown-5 and Their Complexation Thermodynamics with Alkali Cations," Journal of Inclusion Phenomena and Macrocyclic Chemistry, 52(3-4):229-235 (2005).
Mahoney et al., "Functionalization of Csp3-H bond-Sc(OTf)3-catalyzed domino 1,5-hydride shift/cyclization/Friedel-Crafts acylation reaction of benzylidene Meldrum's acids," Tetrahedron Letters, 50(33):4706-4709 (2009).
Majhi et al, "An efficient synthesis of novel dibenzo-fused nine-membered oxacycles using a sequential Baylis-Hillman reaction and radical cyclization," Synthesis, (1):94-100 (2008).
Marchetti et al., "Synthesis and biological evaluation of 5-substituted $O^4$-alkylpyrimidines as CDK2 inhibitors," Org. Biomol. Chem, 8:2397-2407 (2010).
McKay et al., "7,11,15,28-Tetrakis[(2-formylphenoxy)-methyl]-1,21,23,25-tetramethyl-resorcin[4]arene cavitand ethyl acetate clathrate at 173 K," Acta Crystallographica, Section E: Structure Reports Online, E65(4):o692-o693 (2009).
McKay et al., "Microwave-assisted synthesis of a new series of resorcin[4]arene cavitand-capped porphyrin capsules," Organic & Biomolecular Chemistry, 7(19):3958-3968 (2009).
Merlino et al., "Development of second generation amidinohydrazones, thio- and semicarbazones as *Trypanosoma cruzi*-inhibitors bearing benzofuroxan and benzimidazole 1,3-dioxide core scaffolds," Med. Chem. Commun., 1(3):216-228 (2010).
Mesguiche et al., "4-Alkoxy-2,6-diaminopyrimidine derivatives: inhibitors of cyclin dependent kinases 1 and 2," Bioorganic & Medicinal Chemistry Letters, 13:217-222 (2003).
Mitra et al., "Synthesis and biological evaluation of dibenz[b,f][1,5]oxazocine derivatives for agonist activity at k-opioid receptor," European Journal of Medicinal Chemistry, 46(5):1713-1720 (2011).
Mulwad et al., "Synthesis and antimicrobial activity of [6'-methyl-4'-methoxy-2-oxo-2H-[1]-benzopyran)-2",4"-dihydro-[1",2",4"]-triazol-3"-one and 3"-phenylthiazolidin-4"-one-phenoxymethyl derivatives of dipyranoquinoline," Pharmaceutical Chemistry Journal, 45(7):427-432 (2011).

(56) References Cited

OTHER PUBLICATIONS

Neelima et al., "A novel annelation reaction: synthesis of 6H-[1]benzopyrano[4,3-b]quinolines," Chemistry & Industry (London, United Kingdom), (4):141-2 (1986).

Nnamani et al., "Pyridyl derivatives of benzaldehyde as potential antisickling agents", Chemistry & Biodiversity, 5:1762-1769 (2008).

Nonoyama et al., "Cyclometallation of 2-(2-pyridyl)benzo[b]furan and 1-(2-pyridyl and 2-pyrimidyl)indole with palladium(II) and rhodium(III). Structures of unexpectedly formed nitro palladium(II) complexes," Polyhedron, 18:533-543 (1999).

Nyerges et al., "Synthesis of indazole N-oxides via the 1,7-electrocyclization of azomethine ylides," Tetrahedron Letters, 42(30):5081-5083 (2001).

Nyerges et al., "Synthesis of indazole-N-oxides via the 1,7-electrocyclization of azomethine ylides," Tetrahedron, 60(44):9937-9944 (2004).

O'Reilly et al., "Metal-phenoxyalkanoic acid interactions. XXV. The crystal structures of (2-formyl-6-methoxyphenoxy)acetic acid and its zinc(II) complex and the lithium, zinc(II) and cadmium(II) complexes of (2-chlorophenoxy)acetic acid," Australian Journal of Chemistry, 40(7):1147-1159 (1987).

OECD SIDS, "Potassium Hydroxide, SIDS Initial Assessment Report for SIAM 13, CAS No. 1310-58-3," UNEP Publications, pp. 1-96 (2002).

Perez et al., "Preparation of new 1,2-disubstituted ferrocenyl stibine derivatives containing ether/thioether pendant arm from a quaternary ferrocenyl ammonium salt," Polyhedron, 28(14):3115-3119 (2009).

Perkins et al., "Manganese(II), iron(II), cobalt(II), and copper(II) complexes of an extended inherently chiral tris-bipyridyl cage," Proceedings of the National Academy of Sciences of the United States of America, 103(3):532-537 (2006).

Pubchem CID 54009805, create date: Dec. 4, 2011, 3 pages, (2011).

Pubchem CID 54883281, create date: Jan. 24, 2012, 3 pages, (2012).

Rolan et al., "The pharmacokinetics, tolerability and pharmacodynamics of tucaresol (589C80; 4[2-formyl-3-hydroxyphenoxymethyl] benzoic acid), a potential anti-sickling agent, following oral administration to healthy subjects", Br. J. Clin. Pharmacol., 35(4):419-425 (1993).

Ruchirawat et al., "A novel synthesis of aporhoeadanes," Tetrahedron Letters, 25(32):3485-3488 (1984).

Sahakitpichan et al., "A practical and highly efficient synthesis of lennoxamine and related isoindolobenzazepines," Tetrahedron, 60(19):4169-4172 (2004).

Sahm et al., "Synthesis of 2-arylbenzofurans," Justus Liebigs Annalen der Chemie, (4):523-38, includes English language abstract, (1974).

Sainsbury et al., "1,2-Dihydroisoquinolines. IV. Acylation," Tetrahedron, 22(8):2445-2452 (1966).

Sarodnick et al., "Quinoxalines XV. Convenient synthesis and structural study of pyrazolo[1,5-a]quinoxalines," Journal of Organic Chemistry, 74(3):1282-1287 (2009).

Siddiqui et al., "The presence of substitutents on the aryl moiety of the aryl phosphoramidate derivatives of d4T enhances anti-HIV efficacy in cell culture: a structure-activity relationship," J. Med. Chem., 42:393-399 (1999).

Silva et al., "Advances in proddrug design," Mini-Rev. Med. Chem., 5(10):893-914, 2005.

Singh et al., "Reductive-cyclization-mediated synthesis of fused polycyclic quinolines from Baylis-Hillman adducts of acrylonitrile: scope and limitations," European Journal of Organic Chemistry, (20):3454-3466 (2009).

Srivastava et al., "Synthesis and biological evaluation of 4-substituted tetrazolo[4,5-a]quinolines and 2,3-disubstituted quinoline derivatives," Indian Journal of Chemistry, Section B: Organic Chemistry Including Medicinal Chemistry, 28B(7):562-573 (1989).

Starke et al., "Quinoxalines. Part 13: Synthesis and mass spectrometric study of aryloxymethylquinoxalines and benzo[b]furylquinoxalines," Tetrahedron, 60(29):6063-6078 (2004).

Swann et al., "Rates of reductive elimination of substituted nitrophenols from the (indo1-3-yl)methyl position of indolequinones," Journal of the Chemical Society, Perkin Transactions 2, (8):1340-1345 (2001).

Tome, A.C., "13.13, Product class 13: 1,2,3-triazoles," Science of Synthesis: Houben-Weyl Methods of Molecular Transformations, Georg Thieme Verlag publishers, Stuttgart, Germany, pp. 415-601, (2003).

Van Rompaey et al., "A versatile synthesis of 2-substituted 4-amino-1,2,4,5-tetrahydro-2-benzazepine-3-ones," Tetrahedron, 59(24):4421-4432 (2003).

Van Rompaey et al., "Synthesis and evaluation of the β-turn properties of 4-amino-1,2,4,5-tetrahydro-2-benzazepin-3-ones and of their spirocyclic derivative," European Journal of Organic Chemistry, (13):2899-2911 (2006).

Vicente et al., "Carbopalladation of maleate and fumarate esters and 1,1-dimethylallene with ortho-substituted aryl palladium complexes," Organometallics, 29(2):409-416 (2010).

Wang et al., "Studies of benzothiophene template as potent factor IXa (FIXa) inhibitors in thrombosis," Journal of Medicinal Chemistry, 53(4):1465-1472 (2010).

Warshawsky et al., "The synthesis of aminobenzazepinones as anti-phenylalanine dipeptide mimics and their use in NEP inhibition," Bioorganic & Medicinal Chemistry Letters, 6(8):957-962 (1996).

Wendt et al., "Synthesis and SAR of 2-aryl pyrido[2,3-d]pyrimidines as potent mGlu5 receptor antagonists," Bioorganic & Medicinal Chemistry Letters, 17:5396-5399 (2007).

Yan et al., "Synthesis, crystal structure and antibacterial activity of di-n-butyltin carboxylate," Huaxue Tongbao, 70(4):313-316, includes English language abstract, (2007).

Yan et al., "Synthesis, crystal structure and antibacterial activity of di-n-butyltin di-2-(2-formylphenoxy)acetic ester," Yingyong Huaxue, 24(6):660-664, includes English language abstract, (2007).

Yoon et al., "The chirality conversion reagent for amino acids based on salicyl aldehyde," Bull. Korean Chem. Soc., 33(5):1715-18 (2012).

Zhang et al., "DFT study on $Ru^{II}$-catalyzed cyclization of terminal alkynals to cycloalkenes," International Journal of Quantum Chemistry, 109(4):679-687 (2009).

Zwaagstra et at, "Synthesis and structure-activity relationships of carboxylated chalcones: a novel series of Cys-LT1 (LTD4) Receptor Antagonists", Journal of Medicinal Chemistry, 40(7):1075-1089 (1997).

Barnes, et al., "Prospects for new drugs for chronic obstructive pulmonary disease." The Lancet, 2004, 364, 985-996.

Barnes. "COPD: is there light at the end of the tunnel?" Current Opinion in Pharmacology, 2004, 4:263-272.

Bernstein. Crystals in Supramolecular Chemistry. ACA Transactions. 2004; 39:1-14.

Bernstein. Polymorphism in Molecular Crystals. Clarendon Press, Oxford. 2002. 115-118, 272.

Bonaventura, et al., "Molecular Controls of the Oxygenation and Redox Reactions of Hemoglobin." Antioxidants & Redox Signaling, 18(17), 2013, 2298-2313.

Braga, et al. Making crystals from crystals: a green route to crystal engineering and polymorphism. Chem Commun (Camb). Aug. 7, 2005;(29):3635-45. Epub Jun. 15, 2005.

Caira. Crystalline Polymorphism of Organic Compounds. Topics in Current Chemistry, Springer, Berlin, DE. 1998; 198:163-208.

CMU Pharmaceutical polymorphism, internet p. 1-3 (2002) printout Apr. 3, 2008.

Concise Encyclopedia Chemistry, NY: Walter de Gruyter, 1993, 872-873.

Davidovich, et al. Detection of polymorphism by powder x-ray diffraction: interference by preferred orientation. Am. Pharm. Rev. 2004; 10, 12, 14, 16, 100.

Dean. Analytical Chemistry Handbook. University of Tennesse, Knoxville. McGraw-Hill, Inc. 1995; 10.24-10.26.

(56) References Cited

OTHER PUBLICATIONS

Deem. "Red Blood Cells and Hemoglobin in Hypoxic Pulmonary Vasoconstriction" Advances in experimental medicine and biology, (2006) 588, 217-231.
Doelker, English translation of S.T.P, Pratiques (1999), 9(5), 399-409, pp. 1033.
Doelker. English translation of Ann. Pharm. Fr., 2002, 60: 161-176, pp. 1-39.
Einfalt, et al. Methods of amorphization and investigation of the amorphous state. Acta Pharm. 2013; 63:305-334.
European Search Report and Search Opinion dated Jul. 21, 2016 for EP Application No. 14769616.5. 8 pages.
European Search Report and Search Opinion dated Sep. 26, 2016 for EP Application No. 14768759.4. 6 pages.
Extended European Search Report and opinion dated Jul. 20, 2016 for EP Application No. 14768414.6. 10 pages.
Extended European Search Report and Search Opinion dated May 17, 2017 for EP Application No. 15746995.8. 8 pages.
Guillory (in Brittain ed.) Polymorphism in Pharmaceutical Solids. NY, Marcel Dekker, Inc. 1999; 1-2:183-226.
Huckauf, et al., "Oxygen Affinity of Haemoglobin and Red Cell Acid-Base Status in Patients with Severe Chronic Obstructive Lung Disease" Bull. Europe Physiopath. Resp., 1976, 12, 129-142.
International Search Report and Written Opinion dated May 11, 2015 for PCT Application No. PCT/US2015/014589. 5 pages.
International Search Report and Written Opinion dated Nov. 28, 2014 for PCT Application No. PCT/US2014/052576. 10 pages.
International Search Report and Written Opinion dated Oct. 31, 2014 for PCT Application No. PCT/US2014/013575. 10 pages.
Ivanisevic, et al. Uses of x-ray powder diffraction in the pharmaceutical industry. Pharm. Sci. Encycl. 2010; 1-42.
Jain, et al., "Polymorphism in Pharmacy", Indian Drugs, 1986, 23(6) 315-329.
Keidan, et al. Effect of BW12C on oxygen affinity of hemogoblin in sickle-cell disease. The Lancet. 1986; 327(8485):831-834.
Kirk-Othermer Encyclopedia of Chemical Technology. 2002; 8:95-147.
Kratochvil. Chapter 8 Solid Forms of Pharmaceutical Molecues. J. Sestak et al. (eds.), Glassy, Amorphous and Nano-Crystalline Materials. Hot Topics in Thermal Analysis and Calorimetry 8, 2011, pp. 129-140.
Luan, et al. OPS-Mode model of multiplexing neuroprotective effects of drugs and experimental-theoretic study of new 1,3-rasagiline derivatives potentially useful in neurodegenerative diseases. Bioorganic & Medicinal Chemistry. 2013; 21:1870-1879.
Muzaffar, et al., "Polymorphism and Drug Availability: a Review" J of Pharm. (Lahore), 1979, 1(1), 59-66.
Otsuka, et al., "Effect of Polymorphic Forms of Bulk Powders on Pharmaceutical Properties of Carbamazepine Granules." Chem. Pharm. Bull., 47(6) 852-856 (1999).
Prohens, et al. Polymorphism in pharmaceutical industry. The Pharmacist. Apr. 1, 2007; 373:58-68. (in Spanish with English abstract).
Rodriguez-Spong, et al. General principles of pharmaceutical solid polymorphism: a supramolecular perspective. Adv Drug Deliv Rev. Feb. 23, 2004;56(3):241-74.
Safo, et al. Structural basis for the potent antisickling effect of a novel class of five-membered heterocyclic aldehydic compounds. J Med Chem. Sep. 9, 2004;47(19):4665-76.
Seddon. Pseudopolymorph: A Polemic. The QUILL Centre, The Queen's University of Belfast, United Kingdom. Jul. 26, 2004. 2 pages.
Singhal, et al., "Drug Polymorphism and Dosage Form Design: a Practical Perspective" Advanced Drug Delivery reviews 56, p. 335-347 (2004).
Taday, et al., "Using Terahertz Pulse Spectroscopy to Study the Crystalline Structure of a Drug: A Case Study of the Polymorphs of Ranitidine Hydrochloride." J of Pharm. Sci., 92(4), 2003, 831-838.
U.S. Pharmacopia #23, National Formulary #18, 1995, 1843-1844.
Vichinsky. "Emerging 'A' therapies in hemoglobinopathies: agonists, antagonists, antioxidants, and arginine." Hematology 2012, 271-275.
Vippagunta, et al. Crystalline Solids. Advanced Drug Delivery Reviews. 2001; 48:3-26.
Zhang, et al. Current prodrug strategies for improving oral absorption of nucleoside analogues. Asian Journal of Pharmaceutical Sciences. Apr. 2014; 9(2):65-74.
Arya R, et al. "Tucaresol increases oxygen affinity and reduces haemolysis in subjects with sickle cell anaemia," Br. J. Haematol., 93(4):817-21 (1996).
Australian Examination Report dated Nov. 7, 2016 for AU 2016203755.
Babu, et al. Regioselective synthesis and structural elucidation of 1,4-disubstituted 1,2,3-triazole derivatives using 1D and 2D NMR spectral techniques. Magn. Reson. Chem., 49: 824-829. doi:10.1002/mrc.2820.
Beaumont et al., Design of ester prodrugs to enhance oral absorption of poorly permeable compounds: challenges to the discovery scientist. Curr. Drug Metab. 2003, 4:461-85.
Bradbury et al., "New nonpeptide angiotensin II receptor antagonists", Journal of Medicinal Chemistry, 1993, vol. 36, pp. 1245-1254.
CAS Registry No. 1039841-20-7; entry dated Aug. 10, 2008.
CAS Registry No. 1096911-11-3; entry dated Jan. 28, 2009.
CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 631858-40-7; entry dated Dec. 29, 2003.
Congreve et al. Application of Fragment Screening by X-ray Crstallography to the Discovery of Aminopyridimes as Inhibitors of Beta-Secretase. J. Med. Chem. 50:1124-1132 (2007).
Database Pubchem Compound Dec. 4, 2011 XP 003033770 (11 pages).
Desai et al. Preparation of N-[ro-(4-aryl-1-piperazinyl)ethyl/propyl]-3-hydroxyphthalimidines. Indian Journal of Chemistry. 39:455-457 (2000).
Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, 1991, vol. 26, No. 4, pp. 455-460.
Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).
Epsztajn et al., "Application of organolithium", Tetrahedron, Elsevier Science Publishers, Amsterdam, NL, 1991, vol. 47, No. 9, pp. 1697-1706.
European Search Report and Search Opinion dated Aug. 4, 2015 for EP Application No. 12862525.8. 9 pages.
European Search Report and Search Opinion dated May 28, 2015 for EP Application No. 12862096.0. 13 pages.
European Search Report and Search Opinion dated Nov. 16, 2016 for EP Application No. 16194019.2. 13 pages.
Extended European Search Report and Search Opinion dated Jul. 18, 2016 for EP Application No. 14770695.6. 13 pages.
Extended European Search Report and Search Opinion dated Jul. 7, 2016 for EP Application No. 14768317.1. 7 pages.
Extended European Search Report and Search Opinion dated Nov. 23, 2015 for EP Application No. 12862525.8. 16 pages.
Gibson et al., "Novel small molecule bradykinin B2 receptor antagonists", Journal of Medicinal Chemistry, 2009, vol. 52, pp. 4370-4379.
Glasson et al. Metal Template Synthesis of a Tripodal Tris(bipyridyl) Receptor that Encapsulates a Proton and an Iron (ii) Centre in a Pseudo Cage. Aust. J. Chem. 65:1371-1376 (2012).
Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.

(56) References Cited

OTHER PUBLICATIONS

Heimgartner et al., "Stereoselective synthesis of swainsonines from pyridines", Tetrahedron, Elsevier Science Publishers, Amsterdam, NL, 2005, vol. 61, No. 3, pp. 643-655.
Hoffman, et al. 3-Hydroxy-3-methyglutaryl-coenzyme A Reductase Inhibitors, 2. Structural Modification of 7-(Substituted aryl)-3,5-dihydroxy-6-heptenoic Acids and Their Lactone Derivatives. Journal of Medical Chemistry. 29(2):159-169 (1986).
Hong et al., "Potential Anticancer Agents VI: 5-Substituted Pyrimidine-6-Carboxaldehydes", Journal of Pharmaceutical Sciences, American Pharmaceutical Association, Washington, US, 1970, vol. 59, No. 11, pp. 1637-1645.
International Preliminary Report on Patentability for PCT/US2014/022846 dated Sep. 15, 2015. 7 pages.
International Preliminary Report on Patentability for PCT/US2014/022742 dated Sep. 15, 2015. 7 pages.
International Preliminary Report on Patentability for PCT/US2014/022733 dated Sep. 15, 2015. 11 pages.
International Preliminary Report on Patentability for PCT/US2014/022769 dated Sep. 15, 2015. 8 pages.
International Search Report and Written Opinion dated Aug. 19, 2014 for PCT Application No. PCT/US2014/022736. 14 pages.
International Search Report and Written Opinion dated Aug. 27, 2014 for PCT Application No. PCT/US2014/022742. 11 pages.
International Search Report and Written Opinion dated Dec. 8, 2014 for PCT Application No. PCT/US2014/052575. 10 pages.
International Search Report and Written Opinion dated Jul. 22, 2014 for PCT Application No. PCT/US2014/022846. 11 pages.
International Search Report and Written Opinion dated Jul. 31, 2014 for PCT Application No. PCT/US2014/022789. 13 pages.
International Search Report and Written Opinion dated Jul. 4, 2014 for PCT Application No. PCT/US2014/022769. 11 pages.
International Search Report and Written Opinion dated Mar. 5, 2013 for PCT Application No. PCT/US2012/072177. 7 pages.
International Search Report and Written Opinion dated May 20, 2013 for PCT Application No. PCT/US2012/072183. 11 pages.
Israel office action dated Aug. 11, 2016 for 233329. 5 pages.
Klis, et al. Halogen-lithium exchange versus deprotonation: synthesis of diboromic acids derived from aryl-benzyl ethers. Tetrahedron Letters, 48(7):1169-1173 (2007).
Lin et al. Synthesis and anticancer activity of benzyloxybenzaldehyde derivatives against HL-60 cells. Bioorganic & Medicinal Chemistry. 13(5), 1537-1544 (2005).
Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.
Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL FARMACO, 1996, vol. 51, No. 8, 9, pp. 579-587.
Mantyla et al., Synthesis, in vitro evaluation and antileishmanial activity of water-soluble prodrugs of buparvaquone. J. Med. Chem. 2004, 47:188-195.
Nagy et al., Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling. Proc. Natl. Acad. Sci. USA 1993, 90:6373-6376.
Nogrady, Medicinal Chemistry A Biochemical Approach, Oxford University Press, New York, pp. 388-392 (1985).
Notice of Allowance dated Dec. 19, 2014 for U.S. Appl. No. 13/730,730. 11 pages.
Office Action dated Aug. 29, 2014 for U.S. Appl. No. 13/730,730. 17 pages.
Office Action dated Dec. 3, 2013 for U.S. Appl. No. 13/730,674. 8 pages.
Office Action dated Jul. 6, 2015 for U.S. Appl. No. 13/815,874. 14 pages.
Office Action dated Jun. 12, 2015 for CN Application No. 201280070743.5. 13 pages.
Office Action dated Jun. 29, 2015 for U.S. Appl. No. 13/815,810. 19 pages.
Office Action dated Jun. 30, 2014 for U.S. Appl. No. 13/730,674. 9 pages.
Office Action dated Sep. 18, 2013 for U.S. Appl. No. 13/730,674. 10 pages.
Patani, et al. Bioisosterism: A Rational Approach in Drug Design. J. Chem Rev. 1996, 96(8), pp. 3147-3176.
Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.
Remington's Pharmaceutical Sciences, 17th Edition, A. Gennaro editor, Easton Pennsylvania. Table of Contents. (1985).
Rooseboom et al., Enzyme-catalyzed activation of anticancer prodrugs. Pharmacol. Rev. 2004, 56:53-102.
Schudel, et al. Uber die Chemie des Vitamins E. Helvatica Chimica Acta. 1963; 66:636-649.
Shetty et al. Palladium catalyzed alpha-arylation of methyl isobutyrate and isobutyronitrile: an efficient synthesis of 2,5-disubstituted benzyl alcohol and amine intermediates. Tetrahedron Letters, 47:8021-8024 (2006).
Sobolev et al., Effect of acyl chain length and branching on the enantioselectivity of Candida rugosa lipase in the kinetic resolution of 4-(2-difluoromethoxyphenyl)-substituted 1,4-dihydropyridine 3,5-diesters. J. Org. Chem. 2002, 67:401-410.
Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1986; 51:2186-2192.
Table of Compounds, each of which can be found either in Table 1 of U.S. Pat. No. 9,018,210 or Table 1 of U.S. Pat. No. 9,012,450.
Testa et al., Hydrolysis in Drug and Prodrug Metabolism, Jun. 2003, Wiley-VCH, Zurich, 419-534.
Wermuth, Camille G., "Molecular Variations Based on Isosteric Replacements", The Practice of Medicinal Chemistry, 1996, pp. 203-232.
Yang, et al. Structural requirement of chalcones for the inhibitory activity of interleukin-5. Bioorg Med. Chem. 2007, 15(1), 99 104-111.
Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.
Appendix A provided with Israel Office Action dated Aug. 11, 2016 for IL 233329.

COMPOUNDS AND USES THEREOF FOR THE MODULATION OF HEMOGLOBIN

CROSS-REFERENCE TO RELATED APPLICATIONS

This application is the U.S. 371 National Stage application of International Application No. PCT/US2014/022789, filed on Mar. 10, 2014, which is a continuation-in-part of U.S. application Ser. No. 13/815,770, filed on Mar. 15, 2013, now U.S. Pat. No. 9,422,279, and which further claims priority to U.S. Provisional Application No. 61/905,802 filed on Nov. 18, 2013 and U.S. Provisional Application No. 61/905,803 filed on Nov. 18, 2013, the disclosures of each of the above referenced applications are incorporated herein by reference in their entireties and for all purposes.

FIELD OF THE INVENTION

This invention provides compounds and pharmaceutical compositions suitable as allosteric modulators of hemoglobin, methods and intermediates for their preparation, and methods for their use in treating disorders mediated by hemoglobin and disorders that would benefit from tissue and/or cellular oxygenation.

STATE OF THE ART

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin (Hb).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, allowing HbS to become susceptible to polymerization to give the HbS containing red blood cells their characteristic sickle shape. The sickled cells are also more rigid than normal red blood cells, and their lack of flexibility can lead to blockage of blood vessels. U.S. Pat. No. 7,160,910 discloses compounds that are allosteric modulators of hemoglobin. However, a need exists for additional therapeutics that can treat disorders that are mediated by Hb or by abnormal Hb such as HbS.

SUMMARY OF THE INVENTION

This invention relates generally to compounds and pharmaceutical compositions suitable as allosteric modulators of hemoglobin. In some aspects, this invention relates to methods for treating disorders mediated by hemoglobin and disorders that would benefit from tissue and/or cellular oxygenation.

In certain aspects of the invention, a compound of formula (I) is provided:

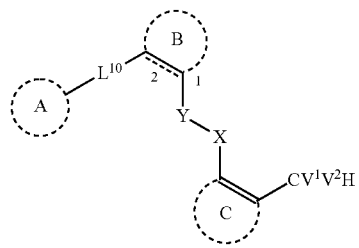

or a tautomer thereof, or a pharmaceutically acceptable salt of each thereof, wherein $L^{10}$ is optionally substituted methylene or, preferably, a bond;

⇜ is a single or a double bond;

each X and Y is independently $(CR^{20}R^{21})_e$, O, S, SO, $SO_2$, or $NR^{20}$; e is 1 to 4, preferably 1; each $R^{20}$ and $R^{21}$ independently is hydrogen or $C_1$-$C_3$ alkyl optionally substituted with 1-3 halo, OH, or $C_1$-$C_6$ alkoxy, or $CR^{20}R^{21}$ is C=O, provided that if one of X and Y is O, S, SO, $SO_2$, then the other is not CO, and X and Y are both not heteroatoms or oxidized forms thereof;

$V^1$ and $V^2$ independently are $C_1$-$C_6$ alkoxy; or $V^1$ and $V^2$ together with the carbon atom they are attached to form a ring of formula:

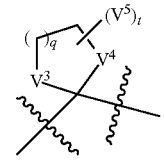

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl optionally substituted with 1-3 OH groups, or $V^5$ is $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl; and $R^{84}$ is optionally substituted $C_1$-$C_6$ alkyl;

provided that the compounds provided herein exclude those disclosed in U.S. patent application Ser. Nos. 13/730,730 and 13/730,674; and provided that the compounds provided herein exclude those in Table 1 hereinbelow;

and A, B, and C are defined as follows.

In one instance, ring A is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted, preferably with 1-4 $C_1$-$C_6$ alkyl and/or $C_1$-$C_6$ alkoxy groups;

ring B is:

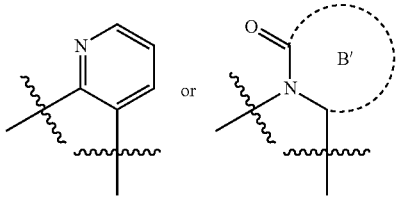 [SMILES: *c1cccnc1* ; *CN(*)C=O]

wherein ring B' including the —N—CO— moiety is a 5-6 membered heterocycle containing up to 3 heteroatoms selected from nitrogen, oxygen, and sulfur and oxidized forms of N and S, wherein each of the heteroaryl and the heterocycle is optionally substituted, preferably with 1-4 $C_1$-$C_6$ alkyl groups;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted, preferably with 1-4: halo, oxo, —$OR^1$, $C_1$-$C_6$ alkyl, —$COOR^1$, and $NR^5R^6$, $R^1$ is a hydrogen, $C_1$-$C_6$ alkyl or a prodrug moiety; wherein the alkyl is optionally substituted with a 5-10 membered heteroaryl containing up to 5 ring heteroatoms, wherein the heteroatom is selected from the group consisting of O, N, S, and oxidized forms of N and S, which is optionally substituted with with a 5-10 membered heteroaryl containing up to 5 ring heteroatoms, wherein the heteroatom is selected from the group consisting of O, N, S, and oxidized forms of N and S, wherein the heteroaryl is optionally substituted with $C_1$-$C_6$ alkyl;

$R^5$ and $R^6$ are each independently hydrogen, optionally substituted $C_1$-$C_6$ alkyl or —$COOR^3$;

$R^3$ is hydrogen or optionally substituted $C_1$-$C_6$ alkyl;

with the proviso that when ring C is $C_6$-$C_{10}$ aryl;
and ring B is optionally substituted 4-10 membered heterocyclyl;
then ring A excludes optionally substituted 5-10 membered heteroaryl;
and provided that when ring C is $C_6$-$C_{10}$ aryl;
and ring B is optionally substituted 5-10 membered heteroaryl;
then ring A is not optionally substituted 4-10 membered heterocycle.

In another instance:

ring A is $C_6$-$C_{10}$ aryl, a $C_3$-$C_8$ cycloalkyl, a 5-10 membered heteroaryl or a 4-10 membered heterocycle containing up to S ring heteroatoms, wherein the heteroatom is selected from the group consisting of O, N, S, and oxidized forms of N and S, wherein each of the aryl, heteroaryl, cycloalkyl, or heterocycle is optionally substituted, preferably with 1-4: halo, $C_1$-$C_6$ alkyl, $C_1$-$C_6$ alkoxy, and/or $C_3$-$C_{10}$ cycloalkyl, wherein the $C_1$-$C_6$ alkyl is optionally substituted with 1-5 halo, $C_1$-$C_6$ alkoxy, and/or $C_3$-$C_{10}$ cycloalkyl;

ring B is a 5-10 membered heteroaryl or a 4-10 membered heterocycle containing up to 5 ring heteroatoms, wherein the heteroatom is selected from the group consisting of O, N, S, and oxidized forms of N and S, wherein each of the heteroaryl and the heterocycle is optionally substituted, preferably with 1-4: halo, $C_1$-$C_6$ alkyl and/or —CO—$C_1$-$C_6$ alkyl, is a single or a double bond;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted, preferably with 1-4: halo, oxo, —$OR^1$, $C_1$-$C_6$ alkyl, —$COOR^1$, and/or $C_1$-$C_6$ alkoxy, wherein the $C_1$-$C_6$ alkyl is optionally substituted with 1-5 halo, $C_1$-$C_6$ alkoxy and/or a 4-10 membered heterocycle containing up to 5 ring heteroatoms, wherein the heteroatom is selected from the group consisting of O, N, S, and oxidized forms of N and S; and $R^1$ is hydrogen or a prodrug moiety;

provided that when ring C is $C_1$-$C_{10}$ aryl;
and ring B is optionally substituted 4-10 membered heterocyclyl;
then ring A excludes optionally substituted 5-10 membered heteroaryl;
and provided that when ring C is $C_6$-$C_{10}$ aryl;
and ring B is optionally substituted 5-10 membered heteroaryl;
then ring A is not optionally substituted 4-10 membered heterocycle.

In certain aspects of the invention, a compound of formula (X-I) is provided:

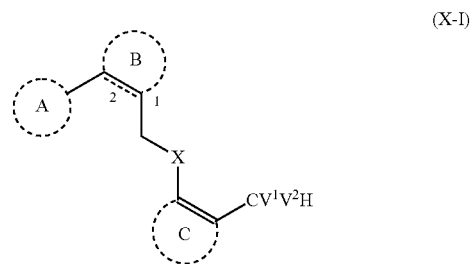

an N-oxide thereof, or a tautomer or each thereof, or a pharmaceutically acceptable salt of each of the preceding, wherein ring A is phenyl optionally substituted with 1-3 halo and/or $C_1$-$C_6$ alkoxy, or is a 4-10 membered heterocycle containing up to 5 ring heteroatoms, wherein the heteroatom is selected from the group consisting of O, N, S, and oxidized forms of N and S, optionally substituted, or is

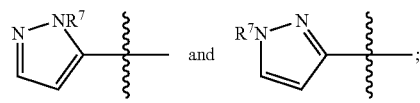

wherein $R^7$ is $C_1$-$C_6$ alkyl, optionally substituted with 3-5 fluoro groups, or is $C_3$-$C_6$ cycloalkyl;
ring B is selected from the group consisting of

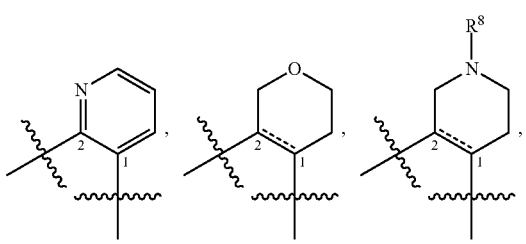

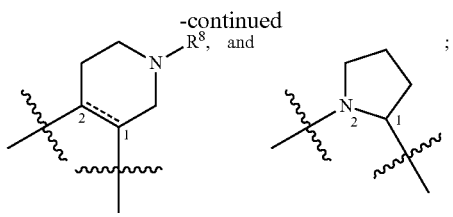

wherein $R^8$ is $C_1$-$C_6$ alkyl, —CO—$C_1$-$C_6$ alkyl or a prodrug moiety and wherein the pyridyl ring is optionally substituted with a halo or an $NR^{25}(CH_2)_2N(R^{25})_2$ group where each $R^{25}$ is independently hydrogen or $C_1$-$C_6$ alkyl;

X is O, S, SO or $SO_2$;

 is a single or a double bond;

ring C is phenyl or a 6 membered nitrogen-containing heteroaryl, each of which is optionally substituted with 1-4: halo, oxo, —$OR^1$, $C_1$-$C_6$ alkyl, —$COOR^1$ and/or $C_1$-$C_6$ alkoxy, wherein the $C_1$-$C_6$ alkyl is optionally substituted with 1-5 halo, $C_1$-$C_6$ alkoxy and/or 4-10 membered heterocycle containing up to 5 ring heteroatoms, wherein the heteroatom is selected from the group consisting of O, N, S, and oxidized forms of N and S; and each $R^1$ is hydrogen or a prodrug moiety R;

$V^1$ and $V^2$ independently are $C_1$-$C_6$ alkoxy; or $V^1$ and $V^2$ together with the carbon atom they are attached to form a ring of formula:

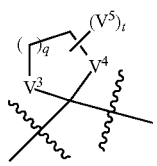

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 1, 2, or 4; or $CV^1V^2$ is C=V, wherein V is O, $NOR^{80}$, or $NNR^{81}R^{82}$;

wherein $R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl;

$R^{84}$ is optionally substituted $C_1$-$C_6$ alkyl;

provided that when ring C is $C_6$-$C_{10}$ aryl;

and ring B is optionally substituted 4-10 membered heterocyclyl;

then ring A excludes optionally substituted 5-10 membered heteroaryl;

provided that when ring C is $C_6$-$C_{10}$ aryl;

and ring B is optionally substituted 5-10 membered heteroaryl;

then ring A is not optionally substituted 4-10 membered heterocycle;

provided that the compounds provided herein exclude those disclosed in U.S. patent application Ser. Nos. 13/730,730 and 13/730,674; and provided that the compounds provided herein exclude those in Table 1 hereinbelow.

Preferably, $V^1$ and $V^2$ together with the carbon atom they are attached to form a ring of formula:

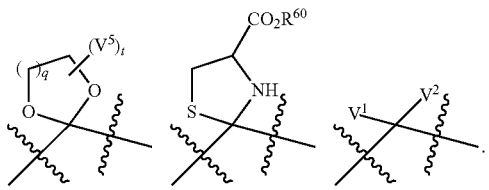

In some embodiments, $V^1$ and $V^2$ independently are $C_1$-$C_6$ alkoxy; or $V^1$ and $V^2$ together with the carbon atom they are attached to form a ring of formula:

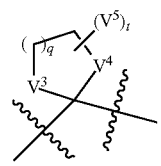

wherein each $V^3$ and $V^4$ are independently O, S, or NH, provided that when one or $V^3$ and $V^4$ is S the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, and wherein the remaining variables are defined herein.

In certain embodiments, a compound of formula (II) is provided:

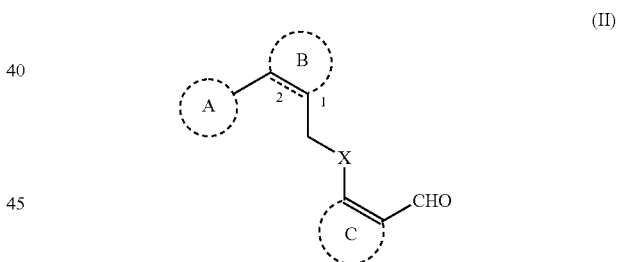

wherein the remaining variables are defined herein.

In certain embodiments, a compound selected from formulas (IIA), (IIB) and (IIC) is provided:

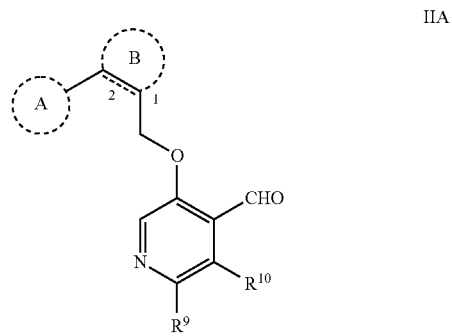

-continued

IIB
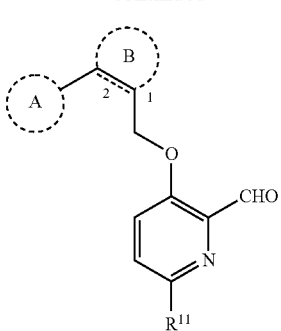

IIC

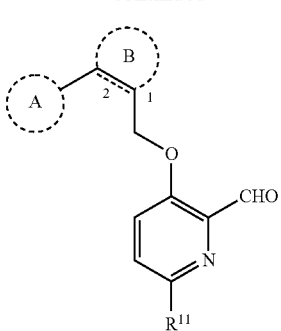

wherein
R⁹ is hydrogen, —OR¹, $C_1$-$C_6$ alkoxy optionally substituted with 1-3 $C_1$-$C_6$ alkoxy or 4-10 membered heterocycle containing up to 5 ring heteroatoms selected from N, O, S or oxidized forms thereof;
$R^{10}$ is hydrogen, hydroxy, halo or $C_1$-$C_6$ alkoxy;
$R^{11}$ is hydrogen or $C_1$-$C_6$ alkyl; and
$R^{12}$ is —OR¹;
wherein $R^1$ is hydrogen or the prodrug moiety R.
In certain aspects of the invention, a compound of formula (I) is provided:
or a tautomer thereof, or a pharmaceutically acceptable salt of each thereof, wherein
$L^{10}$ is optionally substituted methylene or, preferably, a bond;
ring A is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl and/or $C_1$-$C_6$ alkoxy groups;
ring B is:

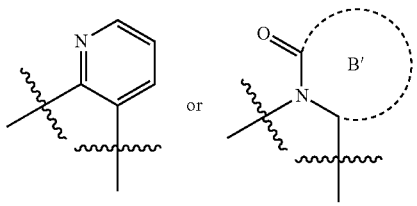 [SMILES: *c1cccnc1* ; *CN(*)C=O]

wherein ring B' including the —N—CO— moiety is a 5-6 membered heterocycle containing up to 3 heteroatoms selected from nitrogen, oxygen, and sulfur and oxidized forms of N and S, wherein each of the heteroaryl and the heterocycle is optionally substituted with 1-4 $C_1$-$C_6$ alkyl groups;
each X and Y is independently $(CR^{20}R^{21})_e$, O, S, SO, $SO_2$, or $NR^{20}$; e is 1 to 4, preferably 1; each $R^{20}$ and $R^{21}$ independently is hydrogen or $C_1$-$C_3$ alkyl optionally substituted with 1-3 halo, OH, or $C_1$-$C_6$ alkoxy, or $CR^{20}R^{21}$ is C=O, provided that if one of X and Y is O, S, SO, $SO_2$, then the other is not CO, and X and Y are both not heteroatoms or oxidized forms thereof;
ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —OR¹, $C_1$-$C_6$ alkyl, —COOR⁵, $NR^5R^6$,
$R^1$ is a hydrogen, $C_1$-$C_6$ alkyl or a prodrug moiety; wherein the alkyl is optionally substituted with a 5-10 membered heteroaryl containing up to 5 ring heteroatoms, wherein the heteroatom is selected from the group consisting of O, N, S, and oxidized forms of N and S, which is optionally substituted with with a 5-10 membered heteroaryl containing up to 5 ring heteroatoms, wherein the heteroatom is selected from the group consisting of O, N, S, and oxidized forms of N and S, wherein the heteroaryl is optionally substituted with $C_1$-$C_6$ alkyl;
$R^5$ and $R^6$ are each independently hydrogen, optionally substituted $C_1$-$C_6$ alkyl or —COOR³;
$R^3$ is hydrogen or optionally substituted $C_1$-$C_6$ alkyl;
$V^1$ and $V^2$ independently are $C_1$-$C_6$ alkoxy; or $V^1$ and $V^2$ together with the carbon atom they are attached to form a ring of formula:

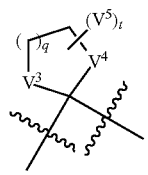

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl optionally substituted with 1-3 OH groups, or $V^5$ is $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;
$R^{80}$ is optionally substituted $C_1$-$C_6$ alkyl;
$R^{81}$ and $R^{82}$ independently are selected from the group consisting of hydrogen, optionally substituted $C_1$-$C_6$ alkyl. $COR^{83}$, or $CO_2R^{84}$;
$R^{83}$ is hydrogen or optionally substituted $C_1$-$C_6$ alkyl; and
$R^{84}$ is optionally substituted $C_1$-$C_6$ alkyl;
with the proviso that when ring C is $C_6$-$C_{10}$ aryl;
and ring B is optionally substituted 4-10 membered heterocyclyl;
then ring A excludes optionally substituted 5-10 membered heteroaryl;
and provided that when ring C is $C_6$-$C_{10}$ aryl;
and ring B is optionally substituted 5-10 membered heteroaryl;
then ring A is not optionally substituted 4-10 membered heterocycle.
In further aspects of the invention, a composition is provided comprising any of the compounds described herein, and at least a pharmaceutically acceptable excipient.

In still further aspects of the invention, a method is provided for increasing oxygen affinity of hemoglobin S in a subject, the method comprising administering to a subject in need thereof a therapeutically effective amount of any of the compounds or compositions described herein.

In further aspects of the invention, a method is provided for treating oxygen deficiency associated with sickle cell anemia, the method comprising administering to a subject in need thereof a therapeutically effective amount of any of the compounds or compositions described herein.

DETAILED DESCRIPTION OF THE INVENTION

Definitions

It must be noted that as used herein and in the appended claims, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

As used herein, $C_m$-$C_n$, such as $C_1$-$C_{12}$, $C_1$-$C_8$, or $C_1$-$C_6$ when used before a group refers to that group containing m to n carbon atoms.

The term "alkoxy" refers to —O-alkyl.

The term "alkyl" refers to monovalent saturated aliphatic hydrocarbyl groups having from 1 to 12 carbon atoms (i.e., $C_1$-$C_{12}$ alkyl) or 1 to 8 carbon atoms (i.e., $C_1$-$C_8$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$CH$—), n-butyl ($CH_3CH_2CH_2CH_2$—), isobutyl (($CH_3$)$_2CHCH_2$—), sec-butyl (($CH_3$)($CH_3CH_2$)$CH$—), t-butyl (($CH_3$)$_3C$—), n-pentyl ($CH_3CH_2CH_2CH_2CH_2$—), and neopentyl (($CH_3$)$_3CCH_2$—).

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom. For example, and without limitation, the following is an aryl group:

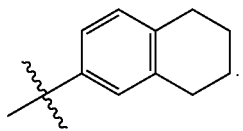 [SMILES: *c1ccc2c(c1)CCCC2]

The term "—$CO_2H$ ester" refers to an ester formed between the —$CO_2H$ group and an alcohol, preferably an aliphatic alcohol. A preferred example included —$CO_2R^E$, wherein $R^E$ is alkyl or aryl group optionally substituted with an amino group.

The term "chiral moiety" refers to a moiety that is chiral. Such a moiety can possess one or more asymmetric centers. Preferably, the chiral moiety is enantiomerically enriched, and more preferably a single enantiomer. Non limiting examples of chiral moieties include chiral carboxylic acids, chiral amines, chiral amino acids, such as the naturally occurring amino acids, chiral alcohols including chiral steroids, and the likes.

The term "cycloalkyl" refers to a monovalent, preferably saturated, hydrocarbyl mono-, bi-, or tricyclic ring having 3-12 ring carbon atoms. While cycloalkyl, refers preferably to saturated hydrocarbyl rings, as used herein, it also includes rings containing 1-2 carbon-carbon double bonds. Nonlimiting examples of cycloalkyl include cyclopropyl, cyclobutyl, cyclopentyl, cyclohexyl, cycloheptyl, adamentyl, and the like. The condensed rings may or may not be non-aromatic hydrocarbyl rings provided that the point of attachment is at a cycloalkyl carbon atom. For example, and without limitation, the following is a cycloalkyl group:

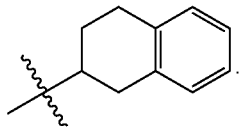 [SMILES: *C1CCc2ccccc2C1]

The term "halo" refers to F, Cl, Br, and/or I.

The term "heteroaryl" refers to a monovalent, aromatic mono-, bi-, or tricyclic ring having 2-16 ring carbon atoms and 1-8 ring heteroatoms selected preferably from N, O, S, and P and oxidized forms of N, S, and P, provided that the ring contains at least 5 ring atoms. Nonlimiting examples of heteroaryl include furan, imidazole, oxadiazole, oxazole, pyridine, quinoline, and the like. The condensed rings may or may not be a heteroatom containing aromatic ring provided that the point of attachment is a heteroaryl atom. For example, and without limitation, the following is a heteroaryl group:

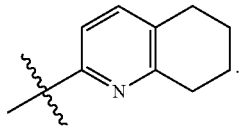 [SMILES: *c1ccc2c(n1)CCCC2]

The term "heterocyclyl" or heterocycle refers to a non-aromatic, mono-, bi-, or tricyclic ring containing 2-12 ring carbon atoms and 1-8 ring heteroatoms selected preferably from N. O, S, and P and oxidized forms of N, S, and P, provided that the ring contains at least 3 ring atoms. While heterocyclyl preferably refers to saturated ring systems, it also includes ring systems containing 1-3 double bonds, provided that the ring is non-aromatic. Nonlimiting examples of heterocyclyl include, azalactones, oxazoline, piperidinyl, piperazinyl, pyrrolidinyl, tetrahydrofuranyl, and tetrahydropyranyl. The condensed rings may or may not contain a non-aromatic heteroatom containing ring provided that the point of attachment is a heterocyclyl group. For example, and without limitation, the following is a heterocyclyl group:

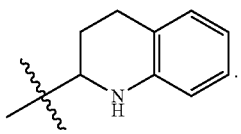 [SMILES: *C1CCc2ccccc2N1]

The term "hydrolyzing" refers to breaking an $R^H$—O—CO—, $R^H$—O—CS—, or an $R^H$—O—SO$_2$— moiety to an $R^H$—OH, preferably by adding water across the broken bond. A hydrolyzing is performed using various methods well known to the skilled artisan, non limiting examples of which include acidic and basic hydrolysis.

The term "oxo" refers to a C=O group, and to a substitution of 2 geminal hydrogen atoms with a C=O group.

The term "optionally substituted," unless defined otherwise, refers to a substituted or unsubstituted group. The group may be substituted with one or more substituents, such as e.g., 1, 2, 3, 4 or 5 substituents. Preferably, the substituents are selected from the group consisting of oxo, halo, —CN, NO$_2$, —N$_2$+, —CO$_2$R$^{100}$, —OR$^{100}$, —S$^{100}$, —SOR$^{100}$, —SO$_2$R$^{100}$, —NR$^{101}$R$^{102}$, —CONR$^{101}$R$^{102}$, —SO$_2$NR$^{101}$R$^{102}$, C$_1$-C$_6$ alkyl, C$_1$-C$_6$ alkoxy, —CR$^{100}$=C(R$^{100}$)$_2$, —CCR$^{100}$, C$_3$-C$_{10}$ cycloalkyl, C$_3$-C$_{10}$ heterocyclyl, C$_6$-C$_{12}$ aryl and C$_2$-C$_{12}$ heteroaryl, wherein each R$^{100}$ independently is hydrogen or C$_1$-C$_8$ alkyl; C$_3$-C$_{12}$ cycloalkyl; C$_3$-C$_{10}$ heterocyclyl; C$_6$-C$_{12}$ aryl; or C$_2$-C$_{12}$ heteroaryl; wherein each alkyl, cycloalkyl, heterocyclyl, aryl, or heteroaryl is optionally substituted with 1-3 halo, 1-3 C$_1$-C$_6$ alkyl, 1-3 C$_1$-C$_6$ haloalkyl or 1-3 C$_1$-C$_6$ alkoxy groups. Preferably, the substituents are selected from the group consisting of chloro, fluoro, —OCH$_3$, methyl, ethyl, isopropyl, cyclopropyl, vinyl, ethynyl, —CO$_2$H, —CO$_2$CH$_3$, —OCF$_3$, —CF$_3$ and —OCHF$_2$.

R$^{101}$ and R$^{102}$ independently is hydrogen; C$_1$-C$_8$ alkyl, optionally substituted with —CO$_2$H or an ester thereof, C$_1$-C$_6$ alkoxy, oxo, —CR$^{103}$=C(R$^{103}$)$_2$, —CCR, C$_3$-C$_{10}$ cycloalkyl, C$_3$-C$_{10}$ heterocyclyl, C$_6$-C$_{12}$ aryl, or C$_2$-C$_{12}$ heteroaryl, wherein each R$^{103}$ independently is hydrogen or C$_1$-C$_8$ alkyl; C$_3$-C$_{12}$ cycloalkyl; C$_3$-C$_{10}$ heterocyclyl; C$_6$-C$_{12}$ aryl; or C$_2$-C$_{12}$ heteroaryl; wherein each cycloalkyl, heterocyclyl, aryl, or heteroaryl is optionally substituted with 1-3 alkyl groups or 1-3 halo groups, or R$^{101}$ and R$^{102}$ together with the nitrogen atom they are attached to form a 5-7 membered heterocycle.

The term "pharmaceutically acceptable" refers to safe and non-toxic for in vivo, preferably, human administration.

The term "pharmaceutically acceptable salt" refers to a salt that is pharmaceutically acceptable.

The term "salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary, and non-limiting cations useful in pharmaceutically acceptable salts include Na, K, Rb, Cs, NH$_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease). The terms further include causing the clinical symptoms not to develop, for example in a subject at risk of suffering from such a disease or disorder, thereby substantially averting onset of the disease or disorder.

The term "effective amount" refers to an amount that is effective for the treatment of a condition or disorder by an intranasal administration of a compound or composition described herein. In some embodiments, an effective amount of any of the compositions or dosage forms described herein is the amount used to treat a disorder mediated by hemoglobin or a disorder that would benefit from tissue and/or cellular oxygenation of any of the compositions or dosage forms described herein to a subject in need thereof.

The term "carrier" as used herein, refers to relatively nontoxic chemical compounds or agents that facilitate the incorporation of a compound into cells, e.g., red blood cells, or tissues.

As used herein, a "prodrug" is a compound that, after administration, is metabolized or otherwise converted to an active or more active form with respect to at least one property. To produce a prodrug, a pharmaceutically active compound can be modified chemically to render it less active or inactive, but the chemical modification is such that an active form of the compound is generated by metabolic or other biological processes. A prodrug may have, relative to the drug, altered metabolic stability or transport characteristics, fewer side effects or lower toxicity. For example, see the reference Nogrady, 1985, Medicinal Chemistry A Biochemical Approach, Oxford University Press, New York, pages 388-392. Prodrugs can also be prepared using compounds that are not drugs.

Compounds

In certain aspects of the invention, a compound of formula (I) is provided:

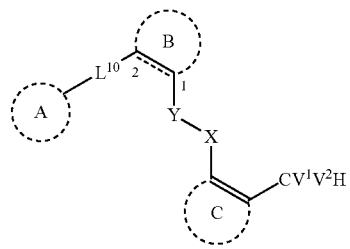

(I)

or a tautomer thereof, or a pharmaceutically acceptable salt of each thereof, wherein $L^{10}$ is optionally substituted methylene or, preferably, a bond;

ring A is $C_6$-$C_{10}$ aryl, a $C_3$-$C_8$ cycloalkyl, a 5-10 membered heteroaryl or a 4-10 membered heterocycle containing up to 5 ring heteroatoms, wherein the heteroatom is selected from the group consisting of O, N, S, and oxidized forms of N and S, wherein each of the aryl, heteroaryl, cycloalkyl, or heterocycle is optionally substituted with 1-4: halo, $C_1$-$C_6$ alkyl, $C_1$-$C_6$ alkoxy, and/or $C_3$-$C_{10}$ cycloalkyl, wherein the $C_1$-$C_6$ alkyl is optionally substituted with 1-5 halo, $C_1$-$C_6$ alkoxy, and/or $C_3$-$C_{10}$ cycloalkyl; or ring A is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl and/or ($C_1$-$C_6$ alkoxy groups;

ring B is a 5-10 membered heteroaryl or a 4-10 membered heterocycle containing up to 5 ring heteroatoms, wherein the heteroatom is selected from the group consisting of O, N, S, and oxidized forms of N and S, wherein each of the heteroaryl and the heterocycle is optionally substituted with 1-4: halo, $C_1$-$C_6$ alkyl and/or —CO—$C_1$-$C_6$ alkyl, or ring B is:

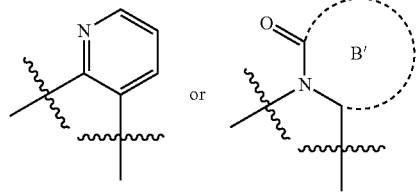 [SMILES: *c1cccnc1* ; *CN(*)C=O]

wherein ring B' including the —N—CO— moiety is a 5-6 membered heterocycle containing up to 3 heteroatoms selected from nitrogen, oxygen, and sulfur and oxidized forms of N and S, wherein each of the heteroaryl and the heterocycle is optionally substituted with 1-4 $C_1$-$C_6$ alkyl groups;

is a single or a double bond;

each X and Y is independently $(CR^{20}R^{21})_e$, O, S, SO, $SO_2$, or $NR^{20}$; e is 1 to 4, preferably 1; each $R^{20}$ and $R^{21}$ independently is hydrogen or $C_1$-$C_3$ alkyl optionally substituted with 1-3 halo, OH, or $C_1$-$C_6$ alkoxy, or $CR^{20}R^{21}$ is C=O, provided that if one of X and Y is O, S, SO, $SO_2$, then the other is not CO, and X and Y are both not heteroatoms or oxidized forms thereof;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —$OR^1$, $C_1$-$C_6$ alkyl, —$COOR^1$, and/or $C_1$-$C_6$ alkoxy, wherein the $C_1$-$C_6$ alkyl is optionally substituted with 1-5 halo, $C_1$-$C_6$ alkoxy, and/or a 4-10 membered heterocycle containing up to 5 ring heteroatoms, wherein the heteroatom is selected from the group consisting of O, N, S, and oxidized forms of N and S; or ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —$OR^1$, $C_1$-$C_6$ alkyl, —$COOR^1$, $NR^5R^6$, $R^1$ is a hydrogen, $C_1$-$C_6$ alkyl or a prodrug moiety; wherein the alkyl is optionally substituted with a 5-10 membered heteroaryl containing up to 5 ring heteroatoms, wherein the heteroatom is selected from the group consisting of O, N, S, and oxidized forms of N and S, which is optionally substituted with with a 5-10 membered heteroaryl containing up to 5 ring heteroatoms, wherein the heteroatom is selected from the group consisting of O, N, S, and oxidized forms of N and S, wherein the heteroaryl is optionally substituted with $C_1$-$C_6$ alkyl;

$R^5$ and $R^6$ are each independently hydrogen, optionally substituted $C_1$-$C_6$ alkyl or —$COOR^3$;

$R^3$ is hydrogen or optionally substituted $C_1$-$C_6$ alkyl;

$V^1$ and $V^2$ independently are $C_1$-$C_6$ alkoxy; or $V^1$ and $V^2$ together with the carbon atom they are attached to form a ring of formula:

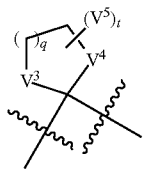

wherein each $V^3$ and $V^4$ are independently O, S, or NH, provided that when one of $V^1$ and $V^4$ is S, the other is NH, and provided that $V^1$ and $V^4$ are both not NH; q is 1 or 2; each $V^5$ is independently $C_1$-$C_6$ alkyl optionally substituted with 1-3 OH groups, or $V^1$ is $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl; and $R^{84}$ is optionally substituted $C_1$-$C_6$ alkyl;

with the proviso that when ring C is $C_6$-$C_{10}$ aryl;

and ring B is optionally substituted 4-10 membered heterocyclyl;

then ring A excludes optionally substituted 5-10 membered heteroaryl;

and provided that when ring C is $C_6$-$C_{10}$ aryl;

and ring B is optionally substituted 5-10 membered heteroaryl;

then ring A is not optionally substituted 4-10 membered heterocycle.

In certain aspects of the invention, a compound of formula (X-I) is provided:

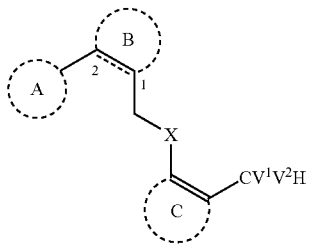

(X-I)

or a tautomer thereof, or a pharmaceutically acceptable salt of each thereof, wherein ring A is $C_6$-$C_{10}$ aryl, a $C_3$-$C_8$ cycloalkyl, a 5-10 membered heteroaryl or a 4-10 membered heterocycle containing up to 5 ring heteroatoms, wherein the heteroatom is selected from the group consisting of O, N, S, and oxidized forms of N and S, wherein each of the aryl, heteroaryl, cycloalkyl, or heterocycle is optionally substituted with 1-4: halo, $C_1$-$C_6$ alkyl, $C_1$-$C_5$ alkoxy, and/or $C_3$-$C_{10}$ cycloalkyl, wherein the $C_1$-$C_6$ alkyl is optionally substituted with 1-5 halo, $C_1$-$C_6$ alkoxy, and/or $C_3$-$C_{10}$ cycloalkyl;

ring B is a 5-10 membered heteroaryl or a 4-10 membered heterocycle containing up to 5 ring heteroatoms, wherein the heteroatom is selected from the group consisting of O, N, S, and oxidized forms of N and S, wherein each of the heteroaryl and the heterocycle is optionally substituted with 1-4: halo, $C_1$-$C_6$ alkyl and/or CO—$C_1$-$C_6$ alkyl, ⋰ is a single or a double bond;

X is O, S, SO, or $SO_2$;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —$OR^1$, $C_1$-$C_6$ alkyl, —$COOR^1$, and/or $C_1$-$C_6$ alkoxy, wherein the $C_1$-$C_6$ alkyl is optionally substituted with 1-5 halo, $C_1$-$C_6$ alkoxy and/or a 4-10 membered heterocycle containing up to 5 ring heteroatoms, wherein the heteroatom is selected from the group consisting of O, N, S, and oxidized forms of N and S; and $R^1$ is hydrogen or a prodrug moiety;

$V^1$ and $V^2$ independently are $C_1$-$C_6$ alkoxy; or $V^1$ and $V^2$ together with the carbon atom they are attached to form a ring of formula:

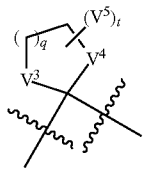

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl;

$R^{84}$ is optionally substituted $C_1$-$C_6$ alkyl;

provided that when ring C is $C_6$-$C_{10}$ aryl;

and ring B is optionally substituted 4-10 membered heterocyclyl;

then ring A excludes optionally substituted 5-10 membered heteroaryl;

and provided that when ring C is $C_6$-$C_{10}$ aryl;

and ring B is optionally substituted 5-10 membered heteroaryl;

then ring A is not optionally substituted 4-10 membered heterocycle.

In certain aspects of the invention, a compound of formula (X-I) is provided:

or a tautomer thereof, or a pharmaceutically acceptable salt of each thereof, wherein ring A is phenyl optionally substituted with 1-3 halo and/or $C_1$-$C_6$ alkoxy, or is a 4-10 membered heterocycle containing up to 5 ring heteroatoms, wherein the heteroatom is selected from the group consisting of O, N, S, and oxidized forms of N and S, optionally substituted, or is

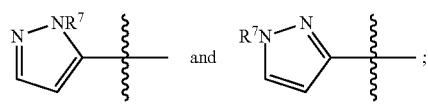

wherein $R^7$ is $C_1$-$C_6$ alkyl, optionally substituted with 3-5 fluoro groups, or is $C_3$-$C_6$ cycloalkyl;

ring B is selected from the group consisting of

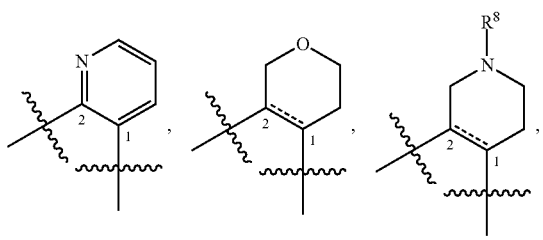

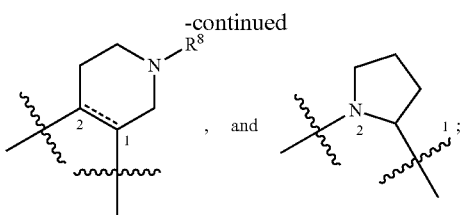

wherein $R^8$ is $C_1$-$C_6$ alkyl, —CO—$C_1$-$C_6$ alkyl or a prodrug moiety;

X is O, S, SO, or $SO_2$;

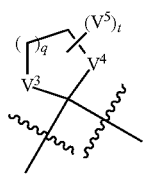 is a single or a double bond;

ring C is phenyl or a 6 membered nitrogen-containing heteroaryl, each of which is optionally substituted with 1-4: halo, oxo, —$OR^1$, $C_1$-$C_6$ alkyl, —$COOR^1$, and/or $C_1$-$C_6$ alkoxy, wherein the $C_1$-$C_6$ alkyl is optionally substituted with 1-5 halo, $C_1$-$C_6$ alkoxy and/or 4-10 membered heterocycle containing up to 5 ring heteroatoms, wherein the heteroatom is selected from the group consisting of O, N, S, and oxidized forms of N and S; and each $R^1$ is hydrogen or a prodrug moiety R;

$V^1$ and $V^2$ independently are $C_1$-$C_6$ alkoxy; or $V^1$ and $V^2$ together with the carbon atom they are attached to form a ring of formula:

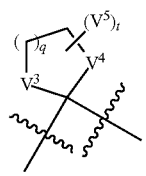

wherein each $V^3$ and $V^4$ are independently O, S, or NH, provided that when one of $V^3$ and $V^4$ is S, the other is NH, and provided that $V^1$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl;

$R^{84}$ is optionally substituted $C_1$-$C_6$ alkyl;

provided that when ring C is $C_6$-$C_{10}$ aryl;

and ring B is optionally substituted 4-10 membered heterocyclyl;

then ring A excludes optionally substituted 5-10 membered heteroaryl;

and provided that when ring C is $C_6$-$C_{10}$ aryl;

and ring B is optionally substituted 5-10 membered heteroaryl;

then ring A is not optionally substituted 4-10 membered heterocycle.

Preferably, $V^1$ and $V^2$ together with the carbon atom they are attached to form a ring of formula:

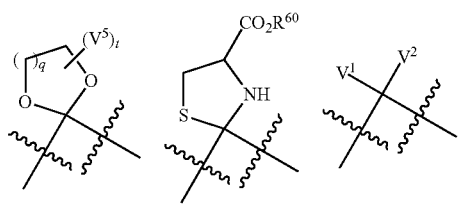

In some embodiments, $V^1$ and $V^2$ independently are $C_1$-$C_6$ alkoxy; or $V^1$ and $V^2$ together with the carbon atom they are attached to form a ring of formula:

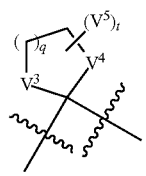

wherein each $V^3$ and $V^4$ are independently O, S, or NH, provided that when one or $V^3$ and $V^4$ is S the other is NH, and provided that $V^3$ and $V^4$ are both not NH; q is 1 or 2; each V is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, and wherein the remaining variables are defined herein.

In certain embodiments, a compound of formula (III) is provided:

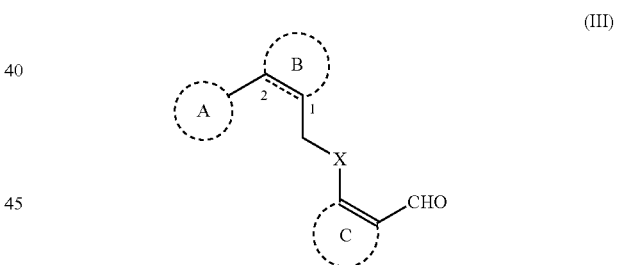

(III)

or a tautomer thereof, or a pharmaceutically acceptable salt of each thereof, wherein ring A is phenyl optionally substituted with 1-3 halo and/or $C_1$-$C_6$ alkoxy, or is a 4-10 membered heterocycle containing up to 5 ring heteroatoms, wherein the heteroatom is selected from the group consisting of O, N, S, and oxidized forms of N and S, optionally substituted, or is

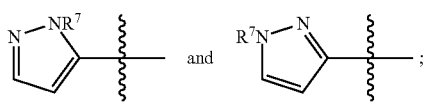

wherein $R^7$ is $C_1$-$C_6$ alkyl, optionally substituted with 3-5 fluoro groups, or is $C_3$-$C_6$ cycloalkyl;

ring B is selected from the group consisting of

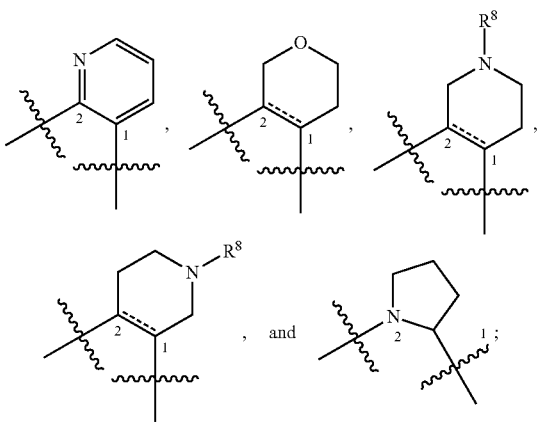

wherein $R^8$ is $C_1$-$C_6$ alkyl, —CO—$C_1$-$C_6$ alkyl or a prodrug moiety;

X is O, S, SO, or $SO_2$;

⋰ is a single or a double bond;

ring C is phenyl or a 6 membered nitrogen-containing heteroaryl, each of which is optionally substituted with 1-4: halo, oxo, —$OR^1$, $C_1$-$C_6$ alkyl —$COOR^1$, and/or $C_1$-$C_6$ alkoxy, wherein the $C_1$-$C_6$ alkyl is optionally substituted with 1-5 halo, $C_1$-$C_6$ alkoxy and/or 4-10 membered heterocycle containing up to 5 ring heteroatoms, wherein the heteroatom is selected from the group consisting of O, N, S, and oxidized forms of N and S; and each $R^1$ is hydrogen or a prodrug moiety R;

$V^1$ and $V^2$ independently are $C_1$-$C_6$ alkoxy; or $V^1$ and $V^2$ together with the carbon atom they are attached to form a ring of formula:

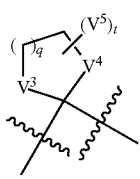

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl;

$R^{84}$ is optionally substituted $C_1$-$C_6$ alkyl;

provided that when ring C is $C_6$-$C_{10}$ aryl;

and ring B is optionally substituted 4-10 membered heterocyclyl;

then ring A excludes optionally substituted 5-10 membered heteroaryl;

and provided that when ring C is $C_6$-$C_{10}$ aryl;

and ring B is optionally substituted 5-10 membered heteroaryl;

then ring A is not optionally substituted 4-10 membered heterocycle.

In certain embodiments, t is 0. In certain embodiments, t is 1. In certain embodiments, t is 2. In certain embodiments, t is 3. In one embodiment, —X—Y— is —$CH_2$—O—. In another embodiment, —X—Y is —O—$CH_2$—.

In certain embodiments, a compound selected from formulas (IIIA), (IIIB) and (IIIC) is provided:

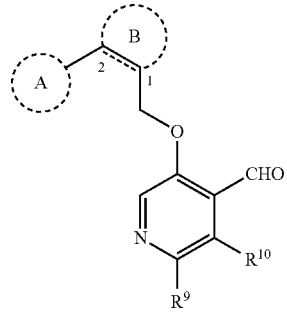

IIIA

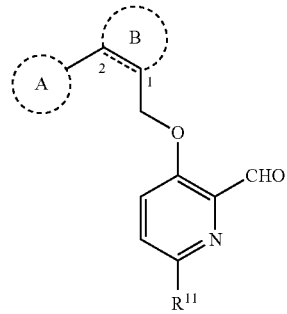

IIIB

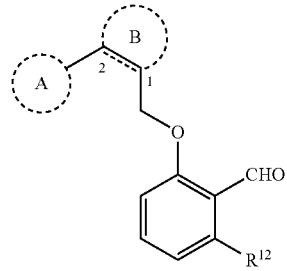

IIIC wherein $R^9$ is hydrogen, —$OR^1$, $C_1$-$C_6$ alkoxy optionally substituted with 1-3 $C_1$-$C_6$ alkoxy or 4-10 membered heterocycle containing up to 5 ring heteroatoms selected from N, O, S or oxidized forms thereof;

$R^{10}$ is hydrogen, halo, hydroxy or $C_1$-$C_6$ alkoxy;

$R^{11}$ is hydrogen or $C_1$-$C_6$ alkyl; and $R^{12}$ is —$OR^1$;

wherein $R^1$ is hydrogen or the prodrug moiety R.

In certain embodiments, ring A is phenyl substituted with 1-3 halo or $C_1$-$C_6$ alkoxy, or $C_3$-$C_8$ heterocyclyl containing 1-3 heteroatoms, wherein the heterocycle is optionally substituted with 1-3 halo.

In certain embodiments, ring A is pyridyl, optionally substituted as defined herein.

In certain embodiments, compounds of formulas (II), (III), (IIIA), (IIIB) and (IIIC) are provided, wherein

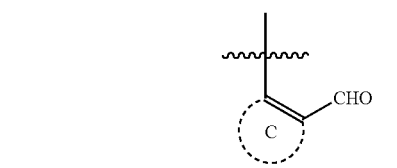
is selected from the group consisting of
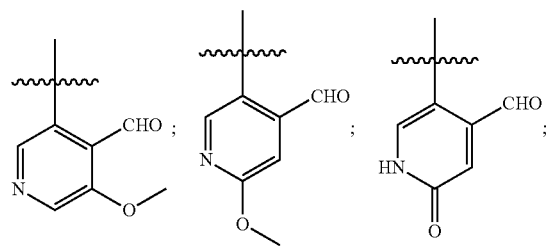
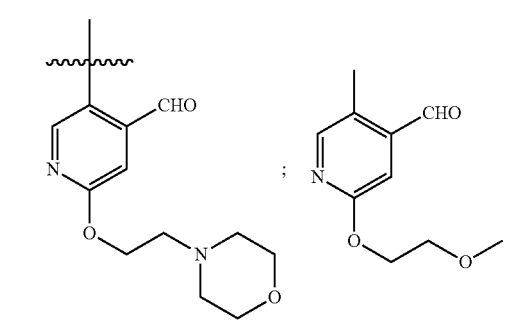
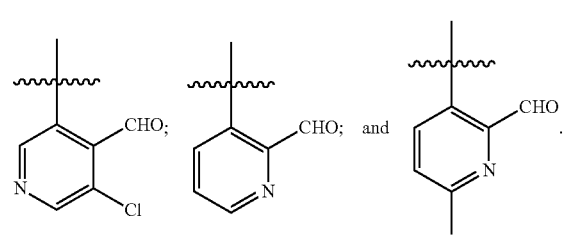
In certain embodiments, compounds of formulas (II), (III), (IIA), (IIB) and (IIIC) are provided, wherein
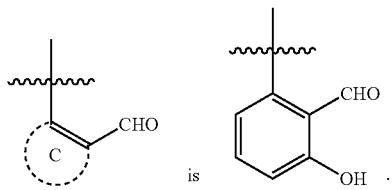 is
In certain embodiments, a compound is provided, wherein the compound selected from the group consisting of:
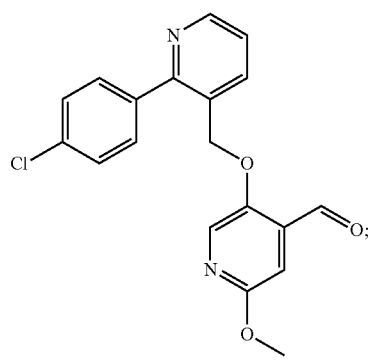
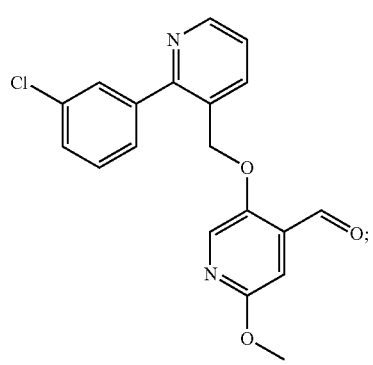
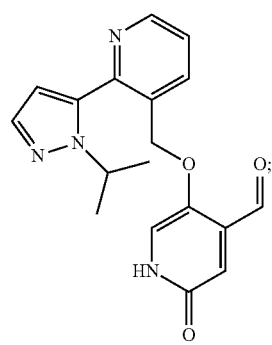
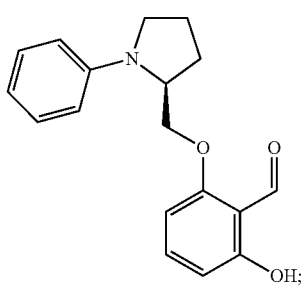
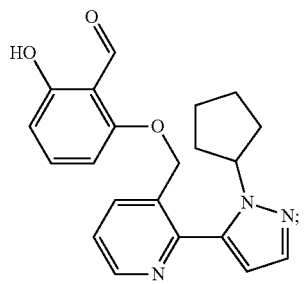

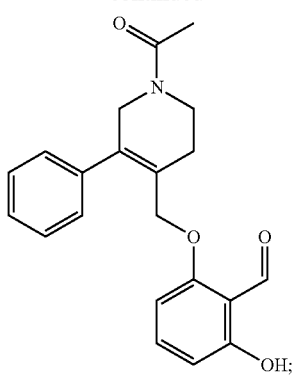
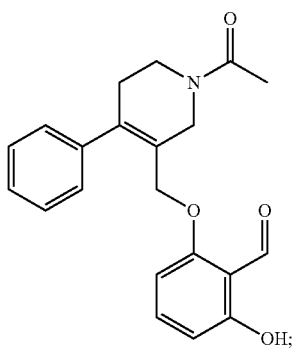
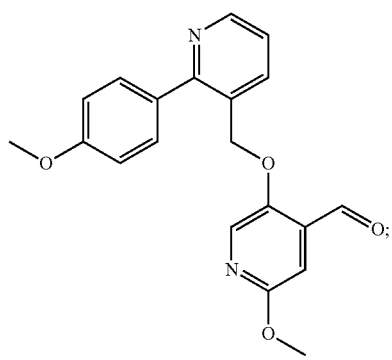
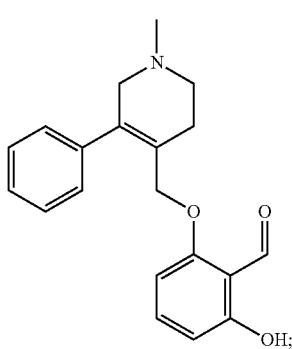
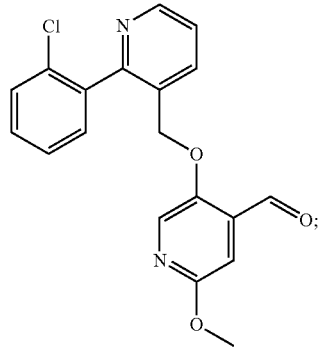
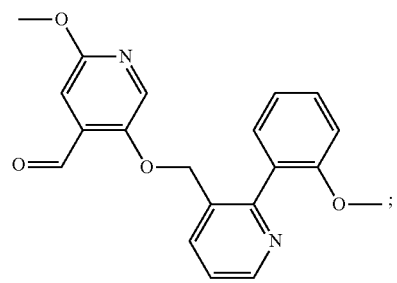
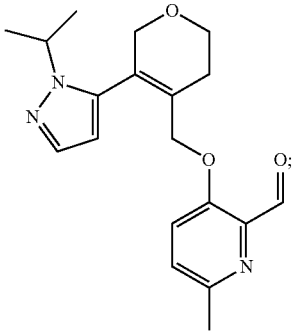
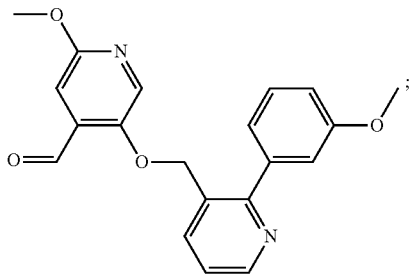
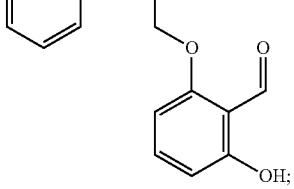

25
-continued
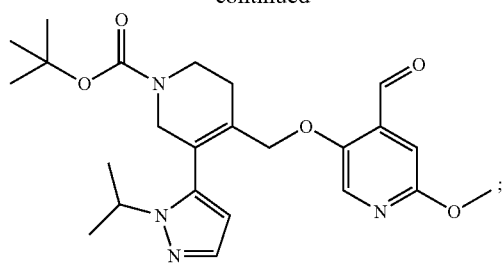
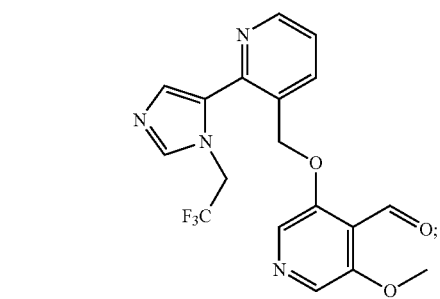
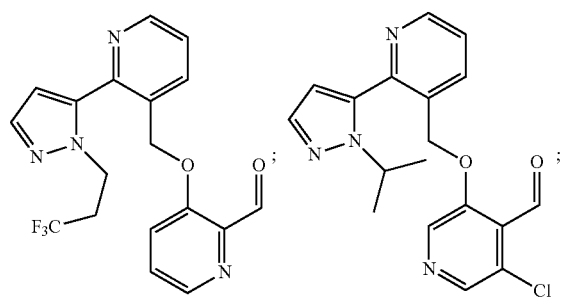
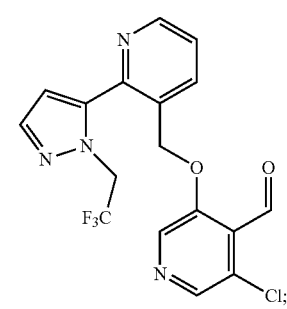
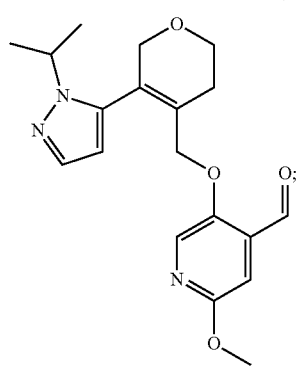
26
-continued
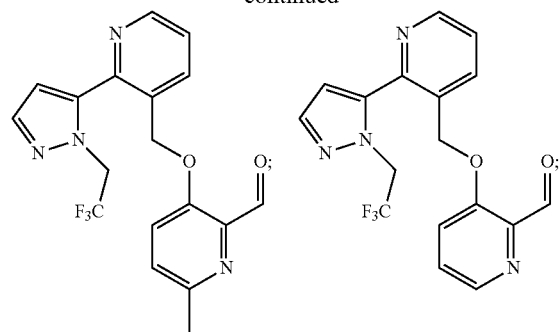
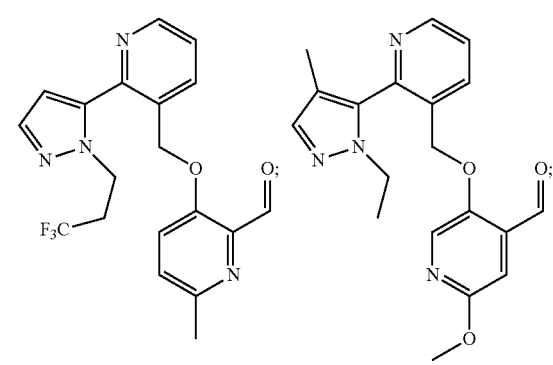
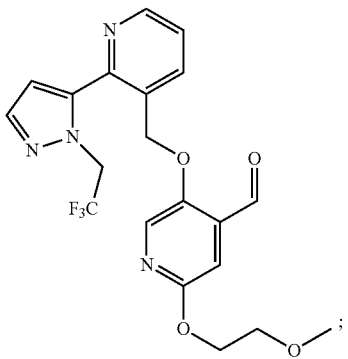
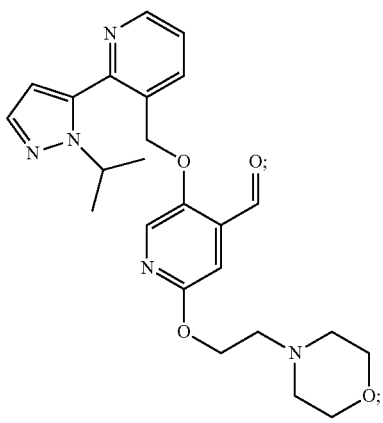

-continued
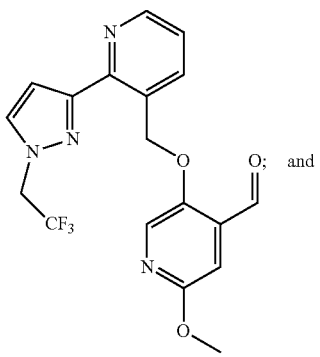
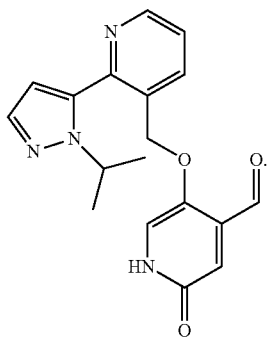
or an N oxides thereof, or a pharmaceutically acceptable salt of each thereof.
In certain embodiments, a compound is provided, wherein the compound selected from the group consisting of:
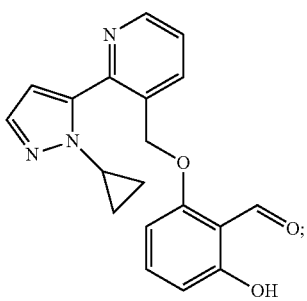
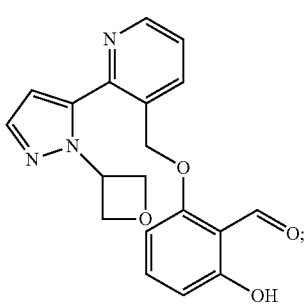
-continued
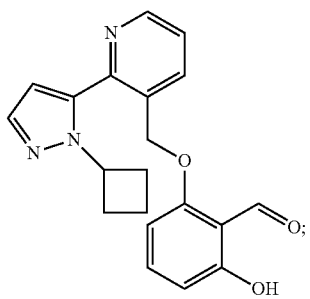
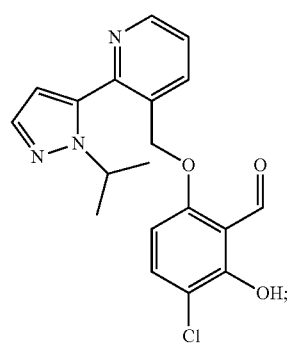
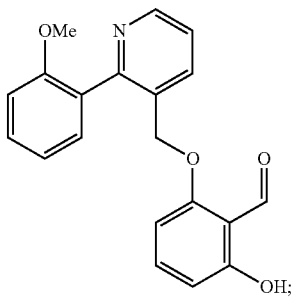
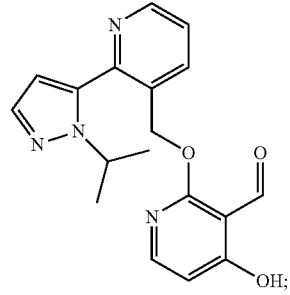
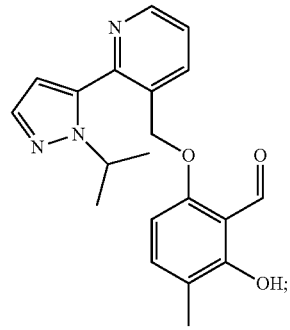

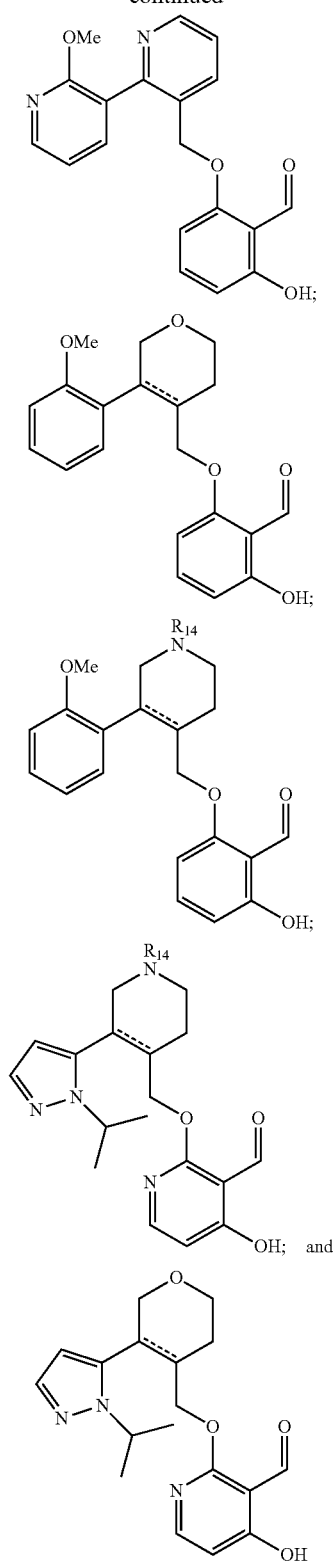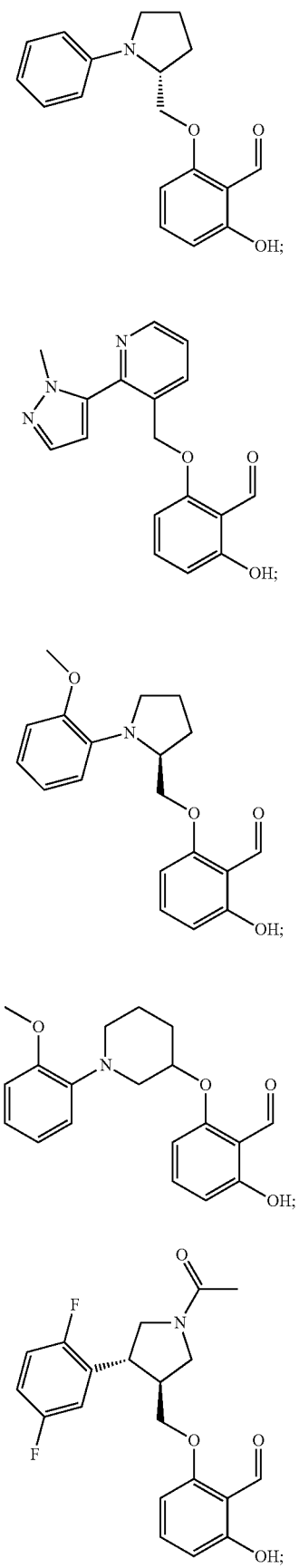
or an N oxides thereof, or a pharmaceutically acceptable salt of each thereof.
In certain aspects of the invention, a compound is provided, wherein the compound is selected from the group consisting of:

31
-continued
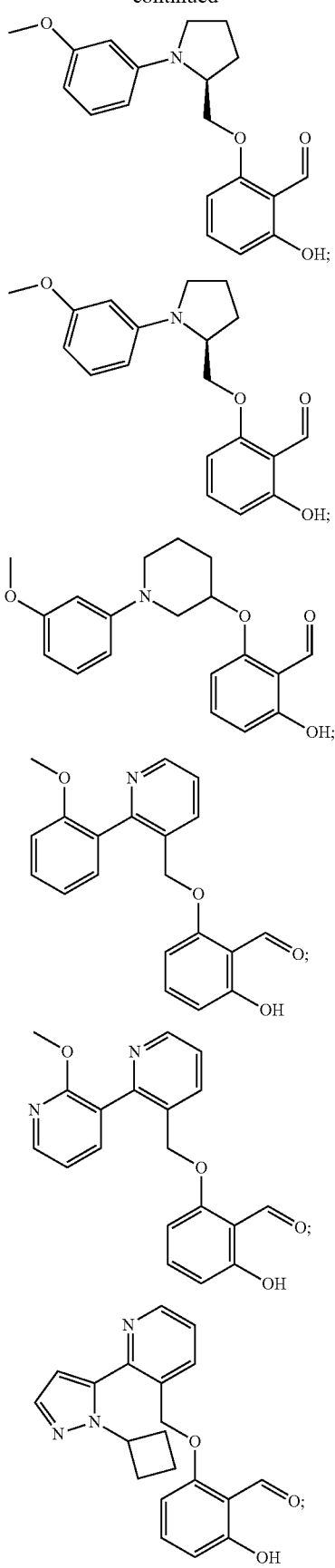
32
-continued
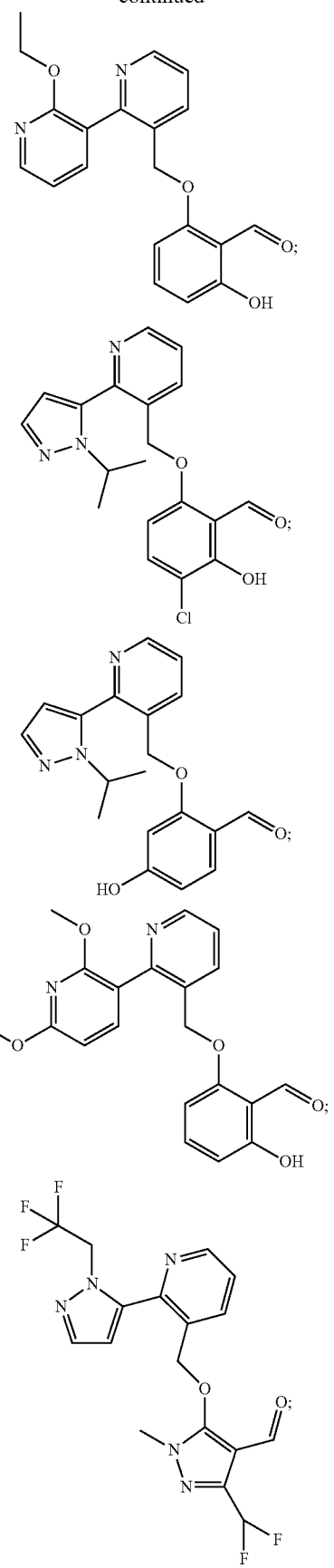

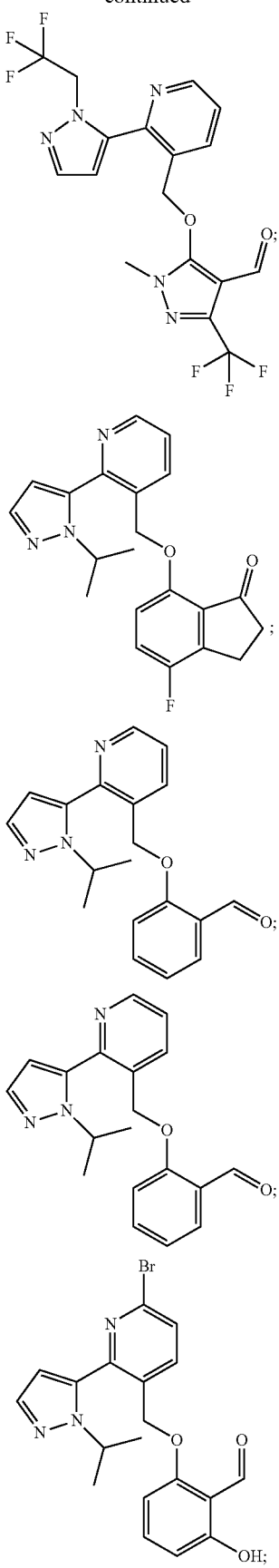

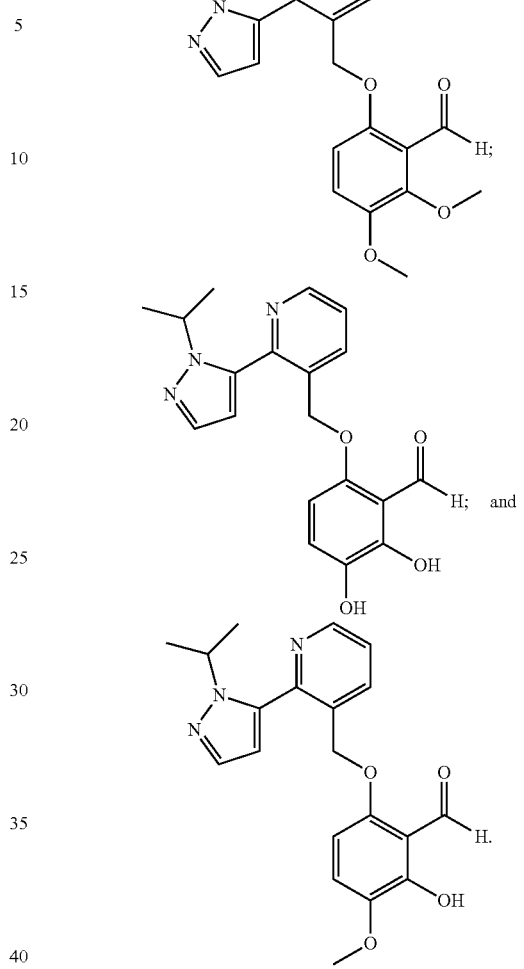

or a prodrug thereof, or a pharmaceutically acceptable salt of each thereof. Other compounds of this invention are illustrated in the Examples section.

In certain aspects of the invention, a compound of formula (I) is provided:

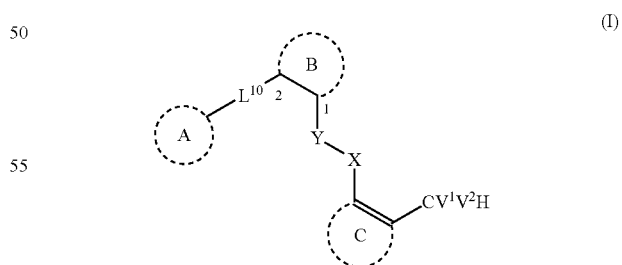

or a tautomer thereof, or a pharmaceutically acceptable salt of each thereof, wherein $L^{10}$ is optionally substituted methylene or, preferably, a bond;

ring A is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl and/or $C_1$-$C_6$ alkoxy groups;

ring B is:

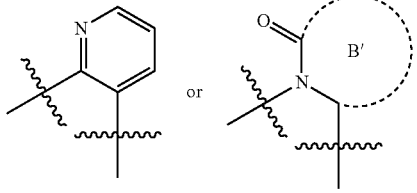

wherein ring B' including the —N—CO— moiety is a 5-6 membered heterocycle containing up to 3 heteroatoms selected from nitrogen, oxygen, and sulfur and oxidized forms of N and S, wherein each of the heteroaryl and the heterocycle is optionally substituted with 1-4 $C_1$-$C_6$ alkyl groups;

each X and Y is independently $(CR^{20}R^{21})_e$, O, S, SO, $SO_2$, or $NR^{20}$; e is 1 to 4, preferably 1; each $R^{20}$ and $R^{21}$ independently is hydrogen or $C_1$-$C_3$ alkyl optionally substituted with 1-3 halo, OH, or $C_1$-$C_6$ alkoxy, or $CR^{20}R^{21}$ is C=O, provided that if one of X and Y is O, S, SO, $SO_2$, then the other is not CO, and X and Y are both not heteroatoms or oxidized forms thereof;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —$OR^1$, $C_1$-$C_6$ alkyl, —$COOR^5$, $NR^5R^6$, $R^1$ is a hydrogen, $C_1$-$C_6$ alkyl or a prodrug moiety; wherein the alkyl is optionally substituted with a 5-10 membered heteroaryl containing up to 5 ring heteroatoms, wherein the heteroatom is selected from the group consisting of O, N, S, and oxidized forms of N and S, which is optionally substituted with with a 5-10 membered heteroaryl containing up to 5 ring heteroatoms, wherein the heteroatom is selected from the group consisting of O, N, S, and oxidized forms of N and S, wherein the heteroaryl is optionally substituted with $C_1$-$C_6$ alkyl;

$R^5$ and $R^6$ are each independently hydrogen, optionally substituted $C_1$-$C_6$ alkyl or —$COOR^3$;

$R^3$ is hydrogen or optionally substituted $C_1$-$C_6$ alkyl;

$V^1$ and $V^2$ independently are $C_1$-$C_6$ alkoxy; or $V^1$ and $V^2$ together with the carbon atom they are attached to form a ring of formula:

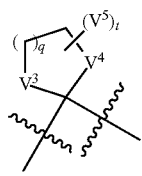

wherein each $V^3$ and $V^4$ are independently O, S, or NH, provided that when one of $V^1$ and $V^4$ is S, the other is NH, and provided that $V^3$ and $V^4$ are both not NH; q is 1 or 2; each $V^5$ is independently $C_1$-$C_6$ alkyl optionally substituted with 1-3 OH groups, or $V^5$ is $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl; and $R^{84}$ is optionally substituted $C_1$-$C_6$ alkyl;

with the proviso that when ring C is $C_6$-$C_{10}$ aryl;

and ring B is optionally substituted 4-10 membered heterocyclyl;

then ring A excludes optionally substituted 5-10 membered heteroaryl;

and provided that when ring C is $C_6$-$C_{10}$ aryl;

and ring B is optionally substituted 5-10 membered heteroaryl;

then ring A is not optionally substituted 4-10 membered heterocycle.

In certain aspects of the invention, a compound of formula (IV) is provided:

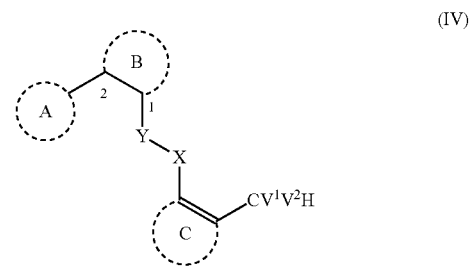

or a tautomer thereof, or a pharmaceutically acceptable salt of each thereof, wherein ring A is $C_6$-$C_{10}$ aryl, or a 5-10 membered heteroaryl, wherein the heteroatom is selected from the group consisting of O, N, S, and oxidized forms of N and S, wherein each of the aryl or heteroaryl is optionally substituted with 1-4 $C_1$-$C_6$ alkyl;

ring B is:

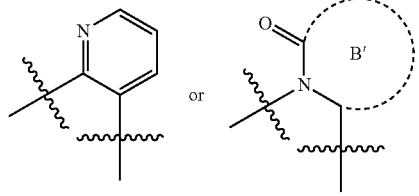

wherein ring B' including the —N—CO— moiety is a 5-6 membered heterocycle containing up to 3 heteroatoms selected from nitrogen, oxygen, and sulfur and oxidized forms of N and S, wherein each of the heteroaryl and the heterocycle is optionally substituted with 1-4 $C_1$-$C_6$ alkyl groups;

each X and Y is independently $CR^{20}R^{21}$, O, S, SO, $SO_2$, or $NR^{10}$; each $R^{20}$ and $R^{21}$ independently is hydrogen or $C_1$-$C_3$ alkyl optionally substituted with 1-3 halo, OH, or $C_1$-$C_6$ alkoxy, or $CR^{20}R^{21}$ is C=O, provided that if one of X and Y is O, S, SO, $SO_2$, then the other is not CO, and X and Y are both not heteroatoms or oxidized forms thereof;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —$OR^1$, $C_1$-$C_6$ alkyl, —$COOR^5$, $NR^5R^6$, $R^1$ is a hydrogen, $C_1$-$C_6$ alkyl or a prodrug moiety; wherein the alkyl is optionally substituted with a 5-10 membered heteroaryl containing up to 5 ring heteroatoms, wherein the heteroatom is selected from the group consisting of O, N, S, and oxidized forms of N and S, which is optionally substituted with with a 5-10 membered heteroaryl containing up to 5 ring heteroatoms, wherein the heteroatom is selected from the group consisting of O, N, S, and oxidized forms of N and S, wherein the heteroaryl is optionally substituted with $C_1$-$C_6$ alkyl;

$R^5$ and $R^6$ are each independently hydrogen, optionally substituted $C_1$-$C_6$ alkyl or —$COOR^3$;

$R^3$ is hydrogen or optionally substituted $C_1$-$C_6$ alkyl;

$V^1$ and $V^2$ independently are $C_1$-$C_6$ alkoxy; or $V^1$ and $V^2$ together with the carbon atom they are attached to form a ring of formula:

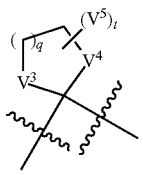

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl optionally substituted with 1-3 OH groups, or $V^5$ is $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl; and $R^{84}$ is optionally substituted $C_1$-$C_6$ alkyl.

In certain embodiments, ring C is substituted with at least one substituent selected from with 1-4: halo, —$OR^1$, $C_1$-$C_6$ alkyl, —$COOR^5$, $NR^5R^6$.

In certain embodiments, X is $CH_2$, O, S, SO, $SO_2$ or NH. In certain embodiments. X is O, S, SO or $SO_2$. Preferably, X is O, and wherein the remaining variables are defined herein.

In certain embodiments, Y is $CR^{20}R^{21}$, O, S. SO, $SO_2$, or $NR^{10}$; wherein each $R^{20}$ and $R^{21}$ independently is hydrogen or $C_1$-$C_3$ alkyl. In certain embodiments, Y is $CR^{20}R^{21}$ wherein each $R^{20}$ and $R^{21}$ independently is hydrogen or $C_1$-$C_3$ alkyl. Preferably, Y is $CH_2$, and wherein the remaining variables are defined herein.

In certain embodiments, t is 0. In certain embodiments, t is 1. In certain embodiments, t is 2. In certain embodiments, t is 3.

Preferably, $CV^1V^2$ is C=V, wherein V is O, and wherein the remaining variables are defined herein.

In certain embodiments, a compound of formula (V) is provided:

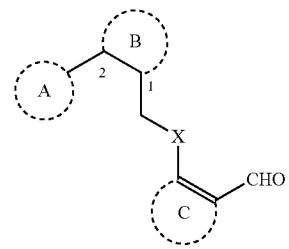

(V)

or a tautomer thereof, or a pharmaceutically acceptable salt of each thereof, wherein ring A is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl and/or $C_1$-$C_6$ alkoxy groups;

ring B is:

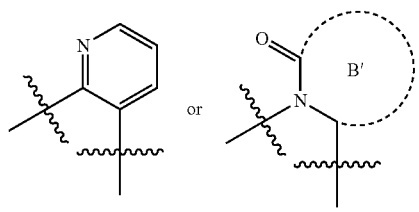 [SMILES: *c1cccnc1* ; *CN(*)C=O]

wherein ring B' including the —N—CO— moiety is a 5-6 membered heterocycle containing up to 3 heteroatoms selected from nitrogen, oxygen, and sulfur and oxidized forms of N and S, wherein each of the heteroaryl and the heterocycle is optionally substituted with 1-4 $C_1$-$C_6$ alkyl groups;

X is O, S, SO or $SO_2$;

ring C is $C_6$-$C_{10}$ aryl or a 5-10 membered heteroaryl containing up to 5 ring heteroatoms, wherein the heteroatom is selected from the group consisting of O, N. S, and oxidized forms of N and S, each of which is optionally substituted with 1-4: halo, oxo, —$OR^1$, $C_1$-$C_6$ alkyl, —$COOR^5$, $NR^5R^6$, $R^1$ is a hydrogen, $C_1$-$C_6$ alkyl or a prodrug moiety R; wherein the alkyl is optionally substituted with a 5-10 membered heteroaryl containing up to 5 ring heteroatoms, wherein the heteroatom is selected from the group consisting of O, N, S, and oxidized forms of N and S, which is optionally substituted with with a 5-10 membered heteroaryl containing up to 5 ring heteroatoms, wherein the heteroatom is selected from the group consisting of O, N, S, and oxidized forms of N and S, wherein the heteroaryl is optionally substituted with $C_1$-$C_6$ alkyl;

$R^5$ and $R^6$ are each independently hydrogen, optionally substituted $C_1$-$C_6$ alkyl or —$COOR^3$; and $R^3$ is hydrogen or optionally substituted $C_1$-$C_6$ alkyl.

In certain embodiments, a compound of formula (VI) or (VII) is provided:

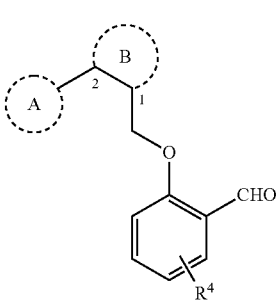

(VI)

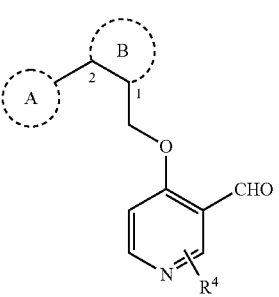

(VII)

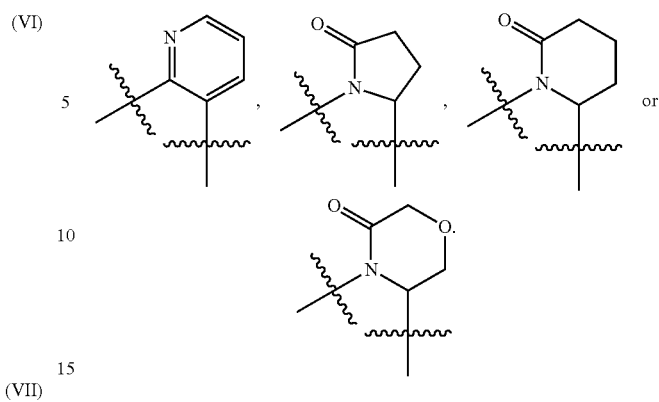

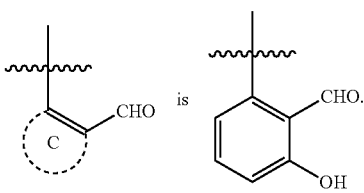

In certain embodiments, compounds of formula (V) are provided, wherein or a tautomer thereof, or a pharmaceutically acceptable salt of each thereof, wherein ring A is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl;

ring B is $C_6$-$C_{10}$ aryl, $C_3$-$C_8$ cycloalkyl, a 5-10 membered heteroaryl containing up to 5 ring heteroatoms or a 4-10 membered heterocycle containing up to 5 ring heteroatoms, wherein the heteroatom is selected from the group consisting of O, N, S, and oxidized forms of N and S, wherein each of the aryl, heteroaryl, cycloalkyl or heterocycle is optionally substituted with 1-4: halo, $C_1$-$C_6$ alkyl, or $C_1$-$C_6$ alkoxy, wherein the $C_1$-$C_6$ alkyl is optionally substituted with 1-5 halo, $C_1$-$C_6$ alkoxy, and/or $C_3$-$C_{10}$ cycloalkyl;

$R^4$ is halo, oxo, —$OR^{18}$, $C_1$-$C_6$ alkyl, $C_1$-$C_6$ alkoxy, —$COOR^1$, and/or $NR^5R^6$;

$R^{18}$ is hydrogen, substituted $C_1$-$C_6$ alkyl, or a prodrug moiety R;

$R^5$ and $R^6$ are each independently hydrogen, optionally substituted $C_1$-$C_6$ alkyl or —$COOR^3$; and $R^3$ is hydrogen, provided that the $COOR^3$ is not joined to a nitrogen atom, or is optionally substituted $C_1$-$C_6$ alkyl.

In one embodiment, $R^4$ is —OH. In another embodiment, $R^4$ is $NH_2$. In one embodiment, $R^4$ is $NH(CH_3)$. In one embodiment, $R^4$ is $N(CH_3)_2$. In one embodiment, $R^4$ is $NHC(O)OC(CH_3)_3$. In one embodiment, $R^4$ is COOH. In one embodiment, $R^4$ is optionally substituted dioxolan. In one embodiment, $R^4$ is a substituted pyridine. As used herein, $R^1$ is hydrogen, provided that the $COOR^3$ is not joined to a nitrogen atom.

In certain embodiments, ring B is selected from the group consisting of:

In certain embodiments, a compound of formula (IV) as disclosed above is provided, with the proviso that:

when ring C is $C_6$-$C_{10}$ aryl;

and ring B is optionally substituted 4-10 membered heterocyclyl;

then ring A excludes optionally substituted 5-10 membered heteroaryl.

In certain embodiments, a compound is provided, wherein the compound is selected from the group consisting of:

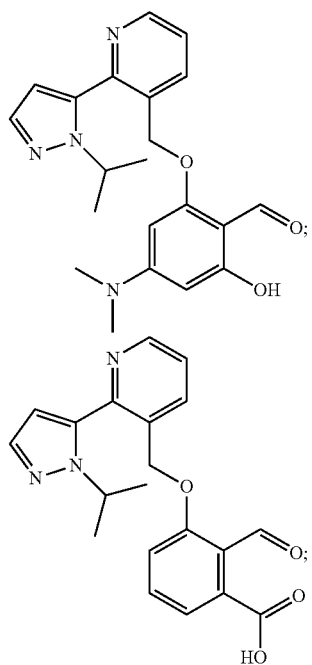

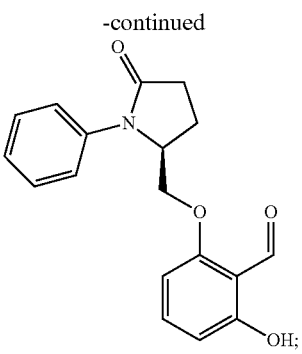
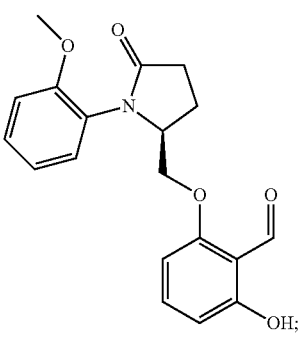
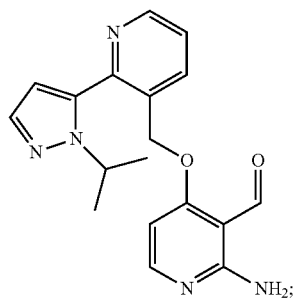
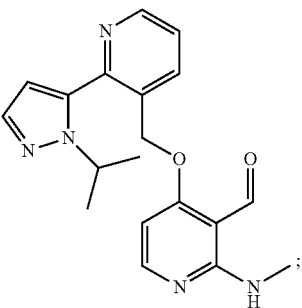
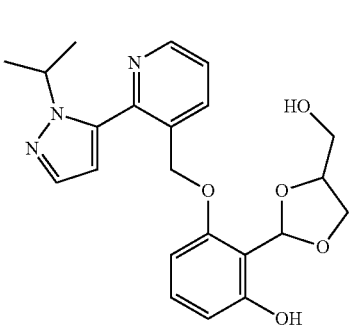

-continued

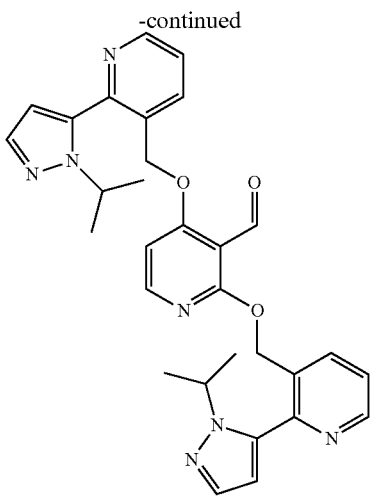

or N oxides thereof, or a pharmaceutically acceptable salt of each thereof.

Compounds provided herein include those in the Examples section.

Prodrug Moiety

In one aspect, R is hydrogen, a phosphate or a diphosphate containing moiety, or another promoiety or prodrug moiety. Preferably the prodrug moiety imparts at least a 2 fold, more preferably a 4 fold, enhanced solubility and/or bioavailability to the active moiety (where R is hydrogen), and more preferably is hydrolyzed in vivo. The promoieties are structurally and functionally defined herein.

In one embodiments, R is —$COR^{90}$, $CO_2R^{91}$, or $CONR^{92}R^{93}$ wherein $R^{90}$ and $R^{91}$ independently are $C_1$-$C_6$ alkyl, $C_3$-$C_8$ cycloalkyl, 4-9 membered heterocycle, or a 5-10 membered heteroaryl, each containing at least 1 basic nitrogen moiety; and $R^{92}$ and $R^{93}$ independently are $C_1$-$C_6$ alkyl; $C_3$-$C_8$ cycloalkyl, 4-9 membered heterocycle, or a 5-10 membered heteroaryl, each containing at least 1 basic nitrogen moiety; or $R^{92}$ and $R^{93}$ together with the nitrogen atom they are bonded to for a 4-9 member heterocycle substituted with at least 1 amino, $C_1$-$C_6$ alkyl amino, or di $C_1$-$C_6$ alkylamino group.

In certain embodiments, R is —$C(O)R^{31}$, $C(O)OR^{31}$, or $CON(R^{13})_2$, each $R^{31}$ is independently a $C_1$-$C_6$ alkyl; $C_3$-$C_8$ cycloalkyl, 4-9 membered heterocycle, or a 5-10 membered heteroaryl, containing at least 1 basic nitrogen moiety; and each $R^{13}$ independently is $C_1$-$C_6$ alkyl; $C_3$-$C_8$ cycloalkyl, 4-9 membered heterocycle, or a 5-10 membered heteroaryl, containing at least 1 basic nitrogen moiety; or both $R^{13}$ together with the nitrogen atom they are bonded to for a 4-9 member heterocycle substituted with at least 1 amino, $C_1$-$C_6$ alkyl amino, or di $C_1$-$C_6$ alkylamino group.

In one aspect, R is $C(O)OR^{31}$, $C(S)OR^{31}$, $C(O)SR^{31}$ or $COR^{31}$, wherein $R^{31}$ is as defined herein.

In one embodiment, $R^{31}$ is a group of the formula $(CR^{32}R^{33})NR^{34}R^{35}$, wherein each $R^{32}$ and $R^{33}$ is independently H, a $C_1$-$C_8$ alkyl, $C_3$-$C_9$ heterocyclyl, $C_3$-$C_8$ cycloalkyl, $C_6$-$C_{10}$ aryl, $C_3$-$C_9$ heteroaryl or $R^{32}$ and $R^{33}$ together with the carbon atom they are bond to form a $C_3$-$C_8$ cycloalkyl, $C_6$-$C_{10}$ aryl, $C_3$-$C_9$ heterocyclyl or $C_3$-$C_9$ heteroaryl ring system, or 2 adjacent $R^{32}$ moieties or 2 adjacent $R^{33}$ moieties together with the carbon atom they are bond to form a $C_3$-$C_8$ cycloalkyl, $C_6$-$C_{10}$ aryl, $C_3$-$C_9$ heterocyclyl or $C_3$-$C_9$ heteroaryl ring system;

each $R^{34}$ and $R^{35}$ is a $C_1$-$C_8$ alkyl, $C_3$-$C_9$ heterocyclyl, $C_3$-$C_8$ cycloalkyl, or $R^{34}$ and $R^{35}$ together with the nitrogen atom they are bond to form a $C_3$-$C_8$ cycloalkyl or $C_3$-$C_9$ heterocyclyl ring system;

each heterocyclic and heteroaryl ring system is optionally substituted with $C_1$-$C_3$ alkyl, —OH, amino and carboxyl groups; and e is an integer of from 1 to 4.

In some less preferred embodiments $R^{34}$ and $R^{35}$ can be hydrogen.

In one embodiment, the subscript e is preferably 2 and each $R^{32}$ and $R^{33}$ is preferably independently selected from the group, H, $CH_3$, and a member in which $R^{32}$ and $R^{33}$ are joined together to form a cyclopropyl, cyclobutyl, cyclopentyl, cyclohexyl, or 1,1-dioxo-hexahydro-1$\Delta^6$-thiopyran-4-yl or tetrahydropyran-4-yl group.

With regard to the prodrug group, preferred embodiments are compounds wherein $NR^{34}R^{35}$ is morpholino.

In one embodiment, R is:

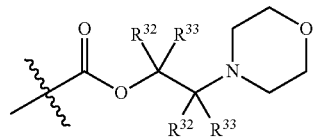

wherein each $R^{32}$ and $R^{33}$ is independently H, $C_1$-$C_8$ alkyl, or optionally, if both present on the same substituent, may be joined together to form a $C_3$-$C_8$ cycloalkyl, $C_6$-$C_{10}$ aryl, $C_3$-$C_9$ heterocyclyl or $C_3$-$C_9$ heteroaryl ring system.

Within this embodiment, each $R^{32}$ and $R^{33}$ is independently, H, $CH_3$, or are joined together to form a cyclopropyl, cyclobutyl, cyclopentyl, cyclohexyl, 1,1-dioxo-hexahydro-1$\lambda^6$-thiopyran-4-yl or tetrahydropyran-4-yl group.

In a preferred embodiment, linkage of the prodrug moiety to the rest of the active molecule is stable enough so that the serum half life of the prodrug is from about 8 to about 24 hours.

In an embodiment of the invention, the prodrug moiety comprises a tertiary amine having a pKa near the physiological pH of 7.5. Any amines having a pKa within 1 unit of 7.5 are suitable alternatives amines for this purpose. The amine may be provided by the amine of a morpholino group. This pKa range of 6.5 to 8.5 allows for significant concentrations of the basic neutral amine to be present in the mildly alkaline small intestine. The basic, neutral form of the amine prodrug is lipophilic and is absorbed through the wall of the small intestine into the blood. Following absorption into the bloodstream, the prodrug moiety is cleaved by esterases which are naturally present in the serum to release an active compound.

Examples of R include, without limitation:

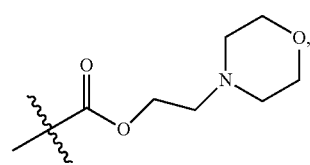

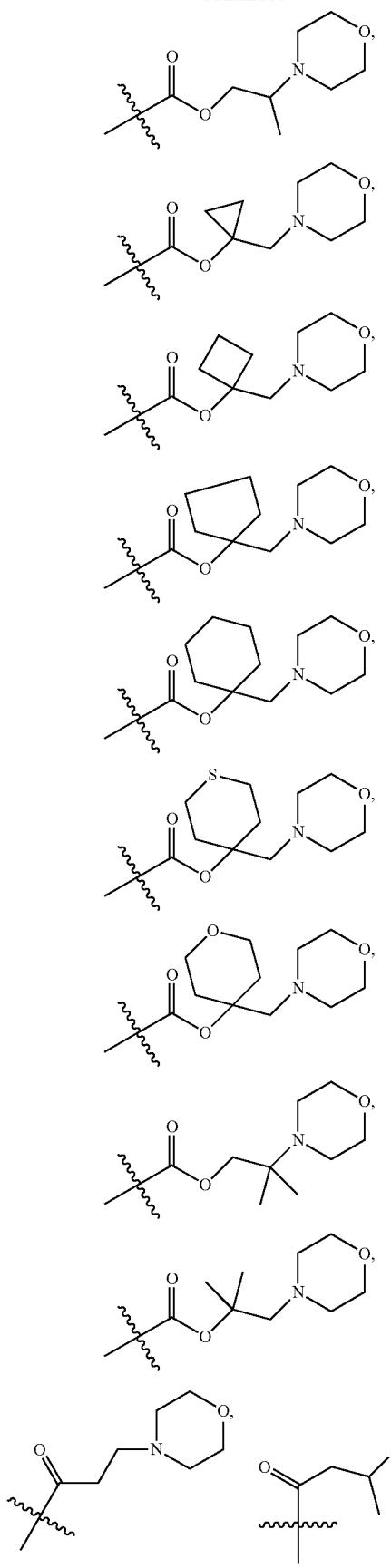
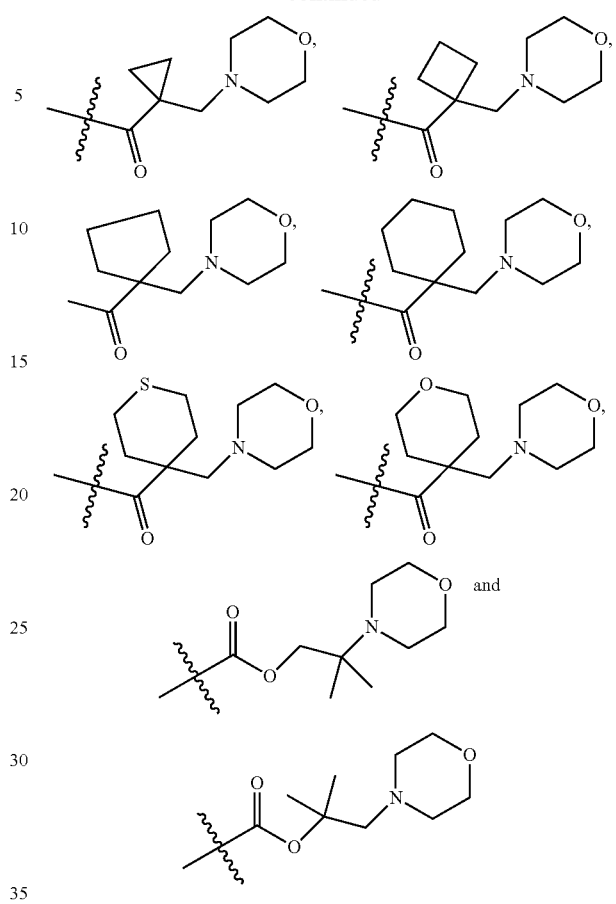

In another embodiment, R is as tabulated below:

| R | m | R$^{34}$ | R$^{35}$ | NR$^{34}$R$^{35}$ |
|---|---|---|---|---|
| C(O)(CH$_2$)$_m$NR$^{34}$R$^{35}$ | 1 | Me | Me | |
| C(O)(CH$_2$)$_m$NR$^{34}$R$^{35}$ | 2 | Me | Me | |
| C(O)(CH$_2$)$_m$NR$^{34}$R$^{35}$ | 3 | Me | Me | |
| C(O)(CH$_2$)$_m$NR$^{34}$R$^{35}$ | 4 | Me | Me | |
| C(O)(CH$_2$)$_m$NR$^{34}$R$^{35}$ | 1 | | | morpholine |
| C(O)(CH$_2$)$_m$NR$^{34}$R$^{35}$ | 2 | | | morpholine |
| C(O)(CH$_2$)$_m$NR$^{34}$R$^{35}$ | 3 | | | morpholine |
| C(O)(CH$_2$)$_m$NR$^{34}$R$^{35}$ | 4 | | | morpholine |
| C(O)O(CH$_2$)$_m$NR$^{34}$R$^{35}$ | 2 | Me | Me | |
| C(O)O(CH$_2$)$_m$NR$^{34}$R$^{35}$ | 3 | Me | Me | |
| C(O)O(CH$_2$)$_m$NR$^{34}$R$^{35}$ | 4 | Me | Me | |

-continued

| R | m | R³⁴ | R³⁵ | NR³⁴R³⁵ |
|---|---|-----|-----|---------|
| C(O)O(CH₂)ₘNR³⁴R³⁵ | 2 | | | 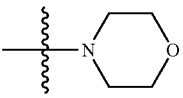 |
| C(O)O(CH₂)ₘNR³⁴R³⁵ | 3 | | | 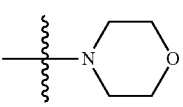 |
| C(O)O(CH₂)ₘNR³⁴R³⁵ | 4 | | | 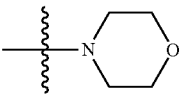 |
| P(O)(OH)₂ | | | | | an N oxide thereof, or a pharmaceutically acceptable salt of each thereof.

In another aspect, R is,

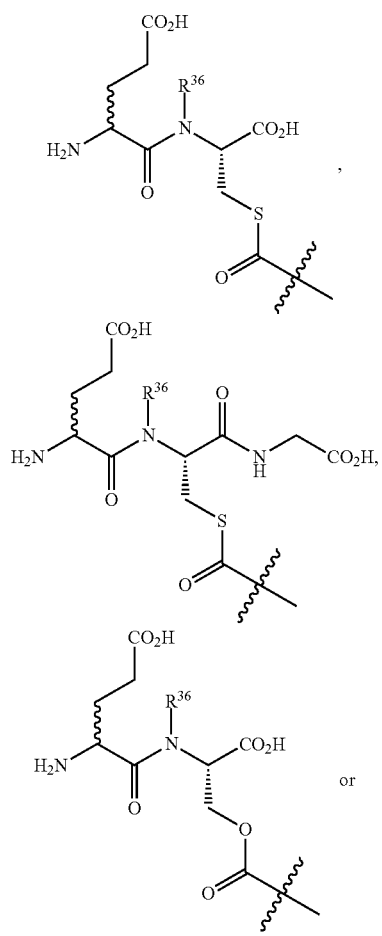

or

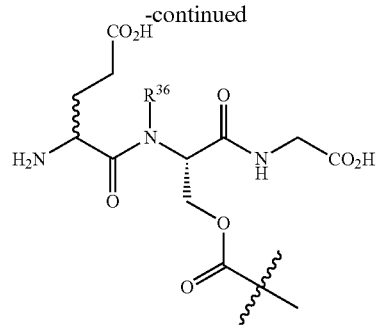

wherein
R³⁶ is lower alkyl (e.g. $C_1$-$C_6$ alkyl).
In yet another aspect, R is:

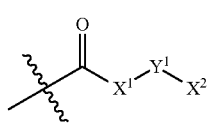

wherein $X^1$, $Y^1$ and $X^2$ are as defined herein.

In one embodiment. $X^1$ is selected from the group consisting of O, S and NR³⁷ wherein R³⁷ is hydrogen or $C_1$-$C_6$ alkyl;

$Y^1$ is —C(R³⁸)₂ or a sugar moiety, wherein each R³⁸ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl;

$X^2$ is selected from the group consisting of halogen, $C_1$-$C_6$ alkoxy, diacylglycerol, amino, $C_1$-$C_6$ alkylamino, $C_1$-$C_6$ dialkylamino, $C_1$-$C_6$ alkylthio, a PEG moiety, a bile acid moiety, a sugar moiety, an amino acid moiety, a di- or tri-peptide, a PEG carboxylic acid, and —U—V wherein U is O or S; and V is selected from the group consisting of $C_1$-$C_6$ alkyl, $C_3$-$C_8$ cycloalkyl, $C_3$-$C_9$ heterocyclyl, $C_6$-$C_{10}$ aryl, $C_3$-$C_9$ heteroaryl, C(W²)X³, PO(X³)₂, and SO₂X³;

wherein W² is O or NR³⁹ wherein R³⁹ is hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl; and each $X^3$ is independently amino, hydroxyl, mercapto, $C_1$-$C_6$ alkyl, heteroalkyl, cycloalkyl, heterocyclyl, aryl, or heteroaryl, $C_1$-$C_6$ alkoxy, $C_1$-$C_6$ alkylamino, $C_1$-$C_6$ dialkylamino, $C_1$-$C_6$ alkylthio, a bile acid based alkoxy group, a sugar moiety, a PEG moiety, and —O—CH₂—CH(OR⁴⁰)CH₂X⁴R⁴⁰, wherein:

$X^4$ is selected from the group consisting of O, S, S=O, and SO₂; and each R⁴⁰ is independently $C_{10}$-$C_{22}$ alkyl, $C_3$-$C_8$ cycloalkyl, $C_3$-$C_9$ heterocyclyl, $C_6$-$C_{10}$ aryl, or $C_3$-$C_9$ heteroaryl, $C_1$-$C_8$ alkylene, or $C_1$-$C_8$ heteroalkylene.

Each heterocyclic and heteroaryl ring system is optionally substituted with $C_1$-$C_3$ alkyl, —OH, amino and carboxyl groups.

In one embodiment, the present invention utilizes the following $Y^1$ groups: CH₂, CHMe, CH(isopropyl), CH(tertiarybutyl), C(Me)₂, C(Et)₂, C(isopropyl)₂, and C(propyl)₂.

In another embodiment, the present invention utilizes the following $X^2$ groups:

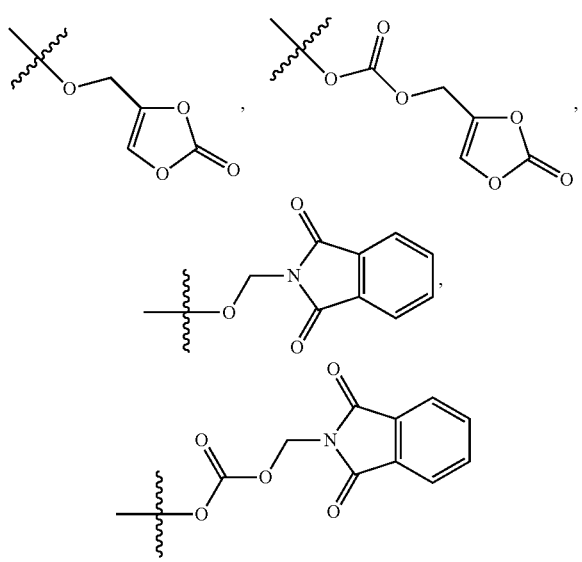

—OMe, —OEt, —O-isopropyl, O-isobutyl, O-tertiarybutyl, —O—COMe, —O—C(=O)(isopropyl), —O—C(=O)(isobutyl), —O—C(=O)(tertiarybutyl), —O—C(=O)—NMe$_2$. —O—C(=O)—NHMe, —O—C(=O)—NH$_2$, —O—C(=O)—N(H)—CH(R$^{41}$)—CO$_2$Et wherein R$^{41}$ is a side chain C$_1$-C$_6$ alkyl, or C$_3$-C$_9$ heterocyclyl group selected from the side chain groups present in essential amino acids; —O—P(=O)(OMe)$_2$, —O—P(=OXO-isopropyl)$_2$, and —O—P(=O)(O-isobutyl)$_2$. Each heterocyclic is optionally substituted with one or more, preferably, 1-3, C$_1$-C$_3$ alkyl, —OH, amino and/or carboxyl groups.

In another embodiment, In one embodiment, R is:

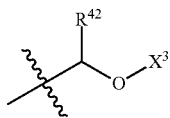

wherein

X$^3$ is independently C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl; and R$^{42}$ is independently hydrogen or C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl.

Each heterocyclic is optionally substituted with one or more, preferably, 1-3, C$_1$-C$_3$ alkyl, —OH, amino and/or carboxyl groups.

In one embodiment, R is:

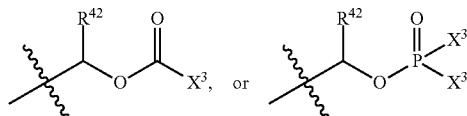

wherein each X$^3$ is independently amino, hydroxyl, mercapto, C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl, C$_1$-C$_6$ alkoxy, C$_1$-C$_6$ alkylamino, C$_1$-C$_6$ dialkylamino, C$_1$-C$_6$ alkylthio, a bile acid based alkoxy group, a sugar moiety, a PEG moiety, and —O—CH$_2$—CH(OR$^{40}$)CH$_2$X$^4$R$^{40}$, wherein:

X$^4$ is selected from the group consisting of O, S, S=O, and SO$_2$; and each R$^{40}$ is independently C$_{10}$-C$_{22}$ alkyl, C$_3$-C$_8$ cycloalkyl, C$_3$-C$_9$ heterocyclyl, C$_6$-C$_{10}$ aryl, C$_3$-C$_9$ heteroaryl, C$_1$-C$_8$ alkylene, or C$_1$-C$_8$ heteroalkylene; and R$^{42}$ is independently hydrogen or C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl.

In some embodiments. R$^{42}$ is independently hydrogen or C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl; and each X$^3$ independently is C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl, C$_1$-C$_6$ alkoxy, C$_1$-C$_6$ alkylamino, C$_1$-C$_6$ dialkylamino, or C$_1$-C$_6$ alkylthio.

In some embodiments, R is represented by the following structures:

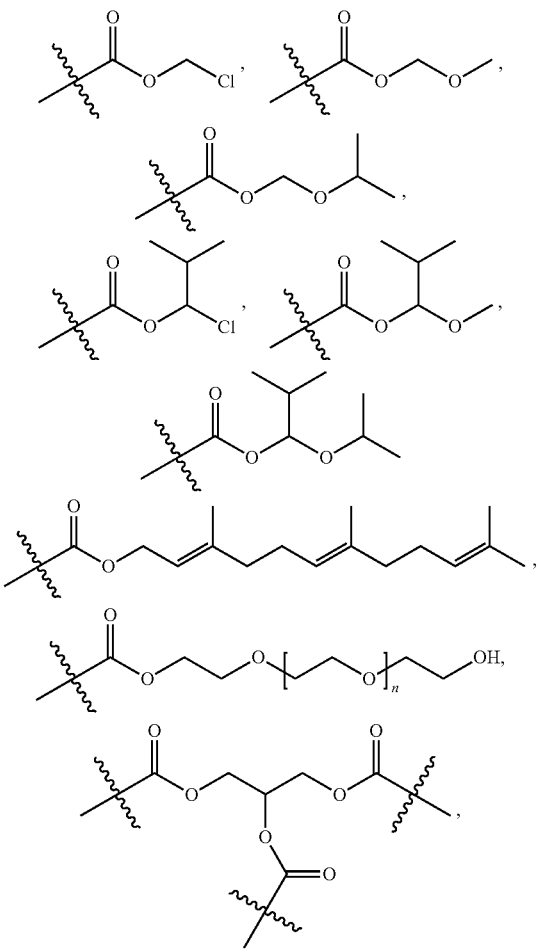

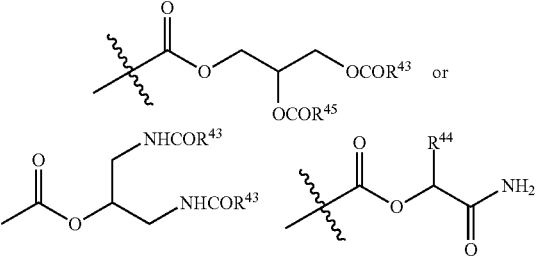

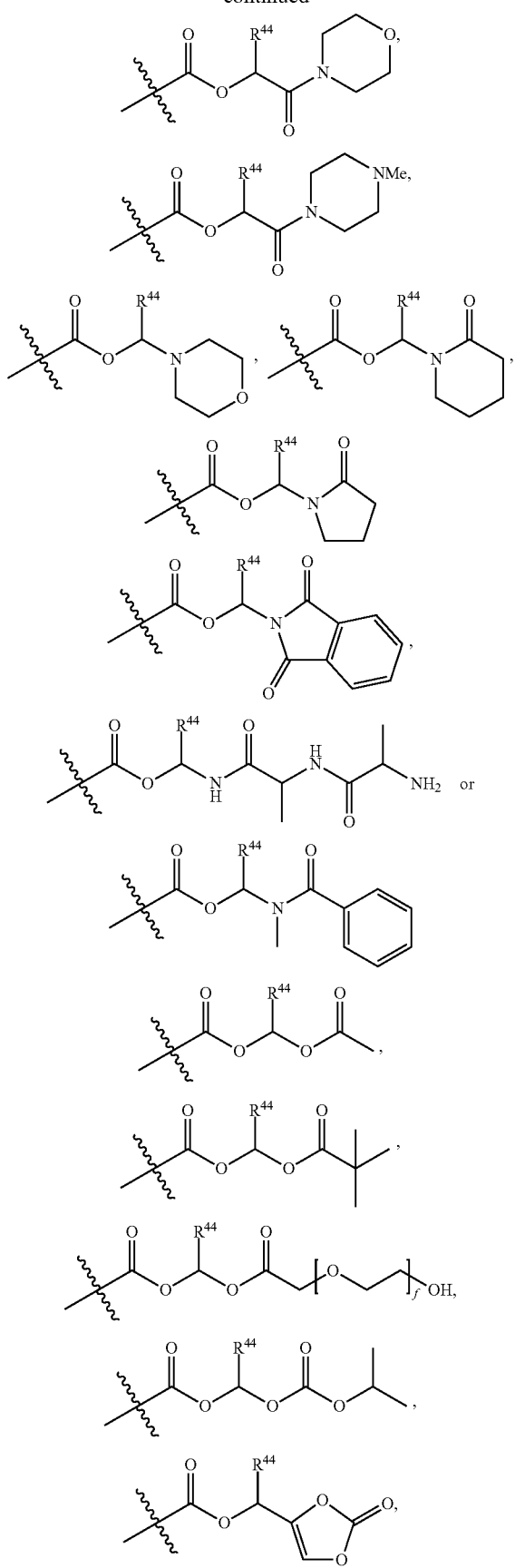

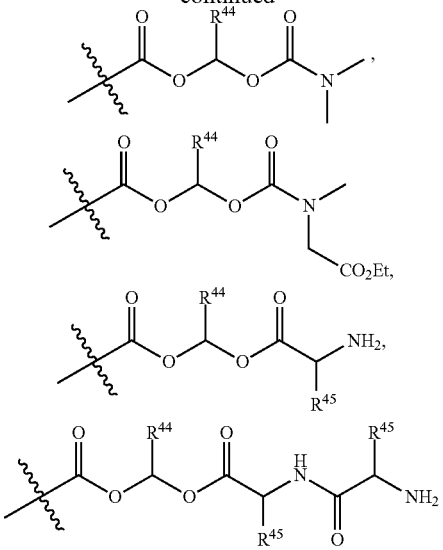

wherein, in the above examples, $R^{43}$ is $C_{10}$-$C_{22}$ alkyl or alkylene, $R^{44}$ is H or $C_1$-$C_6$ alkyl and $R^{45}$ represents side chain alkyl groups present in naturally occurring alpha amino acids;

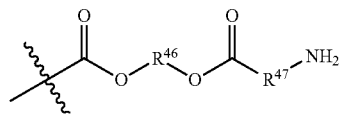

wherein $R^{46}$ is $(CH_2)_n$, f=2-4, and CO—$R^{47}$—$NH_2$ represents an aminoacyl group: or

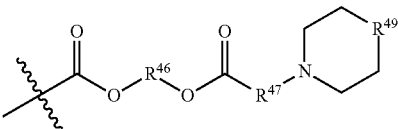

wherein $R^{46}$ is $(CH_2)_n$, n=2-4. $R^{41}$ is $(CH_2)_n$, n=1-3 and $R^{49}$ is O or NMe.

In one embodiment, R is:

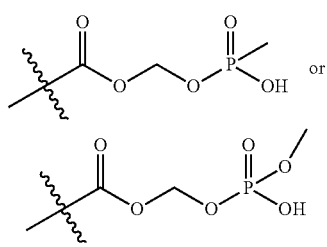

In one aspect, R is —C($R^{200}R^{201}$)O($R^{202}R^{203}$)P(O)OR $NR^{205}R^{206}$, wherein each $R^{200}$, $R^{201}$, $R^{202}$, $R^{203}$, $R^{204}R^{205}$ and $R^{206}$ is independently H, a $C_1$-$C_8$ alkyl, $C_3$-$C_9$ heterocyclyl, $C_3$-$C_8$ cycloalkyl, $C_6$-$C_{10}$ aryl, $C_3$-$C_9$ heteroaryl, wherein each alkyl, heterocyclyl, cycloalkyl, aryl, and heteroaryl is optionally substituted.

In some embodiments, R is —CH($R^{201}$)O$CH_2$P(O)O$R^{204}$NH$R^{206}$, wherein $R^{201}$ is $C_1$-$C_8$ alkyl, $R^{204}$ is phenyl, optionally substituted. In one embodiment, $R^{206}$ is —CH$R^{207}$C(O)O$R^{208}$ wherein $R^{207}$ is selected from the group consisting of the naturally occurring amino acid side chains and —$CO_2$H esters thereof and $R^{208}$ is $C_1$-$C_8$ alkyl. In one embodiment, $R^{206}$ is $C_1$-$C_6$ alkyl, optionally substituted with 1-3, $CO_2$H, SH, $NH_2$, $C_6$-$C_{10}$ aryl, and $C_2$-$C_{10}$ heteroaryl.

In one embodiment, R is:

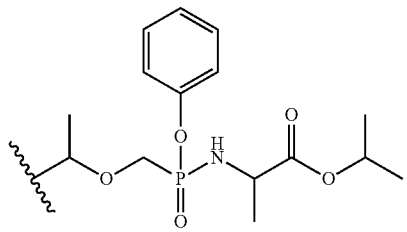

In one embodiment, R is:

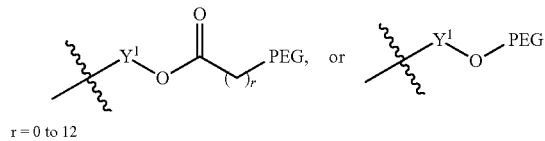

r = 0 to 12 wherein $Y^1$ is —C($R^{38}$)$_2$, wherein each $R^{38}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Various polyethylene glycol (PEG) moieties and synthetic methods related to them that can be used or adapted to make compounds of the invention are described in U.S. Pat. Nos. 6,608,076; 6,395,266; 6,194.580; 6,153.655; 6,127,355; 6,111,107; 5,965,566; 5,880,131; 5,840,900; 6,011,042 and 5,681,567.

In one embodiment, R is

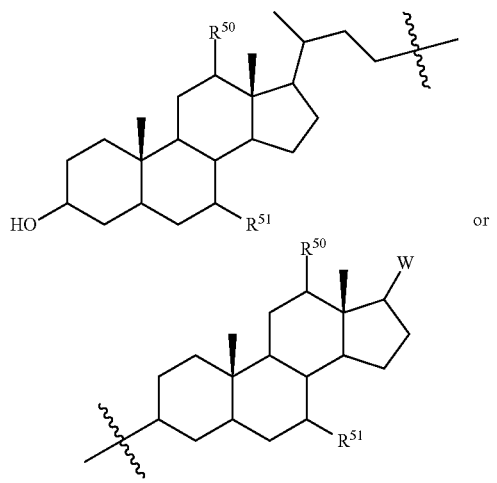

wherein
$R^{50}$ is —OH or hydrogen;
$R^{51}$ is —OH, or hydrogen;
W is —CH($CH_3$)$W^1$;

wherein $W^1$ is a substituted $C_1$-$C_8$ alkyl group containing a moiety which is optionally negatively charged at physiological pH, said moiety is selected from the group consisting of $CO_2$H, $SO_3$H, $SO_2$H, —P(O)(O$R^{52}$)(OH), —OP(O)(O$R^{52}$)(OH), and OS$O_3$H, wherein $R^{52}$ is $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Each heterocyclic and heteroaryl ring system is optionally substituted with one or more, preferably 1-3, $C_1$-$C_3$ alkyl, —OH, amino and/or carboxyl groups.

In one embodiment, R is:

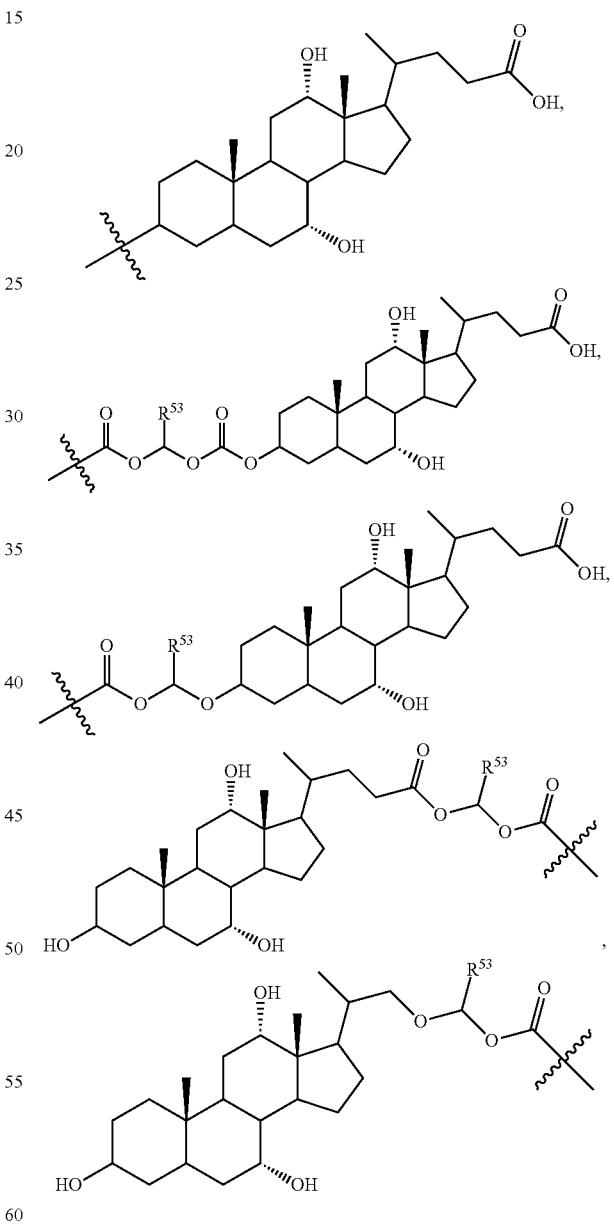

wherein $R^{53}$ is H or $C_1$-$C_6$ alkyl.

In another aspect, R is S$O_3$H.

In another aspect, R comprises a cleavable linker, wherein the term "cleavable linker" refers to a linker which has a short half life in vivo. The breakdown of the linker Z in a compound releases or generates the active compound. In one embodiment, the cleavable linker has a half life of less than ten hours. In one embodiment, the cleavable linker has a half life of less than an hour. In one embodiment, the half life of the cleavable linker is between one and fifteen minutes. In one embodiment, the cleavable linker has at least one connection with the structure: $C^*$—$C(=X^*)X^*$—$C^*$ wherein $C^*$ is a substituted or unsubstituted methylene group, and $X^*$ is S or O. In one embodiment, the cleavable linker has at least one $C^*$—$C(=O)O$—$C^*$ connection. In one embodiment, the cleavable linker has at least one $C^*$—$C(=O)S$—$C^*$ connection. In one embodiment, the cleavable linker has at least one —$C(=O)N^*$—$C^*$—$SO_2$—$N^*$-connection, wherein $N^*$ is —NH— or $C_1$-$C_6$ alkylamino. In one embodiment, the cleavable linker is hydrolyzed by an esterase enzyme.

In one embodiment, the linker is a self-immolating linker, such as that disclosed in U.S. patent publication 2002/0147138, to Firestone; PCT Appl. No. US05/08161 and PCT Pub. No. 2004/087075. In another embodiment, the linker is a substrate for enzymes. See generally Rooseboom et al., 2004. Pharmacol. Rev. 56:53-102.

Pharmaceutical Compositions

In further aspects of the invention, a composition is provided comprising any of the compounds described herein, and at least a pharmaceutically acceptable excipient.

In another aspect, this invention provides a composition comprising any of the compounds described herein, and a pharmaceutically acceptable excipient.

Such compositions can be formulated for different routes of administration. Although compositions suitable for oral delivery will probably be used most frequently, other routes that may be used include transdermal, intravenous, intraarterial, pulmonary, rectal, nasal, vaginal, lingual, intramuscular, intraperitoneal, intracutaneous, intracranial, and subcutaneous routes. Suitable dosage forms for administering any of the compounds described herein include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16th ed., A. Oslo editor, Easton Pa. 1980).

Pharmaceutically acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. In certain embodiments, the compositions provided herein comprises one or more of α-tocopherol, gum arabic, and/or hydroxypropyl cellulose.

In one embodiment, this invention provides sustained release formulations such as drug depots or patches comprising an effective amount of a compound provided herein. In another embodiment, the patch further comprises gum Arabic or hydroxypropyl cellulose separately or in combination, in the presence of alpha-tocopherol Preferably, the hydroxypropyl cellulose has an average MW of from 10.000 to 100.000. In a more preferred embodiment, the hydroxypropyl cellulose has an average MW of from 5,000 to 50,000.

Compounds and pharmaceutical compositions of this invention maybe used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

Methods of Treatment

In aspects of the invention, a method is provided for increasing tissue and/or cellular oxygenation, the method comprising administering to a subject in need thereof a therapeutically effective amount of any of the compounds or compositions described herein.

In aspects of the invention, a method is provided for increasing oxygen affinity of hemoglobin S in a subject, the method comprising administering to a subject in need thereof a therapeutically effective amount of any of the compounds or compositions described herein.

In aspects of the invention, a method is provided for treating a condition associated with oxygen deficiency, the method comprising administering to a subject in need thereof a therapeutically effective amount of any of the compounds or compositions described herein.

In further aspects of the invention, a method is provided for treating oxygen deficiency associated with sickle cell anemia, the method comprising administering to a subject in need thereof a therapeutically effective amount of any of the compounds or compositions described herein.

In further aspects of the invention, a method is provided for treating sickle cell disease, the method comprising administering to a subject in need thereof a therapeutically effective amount of a compound of any of the compounds or compositions described herein. In still further aspects of the invention, a method is provided for treating cancer, a pulmonary disorder, stroke, high altitude sickness, an ulcer, a pressure sore, Alzheimer's disease, acute respiratory disease syndrome, and a wound, the method comprising administering to a subject in need thereof a therapeutically effective amount of a compound of any of the compounds or compositions described herein.

Synthetic Methods

Certain methods for making the compounds described herein are also provided. The reactions are preferably carried out in a suitable inert solvent that will be apparent to the skilled artisan upon reading this disclosure, for a sufficient period of time to ensure substantial completion of the reaction as observed by thin layer chromatography, $^1$H-NMR, etc. If needed to speed up the reaction, the reaction mixture can be heated, as is well known to the skilled artisan. The final and the intermediate compounds are purified, if necessary, by various art known methods such as crystallization, precipitation, column chromatography, and the likes, as will be apparent to the skilled artisan upon reading this disclosure.

An illustrative and non-limiting method for synthesizing a compound of formula (I), is schematically shown below.

In the following Schemes,

refer to rings A, B and C as described herein;

$A^5$ and $B^5$ are independently $NR^{14}$, O, S, S(O)x, NBoC, $CH_2$, $CHR^{14}$, $C(R^{14})_2$ provided that when both $A^5$ and $B^5$ are present in a ring, both are not $CH_2$, $CHR^{14}$, $C(R^{14})_2$, and that when only 1 $A^5$ or $B^5$ is present in a ring the $A^5$ or $B^5$ is not $CH_2$, $CHR^{14}$, $C(R^{14})_2$;

$R^{14}$ is $C_1$-$C_6$ alkyl, $COR^{15}$ or $COOR^{15}$; wherein $R^{15}$ is optionally substituted $C_1$-$C_6$ alkyl, optionally substituted $C_6$-$C_{10}$ aryl, optionally substituted 5-10 membered heteroaryl containing up to 5 ring heteroatoms, or optionally substituted 4-10 membered heterocycle containing up to 5 ring heteroatoms, wherein the heteroatom is selected from the group consisting of O, N, S, and oxidized forms of N and S;

X, and $X^5$ each represents a leaving group and are independently selected from Cl, Br, and I.

$X^6$ represents CR, N, O, S(O)x; wherein x is 0, 1, or 2;

$R^{71}$ is $C_1$-$C_6$ alkyl;

$Y^5$ represents a leaving group selected from Cl, F, Br, I, $OSO_2R^{17}$ and $OSO_2Ar$;

Ar is phenyl optionally substituted with 1-3 halo and/or $C_1$-$C_4$ alkyl;

n is 0, 1, or 2; and

Where variables already used in the structures hereinabove are used in the schemes, the context makes it unambiguous as to what the variable refers to.

General Synthetic Schemes

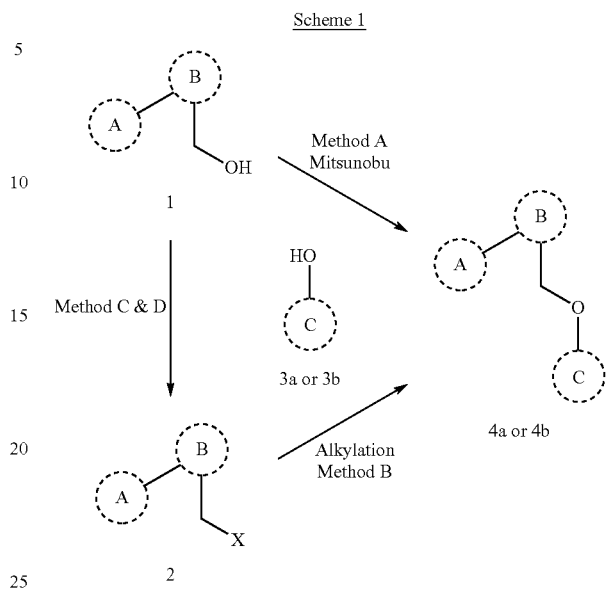

General Method a (Scheme 1) for Preparing Aryloxy/Heteroarylether Analogs (4a/4b) from Substituted Methylene Alcohol (1) and Hydroxyl (Hetero)Aryl Aldehyde Derivatives (3a/3b).

A hydroxyl (hetero)arylaldehyde derivatives (3a/3b) (0.1-2 mmol) mixture with substituted methylene alcohol (1) (0.8 to 1.2 eq) and $PPh_3$ (1-1.5 eq) in anhydrous THF (1-10 mL) was stirred under nitrogen until complete dissolution. The solution was cooled to 0° C. on ice bath and DIAD or DEAD (1.1 eq) in THF or toluene was added dropwise over a 1-20 min period. The ice cooling bath was allowed to expire over 90 min and the mixture was stirred at RT for 2-48 hours. The mixture was stirred for 10 min, then filtered through a pad of silica. The silica was washed with ethyl acetate 2-20 mL. The combined filtrates were evaporated and the residue was dried on highvac. The residue was purified by preparative HPLC or flash silica gel chromatography.

General Method a (Scheme 1) for Preparing Aryloxy/Heteroarylether Analogs (4a/4b) from Substituted Methylene Halide (2) and Hydroxyl (Hetero)Aryl Aldehyde Derivatives (3a/3b).

A mixture of hydroxyl (hetero)arylaldehyde derivatives (3a/3b) (0.1-2 mmol, 1-4 eq.), substituted methylene chloride or bromide (2) (1 eq), and $K_2CO_3$ (2-5 eq.) (catalytic amount of NaI or $Bu_4NI$ may also be added) in DMF or acetonitrile (1 to 10 mL) was stirred at RT or heating up to 120° C. for 0.5-8 h under nitrogen atmosphere. In workup A, water was added to the reaction mixture, the precipitated product was collected, washed with water, and then subjected to preparative HPLC or flash silica gel chromatography purification. In workup B (for products that did not precipitate), diluted HCl or aqueous $NH_4Cl$ was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography using appropriate solvents mixture (e.g., ethyl acetate/hexanes).

General Method C for Preparing Substituted Methylene Chloride (2a). To a solution of substituted methylene alcohol (1) (0.1 to 2 mmol) in DCM (1-10 mL) was added $SOCl_2$ dropwise (2 eq to 5 eq) at 0° C. or RT. The reaction mixture was stirred at RT for 10 min to 6 h, or until reaction is judged complete (LC/MS). The reaction mixture is concentrated to dryness over a rotavap. The crude chloride residue was suspended in toluene, sonicated and concentrated to dryness. The process was repeated three times and dried under vacuum to give the substituted methylene chloride (2), usually as an off-white solid, which was used for next step without further purification. Alternatively, a solution of aqueous 1N $Na_2CO_3$ is then added to produce a solution of pH-8, the mixture was extracted with DCM (3×10-50 mL), dried over sodium sulfate, and concentrated to the crude substituted methylene chloride (2a), which is then purified by column chromatography on silica gel (0-100% ethyl acetate-hexanes).

General Method D for Preparing Substituted Methylene Bromide (2b).

To a solution of substituted methylene alcohol (1) (0.1 to 2 mmol) in DCM (1-10 mL) was added $Ph_3PBr_2$ dropwise (2 eq to 5 eq) at 0° C. or RT. The reaction mixture was stirred at RT for 10 min to 2 h, or until reaction is judged complete (LC/MS). The reaction mixture is concentrated to dryness over a rotavap. The residue purified by column chromatography on silica gel (0-100% ethyl acetate-hexanes) to afford the pure bromide 2b.

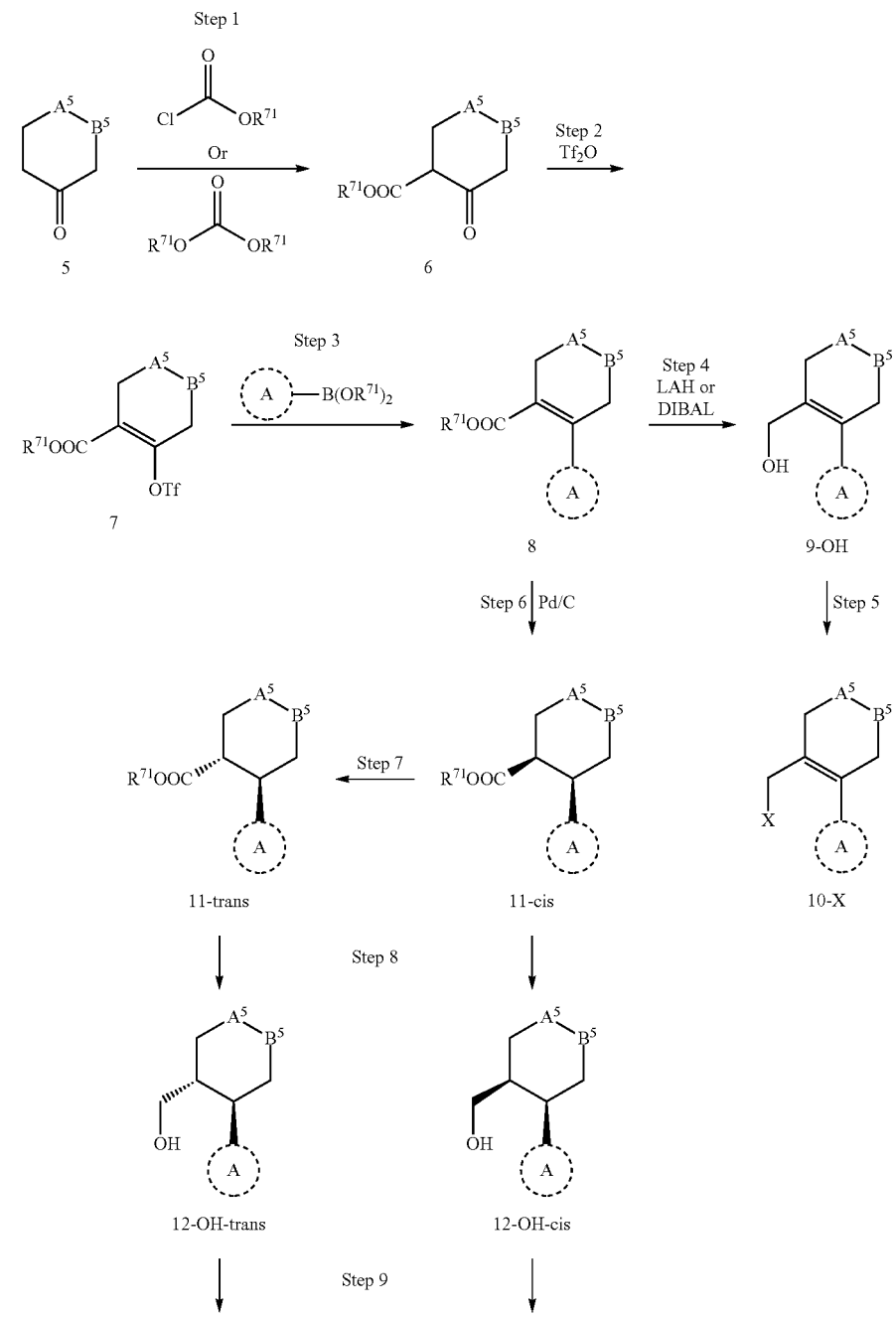

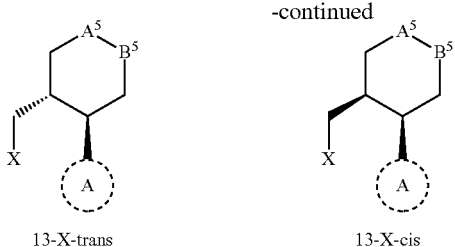

General Method E (Scheme 2) for Preparing Heterocyclic Methylene Derivatives 9, 10, 12 and 13.

Condensation of heterocyclic ketone analog 5 with chloroformate or dialkyl carbonate gives (hetero)cyclic beta-ketone ester 6 (Step 1). The ketone ester 6 is converted to the triflate intermediate 7 by treating with a triflating agent (e.g, triflic anhydride) in the presence of an organic base such as Hunig's base (Step 2). Suzuki coupling of the triflate 7 with a boronic acid or ester affords heterocyclohexene carboxylate 8 (Step 3). Subsequent reduction of the ester group by LAH or DIBAL gives the corresponding alcohol 9-OH (Step 4). Further reaction of the alcohol 9-OH with thionyl chloride, $Ph_3PBr_2$ (or $CBr_4$-$Ph_3P$ or $PBr_3$), or alkyl/aryl sulfonyl chloride produces the corresponding 10-X chloride, bromide or sulfonate (Step 5).

Alternatively, the double bond of heterocyclohexene carboxylate 8 is reduced to give the cis-heterocyclohexane 11-cis carboxylate under palladium catalyzed hydrogenation conditions (Step 6). Reduction of the ester group of 11-cis by LAH or DIBAL yields cis-alcohol 12-OH-cis (Step 8).

Conversion of the alcohol 12-OH-cis to its chloride, bromide or sulfonate (such as mesylate, tosylate) 13-X-cis can be achieved by reacting with thionyl chloride, or $Ph_3PBr_2$, or sulfonyl chloride (such as mesyl chloride or tosyl chloride) (Step 9). The cis-cyclohexane carboxylate 11-cis can also be isomerized to the thermodynamically more stable trans-isomer 11-trans by the treatment with an alcoholic alkoxide (e.g., ethoxide) solution. Analogously, transformation of 11-trans ester to 12-trans alcohol and 13-X-trans halide is accomplished by applying conditions of Step 8 and Step 9 (Scheme 2) similar to these for the corresponding cis-isomers.

Scheme 3

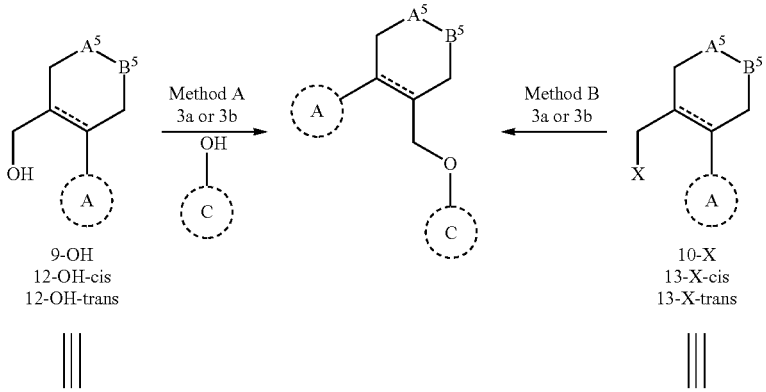

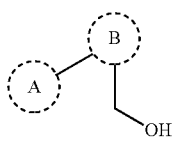

1

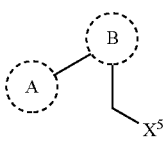

2

Coupling of the (hetero)cyclic methylene derivatives 9, 10, 12 and 13 with hydroxyl (hetero)arylaldehyde derivatives (3a/3b) (Scheme 3) by general method A or B affords the corresponding aryloxy/heteroarylether analogs (4c and 4d).

Similarly, N-linked heterocyclic analogs (compound 5, Scheme 4) can also be synthesized from amination procedures developed by Buchwald and Hartwig.

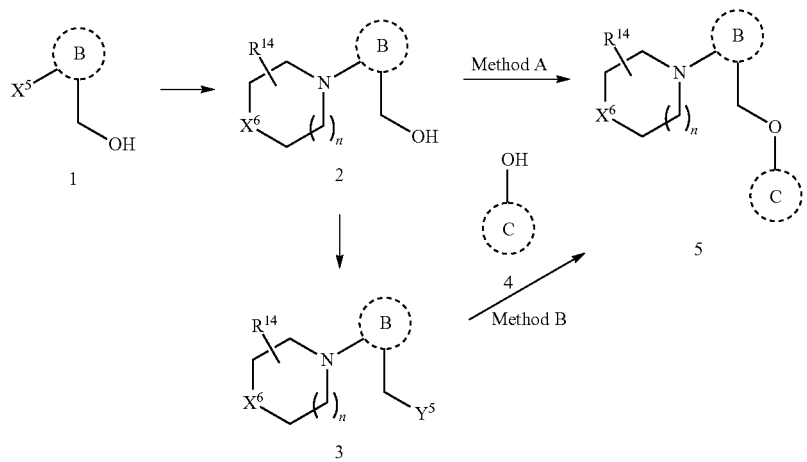

Syntheses of the ester prodrugs start with the free carboxylic acid bearing the tertiary amine. The free acid is activated for ester formation in an aprotic solvent and then reacted with a free alcohol group in the presence of an inert base, such as triethyl amine, to provide the ester prodrug. Activating conditions for the carboxylic acid include forming the acid chloride using oxalyl chloride or thionyl chloride in an aprotic solvent, optionally with a catalytic amount of dimethyl formamide, followed by evaporation. Examples of aprotic solvents, include, but are not limited to methylene chloride, tetrahydrofuran, and the like. Alternatively, activations can be performed in situ by using reagents such as BOP (benzotriazol-1-yloxytris(dimethylamino)phosphonium hexafluorolphosphate, and the like (see Nagy et al., 1993. Proc. Natl. Acad. Sci. USA 90:6373-6376) followed by reaction with the free alcohol. Isolation of the ester products can be affected by extraction with an organic solvent, such as ethyl acetate or methylene chloride, against a mildly acidic aqueous solution; followed by base treatment of the acidic aqueous phase so as to render it basic; followed by extraction with an organic solvent, for example ethyl acetate or methylene chroride; evaporation of the organic solvent layer; and recrystalization from a solvent, such as ethanol. Optionally, the solvent can be acidified with an acid, such as HCl or acetic acid to provide a pharmaceutically acceptable salt thereof. Alternatively the crude reaction can be passed over an ion exchange column bearing sulfonic acid groups in the protonated form, washed with deionized water, and eluted with aqueous ammonia; followed by evaporation.

Suitable free acids bearing the tertiary amine are commercially available, such as 2-(N-morpholino)-propionic acid, N,N-dimethyl-beta-alanine, and the like. Non-commercial acids can be synthesized in straightforward manner via standard literature procedures.

Carbonate and carbamate prodrugs can be prepared in an analogous way. For example, amino alcohols and diamines can be activated using activating agents such as phosgene or carbonyl diimidazole, to provide an activated carbonates, which in turn can react with the alcohol and/or the phenolic hydroxy group on the compounds utilized herein to provide carbonate and carbamate prodrugs.

Various protecting groups and synthetic methods related to them that can be used or adapted to make compounds of the invention can be adapted from the references Testa et al., Hydrolysis in Drug and Prodrug Metabolism, June 2003, Wiley-VCH. Zurich, 419-534 and Beaumont et al., Curr. Drug Metab. 2003, 4:461-85.

Scheme 5 below provides a method of synthesizing an acyloxymethyl version of a prodrug by adapting a method from the reference Sobolev et al., 2002, J. Org. Chem. 67:401-410.

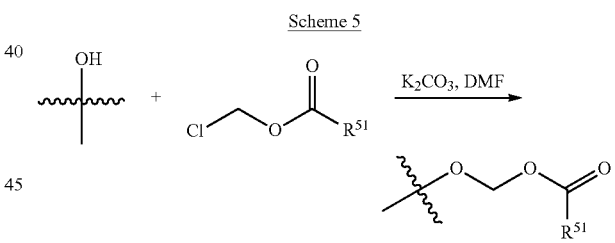

Scheme 5 wherein $R^{51}$ is $C_1$-$C_6$ alkyl.

Scheme 6 below provides a method for synthesizing a phosphonooxymethyl version of a prodrug by adapting a method from Mantyla et al., 2004, J. Med. Chem. 47:188-195.

Scheme 6

Scheme 7 below provides a method of synthesizing an alkyloxymethyl version of a prodrug

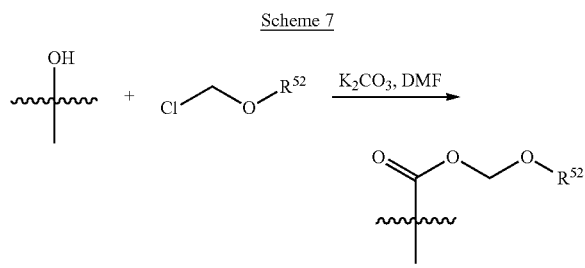

wherein $R^{52}$ is $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

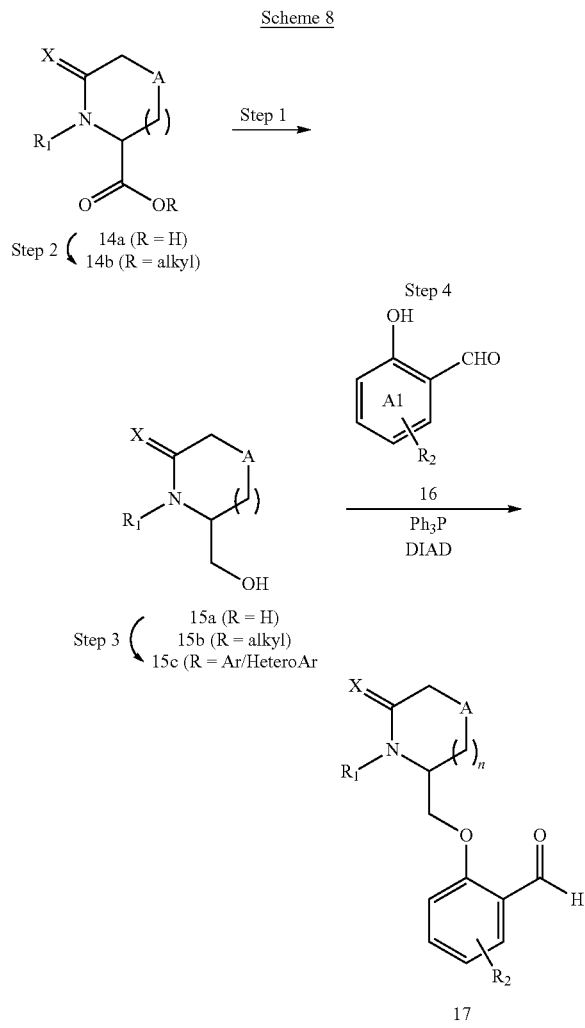

Compounds of structure 17 can be synthesized via general synthetic scheme 8. Reduction of carboxylic acid derivative 14 gives hydroxymethyl analog, which can be N-derivatized at via copper-mediated N-arylation reaction (CuI, Ar—I, base such as N,N-dimethylethylenediamine and potassium phosphate, heat) to give key hydroxymethyl intermediate 15. Coupling of 15 with phenol aldehyde 16 produces the desired aldehyde analog 17 via typical Mitunobu conditions using either triphenylphosphine or polymer supported triphenylphosphine.

General Method Step 1—Reduction of Carboxylic Acid Derivative 14 to Methyl Alcohol 15:

To a suspension of carboxylic acid 14(1-10 mmol) in MeOH or EtOH (2-10 mL) at 0° C. was added $SOCl_2$ (1.5 eq). After stirred at room temperature for 1-12 h, it was concentrated to remove all solvents, dried under high vacuum to give corresponding methyl or ethyl ester. The ester was dissolved in MeOH or EtOH (5-30 mL), to this solution, was added $NaBH_4$ (1-4 eq) at 0° C., the mixture was warmed up to room temperature and stirred for additional 1-24 h. The mixture was quenched with Sat. $NH_4Cl$, filtered off the insolubles and the filtrate was concentrated to give crude product, which was purified by flash silica gel chromatography to give the corresponding hydroxymethylene compound 15.

General Method Step 2—N-Alkylation (14a to 14b):

The carboxylate 14a ($R_1$=H) can be first alkylated and then reduced to give N-alkyl hydroxymethylene analog 14b ($R_1$=alkyl). In a typical procedure, the carboxylate 14a (1-10 mmol) is first dissolved in DMF (2-20 mL); to this was then added a base such as NaH or $Cs_2CO_3$ (1-1.2 eq), followed by the addition of alkyl halide (eg, BnBr) (0.9-1.5 eq). The reaction allowed to proceed at room temperature of heat at 40 to 115° C. for 0.5 to 24 h. In workup A, water was added to the reaction mixture, the precipitated product was collected, washed with water, and then subjected to preparative HPLC or flash silica gel chromatography purification. In workup B (for products that did not precipitate), diluted HCl or aqueous $NH_4Cl$ was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography, reaction appropriate solvents mixture (e.g., ethyl acetate/hexanes).

General Method Step 3—Copper-Mediated N-Arylation from 15a to 15c:

For cyclic amines (X=H, H), to a solution of hydroxymethylene compound 15a (1-10 mmol) and aryl/hetero iodide (1-1.5 eq) in iPrOH (0.5-10 mL) was added ethylene diol (1.3 eq) and CuI (6.7 mol %), followed by $KaPO_4$ (1.3 eq), then it was degassed and heated at 88° C. for 6-24 h. Alternatively, for lactams (X=O), to a solution of hydroxymethylene compound 15a (1-10 mmol) and aryl/hetero iodide (1-1.5 eq) in Dioxane (2-20 mL) was added CuI (0.17 eq), N,N-dimethylethylenediamine (0.17 eq), $K_3PO_4$ (1.7 eq), then it was degassed and heated at 100° C. for 6-48 h.

Workup for both procedures: the reaction mixture was cooled to room temperature the mixture was diluted with EtOAc and water, organic layer was separated and the aqueous layer was extracted with EtOAc, organic layer was combined, washed with brine, dried and concentrated to give crude product, which was purified by flash silica gel chromatography to give N-aryl/heteroaryl compound 15c.

General Method C—Mitsunobu Conditions

A hydroxyl (hetero)arylaldehyde derivatives (17) (0.1-2 mmol) mixture with substituted methylene alcohol (16) (0.8 to 1.2 eq) and (polymer-supported) $PPh_3$ (1-1.5 eq) in anhydrous THF (1-10 mL) was stirred under nitrogen until complete dissolution. The solution was cooled to 0° C. on ice bath and DIAD or DEAD (1.1 eq) in THF or toluene was added dropwise over a 1-20 min period. The ice cooling bath was allowed to expire over 90 min and the mixture was stirred at RT for 2-48 hours. The mixture was filtered through a pad of silica. The silica was washed with ethyl acetate 2-20 mL. The combined filtrates were evaporated and the residue was dried on highvac. The residue was purified by preparative HPLC or flash silica gel chromatography.

at rt for 10 min to 2 h, or until reaction is judged complete (LC/MS). The reaction mixture is concentrated to dryness over a rotavap. The residue purified by column chromatography on silica gel (0-100% ethyl acetate-hexanes) to afford the pure bromide 3b.

Scheme 9

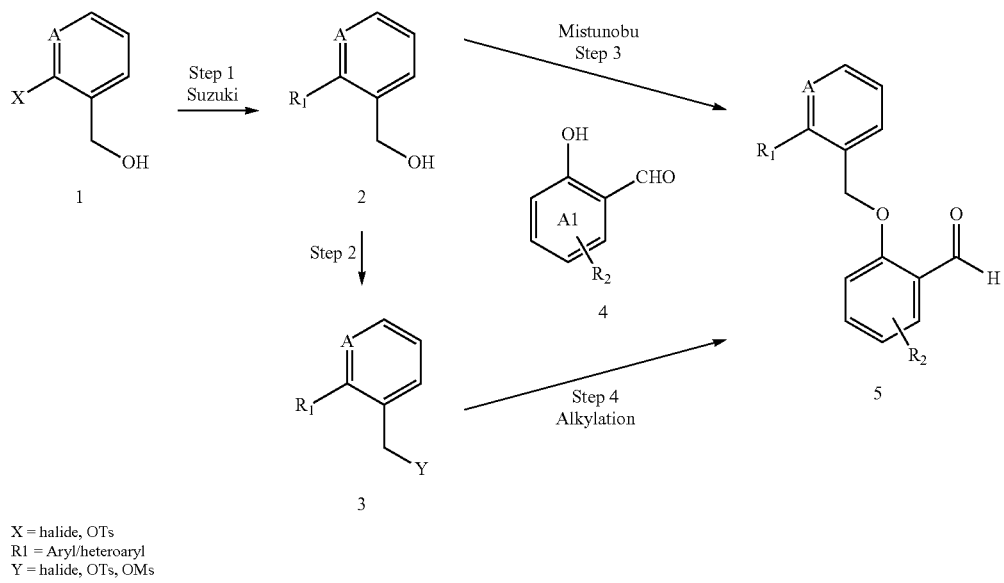

X = halide, OTs
R1 = Aryl/heteroaryl
Y = halide, OTs, OMs

General Method Step 1 (Scheme 9) for Preparing Substituted Methylene Alcohol (2) by Suzuki Coupling Reaction.

To a solution of (2-chloropyridin-3-yl)methanol or (2-bromopyridin-3-yl)methanol (1-100 mmol) and appreciate bronic acid or ester (0.8 to 1.5 eq) in dioxane (2-200 mL) was added a solution of sodium bicarbonate (3 eq) in water (1-100 mL), followed by the addition of Pd(dppf)Cl$_2$ (5 to 10 mol %). After heating at 100° C. for 4-24 h, the reaction mixture was cooled and diluted with EtOAc, organic layer was washed with water, brine, dried and concentrated to give crude product, which was purified by column chromatography.

General Method Step 2 (Scheme 9) for Preparing Substituted Methylene Chloride (3a).

To a solution of substituted methylene alcohol (2) (0.1 to 2 mmol) in DCM (1-10 mL) was added SOCl$_2$ dropwise (2 eq to 5 eq) at 0° C. or rt. The reaction mixture was stirred at rt for 10 min to 6 h, or until reaction is judged complete (LC/MS). The reaction mixture is concentrated to dryness over a rotavap. The crude chloride residue was suspended in toluene, sonicated and concentrated to dryness. The process was repeated three times and dried under vacuum to give the substituted methylene chloride (3a), usually as an off-white solid, which was used for next step without further purification. Alternatively, a solution of aqueous 1N Na$_2$CO$_3$ is then added to produce a solution of pH~8, the mixture was extracted with DCM (3×10-50 mL), dried over sodium sulfate, and concentrated to the crude substituted methylene chloride (3a), which is then purified by column chromatography on silica gel (0-100% ethyl acetate-hexanes).

General Method 2 (Scheme 9) for Preparing Substituted Methylene Bromide (3b).

To a solution of substituted methylene alcohol (2) (0.1 to 2 mmol) in DCM (1-10 mL) was added Ph$_3$P Br$_2$ dropwise (2 eq to 5 eq) at 0° C. or rt. The reaction mixture was stirred General Method Step 3 (Scheme 9) for Preparing Aryloxy/Heteroarylether Analogs (5) from Substituted Methylene Alcohol (2) and Hydroxyl (Hetero)Aryl Aldehyde Derivatives (4).

A hydroxyl (hetero)arylaldehyde derivatives (4) (0.1-2 mmol) mixture with substituted methylene alcohol (2) (0.8 to 1.2 eq) and (polymer-supported)/PPh$_3$ (1-1.5 eq) in anhydrous THF (1-10 mL) was stirred under nitrogen until complete dissolution. The solution was cooled to 0° C. on ice bath and DIAD or DEAD (1.1 eq) in THF or toluene was added drop wise over a 1-20 min period. The ice cooling bath was allowed to expire over 90 min and the mixture was stirred at RT for 2-48 hours. The mixture was stirred for 10 min, then filtered through a pad of silica. The silica was washed with ethyl acetate 2-20 mL. The combined filtrates were evaporated and the residue was dried on highvac. The residue was purified by preparative HPLC or flash silica gel chromatography.

General Method Step 4 (Scheme 9) for Preparing Aryloxy/Heteroarylether Analogs (5) from Substituted Methylene Halide (3) and Hydroxyl (Hetero)Aryl Aldehyde Derivatives (4).

A mixture of hydroxyl (hetero)arylaldehyde derivatives (4) (0.1-2 mmol, 1-4 eq.), substituted methylene chloride or bromide (3) (1 eq), and K$_2$CO$_3$ (2-5 eq.) (catalytic amount of NaI or Bu$_4$NI may also be added) in DMF, acetonitrile, NMP or DMSO (1 to 10 mL) was stirred at RT or heating up to 120° C. for 1-24 h under nitrogen atmosphere. In workup A, water was added to the reaction mixture, the precipitated product was collected, washed with water, and then subjected to preparative HPLC or flash silica gel chromatography purification. In workup B (for products that did not precipitate), diluted HCl or aqueous NH$_4$Cl was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography using appropriate solvents mixture (e.g., ethyl acetate/hexanes).

EXAMPLES

In the examples below as well as throughout the application, the following abbreviations have the following meanings. If not defined, the terms have their generally accepted meanings.

° C.=degrees Celsius
RT=Room temperature
min=minute(s)
h=hour(s)
µL=Microliter
mL=Milliliter
mmol=Millimole
eq=Equivalent
mg=Milligram
ppm=Parts per million
atm=Atmospheric pressure
MS=Mass spectrometry
LC-MS=Liquid chromatography-mass spectrometry
HPLC=High performance liquid chromatography
NMR=Nuclear magnetic resonance
Sat./sat. Saturated
MeOH=Methanol
EtOH=Ethanol
EtOAc=Ethyl acetate
Et$_3$N=Triethylamine
ACN=Acetonitrile
Ac$_2$O=Acetic anhydride
Na(OAc)$_3$BH=Sodium triacetoxy borohydride
PBr$_3$=phosphorus tribromide
Ph$_3$P=Triphenylphosphine
Ph$_3$PBr$_2$=Triphenylphosphine dibromide
CBr$_4$=Tetrabromomethane
DMF=N,N-Dimethylformamide
DCM=Dichloromethane
LAH/LiAlH$_4$=Lithium aluminum hydride
THF=Tetrahydrofuran
DIBAL=Diisobutylaluminium hydride
DIAD=Diisopropyl azodicarboxylate
DEAD=Diethyl azodicarboxylate
DIPEA=N,N-Diisopropylethylamine
Tf$_2$O=Trifluoromethanesulfonic (triflic) anhydride
Pd(dppf)Cl$_2$=[1,1'-Bis(diphenylphosphino)ferrocene]dichloropalladium(II), complex The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Experimental Procedures for Intermediates (E)-1-(3-(((tert-butyldimethylsilyl)oxy)methyl)pyridin-2-yl)-3-(dimethylamino)prop-2-en-1-one (INT-1)

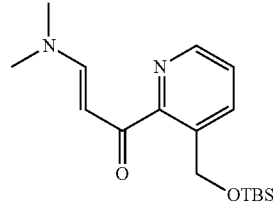

INT-1

Step 1

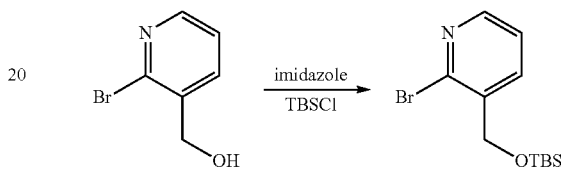

To a mixture of (2-bromopyridin-3-yl)methanol (20.0 g, 106.4 mmol, 1 eq.; refer to example 14) and imidazole (14.5 g, 212.8 mmol, 2 eq.) in DMF (50.0 mL) was added TBSCl (19.2 g, 150.7 mmol, 1.2 eq.) at RT. The mixture was stirred at RT for 1 h and diluted with a mixture of water (100 mL) and EtOAc (300 mL). The organic layer was washed with NH$_4$Cl$_{(sat.)}$ solution and brine, dried over Na$_2$SO$_4$, concentrated, and purified on silica gel using 10% EtOAc/hexanes as eluent to give 2-bromo-3-((tert-butyldimethylsilyloxy)methyl)pyridine (30.1 g, 94%) as a colorless oil. MS (ESI) m/z 302.0 [M+H]$^+$.

Step 2

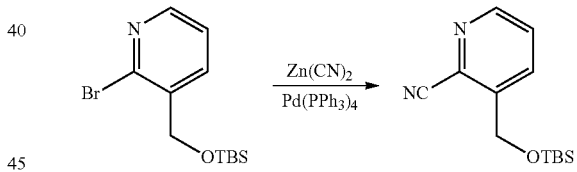

A mixture of 2-bromo-3-((tert-butyldimethylsilyloxy)methyl)pyridine (30.1 g, 100.0 mmol, 1 eq.) and Zn(CN)$_2$ (23.5 g, 200.0 mmol, 2.0 eq.) in DMF (100.0 mL) was purged with N$_2$ for 5 min and added Pd(PPh$_3$)$_4$ (5.78 g, 5.0 mmol, 0.05 eq.). The mixture was heated at 120° C. for 2 h under N$_2$, cooled, filtered, concentrated, and purified on silica gel using a mixture of EtOAc and hexanes as eluent to give 3-((tert-butyldimethylsilyloxy)methyl)picolinonitrile (20.4 g, 82%) as a colorless oil. MS (ESI) m/z 249.1 [M+H]$^+$.

Step 3:

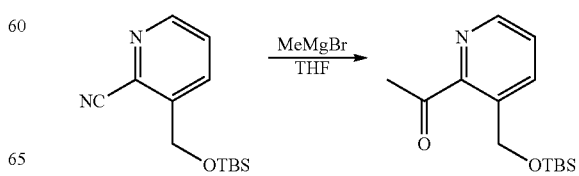

Methylmagnesium bromide (3M/ether, 41.0 mL, 123.4 mmol) was added to a stirred solution of 3-((tert-butyldimethylsilyloxy)methyl)picolinonitrile (20.4 g, 82.25 mmol) in THF (100.0 mL) at −78° C. The reaction mixture was warm to RT, quenched with aqueous citric acid solution, and extracted with EtOAc (50 mL) twice. The combined organic layers were washed with $NaHCO_{3\,(sat)}$ solution and brine, dried over $Na_2SO_4$, concentrated, and purified on silica gel using a mixture of EtOAc/hexanes as eluent to give 1-(3-((tert-butyldimethylsilyloxy)methyl)pyridin-2-yl)ethanone (12.9 g, 59%) as a colorless oil. MS (ESI) m/z 266.2 $[M+H]^+$.

Step 4:

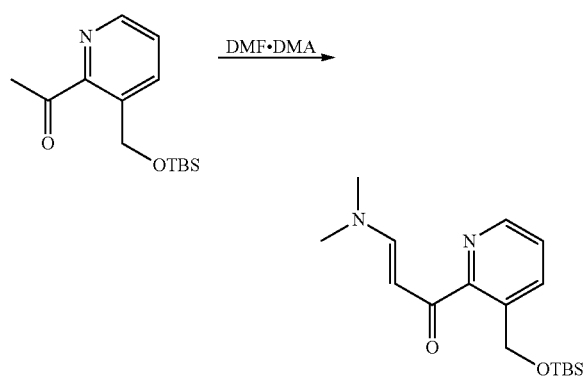

1-(3-((tert-butyldimethylsilyloxy)methyl)pyridin-2-yl)ethanone (10.8 g, 40.75 mmol) in dimethoxy-N,N-dimethylmethanamine (15.0 mL) was heated to reflux for 3 days. The mixture was concentrated and used for next step without further purification. MS (ESI) m/z 321.1 $[M+H]^+$.

Preparation of 3-(chloromethyl)-2-(1-(2,2,2-trifluoroethyl)-1H-pyrazol-5-yl)pyridine (INT-2)

INT-2

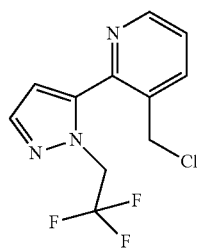

Step 1:

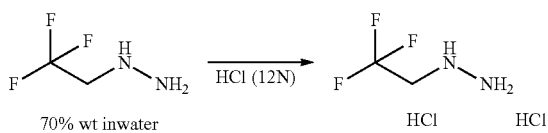 [SMILES: NNCC(F)(F)F ; NNCC(F)(F)F ; Cl ; Cl]

To (3,3,3-trifluoroethyl)hydrazine (25 g, 50% wt in water, 153.5 mmol, 1 eq.) in a RB flask (250 mL) was added HCl (12 N, 25.6 mL, 307.0 mmol, 2 eq.). The mixture was concentrated to give (3,3,3-trifluoroethyl)hydrazine dihydrochloride (1.07 g) as a yellow solid. MS (ESI) m/z 115.1 $[M+H]^+$.

Step 2:

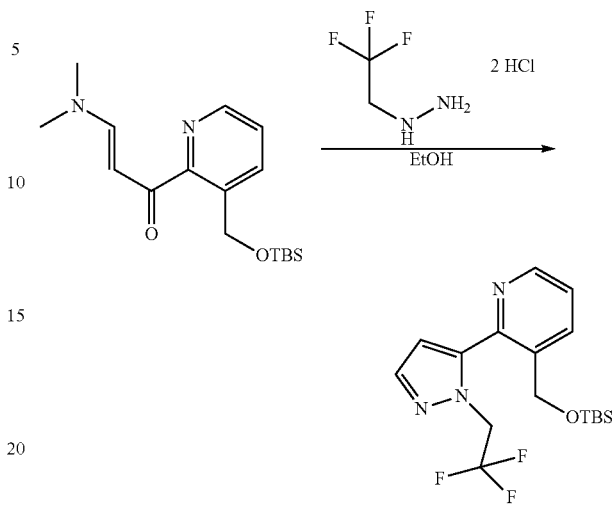

To (E)-1-(3-((tert-butyldimethylsilyloxy)methyl)pyridin-2-yl)-3-(dimethylamino)prop-2-en-1-one (crude above, 5.91 g, 18.44 mmol, 1 eq.) in EtOH (20 mL) was added (3,3,3-trifluoroethyl)hydrazine dihydrochloride (4.13 g, crude above, 22.13 mmol, 1.2 eq.) at RT. The mixture was heated at 80° C. for 1 h, concentrated, and diluted with EtOAc (50 mL) and $NaHCO_{3(sat)}$ solution (10 mL). The layers were separated and aqueous layer was extracted with EtOAc three times. The combined organic layers were dried over $Na_2SO_4$, concentrated, and purified on silica gel using a mixture of EtOAc and hexanes as eluent to give 3-((tert-butyldimethylsilyloxy)methyl)-2-(1-(3,3,3-trifluoroethyl)-1H-pyrazol-5-yl)pyridine (5.90 g; 86% for 2 steps). MS (ESI) m/z 372.2 $[M+H]^+$.

Step 3:

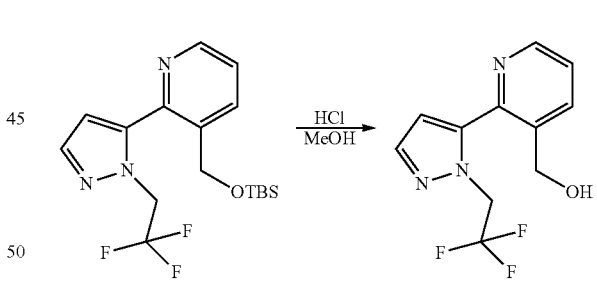

To 3-((tert-butyldimethylsilyloxy)methyl)-2-(1-(3,3,3-trifluoroethyl)-1H-pyrazol-5-yl)pyridine (5.91 g, 15.93 mmol) in MeOH (20 mL) was added HCl (4 N, 8.0 mL). The mixture was stirred at RT for 1 h, concentrated, and diluted with EtOAc (50 mL) and $NaHCO_{3(sat)}$ solution (10 mL). The layers were separated and aqueous layer was extracted with EtOAc three times. The combined organic layers were dried over $Na_2SO_4$, and concentrated to give (2-(1-(3,3,3-trifluoroethyl)-1H-pyrazol-5-yl)pyridin-3-yl)methanol (4.1 g, quantitative yield) as colorless oil. $^1$H NMR (400 MHz, $CDCl_3$) δ 8.54 (dd, J=4.7, 1.5 Hz, 1H), 7.92 (dd, J=7.9, 1.2 Hz, 1H), 7.57 (d, J=1.9 Hz, 1H), 7.30 (dd, J=7.8, 4.8 Hz, 1H), 6.50 (d, J=1.9 Hz, 1H), 5.09 (q, J=8.6 Hz, 2H), 4.63 (s, 2H), 1.76 (s, 1H). MS (ESI) m/z 258.1 $[M+H]^+$.

Step 4:

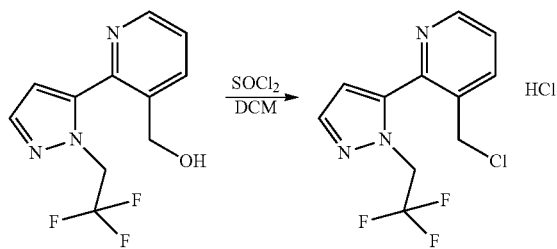

To (2-(1-(2,2,2-trifluoroethyl)-1H-pyrazol-5-yl)pyridin-3-yl)methanol (408 mg, 1.59 mmol) in DCM (5 mL) was added $SOCl_2$ (1.5 mL) at RT. The reaction mixture was stirred at RT for 4 h and concentrated to dryness. The crude solid was suspended in toluene and concentrated to dryness. The process was repeated three times and dried under vacuum to give 3-(chloromethyl)-2-(1-(2,2,2-trifluoroethyl)-1H-pyrazol-5-yl)pyridine hydrochloride (498 mg) as an off-white solid, which was used for next step without further purification.

Preparation of 3-(chloromethyl)-2-(1-(3,3,3-trifluoropropyl)-1H-pyrazol-5-yl)pyridine (INT-3)

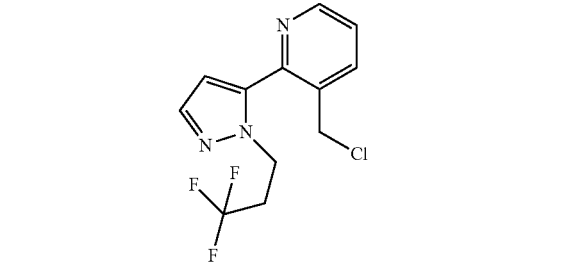

INT-3

Step 1:

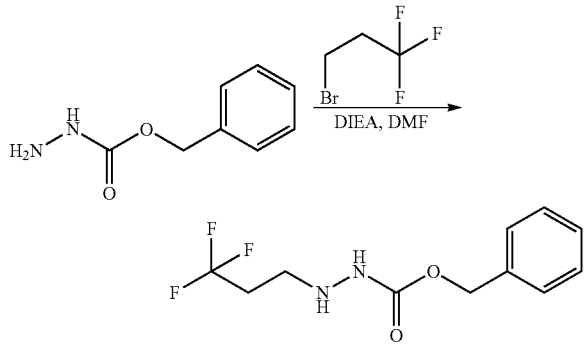

To a mixture of benzyl hydrazinecarboxylate (5.0 g, 30.3 mmol, 1 eq.) and DIEA (15.0 mL, 90.9 mmol, 3 eq.) in DMF (20 mL) was added 3,3,3-trifluoropropyl bromide (10.7 g 60.6 mmol, 2 eq.) at RT. The mixture was heated at 80° C. for 20 h, concentrated, and purified on silica gel using a mixture of EtOAc and hexanes as eluent to benzyl 2-(3,3,3-trifluoropropyl) hydrazinecarboxylate (4.2 g; 53%) as a white solid. $^1H$ NMR (400 MHz, $CDCl_3$) δ 7.33-7.17 (m, 5H), 6.11 (s, 1H), 5.01 (s, 2H), 4.00 (s, 1H), 3.00 (dd, J=12.2, 7.1 Hz, 2H), 2.17 (qt, J=10.8, 7.3 Hz, 2H). MS (ESI) m/z 263.1 $[M+H]^+$.

Step 2:

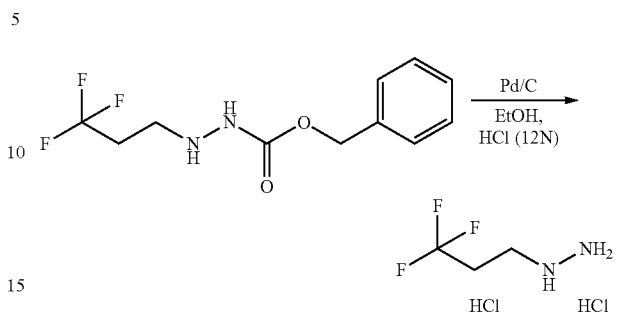

To benzyl 2-(3,3,3-trifluoropropyl)hydrazinecarboxylate (1.7 g, 6.49 mmol, 1 eq.) in a mixture of EtOH (30 mL) were added Pd/C (1.0 g) and HCl (12 N, 2.0 mL). The mixture was charged with $H_2$ (60 psi), stirred at RT for 1 h, filtered, and concentrated to give (3,3,3-trifluoropropyl)hydrazine dihydrochloride (1.07 g) as a yellow solid. MS (ESI) m/z 129.1 $[M+H]^+$.

Step 3:

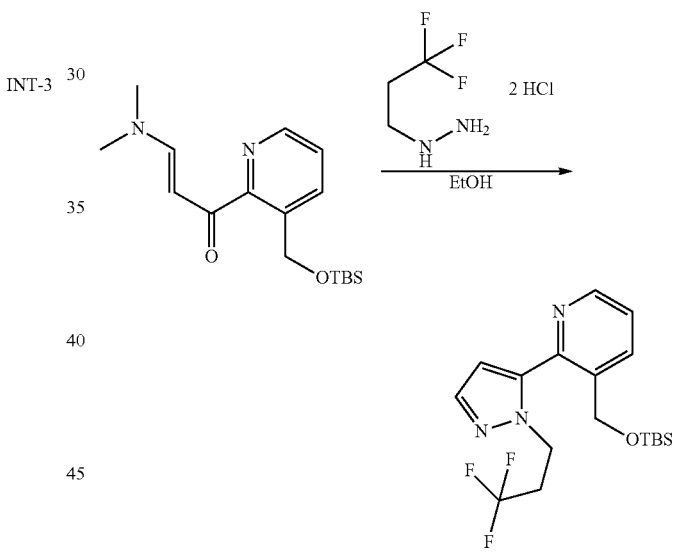

To (E)-1-(3-((tert-butyldimethylsilyloxy)methyl)pyridin-2-yl)-3-(dimethylamino)prop-2-en-1-one (crude above, 1.73 g, 5.41 mmol, 1 eq.) in EtOH (10 mL) was added (3,3,3-trifluoropropyl)hydrazine dihydrochloride (1.30 g, crude above, 6.49 mmol, 1.2 eq.) at RT. The mixture was heated at 80° C. for 1 h, concentrated, and diluted with EtOAc (50 mL) and $NaHCO_{3(sat)}$ solution (10 mL). The layers were separated and aqueous layer was extracted with EtOAc three times. The combined organic layers were dried over $Na_2SO_4$, concentrated, and purified on silica gel using a mixture of EtOAc and hexanes as eluent to give 3-((tert-butyldimethylsilyloxy)methyl)-2-(1-(3,3,3-trifluoropropyl)-1H-pyrazol-5-yl)pyridine (1.58 g; 76% for 2 steps). $^1H$ NMR (400 MHz, $CDCl_3$) δ 8.53 (dd, J=4.7, 1.6 Hz, 1H), 7.96-7.88 (m, 1H), 7.51 (d, J=1.9 Hz, 11H), 7.29 (dd, J=7.9, 4.7 Hz, 1H), 6.34 (d, J=1.9 Hz, 1H), 4.62 (s, 2H), 4.45-4.33 (m, 2H), 2.82-2.61 (m, 2H), 0.85 (s, 8H), −0.00 (s, 5H). MS (ESI) m/z 386.2 $[M+H]^+$.

Step 4:

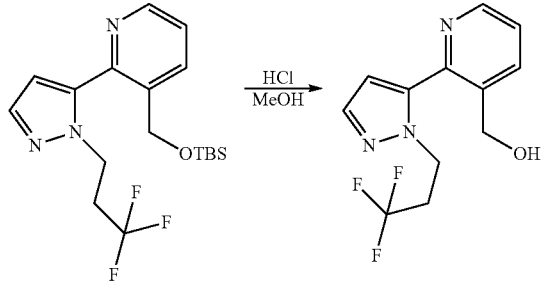 [SMILES: "MeOH" ; CC(C)(C)[Si](C)(C)OCc1cccnc1-c1ccnn1CCC(F)(F)F ; Cl ; OCc1cccnc1-c1ccnn1CCC(F)(F)F]

To 3-((tert-butyldimethylsilyloxy)methyl)-2-(1-(3,3,3-trifluoropropyl)-1H-pyrazol-5-yl)pyridine (1.58 g, 4.1 mmol) in MeOH (20 mL) was added HCl (4 N, 4.0 mL). The mixture was stirred at RT for 1 h, concentrated, and diluted with EtOAc (50 mL) and NaHCO$_{3(sat)}$ solution (10 mL). The layers were separated and aqueous layer was extracted with EtOAc three times. The combined organic layers were dried over Na$_2$SO$_4$, and concentrated to give (2-(1-(3,3,3-trifluoropropyl)-1H-pyrazol-5-yl)pyridin-3-yl)methanol (1.1 g, 99%) as colorless oil. $^1$H NMR (400 MHz, CDCl$_3$) δ 8.64 (dd, J=4.7, 1.7 Hz, 1H), 8.00 (dd, J=7.9, 1.7 Hz, 1H), 7.57 (d, J=1.9 Hz, 1H), 7.38 (dd, J=7.9, 4.8 Hz, 1H), 6.48 (d, J=1.9 Hz, 1H), 4.69 (s, 2H), 4.51-4.43 (m, 2H), 2.85-2.72 (m, 2H), 2.70 (s, 1H). MS (ESI) m/z 272.1 [M+H]$^+$.

Step 5:

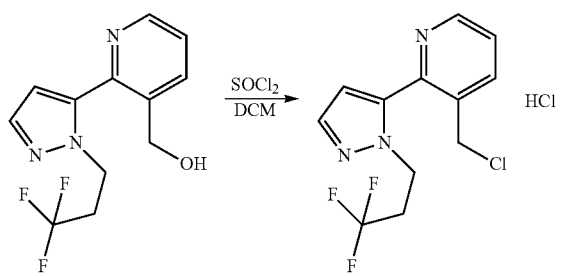

To (2-(1-(2,2,2-trifluoropropyl)-1H-pyrazol-5-yl)pyridin-3-yl)methanol (140 mg, 0.52 mmol) in DCM (5 mL) was added SOCl$_2$ (2.0 mL) at RT. The reaction mixture was stirred at RT for 4 h and concentrated to dryness. The crude solid was suspended in toluene and concentrated to dryness. The process was repeated three times and dried under vacuum to give 3-(chloromethyl)-2-(1-(2,2,2-trifluoropropyl)-1H-pyrazol-5-yl)pyridine hydrochloride (498 mg) as an off-white solid, which was used for next step without further purification.

Preparation of 3-(chloromethyl)-2-(1-isopropyl-1H-pyrazol-5-yl)pyridine (INT-4)

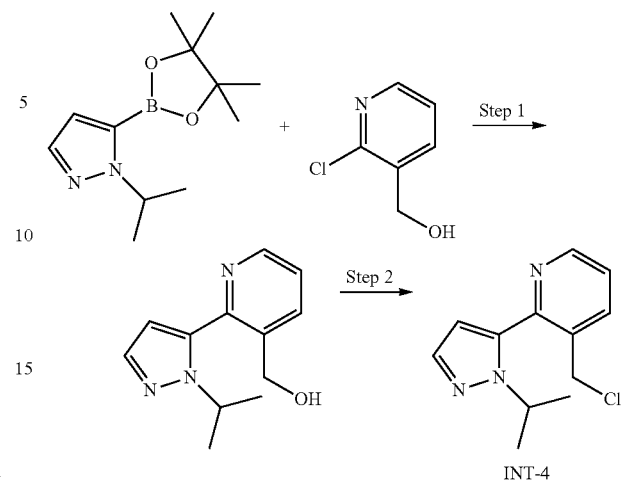

Step 1:

To a 500-mL flask containing the pyrazole boronate (9.0 g, 38.1 mmol), 2-chloropyridine (5.47 g, 38.1 mmol), Pd(dppf)Cl$_2$ ([1,1-bis(diphenylphosphino)ferrocene]dichloropalladium) (1.39 g, 1.91 mmol, 5% mol), and sodium bicarbonate (9.61 g, 114.4 mmol, 3 equiv) was added 100 mL of dioxane and 30 mL of water. The mixture was heated under nitrogen at 100° C. for 12 hrs. Then solvents were removed on a rotavap at 40° C. undervacum. The resulting brown residue was suspended in 20% EtOAc/DCM (60 mL), filtered through a pad of silica gel (15 g); washed with 20% EtOAc/DCM (4×20 mL). The combined filtrate were concentrated to afford a brown oil (13 g). The residue was dissolved 10% EtOAc/hexanes (20 mL) and loaded on a Biotage 100 g snap SiO2 column and eluted with 0-50% EtOAc. (2-(1-isopropyl-1H-pyrazol-5-yl)pyridin-3-yl)methanol was obtained as a light brown oil (3.32 g, 40%). MS (ESI) m/z 218 [M+H]$^+$.

Step 2:

To a solution of (2-(1-isopropyl-1H-pyrazol-5-yl)pyridin-3-yl)methanol) (440 mg, 2.02 mmol) in DCM (4 mL) was added SOCl$_2$ (2 eq) at 0° C. The reaction mixture was stirred at RT for 15 mins and concentrated to dryness. The crude solid was suspended in toluene and concentrated to dryness. The process was repeated three times and dried under vacuum to give 3-(chloromethyl)-2-(1-isopropyl-1H-pyrazol-5-yl)pyridine hydrochloride (432 mg) as an off-white solid, which was used for next step without further purification. MS (ESI) m/z 236.5 [M+H]$^+$.

Preparation of 3-(chloromethyl)-2-(1-cyclopentyl-1H-pyrazol-5-yl)pyridine (INT-5)

INT-4

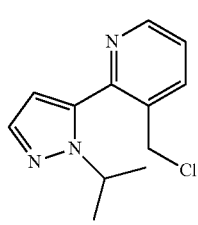

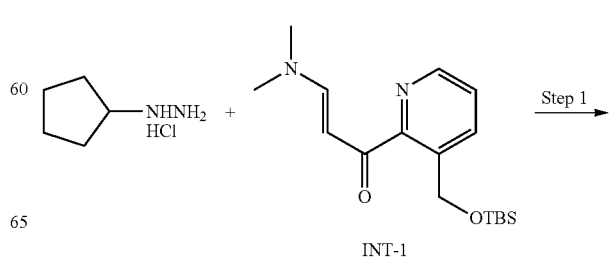

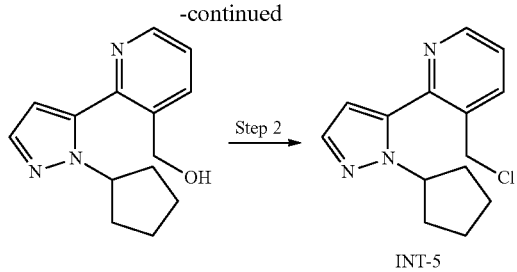

Step 1:

To (E)-1-(3-((tert-butyldimethylsilyloxy)methyl)pyridin-2-yl)-3-(dimethylamino)prop-2-en-1-one (crude, 3.205 g, 10.0 mmol, 1 eq.) in EtOH (30 mL) was added cyclopentylhydrazine HCl salt (1.639 g, 12.0 mmol, 1.2 eq) at RT. The mixture was heated at 80° C. for 2 h, concentrated, and purified on silica gel using a mixture of EtOAc and hexanes as eluent to give a mixture of regio-isomers, the less polar (2-(1-cyclopentyl-1H-pyrazol-5-yl)pyridin-3-yl)methanol was obtained as a light brown oil (440 mg). MS (ESI) m/z 244.2 [M+H]$^+$.

Step 2:

To a solution of (2-(1-cyclopentyl-1H-pyrazol-5-yl)pyridin-3-yl)methanol (301 mg, 1.24 mmol) in DCM (3 mL) was added SOCl$_2$ (3 eq) at 0° C. The reaction mixture was stirred at RT for 15 mins (thew reaction was done in 10 mins by LCMS) and concentrated to dryness. The crude solid was suspended in toluene and concentrated to dryness. The process was repeated three times and dried under vacuum to give 3-(chloromethyl)-2-(1-cyclopentyl-1H-pyrazol-5-yl)pyridine hydrochloride (305 mg) as an off-white solid, which was used for next step without further purification. MS (ESI) m/z 262.2 [M+H]$^+$.

Preparation of 5-hydroxy-2-(2-methoxyethoxy)isonicotinaldehyde (INT-6)

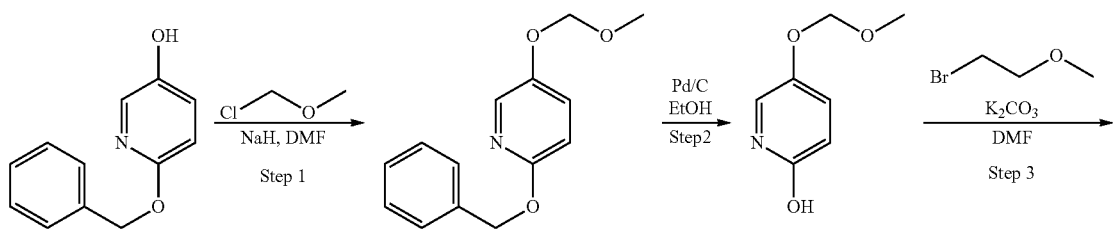

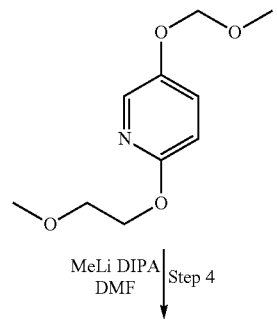

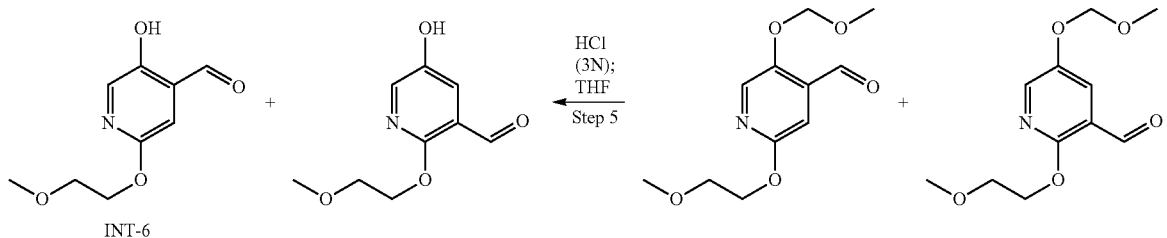

Step 1

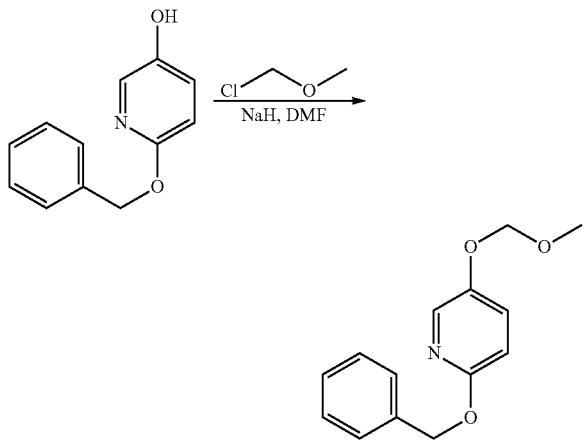

To a solution of 6-(benzyloxy)pyridin-3-ol (2.0 g, 10 mmol, 1 eq.) in DMF (20 mL) was added NaH (60% in mineral oil; 0.6 g, 15 mmol, 1.5 eq.) at 0-5° C. portion-wise. Upon the completion of addition, the mixture was continued to stir at 0-5° C. for 15 min. added chloromethyl methyl ether (0.88 g, 11 mmol, 1.1 eq.), stirred at 0-5° C. for another 20 min. and quenched with NH$_4$Cl$_{(sat.)}$ solution. The aqueous layer was extracted with EtOAc (3×20 mL) and the combined organic layers were washed with water and brine, dried over Na$_2$SO$_4$, concentrated, and purified on silica gel using 25% EtOAc/hexanes as eluent to give 2-(benzyloxy)-5-(methoxymethoxy)pyridine (2.1 g, 87%) as a colorless oil. MS (ESI) m/z 246.1 [M+H]$^+$.

Step 2

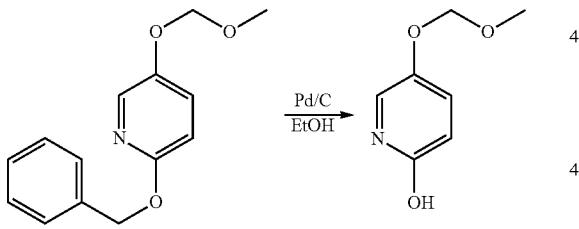

To 2-(benzyloxy)-5-(methoxymethoxy)pyridine (1.8 g, 8.71 mol) in EtOH was added Pd/C (1.0 g). The mixture was charged with H2 (15 psi), stirred at RT for 45 min, filtered, and concentrated to give 5-(methoxymethoxy)pyridin-2-ol (1.35 g, quantitative yield) as a pale yellow solid. MS (ESI) m/z 156.1 [M+H]$^+$.

Step 3

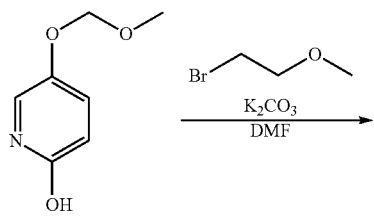

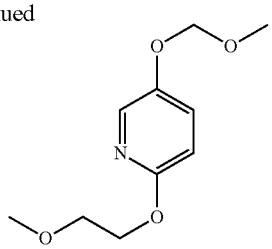

To a mixture of 5-(methoxymethoxy)pyridin-2-ol (1.35 g, 8.71 mmol, 1 eq.) and K$_2$CO$_3$ (6.01 g, 43.6 mmol, 5.0 eq.) in DMF (30.0 mL) was added 1-bromo-2-methoxyethane (3.61 g, 26.1 mmol, 3 eq.). The mixture was heated at 60° C. for 2 h, cooled, filtered, concentrated, and purified on silica gel using a mixture of EtOAc and hexanes as eluent to give 2-(2-methoxyethoxy)-5-(methoxymethoxy)pyridine (500 mg, 27%) as a colorless oil. $^1$H NMR (400 MHz, CDCl$_3$) δ 7.94 (d, J=3.0 Hz, 1H), 7.35 (ddd, 0.1=8.9, 3.0, 1.0 Hz, 1H), 6.76 (dd, J=8.9, 1.0 Hz, 1H), 5.11 (s, 2H), 4.48-4.40 (m, 2H), 3.79-3.71 (m, 2H), 3.50 (s, 3H), 3.45 (s, 3H). MS (ESI) m/z 214.1 [M+H]$^+$.

Step 4

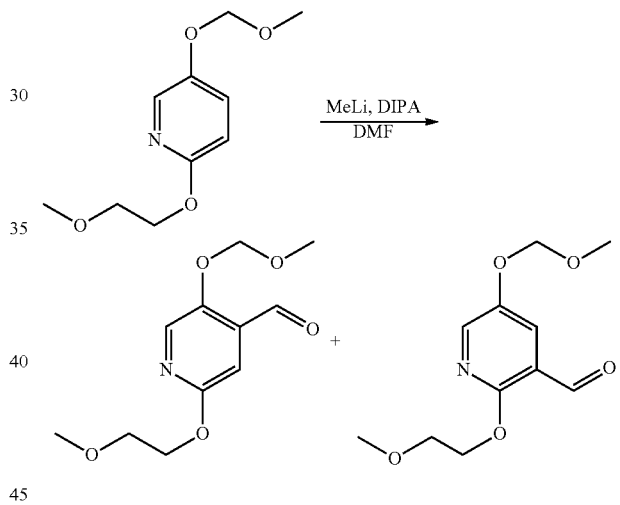

To a mixture of 2-(2-methoxyethoxy)-5-(methoxymethoxy)pyridine (1.34 g, 6.3 mol, 1 eq.) and diisopropylamine (17.5 uL, 0.13 mmol, 0.02 eq.) in THF (50 mL) was added methyl lithium (1.6 M/THF, 7 mL, 11.3 mol, 1.8 eq.) at −40° C. Upon the completion of addition, the mixture was warmed to 0° C., continued to stir at 0° C. for 3 h, cooled back down to −40° C., and added DMF (0.83 mL, 11.3 mol, 1.8 eq.) slowly. The mixture was then stirred at −40° C. for 1 h, quenched with a mixture of HCl (12 N, 12 mL) and THF (28 mL), warmed to RT, and added water (20 mL). The pH of the mixture was adjusted to pH 8-9 with solid K$_2$CO$_3$. The aqueous layer was extracted with EtOAc (30 mL) twice. The combined organic layers were dried over Na$_2$SO$_4$, concentrated, and purified on silica gel using a mixture of EtOAc and hexanes as eluent to give a mixture of 2-(2-methoxyethoxy)-5-(methoxymethoxy)isonicotinaldehyde and 2-(2-methoxyethoxy)-5-(methoxymethoxy) nicotinaldehyde (5/1, 1.27 g, 83.6%) as a pale yellow oil. $^1$H NMR (400 MHz, CDCl$_3$) δ 10.45 (s, 1H), 8.23 (s, 1H), 7.16 (s, 1H), 5.27 (s, 2H), 4.46 (dd, J=5.4, 3.9 Hz, 2H), 4.14 (q, J=7.1 Hz, 1H), 3.77-3.71 (m, 2H), 3.56 (s, 3H), 3.46 (s, 3H) and $^1$H NMR (400 MHz, CDCl$_3$) δ 10.41 (s, 1H), 8.18 (d, J=3.2 Hz, 1H), 7.85 (d, J=3.1 Hz, 1H), 5.16 (s, 2H), 4.64-4.57 (m, 2H), 3.85-3.79 (m, J=5.4, 4.0 Hz, 2H), 3.50 (s, 3H), 3.46 (s, 3H); MS (ESI) m/z 242.1 [M+H]$^+$.

Step 5

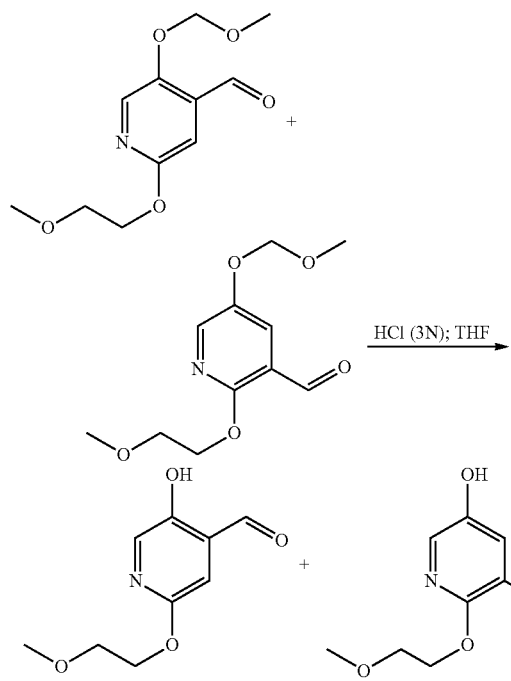

To a solution of 2-methoxy-5-(methoxymethoxy)isonicotinaldehyde (1.27 g, 5.29 mol) in THF (5 mL) was added HCl (3 N, 4 mL). The reaction was stirred at 50° C. for 1 h, cooled to RT, and diluted with water (5 mL). The mixture was neutralized to pH 7-8 with solid $K_2CO_3$ and the aqueous layer was extracted with EtOAc (100 mL) twice. The combined organic layers were dried over $Na_2SO_4$, concentrated, and purified on silica gel using a mixture of EtOAc and hexanes to give 5-hydroxy-2-(2-methoxyethoxy)isonicotinaldehyde (630 mg, 60%) and 5-hydroxy-2-(2-methoxyethoxy)nicotinaldehyde (120 mg, 11%). Data for 5-hydroxy-2-(2-methoxyethoxy)isonicotinaldehyde: $^1$H NMR (400 MHz, CDCl$_3$) δ 9.98 (s, 1H), 9.50 (s, 1H), 8.07 (s, 1H), 7.02 (s, 1H), 4.51-4.39 (m, 2H), 3.81-3.72 (m, 2H), 3.47 (s, 3H). LRMS (M+H$^+$) m/z 198.1. Data for and 5-hydroxy-2-(2-methoxyethoxy) nicotinaldehyde: $^1$H NMR (400 MHz, CDCl$_3$) δ 10.3 (s, 1H), 7.99 (d, J=3.2 Hz, 1H), 7.58 (d, J=3.2 Hz, 1H), 7.18-7.07 (br, 1H), 4.54 (dd, J=5.4, 3.7 Hz, 21H), 3.84 (dd, J=5.4, 3.7 Hz, 2H), 3.49 (s, 3H); MS (ESI) m/z 198.1 [M+H]$^+$.

Preparation of 2,6-dihydroxybenzaldehyde (INT-7)

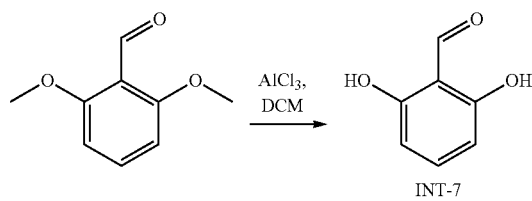

Into a 3000-mL three neck round-bottom flask, was placed a solution of AlCl$_3$ (240 g, 1.80 mol, 3.00 equiv) in dichloromethane (1200 mL). A solution of 2,6-dimethoxybenzaldehyde (100 g, 601.78 mmol, 1.00 equiv) in dichloromethane (800 ml) was added to the reaction mixture dropwise at 0° C. The resulting solution was stirred overnight at room temperature, and then it was quenched with 200 mL of diluted HCl (2M). The resulting solution was extracted with 2×200 mL of dichloromethane. The combined organic layers were concentrated under vacuum. The residue was applied onto a silica gel column with ethyl acetate/petroleum ether (1:200-1:50) as eluent to furnish 40 g (48%) of 2,6-dihydroxybenzaldehyde as a yellow solid.

$^1$HNMR (300 MHz, DMSO-d$_6$) δ 11.25 (s, 2H), 10.25 (s, 1H), 7.36 (m, 1H), 6.36 (d, J=8.4 Hz 2H); MS (ESI) m/z 139 [M+H]$^+$.

Preparation of 5-hydroxy-2-methoxyisonicotinaldehyde (INT-8)

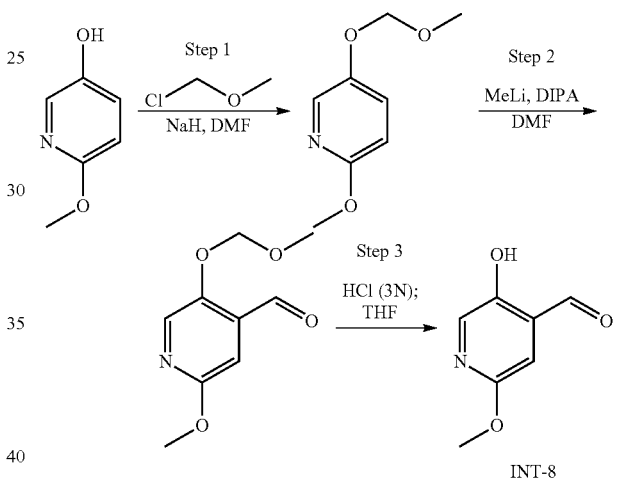

Step 1:

To a solution of 6-methoxypyridin-3-ol (20 g, 0.16 mol) in DMF (200 mL) was added NaH (60% in mineral oil; 9.6 g, 0.24 mol) at 0-5° C. portion-wise. Upon the completion of addition, the mixture was continued to stir at 0-5° C. for 15 min followed by additional of chloromethyl methyl ether. The mixture was stirred at 0-5° C. for another 20 min and quenched with aqueous NH$_4$Cl$_{(sat.)}$. The aqueous layer was extracted with EtOAc (3×100 mL) and the combined organic layer was washed with water and brine, dried over Na$_2$SO$_4$, and concentrated under reduced pressure. The residue was purified on silica gel with 25% EtOAc/hexanes as eluent to give 2-methoxy-5-(methoxymethoxy)pyridine (24.1 g, 89.3%) as a colorless oil. $^1$H NMR (400 MHz; CDCl$_3$) 7.97 (d, 1H), 7.35 (dd, 1H), 6.70 (d, 1H), 5.12 (s, 2H), 3.91 (s, 3H), 3.51 (s, 3H); MS (ESI) m/z 170.1 [M+H]$^+$.

Step 2: To a mixture of 2-methoxy-5-(methoxymethoxy) pyridine (30 g, 0.178 mol) and diisopropylamine (507 uL, 3.6 mmol) in THF (500 mL) was added methyl lithium (1.6 M/THF, 200 mL, 0.32 mol) at −40° C. Upon the completion of addition, the mixture was warmed to 0° C. and continued to stir at 0° C. for 3 h. The reaction mixture was then cooled back down to −40° C. followed by addition of DMF (24.7 mL, 0.32 mol) slowly. The mixture was then stirred at −40° C. for 1 h and quenched with a mixture of HCl (12 N, 120 mL) and THF (280 mL). Water (200 mL) was added and the pH of the mixture was adjusted to pH 8-9 with solid K$_2$CO$_3$. The mixture was extracted with EtOAc (300 mL) twice. The organic layer was combined, dried over Na$_2$SO$_4$, and concentrated to give 2-methoxy-5-(methoxymethoxy)isonicotinaldehyde (33.5 g, 95.7%) as a brown solid, which was used for next step without further purification. $^1$H NMR (400 MHz; CD$_3$OD) 7.90 (s, 1H), 6.92 (s, 1H), 5.64 (s, 1H), 5.20 (s, 2H), 3.84 (s, 3H), 3.48 (s, 3H); MS (ESI) m/z 198.1 [M+H]$^+$.

Step 3:

To a solution of 2-methoxy-5-(methoxymethoxy)isonicotinaldehyde (33.5 g, 0.17 mol) in THF (150 mL) was added HCl (3 N, 250 mL). The reaction was stirred at 50° C. for 1 h, cooled to RT and diluted with water (500 mL). The mixture was neutralized to pH 7-8 with solid K$_2$CO$_3$. The pale yellow solid was collected, washed with water, and dried in vacuum oven (40° C.) overnight to give 5-hydroxy-2-methoxyisonicotinaldehyde (17.9 g, 74.6%). $^1$H NMR (400 MHz; DMSO) δ=10.31 (s, 1H), 8.03 (s, 1H), 6.89 (s, 1H), 3.80 (s, 3H); MS (ESI) m/z 154.0 [M+H]$^+$.

Experimental Procedures for Examples:

GBT527 Preparation of 2-methoxy-5-[[2-[1-(2,2,2-trifluoroethyl)pyrazol-3-yl]pyridin-3-yl]methoxy]pyridine-4-carbaldehyde GTB527 was prepared using general method B from 5-hydroxy-2-methoxyisonicotinaldehyde and INT-2.

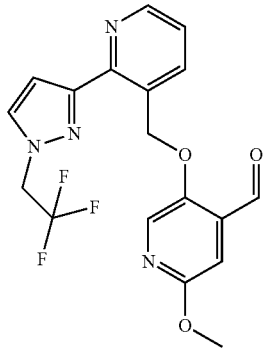 [SMILES: COc1cc(C=O)c(OCc2cccnc2-c2ccn(CC(F)(F)F)n2)cn1]

GBT576 Preparation of 2-oxo-5-[[2-(2-propan-2-ylpyrazol-3-yl)pyridin-3-yl]methoxy]-1H-pyridine-4-carbaldehyde

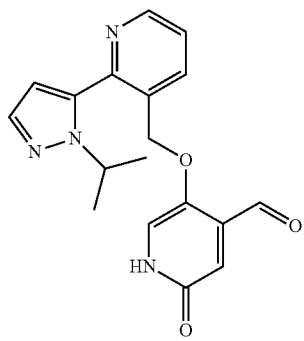 [SMILES: CC(C)n1nccc1-c1ncccc1COc1c[nH]c(=O)cc1C=O]

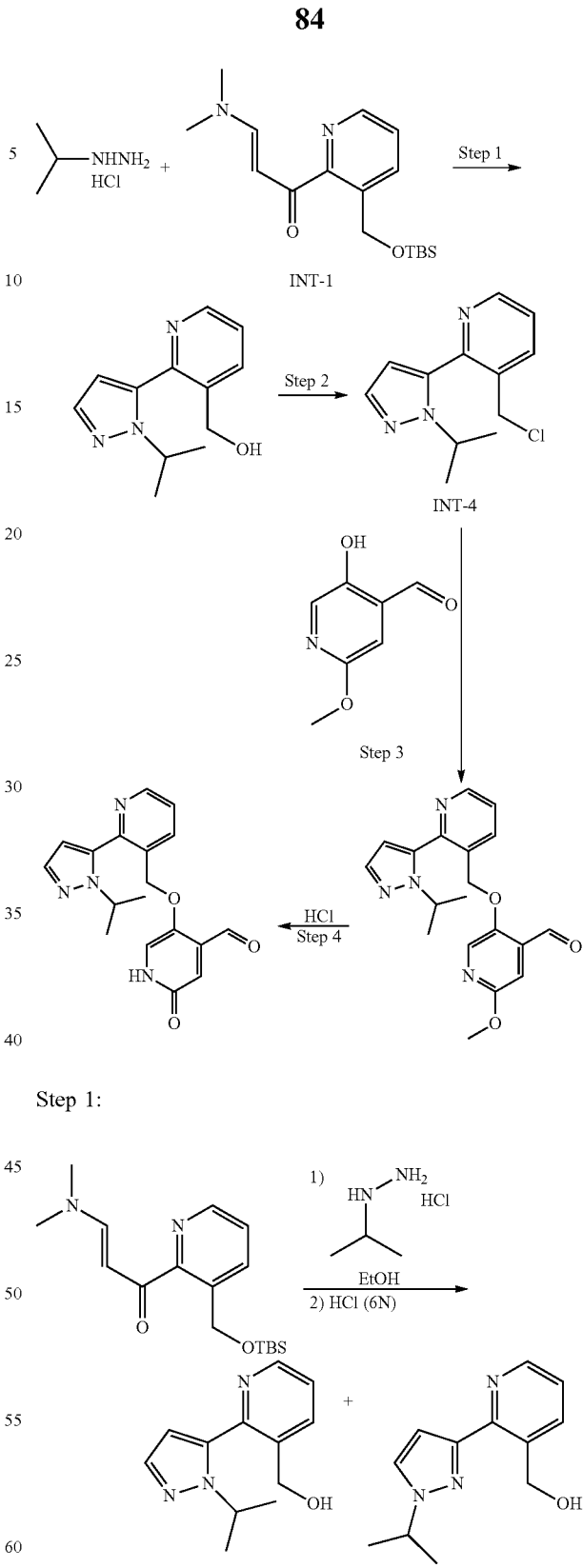

Step 1:

To (E)-1-(3-((tert-butyldimethylsilyloxy)methyl)pyridin-2-yl)-3-(dimethylamino)prop-2-en-1-one (crude, 1.03 g, 3.22 mmol, 1 eq.; INT-1) in EtOH (10 mL) was added isopropylhydrazine hydrochloride (430 mg, 3.86 mmol, 1.2 eq.). The mixture was heated at 80° C. for 2 h, cooled, added HCl (6 N, 0.5 mL), and stirred O/N. The mixture was concentrated and diluted with EtOAc (80 mL) and NaHCO$_{3(sat)}$ (10 mL) solution. The layers were separated and the aqueous layer was extracted with EtOAc three times. The combined organic layers were dried over Na$_2$SO$_4$, concentrated, and purified on silica gel using EtOAc as eluent to give (2-(1-isopropyl-1H-pyrazol-5-yl)pyridin-3-yl)methanol (500 mg, 71%) and (2-(1-isopropyl-1H-pyrazol-3-yl)pyridin-5-yl)methanol (55 mg, 25%) as pale yellow oils. Data for 2-(1-isopropyl-1H-pyrazol-5-yl)pyridin-3-yl)methanol: $^1$H NMR (400 MHz, CDCl$_3$) δ 8.67 (dd, J=4.7, 1.5 Hz, 1H), 8.0 (d, J=7.8 Hz, 1H), 7.61 (d, J=1.8 Hz, 1H), 7.39 (dd, J=7.8, 4.8 Hz, 1H), 6.37 (d, J=1.8 Hz, 1H), 4.67 (s, 2H), 4.55 (sep, J=6.6 Hz 1H), 1.98-2.05 (br, 1H), 1.47 (d, J=6.6 Hz, 6H). LRMS (M+H$^+$) m/z 218.1 Data for (2-(1-isopropyl-1H-pyrazol-3-yl)pyridin-5-yl)methanol: $^1$H NMR (400 MHz, CDCl$_3$) δ 8.62 (dd, J 4.8, 1.6 Hz, 1H), 7.72 (d, J=7.6 Hz, 1H), 7.55 (d, J=2.4 Hz, 1H), 7.23 (dd, J=7.6, 4.8 Hz, 1H), 6.99 (dd, J=8.0, 6.5 Hz, 1H), 6.07 (t, J=7.6 Hz, 1H), 4.67 (d, J=7.6 Hz, 2H), 4.58 (sep. J=6.7 Hz, 1H), 1.60 (d, J=6.7 Hz, 1H). MS (ESI) m/z 218.1 [M+H]$^+$.

Step 2:

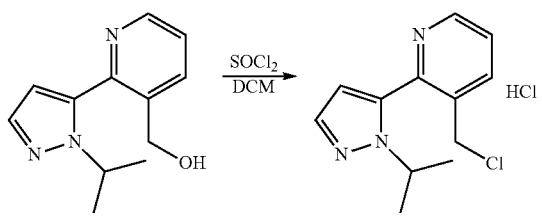

To (2-(1-isopropyl-1H-pyrazol-5-yl)pyridin-3-yl)methanol (560 mg, 2.58 mmol) in DCM (10 mL) was added SOCl$_2$ (3.0 mL) at RT. The reaction mixture was stirred at RT for 4 h and concentrated to dryness. The crude solid was suspended in toluene and concentrated to dryness. The process was repeated three times and dried under vacuum to give 3-(chloromethyl)-2-(1-isopropyl-1H-pyrazol-5-yl)pyridine hydrochloride (700 mg) as an off-white solid, which was used for next step without further purification.

Step 3:

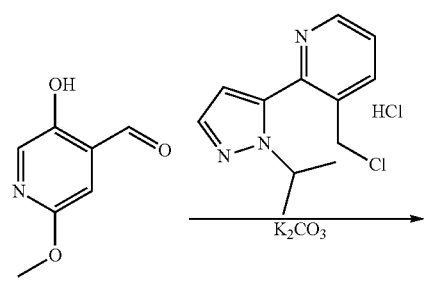

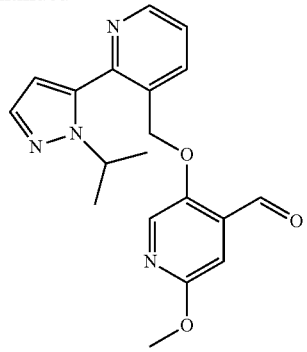

A mixture of 5-hydroxy-2-methoxyisonicotinaldehyde (395 mg, 2.58 mmol, 1 eq.), 3-(chloromethyl)-2-(1-isopropyl-1H-pyrazol-5-yl)pyridine hydrochloride (700 mg, 2.58 mmol, 1 eq.), and K$_2$CO$_3$ (1.4 g, 10.32 mmol, 4 eq.) in DMF (10.0 mL) was heated at 70° C. for 2 h. The mixture was cooled, filtered, concentrated, and purified on silica gel using a mixture of EtOAc and hexanes as eluent to give 5-((2-(1-isopropyl-1H-pyrazol-5-yl)pyridin-3-yl)methoxy)-2-methoxyisonicotinaldehyde (590 mg, 65%) as an off-white solid. $^1$H NMR (400 MHz, CDCl$_3$) δ 10.41 (s, 1H), 8.76 (dd, J=4.7, 1.6 Hz, 1H), 8.04 (dd, J=7.9, 1.6 Hz, 1H), 7.90 (s, 1H), 7.61 (d, J=1.8 Hz, 1H), 7.44 (dd, J=7.9, 4.8 Hz, 1H), 7.10 (s, 1H), 6.37 (d, J=1.8 Hz, 1H), 5.14 (s, 2H), 4.65 (sep, J=6.6 Hz, 1H), 3.91 (s, 3H), 1.49 (d, J=6.6 Hz, 6H); MS (ESI) m/z 353.1 [M+H]$^+$.

To 5-((2-(1-isopropyl-1H-pyrazol-5-yl)pyridin-3-yl)methoxy)-2-methoxyisonicotinaldehyde (590 mg) suspended in water (5.0 mL) was added HCl (6 N, 4 mL). Once the mixture turned into a homogeneous solution, it was freeze at −78° C. to an solid and pump under high vacuum O/N. The yellow solid was continued to pump at 45° C. for 20 h, dissolved in water (2.0 mL), and basified to pH 11 with NaOH (2 N). The aqueous layer was washed with DCM three times and the pH of the mixture was adjusted to pH 6-7. The solid was collected and dried to give 2-oxo-5-[[2-(2-propan-2-ylpyrazol-3-yl)pyridin-3-yl]methoxy]-1H-pyridine-4-carbaldehyde as a yellow solid. $^1$H NMR (400 MHz, CDCl$_3$) δ 10.3 (s, 1H), 8.8 (dd, J=4.7, 1.6 Hz, 1H), 8.1 (dd, J=7.9, 1.5 Hz, 1H), 7.6 (s, 1H), 7.5 (d, J=1.8 Hz, 1H), 7.1 (s, 1H), 7.0 (s, 1H), 6.6 (d, J=1.8 Hz, 1H), 4.9 (s, 2H), 4.7 (sep, J=6.6 Hz, 1H), 1.5 (d, J=6.6 Hz, 6H); MS (ESI) m/z 339.4 [M+H]$^+$.

GHT779 Preparation of 2-(2-morpholin-4-ylethoxy)-5-[[2-(2-propan-2-ylpyrazol-3-yl)pyridin-3-yl]methoxy]pyridine-4-carbaldehyde GTB779 was prepared according to general method B from 5-hydroxy-2-(2-morpholinoethoxy)isonicotinaldehyde and INT-4.

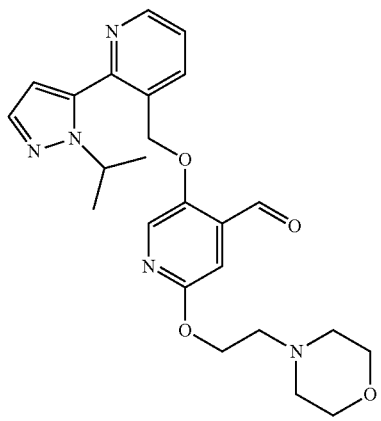 [SMILES: CC(C)n1nccc1-c1ncccc1COc1cnc(OCCN2CCOCC2)cc1C=O]

¹H NMR (400 MHz, Chloroform-d) δ 10.33 (s, 1H), 8.68 (dd, J=4.8, 1.7 Hz, 1H), 7.95 (dd, J=7.9, 1.7 Hz, 1H), 7.79 (s, 1H), 7.53 (d, J=1.8 Hz, 1H), 7.36 (dd, J=7.9, 4.7 Hz, 1H), 7.04 (s, 1H), 6.28 (d, J=1.8 Hz, 1H), 5.06 (s, 2H), 4.57 (s, OH), 4.32 (t, J=5.7 Hz, 2H), 3.69-3.62 (m, 4H), 2.70 (t, J=5.7 Hz, 2H), 2.53-2.45 (m, 4H), 1.41 (d, J=6.6 Hz, 6H); MS (ESI) m/z 452 [M+H]⁺.

GBTS32 Preparation of 2-(2-methoxyethoxy)-5-[[2-[2-(2,2,2-trifluoroethyl)pyrazol-3-yl]pyridin-3-yl]methoxy]pyridine-4-carbaldehyde GTB832 was prepared according to general method B from 5-hydroxy-2-(2-methoxyethoxy)isonicotinaldehyde (INT-5) and INT-2.

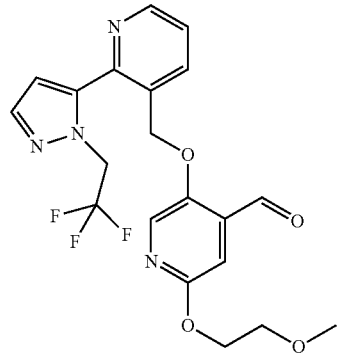 [SMILES: COCCOc1cc(C=O)c(OCc2cccnc2-c2ccnn2CC(F)(F)F)cn1]

¹H NMR (400 MHz, CDCl₃) δ 10.32 (s, 1H), 8.67 (dd, J=4.8, 1.6 Hz, 1H), 7.97 (dd, J=7.9, 1.5 Hz, 1H), 7.87 (s, 1H), 7.59 (d, J=1.9 Hz, 1H), 7.38 (dd, J=7.9, 4.8 Hz, 1H), 7.11 (s, 1H), 6.47 (d, J=1.9 Hz, 1H), 5.17 (q, J=8.6 Hz, 2H), 5.10 (s, 2H), 4.39-4.32 (m, 2H), 3.70-3.63 (m, 21H); MS (ESI) m/z 437 [M+H]⁺.

GBT835 Preparation of 6-methyl-3-[[2-[2-(2,2,2-trifluoroethyl)pyrazol-3-yl]pyridin-3-yl]methoxy]pyridine-2-carbaldehyde GTB835 was prepared according to general method B from 3-hydroxy-6-methylpicolinaldehyde and INT-2.

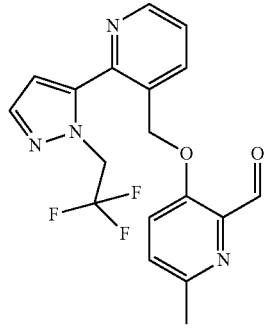 [SMILES: Cc1ccc(OCc2cccnc2-c2ccnn2CC(F)(F)F)c(C=O)n1]

¹H NMR (400 MHz, CDCl₃) δ 10.23 (s, 1H), 8.64 (dd, J=4.7, 1.6 Hz, 1H), 8.16 (dd, J=7.9, 1.5 Hz, 1H), 7.61 (d, J=1.9 Hz, 1H), 7.38 (dd, J=7.9, 4.8 Hz, 1H), 7.21 (d, J=8.6 Hz, 1H), 7.10 (d, J=8.6 Hz, 1H), 6.47 (d, J=1.9 Hz, 1H), 5.19 (q, J=8.6 Hz, 2H), 5.12 (d, J=6.1 Hz, 2H), 2.51 (s, 3H); MS (ESI) m/z 377 [M+H]⁺.

GBT836 Preparation of 6-methyl-3-[[2-[2-(3,3,3-trifluoropropyl)pyrazol-3-yl]pyridin-3-yl]methoxy]pyridine-2-carbaldehyde GTB836 was prepared according to general method B from 3-hydroxy-6-methylpicolinaldehyde and INT-3.

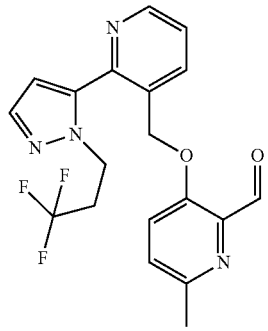 [SMILES: Cc1ccc(OCc2cccnc2-c2ccnn2CCC(F)(F)F)c(C=O)n1]

¹H NMR (400 MHz, CDCl₃) δ 10.31 (s, 1H), 8.75 (dd, J=4.7, 1.7 Hz, 1H), 8.27 (dd, J=7.9, 1.6 Hz, 1H), 7.62 (d, J=1.9 Hz, 1H), 7.49 (dd, J=7.9, 4.8 Hz, 1H), 7.33 (d, J=8.6 Hz, 1H), 7.24 (d, J=8.6 Hz, 1H), 6.46 (d, J=1.9 Hz, 1H), 5.18 (s, 2H), 4.61-4.44 (m, 2H), 2.96-2.75 (m, 2H), 2.62 (s, 3H); MS (ESI) m/z 391 [M+H]⁺.

GBT839 Preparation of 3-[[2-[2-(2,2,2-trifluoroethyl)pyrazol-3-yl]pyridin-3-yl]methoxy]pyridine-2-carbaldehyde GTB839 was prepared according to general method B from 3-hydroxypicolinaldehyde and INT-2.

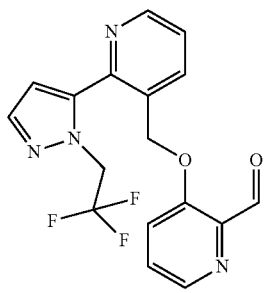 [SMILES: O=Cc1ncccc1OCc1cccnc1-c1ccnn1CC(F)(F)F]

¹H NMR (400 MHz, CDCl₃) δ 10.26 (s, 1H), 8.65 (dd, J=4.7, 1.5 Hz, 1H), 8.38 (dd, J=4.4, 1.0 Hz, 1H), 8.19 (dd, J=7.9, 1.0 Hz, 1H), 7.61 (d, J=1.9 Hz, 1H), 7.43-7.33 (m, 2H), 7.21 (d, J=8.6 Hz, 1H), 6.48 (d, J=1.9 Hz, 1H), 5.19 (q, J=8.6 Hz, 2H), 5.15 (s, 2H); MS (ESI) m/z 363.1 [M+H]⁺.

GBT840 Preparation of 3-[[2-[2-(3,3,3-trifluoropropyl)pyrazol-3-yl]pyridin-3-yl]methoxy]pyridine-2-carbaldehyde GTB839 was prepared according to general method B from 3-hydroxypicolinaldehyde and INT-3.

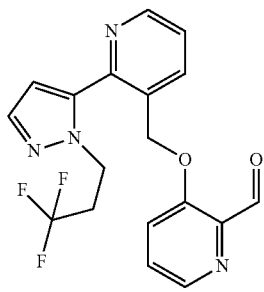 [SMILES: O=Cc1ncccc1OCc1cccnc1-c1ccnn1CCC(F)(F)F]

¹H NMR (400 MHz, CDCl₃) δ 10.24 (s, 1H), 8.66 (dd, J=4.7, 1.6 Hz, 1H), 8.39 (dd, J=4.5, 1.1 Hz, 1H), 8.21 (dd, J=7.9, 1.6 Hz, 1H), 7.53 (d, J=1.9 Hz, 1H), 7.44-7.37 (m, 2H), 7.26 (d, J=8.5 Hz, 1H), 6.37 (d, J=1.9 Hz, 1H), 5.13 (s, 2H), 4.49-4.40 (m, 2H), 2.87-2.64 (m, 2H); MS (ESI) m/z 377.1 [M+H]⁺.

GBT841 Preparation of 3-chloro-5-[[2-(2-propan-2-ylpyrazol-3-yl)pyridin-3-yl]methoxy]pyridine-4-carbaldehyde GTB841 was prepared according to general method B from 3-chloro-5-hydroxyisonicotinaldehyde and INT-4.

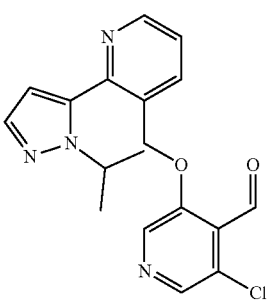 [SMILES: CC(C)n1nccc1-c1ncccc1COc1cncc(Cl)c1C=O]

¹H NMR (400 MHz, CDCl₃) δ 10.51 (s, 1H), 8.77 (dd, J=4.7, 1.6 Hz, 1H), 8.41 (s, 1H), 8.28 (s, 1H), 8.13 (dd, J=7.9, 1.5 Hz, 1H), 7.63 (d, J=1.8 Hz, 1H), 7.47 (dd, J=7.9, 4.8 Hz, 1H), 6.37 (d, J=1.8 Hz, 1H), 5.23 (s, 2H), 4.66 (sep, J=6.6 Hz, 1H), 1.49 (d, J=6.6 Hz, 6H); MS (ESI) m/z 357 [M+H]⁺.

GBT844 Preparation of 3-chloro-5-[[2-[2-(2,2,2-trifluoroethyl)pyrazol-3-yl]pyridin-3-yl]methoxy]pyridine-4-carbaldehyde GTB844 was prepared according to general method B from 3-chloro-5-hydroxyisonicotinaldehyde and INT-2.

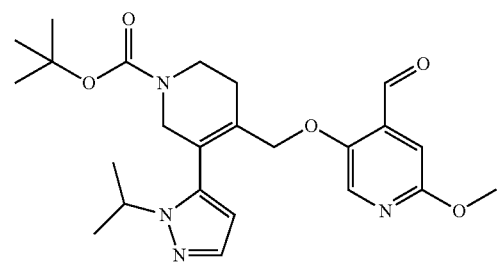

¹H NMR (400 MHz, CDCl₃) δ 10.43 (s, 1H), 8.67 (dd, J=4.7, 1.5 Hz, 1H), 8.35 (s, 1H), 8.26 (s, 1H), 8.06 (dd, J=7.9, 1.3 Hz, 1H), 7.61 (d, J=1.9 Hz, 1H), 7.40 (dd, J=7.9, 4.8 Hz, 1H), 6.47 (d, J=1.9 Hz, 1H), 5.21-5.10 (m, 4H); MS (ESI) m/z 397 [M+H]⁺.

GBT860 Preparation of tert-butyl 4-(((4-formyl-6-methoxypyridin-3-yl)oxy)methyl)-5-(1-isopropyl-1H-pyrazol-5-yl)-3,6-dihydropyridine-1(2H)-carboxylate

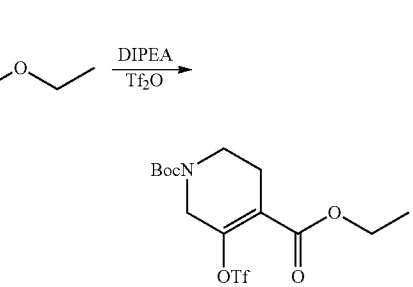

Step 1:
To a solution of 1-tert-butyl 4-ethyl 3-oxopiperidine-1,4-dicarboxylate (2.0 g, 7.37 mmol) in DCM (45 mL) was added DIPEA (1.54 ml, 8.84 mmol) and Tf₂O (1.36 mL, 8.11 mmol) at −78° C., then the temperature was warmed up to room temperature and the solution was stirred at RT for 1.5 h, the mixture was diluted with DCM (100 mL), organic layer was washed with Sat. NaHCO₃, brine, dried and concentrated to give 1-(tert-butyl) 4-ethyl 5-(((trifluoromethyl)sulfonyl)oxy)-3,6-dihydropyridine-1,4(2H)-dicarboxylate, which was used for next step without purification.

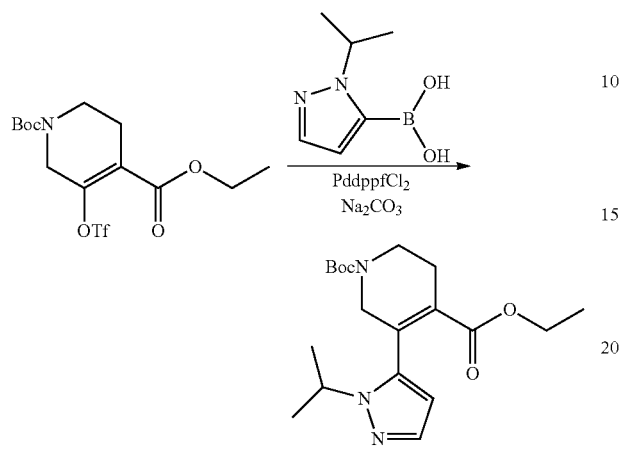

Step 2:

To a solution of 1-tert-butyl 4-ethyl 3-(((trifluoromethyl)sulfonyl)oxy)-5,6-dihydropyridine-1,4(2H)-dicarboxylate (1.49 g, 3.7 mmol) and (1-isopropyl-1H-pyrazol-5-yl)boronic acid (0.57 g, 3.7 mmol) in dioxane (10 mL) was added Pd(dppf)Cl₂ (0.27 g, 0.37 mmol) and a solution of sodium carbonate (1.18 g, 11.10) in water (3 ml), the mixture was degassed with N₂ for 5 min, and was heated at 100° C. for 15 h, after cooling to room temperature the mixture was diluted with EtOAc and washed with Sat. NaHCO₃ and brine, organic layer was combined, dried and concentrated to give crude product, which was purified by column chromatography (Hexanes/EtOAc-3:1) to give desired product 830 mg (62%).

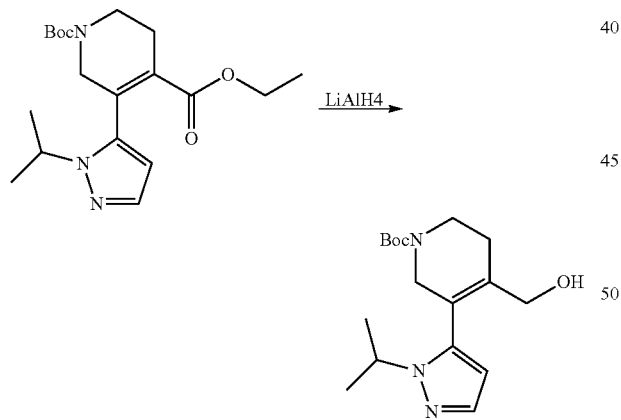

Step 3:

To a solution of 1-(tert-butyl) 4-ethyl 5-(1-isopropyl-1H-pyrazol-5-yl)-3,6-dihydropyridine-1,4(2H)-dicarboxylate (450 mg, 1.24 mmol) in THF (6 mL) was added LiAlH₄ (1M in THF, 1.49 mL, 1.49 mmol) at −20° C., the reaction was stirred at −20° C. for 30 min, and was quenched with Sat. NH₄Cl, the aqueous layer was extracted with EtOAc, the combined organics were washed with brine, dried and concentrated to give crude oil, which was purified by column (Hexanes/EtOAc=100:0 to 40:60) to give tert-butyl 4-(hydroxymethyl)-5-(1-isopropyl-1H-pyrazol-5-yl)-3,6-dihydropyridine-1(2H)-carboxylate (370 mg, 91%).

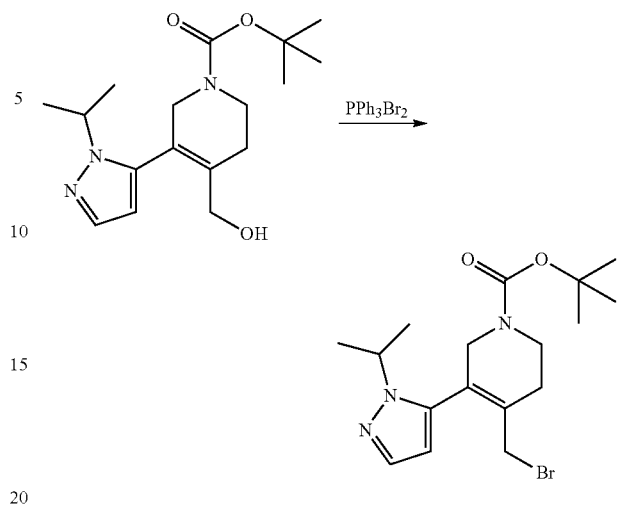

Step 4:

To a solution of give tert-butyl 4-(hydroxymethyl)-5-(1-isopropyl-1H-pyrazol-5-yl)-3,6-dihydropyridine-1(2H)-carboxylate (25 mg, 0.08 mmol) in DCM (1 mL) was added triphenylphosphine bromine adduct (40 mg, 0.09 mmol) at room temperature, after stirring for 30 min, it was diluted with DCM, washed with Sat. NaHCO3, brine, dried and concentrated to give crude product, which was purified by column to give tert-butyl 4-(bromomethyl)-5-(1-isopropyl-1H-pyrazol-5-yl)-3,6-dihydropyridine-1(2H)-carboxylate (18 mg).

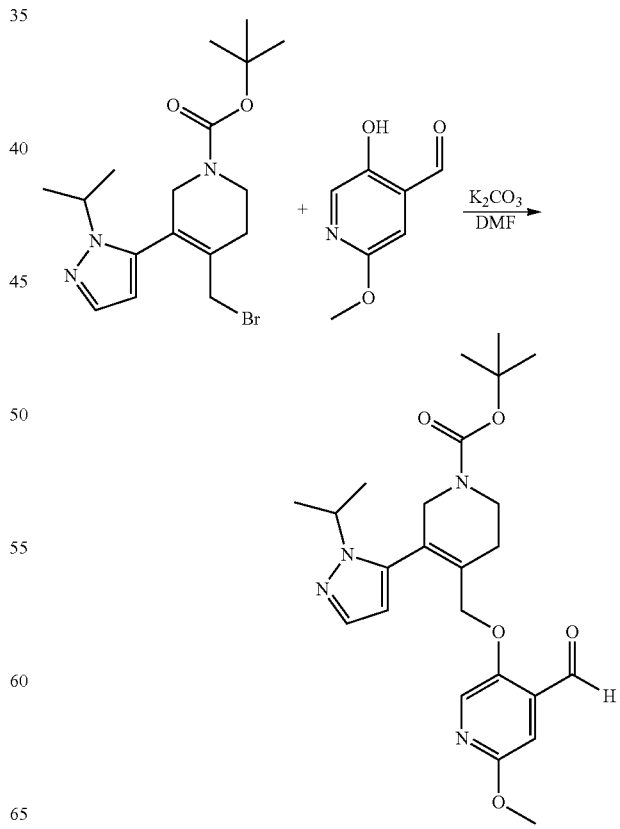

Step 5:

To a solution of tert-butyl 4-(bromomethyl)-5-(1-isopropyl-1H-pyrazol-5-yl)-3,6-dihydropyridine-1(2H)-carboxylate (18 mg, 0.05 mmol) and 5-hydroxy-2-methoxyisonicotinaldehyde (10 mg, 0.06 mmol) in DMF (1 mL) was added K$_2$CO$_3$ (14 mg, 0.1 mmol). After stirred at room temperature for 1 h, it was diluted with water and EtOAc, organic layer was separated, and the aqueous layer was extracted with EtOAc, organic layer was combined, washed with brine, dried and concentrated to give crude product, which was purified by column (Hexanes/EtOAc=2:1) to give tert-butyl 4-(((4-formyl-6-methoxypyridin-3-yl)oxy)methyl)-3-(1-isopropyl-1H-pyrazol-5-yl)-5,6-dihydropyridine-1(2H)-carboxylate (7.2 mg). 1H NMR (400 MHz, CDCl$_3$) (ppm) 10.39 (s, 1H), 7.79 (s, 1H), 7.56 (d, J=1.6 Hz, 1H), 7.05 (s, 1H), 6.11 (d, J=1.6 Hz, 1H), 4.40 (s, 2H), 4.38 (m, 1H), 4.01 (s, 2H), 3.88 (s, 3H), 3.66 (bs, 2H), 2.46 (bs, 2H), 1.48 (s, 9H), 1.43 (d, 6.4 Hz, 6H). MS (ESI) m/z 457.3 [M+H]$^+$.

GBT861 Preparation of 2-hydroxy-6-((5-(1-isopropyl-1H-pyrazol-5-yl)-3,6-dihydro-2H-pyran-4-yl)methoxy)benzaldehyde

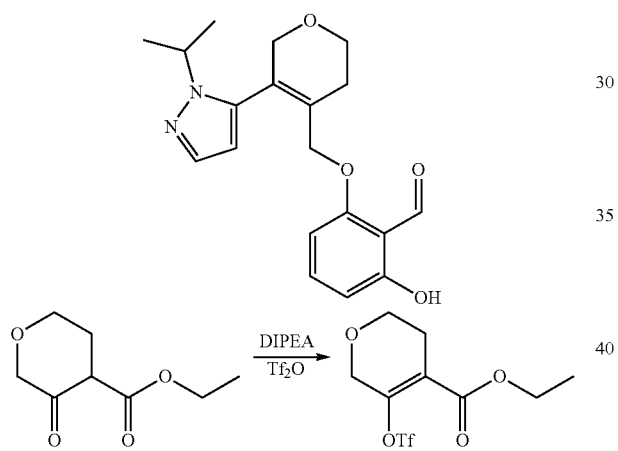

Step 1:

To a solution of ethyl 3-oxotetrahydro-2H-pyran-4-carboxylate (1.0 g, 5.81 mmol) in DCM (30 mL) was added DIPEA (1.22 mL, 6.97 mmol) and Tf$_2$O (1.08 mL, 6.39 mmol) at −78° C., then it was warmed up to room temperature and stirred at room temperature for 2 h, the solution was diluted with DCM, washed with Sat. NaHCO3, brine, dried and concentrated to give ethyl 5-(((trifluoromethyl)sulfonyl)oxy)-3,6-dihydro-2H-pyran-4-carboxylate as crude product (2 g).

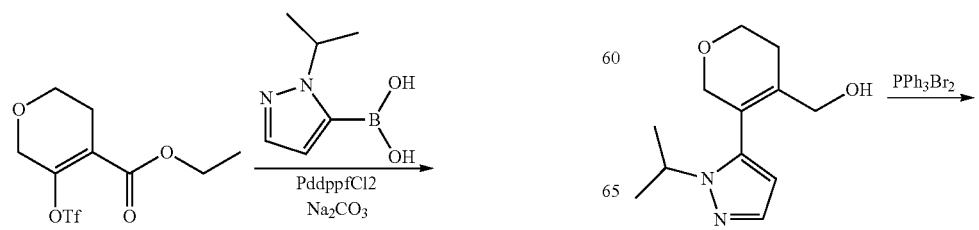

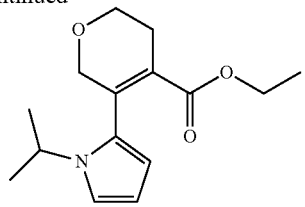

Step 2:

To a solution of ethyl 5-(((trifluoromethyl)sulfonyl)oxy)-3,6-dihydro-2H-pyran-4-carboxylate (crude from step 1) and 1-isopropyl-5-(4,4,5,5-tetramethyl-1,3,2-dioxaborolan-2-yl)-1H-pyrazole (1.37 g, 5.82 mmol) in dioxane (20 ml) was added Pd(dppf)Cl$_2$ (430 mg, 0.58 mmol) and Na$_2$CO$_3$ (1.85 g, 17.46 mmol) in water (6 mL), the mixture was degassed with N2 for 5 min, and was heated at 100° C. for 15 h, after cooling to room temperature the mixture was diluted with EtOAc and washed with Sat. NaHCO$_3$ and brine, organic layer was combined, dried and concentrated to give crude product, which was purified by column chromatography (Hexanes/EtOAc=3:1) to give ethyl 5-(1-isopropyl-1H-pyrazol-5-yl)-3,6-dihydro-2H-pyran-4-carboxylate (850 mg).

Step 3:

To a solution of ethyl 5-(1-isopropyl-1H-pyrazol-5-yl)-3,6-dihydro-2H-pyran-4-carboxylate (600 mg, 2.27 mmol) in THF (10 mL) was added LiAlH$_4$ (1M in THF, 2.72 mL, 2.72 mmol) at −20° C., the reaction was stirred at −20° C. for 30 min, and was quenched with Sat. NH$_4$Cl, the aqueous layer was extracted with EtOAc, the combined organics were washed with brine, dried and concentrated to give crude oil, which was purified by column (Hexanes/EtOAc=100:0 to 20:80) to give (5-(1-isopropyl-1H-pyrazol-5-yl)-3,6-dihydro-2H-pyran-4-yl)methanol (500 mg).

-continued

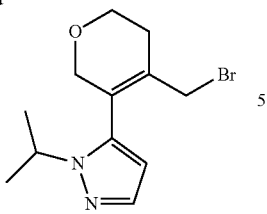

Step 4:
To a solution of (5-(1-isopropyl-1H-pyrazol-5-yl)-3,6-dihydro-2H-pyran-4-yl)methanol (300 mg, 1.35 mmol) in DCM (5 mL) was added dibromotriphenylphosphorane (630 mg, 1.35 mmol) at room temperature, after stirring for 30 min, it was diluted with DCM, organic layer was washed with Sat. NaHCO₃, brine, dried and concentrated to give crude product, which was purified by column(Hexanes/EtOAc=4:1) to give 5-(4-(bromomethyl)-5,6-dihydro-2H-pyran-3-yl)-1-isopropyl-1H-pyrazole (360 mg).

Step 5:
To a solution of 5-(4-(bromomethyl)-5,6-dihydro-2H-pyran-3-yl)-1-isopropyl-1H-pyrazole (110 mg, 0.38 mmol) and 2,6-dihydroxybenzaldehyde (10(0 mg, 0.76 mmol) in DMF (6 mL) was added K₂CO₃ (110 mg, 0.76 mmol). After stirred at room temperature for 1 h, it was diluted with water and EtOAc, organic layer was separated, and the aqueous layer was extracted with EtOAc. Organic layer was combined, washed with brine, dried and concentrated to give crude product, which was purified by column (Hexanes/EtOAc=1:1) to give 2-hydroxy-6-((5-(1-isopropyl-1H-pyrazol-5-yl)-3,6-dihydro-2H-pyran-4-yl)methoxy)benzaldehyde (90 mg). 1H NMR (400 MHz, CDCl₃) δ (ppm) 11.89 (s, 1H), 10.33 (s, 1H), 7.53 (d, J=1.6 Hz, 1H), 7.33 (t, J=8.8 Hz, 1H), 6.51 (d, J=8.8 Hz, 1H), 6.16 (d, J=8.0 Hz, 1H), 6.08 (d, J=2.0 Hz, 1H), 4.40 (dd, J=12.8, 6.4 Hz, 1H), 4.35 (s, 2H), 4.18 (s, 2H), 3.97 (t, J=5.2 Hz, 2H), 2.44 (s, 2H), 1.40 (d, J=6.4 Hz, 6H); MS (ESI) m/z 343.3 [M+H]⁺.

GBT863 Preparation of 2-methoxy-5-[[5-(2-propan-2-ylpyrazol-3-yl)-3,6-dihydro-2H-pyran-4-yl]methoxy]pyridine-4-carbaldehyde

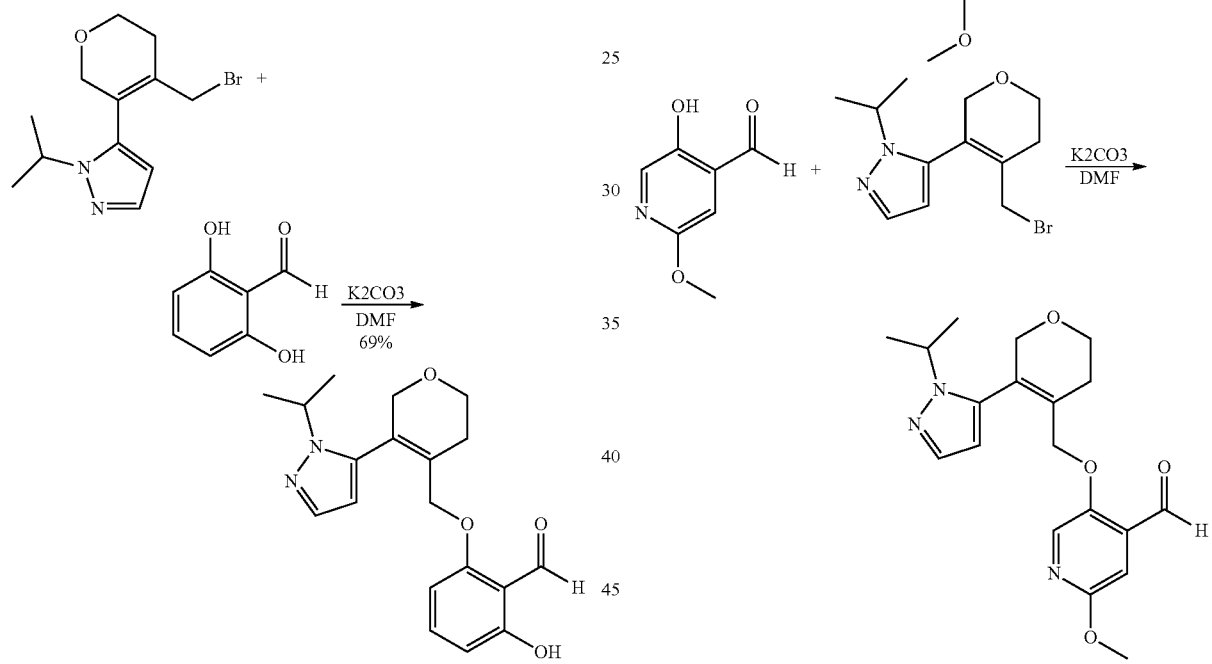

To a solution of 5-(4-(bromomethyl)-5,6-dihydro-2H-pyran-3-yl)-1-isopropyl-1H-pyrazole (50 mg, 0.19 mmol) (see the synthesis of GBT861) and 5-hydroxy-2-methoxy-isonicotinaldehyde (30 mg, 0.23 mmol) in DMF (1 mL) was added K₂CO₃ (50 mg, 0.38 mmol). After stirred at room temperature for 3 h, it was diluted with water and EtOAc, organic layer was separated, and the aqueous layer was extracted with EtOAc, organic layer was combined, washed with brine, dried and concentrated to give crude product, which was purified by column (Hexanes/EtOAc=1:1) to give 5-((5-(1-isopropyl-1H-pyrazol-5-yl)-3,6-dihydro-2H-pyran-4-yl)methoxy)-2-methoxyisonicotinaldehyde (26 mg). 1H NMR (400 MHz, CDCl₃) δ (ppm) 10.40 (s, 1H), 7.81 (s, 1H), 7.54 (d, J=1.6 Hz, 1H), 7.05 (s, 1H), 6.08 (d, J=1.6 Hz, 1H), 4.42 (s, 2H), 4.40 (m, 1H), 4.19 (s, 2H), 3.98 (t, J=5.6 Hz, 2H), 3.88 (s, 3H), 2.47 (s, 2H), 1.41 (d, J=6.8 Hz, 6H); MS (ESI) m/z 358.4 [M+H]⁺.

GBT864 Preparation of 6-methyl-3-[[5-(2-propan-2-ylpyrazol-3-yl)-3,6-dihydro-2H-pyran-4-yl]methoxy]pyridine-2-carbaldehyde

GBT867 Preparation of 2-hydroxy-6-[(5-phenyl-3,6-dihydro-2H-pyran-4-yl)methoxy]benzaldehyde

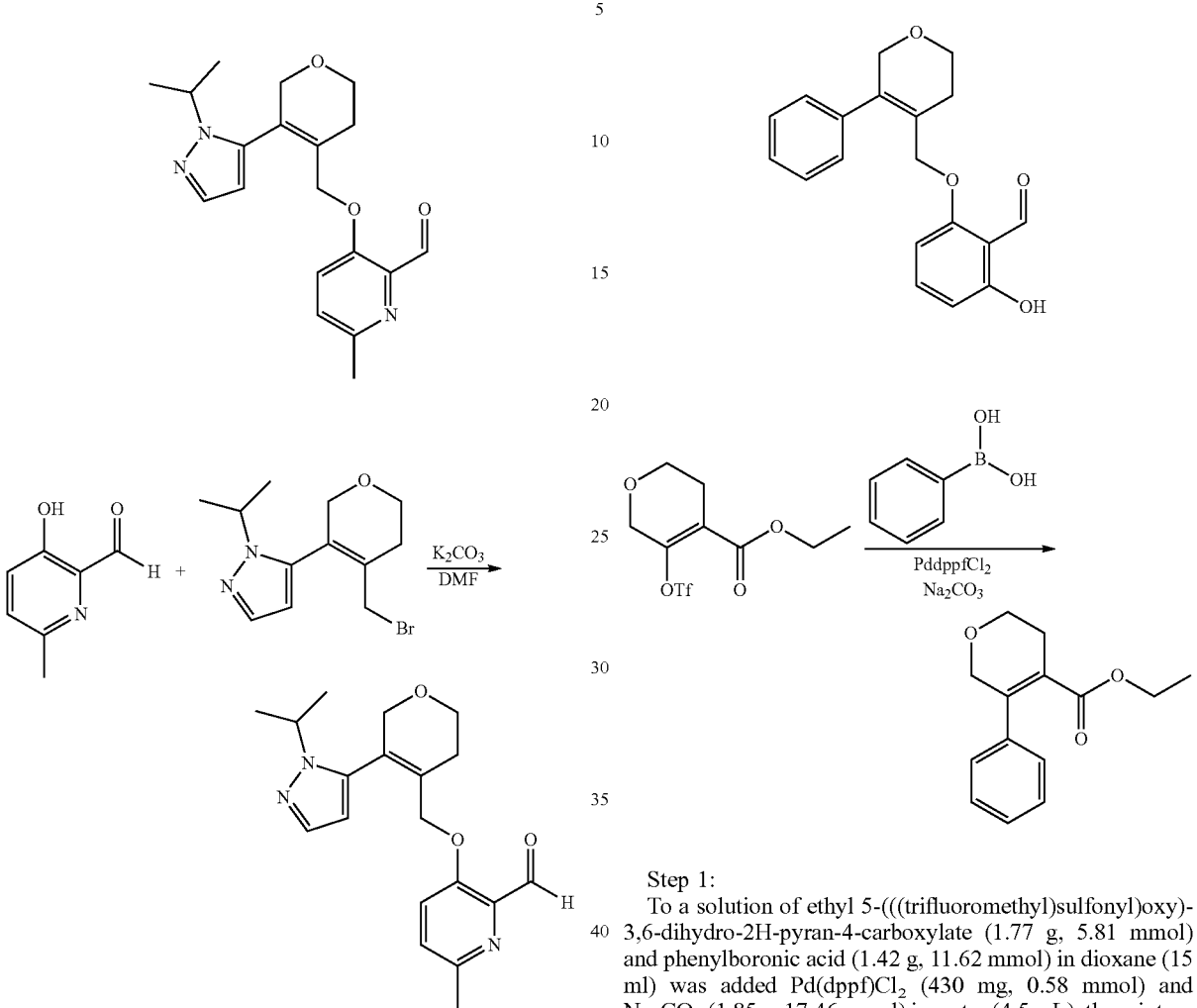

To a solution of 5-(4-(bromomethyl)-5,6-dihydro-2H-pyran-3-yl)-1-isopropyl-1H-pyrazole (50 mg, 0.19 mmol) (see the synthesis of GBT861) and 3-hydroxy-6-methylpicolinaldehyde (30 mg, 0.24 mmol) in DMF (1 mL) was added K$_2$CO$_3$ (50 mg, 0.38 mmol). After stirred at room temperature for 3 h, it was diluted with water and EtOAc, organic layer was separated, and the aqueous layer was extracted with EtOAc, organic layer was combined, washed with brine, dried and concentrated to give crude product, which was purified by column (Hexanes/EtOAc=40:60) to give 5-((5-(1-isopropyl-1H-pyrazol-5-yl)-3,6-dihydro-2H-pyran-4-yl)methoxy)-2-methoxyisonicotinaldehyde (37 mg). 1H NMR (400 MHz, CDCl$_3$) δ (ppm) 10.30 (s, 1H), 7.54 (d, J=1.6 Hz, 1H), 7.24 (d, J=8.4 Hz, 1H), 7.09 (d, J=9.2 Hz, 1H), 6.08 (d, J=2.0 Hz, 1H), 4.42 (m, 1H), 4.38 (s, 2H), 4.18 (s, 2H), 3.98 (t, J=5.6 Hz, 2H), 2.56 (s, 3H), 2.51 (s, 2H), 1.39 (d, J=6.4 Hz, 6H); MS (ESI) m/z 342.4 [M+H]$^+$.

Step 1:
To a solution of ethyl 5-(((trifluoromethyl)sulfonyl)oxy)-3,6-dihydro-2H-pyran-4-carboxylate (1.77 g, 5.81 mmol) and phenylboronic acid (1.42 g, 11.62 mmol) in dioxane (15 ml) was added Pd(dppf)Cl$_2$ (430 mg, 0.58 mmol) and Na$_2$CO$_3$ (1.85 g, 17.46 mmol) in water (4.5 mL), the mixture was degassed with N2 for 5 min, and was heated at 100° C. for 15 h, after cooling to room temperature the mixture was diluted with EtOAc and washed with Sat. NaHCO$_3$ and brine, organic layer was combined, dried and concentrated to give crude product, which was purified by column chromatography (Hexanes/EtOAc=4:1) to give ethyl 5-phenyl-3,6-dihydro-2H-pyran-4-carboxylate (1.05 g, 78%).

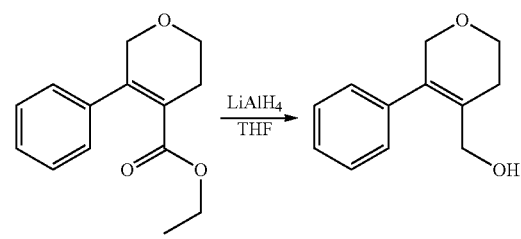

Step 2:
To a solution of ethyl 5-phenyl-3,6-dihydro-2H-pyran-4-carboxylate (1.05 g, 4.52 mmol) in THF (20 mL) was added LiAlH$_4$ (1M in THF, 5.42 mL, 5.42 mmol) at −20° C., the reaction was stirred at −20° C. for 30 min, and was quenched with Sat. NH4Cl, the aqueous layer was extracted with EtOAc, the combined organics were washed with brine, dried and concentrated to give crude oil, which was purified by column (Hexanes/EtOAc=100:0 to 35:65) to give (5-phenyl-3,6-dihydro-2H-pyran-4-yl)methanol (720 mg).

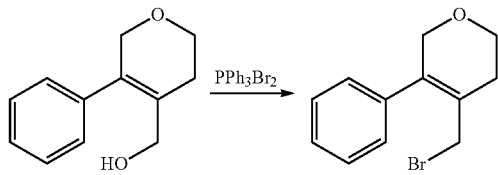 [SMILES: OCC1=C(c2ccccc2)COCC1 ; BrCC1=C(c2ccccc2)COCC1 ; "PPh3Br2"]

Step 3:
To a solution of (5-phenyl-3,6-dihydro-2H-pyran-4-yl)methanol (360 mg, 1.89 mmol) in DCM (6 mL) was added dibromotriphenylphosphorane (880 mg, 2.08 mmol) at room temperature, after stirring for 30 min, it was diluted with DCM, organic layer was washed with Sat. NaHCO3, brine, dried and concentrated to give crude product, which was purified by column(Hexanes/EtOAc=9:1) to give 4-(bromomethyl)-5-phenyl-3,6-dihydro-2H-pyran (380 mg).

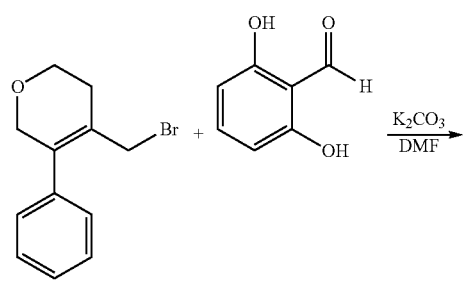

Step 4:
To a solution of 4-(bromomethyl)-5-phenyl-3,6-dihydro-2H-pyran (110 mg, 0.45 mmol) and 2,6-dihydroxybenzaldehyde (120 mg, 0.90 mmol) in DMF (3 mL) was added K2CO3 (120 mg, 0.90 mmol). After stirred at room temperature for 1 h, it was diluted with water and EtOAc, organic layer was separated, and the aqueous layer was extracted with EtOAc. Organic layer was combined, washed with brine, dried and concentrated to give crude product, which was purified by column (Hexanes/EtOAc-3:1) to give 2-hydroxy-6-((5-phenyl-3,6-dihydro-2H-pyran-4-yl)methoxy) benzaldehyde (120 mg). 1H NMR (400 MHz, CDCl3) δ (ppm) 11.92 (s, 1H), 10.36 (s, 1H), 7.35 (m, 4H), 7.18 (m, 2H), 6.49 (d, J=8.0 Hz, 1H), 6.13 (d, J=8.0 Hz, 1H), 4.48 (s, 2H), 4.32 (s, 2H), 3.95 (t, J=5.6 Hz, 2H), 2.41 (m, 2H); MS (ESI) m/z 309.

GBT868 Preparation of 3-methoxy-5-[[2-[2-(2,2,2-trifluoroethyl)pyrazol-3-yl]pyridin-3-yl]methoxy]pyridine-4-carbaldehyde

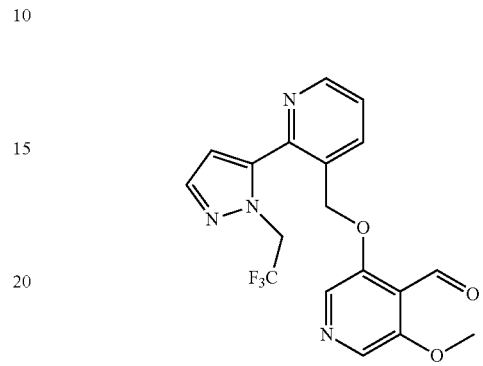

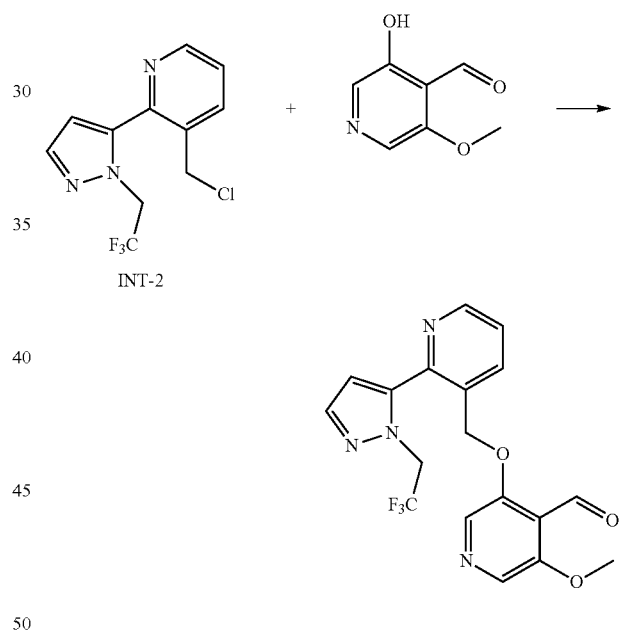

To a solution of 3-hydroxy-5-methoxyisonicotinaldehyde (0.13 g, 0.88 mmol) in DMF was added 3-(chloromethyl)-2-(1-(2,2,2-trifluoroethyl)-1H-pyrazol-5-yl)pyridine (0.24 g, 0.88 mmol) (INT-2) and potassium carbonate (0.49 g, 3.52 mmol) and the reaction mixture was heated (60° C.). After 3 hours, the reaction mixture was filtered through a plug of silica (MeOH/CH2Cl2, 0-20%). Purification of the resulting residue by Prep-HPLC, provided 2-methoxy-6-((2-(1-(2,2,2-trifluoroethyl)-1H-pyrazol-5-yl)pyridin-3-yl)methoxy)benzaldehyde (12 mg, 5% yield). 1H NMR (400 MHz, Chloroform-d) δ 10.54 (s, 1H), 8.71 (dd, J=5.0, 1.8 Hz, 1H), 8.23 (s, 1H), 8.21 (ddd, J=7.9, 1.7, 0.7 Hz, 1H), 8.10 (s, 1H), 7.67 (dd, J=1.9, 0.5 Hz, 1H), 7.46 (dd, J=8.0, 4.5 Hz, 1H), 7.26 (d, J=0.5 Hz, 3H), 6.56 (dd, J=1.9, 0.5 Hz, 1H), 5.23 (s, 2H), 5.28-5.15 (m, 2H), 4.04 (s, 3H); MS (ESI) m/z 393 [M+H]+.

GBT870 Preparation of 2-methoxy-5-[[2-(2-methoxyphenyl)pyridin-3-yl]methoxy]pyridine-4-carbaldehyde

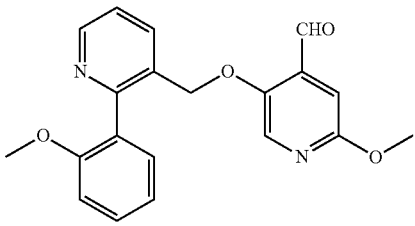

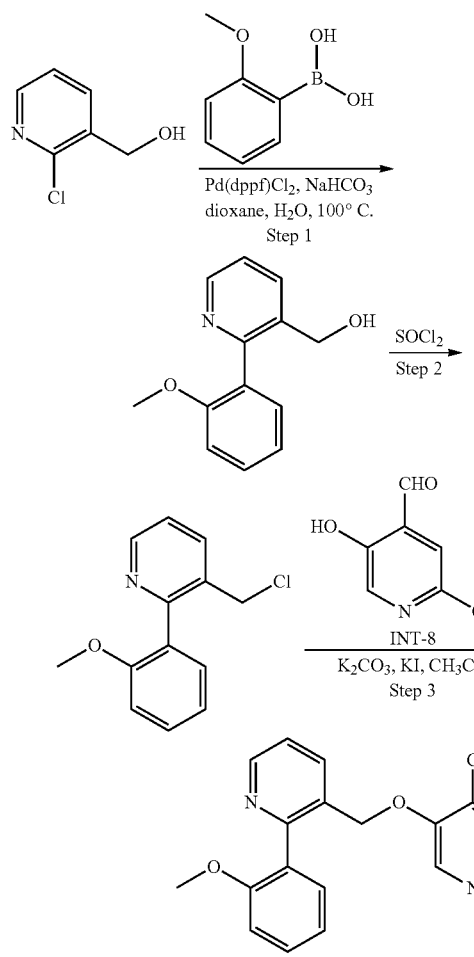

Step 1:

Into a 50-mL round-bottom flask, was placed a solution of (2-chloropyridin-3-yl)methanol (500 mg, 3.48 mmol, 1.00 equiv) in a solvent mixture of dioxane and H$_2$O (10/10 mL). (2-Methoxyphenyl)boronic acid (532 mg, 3.50 mmol, 1.20 equiv), sodium bicarbonate (882 mg, 10.50 mmol, 3.00 equiv), and Pd(dppf)Cl$_2$ (286 mg, 0.39 mmol, 0.10 equiv) were added to the reaction mixture. The resulting solution was stirred for 2 h at 100° C., and then it was diluted with 100 mL of H$_2$O. The resulting solution was extracted with 2×100 mL of ethyl acetate, and the combined organic layers were concentrated under vacuum. The residue was applied onto a silica gel column with ethyl acetate/petroleum ether (1:5) as eluent to furnish 650 mg (87%) of [2-(2-methoxyphenyl)pyridin-3-yl]methanol as a yellow solid.

Step 2:

Into a 50-mL round-bottom flask, was placed a solution of [2-(2-methoxyphenyl)pyridin-3-yl]methanol (600 mg, 2.79 mmol, 1.00 equiv) in thionyl chloride (10 mL). The resulting solution was heated to reflux for 2 hr. and then it was concentrated under vacuum. This resulted in 600 mg (92%) of 3-(chloromethyl)-2-(2-methoxyphenyl)pyridine as a yellow solid.

Step 3:

Into a 100-mL round-bottom flask, was placed a solution of 3-(chloromethyl)-2-(2-methoxyphenyl)pyridine (306 mg, 1.31 mmol, 1.00 equiv) in CH$_3$CN (20 mL). 5-Hydroxy-2-methoxypyridine-4-carbaldehyde (200 mg, 1.31 mmol, 1.00 equiv), potassium carbonate (364 mg, 2.63 mmol, 2.00 equiv), and KI (44 mg, 0.27 mmol, 0.20 equiv) were added to the reaction mixture. The resulting solution was stirred for 5 h at 60° C., and then it was concentrated under vacuum. The crude product (200 mg) was purified by Prep-HPLC with the following conditions (Prep-HPLC-010): Column, SunFire Prep C18 OBD Column, 5 um, 19*150 mm; mobile phase, water with 0.1% HCOOH and MeCN (10.0% MeCN up to 40.0% in 10 min, up to 95.0% in 2 min, down to 10.0% in 2 min); Detector, Waters2545 UvDector 254&220 nm. This resulted in 65 mg (9%) of 2-methoxy-5-[[2-(2-methoxyphenyl)pyridin-3-yl]methoxy]pyridine-4-carbaldehyde bis(trifluoroacetic acid) as a yellow solid. The compound exhibited a melting point of 105-107° C. $^1$HNMR (300 MHz. CDCl$_3$) δ 10.32 (s, 1H), 8.69 (s, 1H), 7.93 (m, 2H), 7.36 (m, 3H), 6.99 (m, 3H), 5.35 (s, 2H), 3.86 (m, 6H); MS (ESI) m/z 351 [M+H]$^+$.

GBT871 Preparation of 2-methoxy-5-[[2-(3-methoxyphenyl)pyridin-3-yl]methoxy]pyridine-4-carbaldehyde

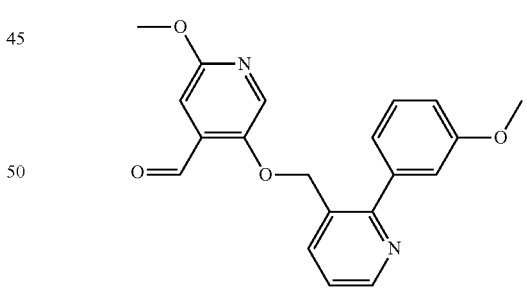

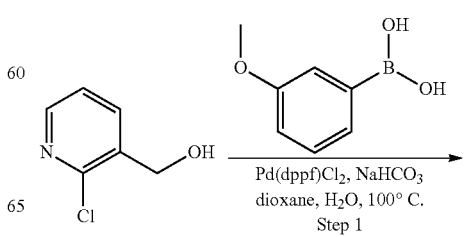

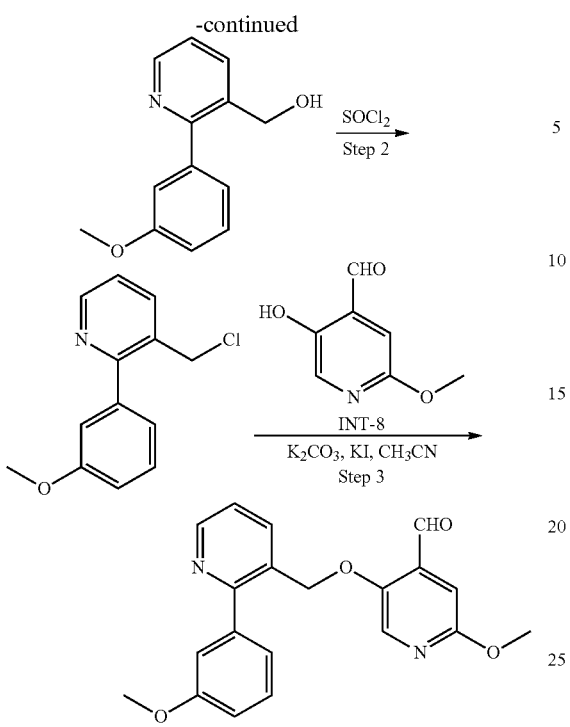

Step 1: Into a 50-mL round-bottom flask, which was purged and maintained with an inert atmosphere of nitrogen, was placed a solution of (3-methoxyphenyl)boronic acid (1.6 g, 10.53 mmol, 1.20 equiv), (2-chloropyridin-3-yl)methanol (1 g, 6.97 mmol, 1.00 equiv), sodium bicarbonate (1.7 g, 20.24 mmol, 3.00 equiv), Pd(dppf)Cl$_2$ (0.57 g, 0.10 equiv) in a solvent mixture of dioxane (10 mL) and water (10 mL). The resulting solution was stirred for 1.5 h at 100° C., and then it was diluted with 20 mL of H$_2$O. The resulting solution was extracted with 2×50 mL of ethyl acetate, and the combined organic layers were concentrated under vacuum. The residue was applied onto a silica gel column with ethyl acetate/petroleum ether (1:50-1:1) as eluent to yield 1.3 g (87%) of [2-(3-methoxyphenyl)pyridin-3-yl]methanol as a colorless oil.

Step 2:
Into a 50-mL round-bottom flask, was placed a solution of [2-(3-methoxyphenyl)pyridin-3-yl]methanol (1 g, 4.65 mmol, 1.00 equiv) in thionyl chloride (20 mL). The resulting solution was stirred for 2 h at reflux. The resulting mixture was concentrated under vacuum to furnish 600 mg (55%) of 3-(chloromethyl)-2-(3-methoxyphenyl)pyridine as a white solid.

Step 3:
Into a 100-mL round-bottom flask, was placed a solution of 3-(chloromethyl)-2-(3-methoxyphenyl)pyridine (234 mg, 1.00 mmol, 1.00 equiv), 5-hydroxy-2-methoxypyridine-4-carbaldehyde (153 mg, 1.00 mmol, 1.00 equiv), and potassium carbonate (278 mg, 2.01 mmol, 2.00 equiv) in CH$_3$CN (30 mL). The resulting solution was stirred for 4 h at 70° C., and then it was concentrated under vacuum. The crude product (200 mg) was purified by Prep-HPLC with the following conditions (Prep-HPLC-010): Column, SunFire Prep C18 OBD Column, 5 um, 19*150 mm; mobile phase, water with 0.1% TFA and MeCN (20% MeCN up to 40% in 10 min, up to 95% in 2 min, down to 20% in 1 min); Detector, Waters2545 UvDector 254&220 nm. This resulted in 100.8 mg (17%) of 2-methoxy-5-[[2-(3-methoxyphenyl) pyridin-3-yl]methoxy]pyridine-4-carbaldehyde bis(trifluoroacetic acid) as a yellow solid.

$^1$HNMR (300 MHz, DMSO-d$_6$) δ 10.01 (s, 1H), 8.65 (m, 1H), 8.39 (s, 1H), 8.10 (m, 2H), 7.57 (d, J=9 Hz, 2H), 7.42 (m, 1H), 6.97 (m, 3H), 5.33 (s, 2H) 3.80 (m, 6H); MS (ESI) m/z 351 [M+H]$^+$.

GBT874 Preparation of 2-hydroxy-6-[(1-methyl-5-phenyl-3,6-dihydro-2H-pyridin-4-yl)methoxy]benzaldehyde

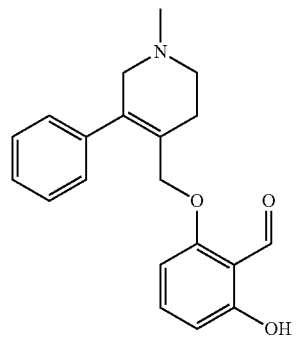 [SMILES: CN1CCC(COc2cccc(O)c2C=O)=C(c2ccccc2)C1]

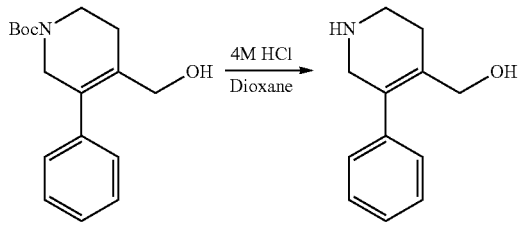 [SMILES: CC(C)(C)OC(=O)N1CCC(CO)=C(c2ccccc2)C1 ; OCC1=C(c2ccccc2)CNCC1]

Step 1:
To a solid of tert-butyl 4-(hydroxymethyl)-3-phenyl-5,6-dihydropyridine-1(21H)-carboxylate (300 mg, 1.04 mmol) in round bottom flask was added 4N HCl in dioxane (6 mL) at room temperature, after stirring for 1 h, the mixture was concentrated and dried under high vacuum to give (5-phenyl-1,2,3,6-tetrahydropyridin-4-yl)methanol as HCl salt.

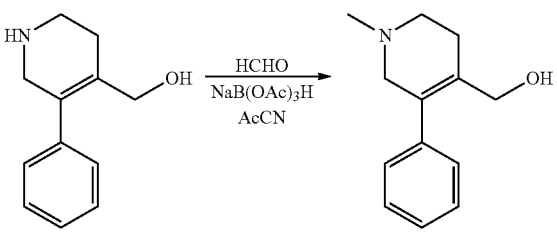

Step 2:
To a solution of (5-phenyl-1,2,3,6-tetrahydropyridin-4-yl)methanol hydrochloride (230 mg, 1.04 mmol) in ACN (10 mL) was added Et$_3$N (0.15 mL, 1.04 mmol) followed by formalin (340 mg, 4.16 mmol). After stirred at room temperature for 10 min, it was added Na(OAc)$_3$BH (440 mg, 2.08 mmol) and was stirred for 30 min. the mixture was concentrated to remove most of the ACN, and the residue was diluted with CHCl$_3$, organic layer was washed with Sat.

NaHCO₃, brine, dried and concentrated to give crude product, which was purified by column (DCM/MeOH=9:1) to give (1-methyl-5-phenyl-1,2,3,6-tetrahydropyridin-4-yl)methanol (140 mg).

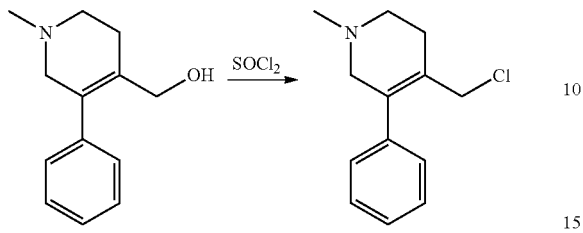

Step 3:

To a solution of (1-methyl-5-phenyl-1,2,3,6-tetrahydropyridin-4-yl)methanol (130 mg, 0.64 mmol) in DCM (4 mL) was added SOCl₂ (1.16 mL, 16 mmol) at room temperature, after stirred at room temperature for 30 min, the mixture was concentrated, dried under high vacuum to give 4-(chloromethyl)-1-methyl-5-phenyl-1,2,3,6-tetrahydropyridine as crude HCl salt.

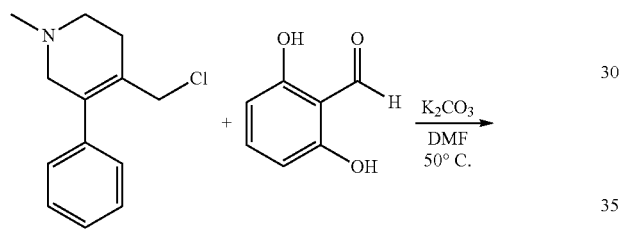

Step 4:

To a suspension of K₂CO₃ (350 mg, 2.56 mmol) and 2,6-dihydroxybenzaldehyde (180 mg, 1.28 mmol) in DMF (3 ml) was added a solution of 4-(chloromethyl)-1-methyl-5-phenyl-1,2,3,6-tetrahydropyridine (140 mg, 0.64 mmol) in DMF (4 mL), the mixture was heated at 50° C. for 3 h, cooled to room temperature, and was diluted with EtOAc, organic layer was separated and aqueous layer was extracted with EtOAc. EtOAc layers were combined, washed with Sat. NaHCO3, brine, dried over Na₂SO₄, and was concentrated to give crude oil, which was purified by column (Hexane/EtOAc=1:1 followed by DCM/MeOH=90:10) to give 2-hydroxy-6-((1-methyl-5-phenyl-1,2,3,6-tetrahydropyridin-4-yl)methoxy)benzaldehyde (55 mg). 1H NMR (400 MHz, CDCl₃) δ (ppm) 11.92 (s, 1H), 10.35 (s, 1H), 7.34 (m, 5H), 7.19 (dd, J=8.4, 8.0 Hz, 1H), 6.46 (d, J=8.4 Hz, 1H), 6.16 (d, J=8.0 Hz, 1H), 4.45 (s, 2H), 3.20 (s, 2H), 2.68 (t, J=5.6 Hz, 2H), 2.47 (m, 2H), 2.42 (s, 3H); MS (ESI) m/z 324.3 [M+H]⁺.

GBT875 Preparation of 2-methoxy-5-[[2-(4-methoxyphenyl)pyridin-3-yl]methoxy]pyridine-4-carbaldehyde

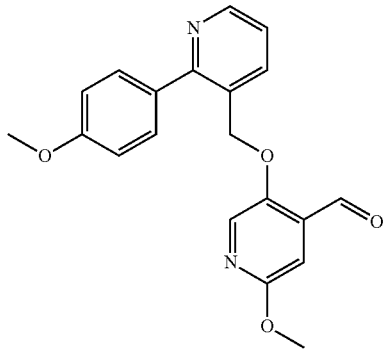 [SMILES: COc1ccc(-c2ncccc2COc2cnc(OC)cc2C=O)cc1]

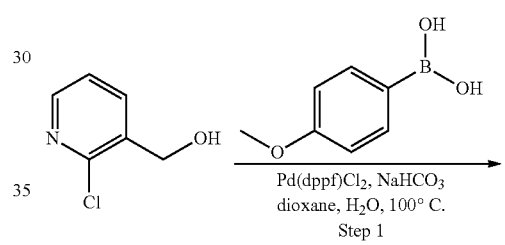

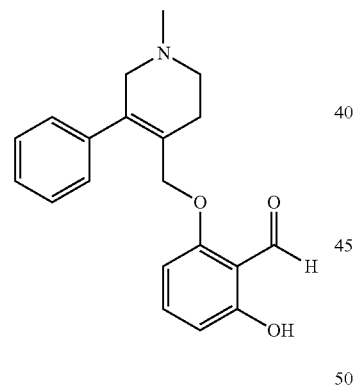

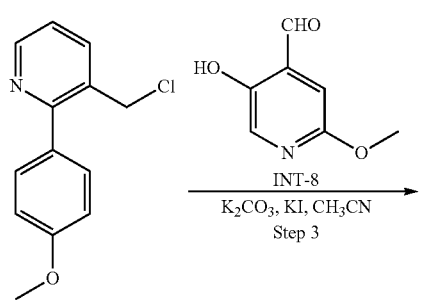

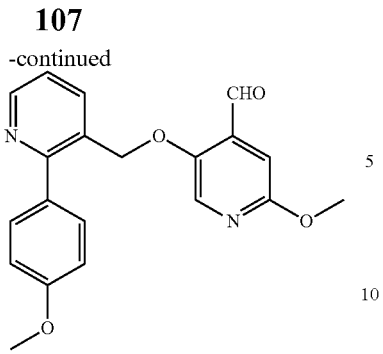

Step 1: Into a 50-mL round-bottom flask, which was purged and maintained with an inert atmosphere of nitrogen, was placed a solution of (4-methoxyphenyl)boronic acid (1.6 g, 10.53 mmol, 1.20 equiv), (2-chloropyridin-3-yl)methanol (1 g, 6.97 mmol, 1.00 equiv), sodium bicarbonate (1.7 g, 20.24 mmol, 3.00 equiv), Pd(dppf)Cl$_2$ (0.57 g, 0.10 equiv) in a solvent mixture of dioxane (10 mL) and water (10 mL). The resulting solution was stirred for 1.5 h at 100° C., and then it was diluted with 20 mL of H$_2$O. The resulting solution was extracted with 2×50 mL of ethyl acetate, and the combined organic layers were concentrated under vacuum. The residue was applied onto a silica gel column with ethyl acetate/petroleum ether (1:50-1:1) as eluent to furnish 1 g (67%) of [2-(4-methoxyphenyl)pyridin-3-yl]methanol as a colorless oil.

Step 2:

Into a 50-mL round-bottom flask, was placed a solution of [2-(4-methoxyphenyl)pyridin-3-yl]methanol (1 g, 4.65 mmol, 1.00 equiv) in thionyl chloride (20 mL). The resulting solution was stirred for 2 h at reflux. The resulting mixture was concentrated under vacuum to yield 600 mg (55%) of 3-(chloromethyl)-2-(4-methoxyphenyl)pyridine as a white solid.

Step 3:

Into a 50-mL round-bottom flask, was placed a solution of 3-(chloromethyl)-2-(2-methoxyphenyl)pyridine (234 mg, 1.00 mmol, 1.00 equiv), 5-hydroxy-2-methoxypyridine-4-carbaldehyde (153 mg, 1.00 mmol, 1.00 equiv), and potassium carbonate (278 mg, 2.01 mmol, 2.00 equiv) in CH$_3$CN (20 mL). The resulting solution was stirred for 4 h at 70° C., and then it was concentrated under vacuum. The crude product (300 mg) was purified by Prep-HPLC with the following conditions (Prep-HPLC-010): Column, SunFire Prep C18 OBD Column, 5 um, 19*150 mm; mobile phase, water with 0.1% TFA and MeCN (20.0% MeCN up to 50.0% in 10 min, up to 95.0% in 2 min, down to 20.0% in 1 min); Detector, Waters2545 UvDector 254&220 nm. This resulted in 265.1 mg (46%) of 2-methoxy-5-[[2-(4-methoxyphenyl)pyridin-3-yl]methoxy]pyridine-4-carbaldehyde; bis(trifluoroacetic acid) as a brown oil.

$^1$HNMR (300 MHz, DMSO-d$_6$) δ 10.08 (s, 1H), 8.69 (m, 1H), 8.15 (m, 2H), 7.50 (m, 1H), 7.37 (m, 1H), 7.18 (m, 2H), 7.16 (m, 1H), 6.99 (m, 1H), 5.34 (s, 2H), 3.86 (s, 3H), 3.77 (s, 3H);

MS (ESI) m/z 351 [M+H]$^+$.

GBT877 Preparation of 5-[[2-(2-chlorophenyl)pyridin-3-yl]methoxy]-2-methoxypyridine-4-carbaldehyde

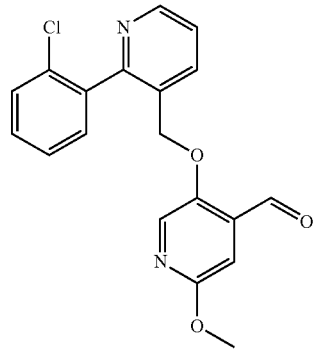 [SMILES: COc1cc(C=O)c(OCc2cccnc2-c2ccccc2Cl)cn1]

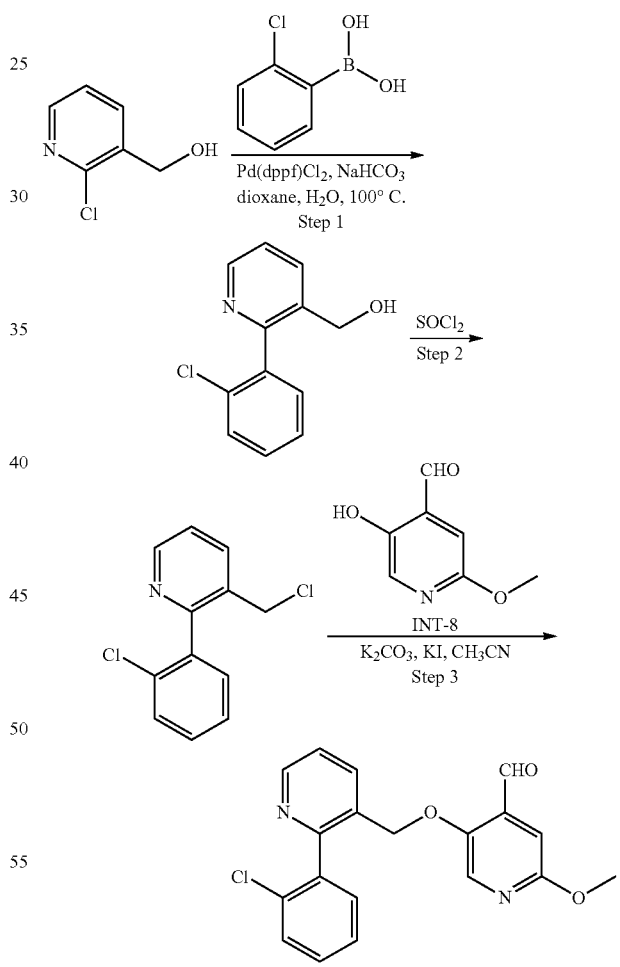

Step 1:

Into a 50-mL round-bottom flask, was placed a solution of (2-chlorophenyl)boronic acid (1.6 g, 10.23 mmol, 1.20 equiv), (2-chloropyridin-3-yl)methanol (1 g, 6.97 mmol, 1.00 equiv), Pd(dppf)Cl$_2$ (570 mg, 0.78 mmol, 0.10 equiv), and sodium bicarbonate (1.7 g, 20.24 mmol, 3.00 equiv) in a solvent mixture of dioxane (10 mL) and water (10 mL).

The resulting solution was stirred for 3 h at 70° C., and then it was diluted with 20 mL of H₂O. The resulting solution was extracted with 2×20 mL of dichloromethane, and the combined organic layers were concentrated under vacuum. The residue was applied onto a silica gel column with ethyl acetate/petroleum ether (1:100-1:5) as eluent to furnish 1 g (65%) of [2-(2-chlorophenyl)pyridin-3-yl]methanol as a white solid.

Step 2:
Into a 25-mL round-bottom flask, was placed a solution of [2-(2-chlorophenyl)pyridin-3-yl]methanol (1 g, 4.55 mmol, 1.00 equiv) in thionyl chloride (5 mL). The resulting solution was stirred for 1 h at reflux. The resulting mixture was concentrated under vacuum to yield 1 g (92%) of 3-(chloromethyl)-2-(2-chlorophenyl)pyridine as a white solid.

Step 3:
Into a 50-mL round-bottom flask, was placed a solution of 3-(chloromethyl)-2-(2-chlorophenyl)pyridine (309 mg, 1.30 mmol, 1.00 equiv), 5-hydroxy-2-methoxypyridine-4-carbaldehyde (200 mg, 1.31 mmol, 1.00 equiv), and potassium carbonate (361 mg, 2.61 mmol, 1.50 equiv) in CH₃CN (20 mL). The resulting solution was stirred for 4 h at 70° C., and then it was concentrated under vacuum. The residue was purified by prep-HPLC. This resulted in 86.2 mg (11%) of 5-[[2-(2-chlorophenyl)pyridin-3-yl]methoxy]-2-methoxy-pyridine-4-carbaldehyde; bis(trifluoroacetic acid) as a brown oil.

¹H NMR (300 MHz, DMSO-d₆) δ 10.06 (s, 1H), 8.69 (m, 1H), 8.19 (m, 1H), 8.05 (s, 1H), 7.56 (m, 2H), 7.41 (m, 3H), 6.92 (s, 1H), 5.14 (m, 2H), 3.81 (s, 3H); MS (ESI) m/z 355 [M+H]⁺.

GBT878 Preparation of 2-[(1-acetyl-5-phenyl-3,6-dihydro-2H-pyridin-4-yl)methoxy]-6-hydroxybenzaldehyde

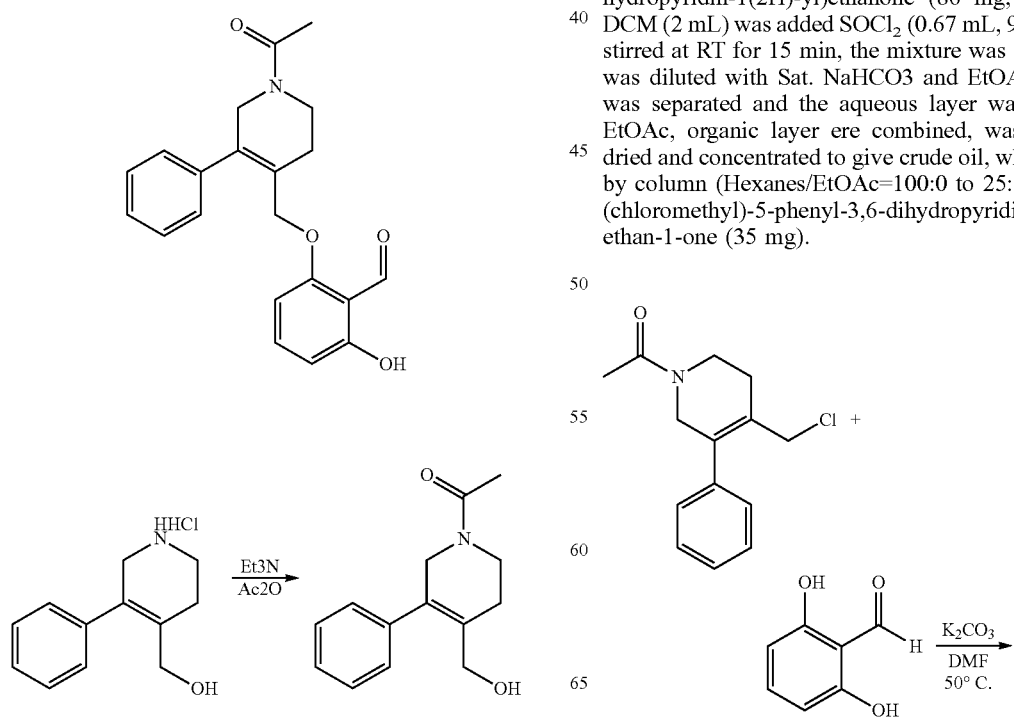

Step 1:
To a solution of (5-phenyl-1,2,3,6-tetrahydropyridin-4-yl)methanol hydrochloride (90 mg, 0.38 mmol) in DCM (2 mL) at 0° C. was added Et3N (0.11 mL, 0.76 mmol) and a solution of Ac2O (0.04 mL, 0.38 mmol) in DCM (0.4 mL), after stirred for 15 min, it was diluted with Sat. NH₄Cl and EtOAc, organic layer was separated and the aqueous layer was further extracted with EtOAc, organic layers were combined, washed with Sat. NaHCO₃, brine, dried over Na₂SO₄, and was concentrated to give 1-(4-(hydroxymethyl)-5-phenyl-3,6-dihydropyridin-1(2H)-yl)ethan-1-one as crude product (95 mg).

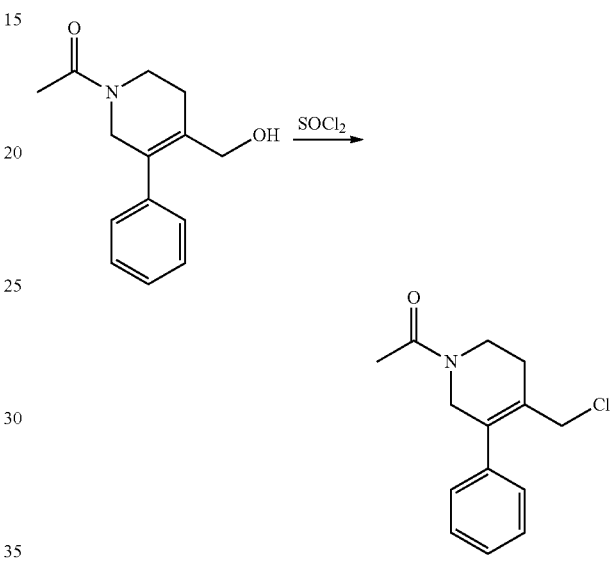

Step 2:
To a solution of 1-(4-(hydroxymethyl)-3-phenyl-5,6-dihydropyridin-1(2H)-yl)ethanone (86 mg, 0.37 mmol) in DCM (2 mL) was added SOCl₂ (0.67 mL, 9.25 mmol). After stirred at RT for 15 min, the mixture was concentrated and was diluted with Sat. NaHCO3 and EtOAc, organic layer was separated and the aqueous layer was extracted with EtOAc, organic layer ere combined, washed with brine, dried and concentrated to give crude oil, which was purified by column (Hexanes/EtOAc=100:0 to 25:75) to give 1-(4-(chloromethyl)-5-phenyl-3,6-dihydropyridin-1(2H)-yl)ethan-1-one (35 mg).

111

-continued

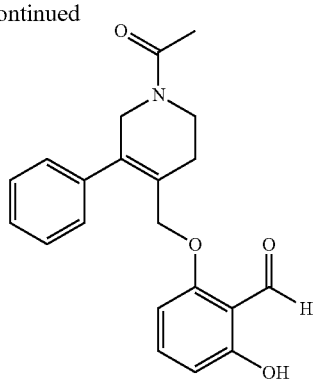

Step 3:
To a suspension of K₂CO₃ (40 mg, 0.28 mmol) and 2,6-dihydroxybenzaldehyde (40 mg, 0.28 mmol) in DMF (1 mL) was added a solution of 1-(4-(chloromethyl)-5-phenyl-3,6-dihydropyridin-1(2H)-yl)ethan-1-one (35 mg, 0.14 mmol) in DMF (1 mL), the mixture was heated at 50° C. for 3 h, cooled to room temperature, and was diluted with EtOAc, organic layer was separated and aqueous layer was extracted with EtOAc. EtOAc layers were combined, washed with Sat. NaHCO3, brine, dried over Na₂SO₄, and was concentrated to give crude oil, which was purified by column (DCM/MeOH=90:10) to give 2-((1-acetyl-5-phenyl-1,2,3,6-tetrahydropyridin-4-yl)methoxy)-6-hydroxybenzaldehyde (17 mg). 1H NMR (400 MHz, CDCl₃, NMR shows rotamer exist, only one set of signal was reported) □ (ppm) 11.93 (s, 1H), 10.36 (s, 1H), 7.34 (m, 5H), 7.22 (m, 1H), 6.49 (d, J=8.8 Hz, 1H), 6.10 (d, J=8.8 Hz, 1H), 4.47 (s, 2H), 4.32 (s, 2H), 3.68 (t, J=6.0 Hz, 2H), 2.47 (m, 2H), 2.18 (s, 3H); MS (ESI) m/z 352.5 [M+H]⁺.

GBT881 Preparation of 2-[(1-acetyl-4-phenyl-3,6-dihydro-2H-pyridin-5-yl)methoxy]-6-hydroxybenzaldehyde

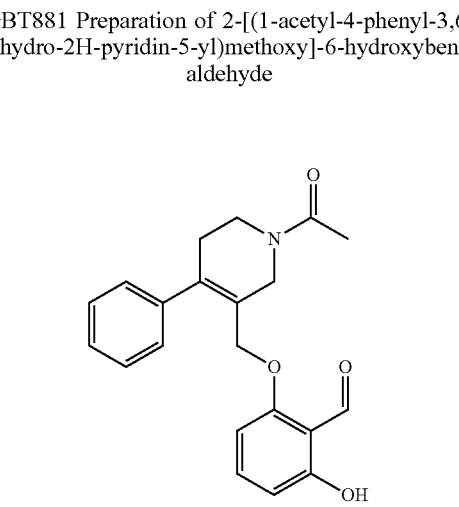

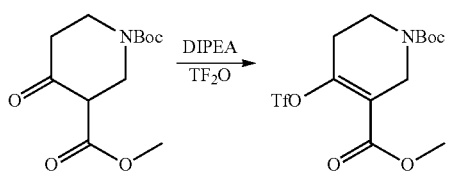

112

Step 1:
To a solution of 1-tert-butyl 3-methyl 4-oxopiperidine-1,3-dicarboxylate (2.50 g, 9.72 mmol) in DCM (50 mL) was added DIPEA (2.03 mL, 11.66 mmol) and Tf₂O (1.80 mL, 10.69 mmol) at −78° C., and then it was warmed up to room temperature and stirred further for 2 h, the solution was diluted with DCM and the organic layer was washed with Sat. NaHCO₃, dried and concentrated to give 1-tert-butyl 3-methyl 4-(((trifluoromethyl)sulfonyl)oxy)-5,6-dihydropyridine-1,3(2H)-dicarboxylate as crude product (4.4 g).

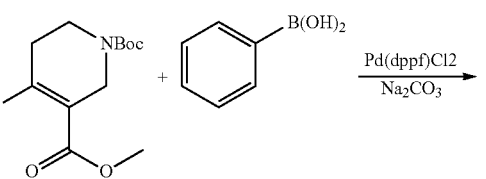

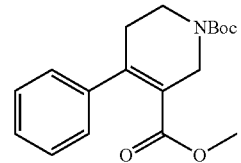

Step 2:
To a solution of 1-tert-butyl 3-methyl 4-(((trifluormethyl)sulfonyl)oxy)-5,6-dihydropyridine-1,3(2H)-dicarboxylate (1.95 g, 5 mmol) and phenylboronic acid (1.22 g, 10 mmol) in Dioxane (20 ml) was added Pd(dppf)Cl₂ and a solution of Na₂CO₃ (3.18 g, 30 mmol) in water (6 mL), after degassed with N₂ for 5 min, the reaction was heated at 100° C. for 15 h, the mixture was cooled to room temperature, diluted with EtOAc, organic layer was washed with water, brine, dried and concentrated to give crude product, which was purified by column (Hexanes/EtOAc=3:1) to give 1-tert-butyl 3-methyl 4-phenyl-5,6-dihydropyridine-1,3(2H)-dicarboxylate (740 mg).

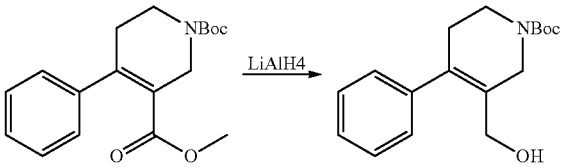 [SMILES: COC(=O)C1=C(c2ccccc2)CCN(C(=O)OC(C)(C)C)C1 ; "LiAlH4" ; CC(C)(C)OC(=O)N1CCC(c2ccccc2)=C(CO)C1]

Step 3:
To a solution of 1-tert-butyl 3-methyl 4-phenyl-5,6-dihydropyridine-1,3(2H)-dicarboxylate (740 mg, 2.33 mmol) in THF (7.2 mL) was added 1M LiAlH₄ in THF (2.80 mL, 2.80 mmol) at −20° C. dropwise, after stirring at −20° C. for 30 min, it was quenched with Sat. NH₄Cl, the mixture was extracted with EtOAc. Organic layers were combined, washed with brine, dried and concentrated to give crude product, which was purified by column (Hexanes/EtOAc=60:40) to give tert-butyl 5-(hydroxymethyl)-4-phenyl-3,6-dihydropyridine-1(2H)-carboxylate (512 mg).

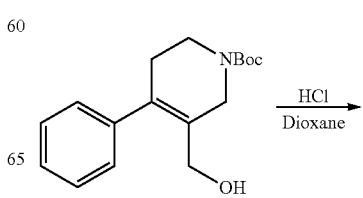

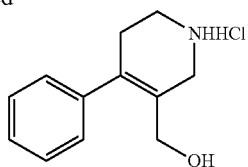

Step 4:

To tert-butyl 3-(hydroxymethyl)-4-phenyl-5,6-dihydropyridine-1(2H)-carboxylate (510 mg, 1.76 mmol) was added 4N HCl in Dioxane (3 ml), after stirring at room temperature for 1 h, it was concentrated to give (4-phenyl-1,2,5,6-tetrahydropyridin-3-yl)methanol as HCl salt.

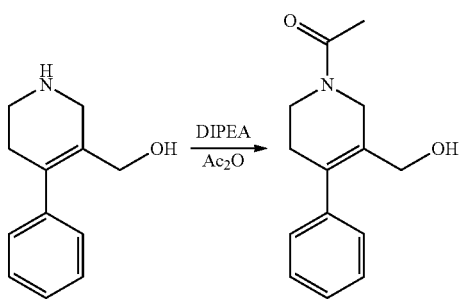 [SMILES: "Ac2O" ; OCC1=C(c2ccccc2)CCNC1 ; CC(=O)N1CCC(c2ccccc2)=C(CO)C1]

Step 5:

To a solution of (4-phenyl-1,2,5,6-tetrahydropyridin-3-yl)methanol hydrochloride (110 mg, 0.49 mmol) in DCM (2 mL) was added DIPEA (0.17 mL, 0.98 mmol) and Ac$_2$O (0.05 g, 0.49 mmol), 15 min later, it was diluted with water and extracted with DCM. Organic layers were combined, dried and concentrated, the resulting crude oil was purified by column (EtOAc followed by DCM/MeOH 9:1) to give 1-(5-(hydroxymethyl)-4-phenyl-3,6-dihydropyridin-1(2H)-yl)ethan-1-one (88 mg).

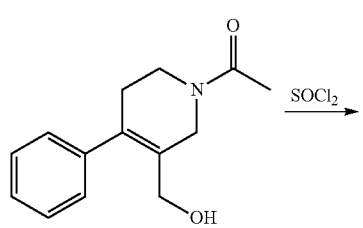

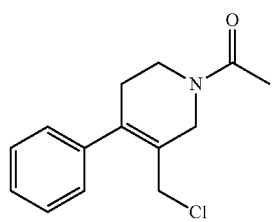

Step 6:

To a solution of 1-(3-(hydroxymethyl)-4-phenyl-5,6-dihydropyridin-1(2H)-yl)ethanone (88 mg, 0.38 mmol) in DCM (2 mL) was added SOCl$_2$ (0.67 mL, 9.50 mmol) at 0° C. After stirring at 0° C. for 15 min, the solution was concentrated to remove SOCl$_2$, dried under high vacuum to give 1-(5-(chloromethyl)-4-phenyl-3,6-dihydropyridin-1(2H)-yl)ethan-1-one as crude product.

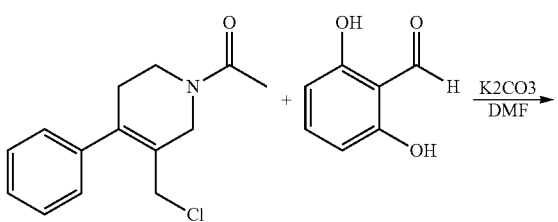

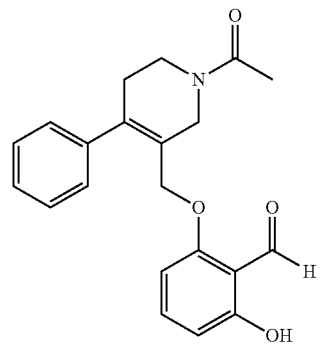

Step 7:

To a solution of 1-(3-(chloromethyl)-4-phenyl-5,6-dihydropyridin-1(2H)-yl)ethanone (100 mg, 0.40 mmol) and 2,6-dihydroxybenzaldehyde (110 mg, 0.80 mmol) in DMF (2.5 mL) was added K$_2$CO$_3$ (170 mg, 1.20 mmol), after heated at 50 degree for 2 h, the reaction was diluted with EtOAc, organic layer was separated and aqueous layer was extracted with EtOAc. EtOAc layers were combined, washed with Sat. NaHCO$_3$, brine, dried over Na$_2$SO$_4$, and was concentrated to give crude oil, which was purified by preparative HPLC (eluted with ACN/H$_2$O) to give 2-((1-acetyl-4-phenyl-1,2,5,6-tetrahydropyridin-3-yl)methoxy)-6-hydroxybenzaldehyde (26 mg). 1H NMR (400 MHz, CDCl$_3$, NMR shows rotamers exist, only one set of signal was reported) δ (ppm) 11.97 (s, 1H), 10.34 (s, 1H), 7.34 (m, 4H), 7.17 (m, 2H), 6.49 (d, J=8.0 Hz, 1H), 6.11 (d, J=8.8 Hz, 1H), 4.48 (s, 2H), 4.33 (s, 2H), 3.69 (t, J=6.0 Hz, 2H), 2.55 (m, 2H), 2.18 (s, 3H); MS (ESI) m/z 352.3 [M+H]$^+$.

GBT887 Preparation of 2-((2-(1-cyclopentyl-1H-pyrazol-5-yl)pyridin-3-yl)methoxy)-6-hydroxybenzaldehyde

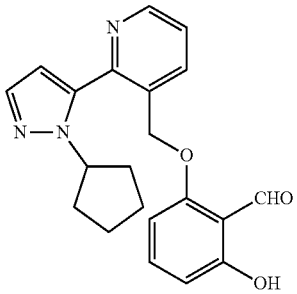 [SMILES: O=Cc1c(O)cccc1OCc1cccnc1-c1ccnn1C1CCCC1]

115

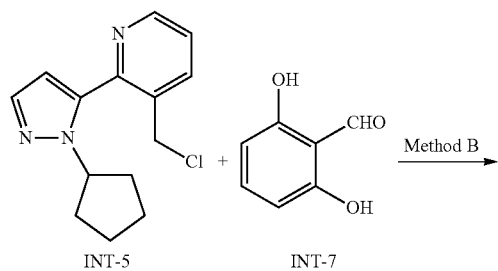

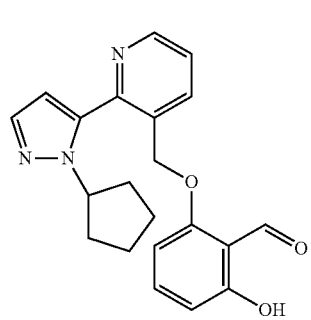

To a mixture of 3-(chloromethyl)-2-(1-cyclopentyl-1H-pyrazol-5-yl)pyridine hydrochloride (44.7 mg, 0.15 mmol) and 2,6-dihydroxybenzaldehyde (83 mg, 0.6 mmol, 4 eq) and potassium carbonate (41.5 mg, 0.3 mmol, 2 eq) were added 1 mL anhydrous DMF. The mixture was heated to 80° C. for 40 mins. The reaction was almost done by LCMS. Solvent was removed at 50° C. on a rotavap. Water 3 mL and 0.3 mL of formic acid were added to the resulting brown residue, the mixture was sonicated to make sure all carbonate was neutralized. Solvents were then removed at 45° C. on a rotavap. DCM (4×1 ml) was added to the yellow residue, the mixture was sonicated and filtered. The filtrate was concentrated to give the crude product as a yellow-light brown film. It contains the product, 2,6-dihydroxybenzaldehyde, and some starting chloride, no bis-alkylation product was observed. The residue was taken up in 2 ml DCM, filtered and loaded on a 4 g ZAP SiO2 column. It was purified on Biotage Isolera One system eluted with 5%-100% EtOAc (the product came out around 25% EtOAc, 2nd peak; the 1st peak is dihydroxybenzaldehyde). The product as a yellow film was contained after removing solvents, the residue was re-dissolved in 0.3 mL CH$_3$CN and to this was added 0.5 mL of water. This suspension was freezed and put on a lyophilizer over the weekend. The product was obtained as a light brown film (18.6 mg, 34% yield). $^1$H NMR (400 MHz, CDCl$_3$-d) δ 11.94 (s, 1H), 10.37 (s, 1H), 8.75 (dd, J=4.8, 1.7 Hz, 1H), 7.97 (dd, J=8.0, 1.4 Hz, 1H), 7.59 (d, J=2.0 Hz, 1H), 7.42 (dd, =7.7, 4.8 Hz, 1H), 7.37 (t, J=8.3 Hz, 1H), 6.56 (d, J=8.6 Hz, 1H), 6.35 (d, J=1.9 Hz, 1H), 6.25 (d, J=8.3 Hz, 1H), 5.07 (s, 2H), 4.79-4.67 (m, 1H), 2.18-1.95 (m, 4H), 1.95-1.84 (m, 2H), 1.66-1.50 (m, 2H); MS (ESI) m/z 364.3 [M+H]$^+$.

116

GBT888 Preparation of 2-hydroxy-6-[[(2S)-1-phenylpyrrolidin-2-yl]methoxy]benzaldehyde

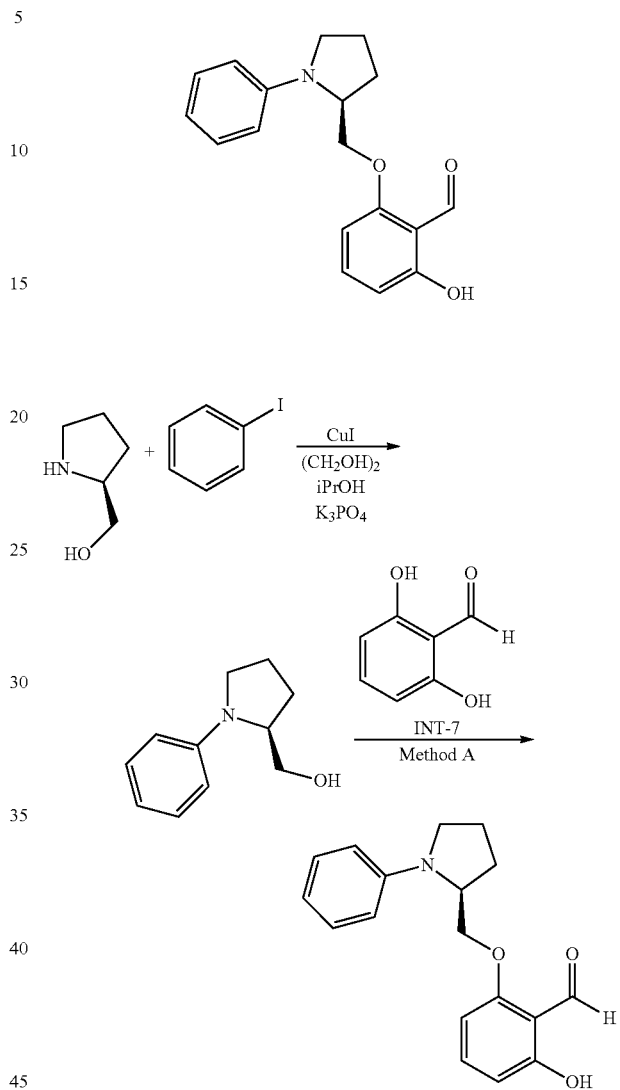

Step 1:
To a solution of (S)-pyrrolidin-2-ylmethanol (1.52 g, 15 mmol) and CuI (190 mg, 1 mmol) in iPrOH (10 mL) was added (CH$_2$OH)$_2$ (1.11 mL, 20 mmol), iodobenzene (2.04 g, 20 mmol) and K$_3$PO$_4$ (4.25 g, 20 mmol), after degassed with N2, the mixture was heated at 88° C. for 15 h. Water and ether was added, organic layer was separated and aqueous layer was further extracted with ether. Organic layers were combined, concentrated and the resulting crude oil was purified by column (hexanes/EtOAc=2:1) to give (S)-(1-phenylpyrrolidin-2-yl)methanol (1.6 g).

Step 2:
To a solution of (S)-(1-phenylpyrrolidin-2-yl)methanol (45 mg, 0.23 mmol) and 2,6-dihydroxybenzaldehyde (60 mg, 0.46 mmol) in THF (1 ml) was added PPh$_3$ (0.12 g, 0.46 mmol), followed by DIAD (90 mg, 0.46 mmol) at room temperature. After stirrer for 10 min, the mixture was concentrated and the residue was purified by column (Hexanes/EtOAc=9:1) to give (S)-2-hydroxy-6-((1-phenylpyrrolidin-2-yl)methoxy)benzaldehyde (14 mg). 1H NMR (400 MHz, CDCl₃ (ppm) 11.96 (s, 1H), 10.37 (s, 1H), 7.35 (t, J=8.0 Hz, 1H), 7.25 (nm, 2H), 6.73 (m, 3H), 6.53 (d, J=8.4 Hz, 1H), 6.33 (d, J=9.2 Hz, 1H), 4.21 (m, 1H), 4.15 (d, J=3.6 Hz, 1H), 3.83 (t, J=8.0 Hz, 1H), 3.53 (m, 1H), 3.22 (m, 1H), 2.11 (m, 4H); MS (ESI) m/z 298.4

GBT892 Preparation of 5-[[2-(3-chlorophenyl)pyridin-3-yl]methoxy]-2-methoxypyridine-4-carbaldehyde

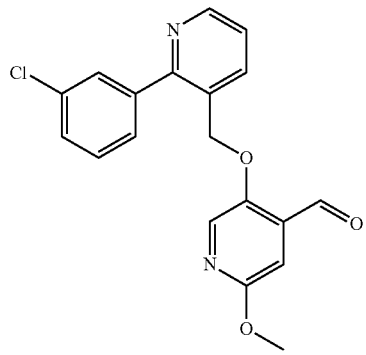 [SMILES: COc1cc(C=O)c(OCc2cccnc2-c2cccc(Cl)c2)cn1]

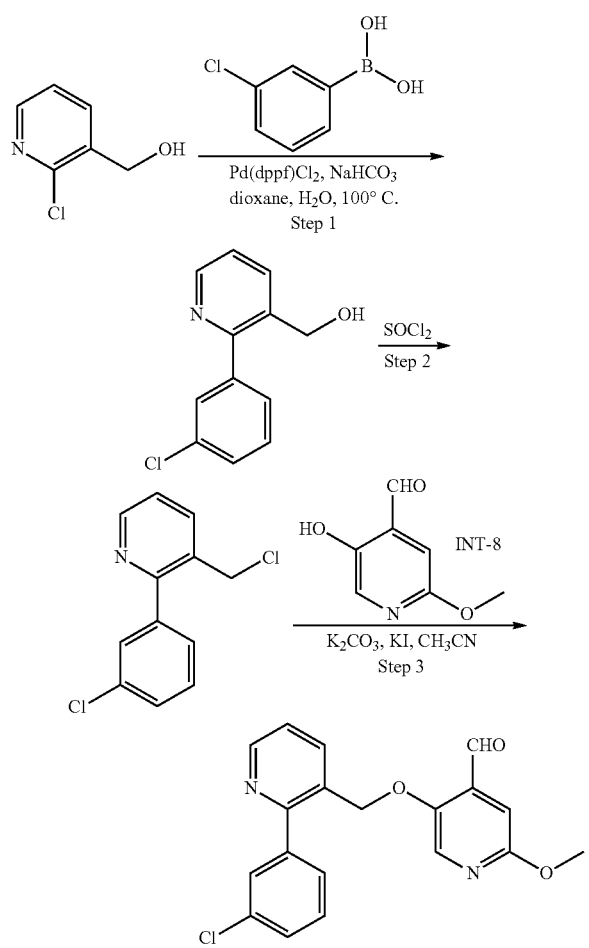

Step 1:

Into a 50-mL round-bottom flask, was placed a solution of (3-chlorophenyl)boronic acid (1.6 g, 10.23 mmol, 1.20 equiv), (2-chloropyridin-3-yl)methanol (1 g, 6.97 mmol, 1.00 equiv), Pd(dppf)Cl₂ (570 mg, 0.78 mmol, 0.10 equiv), and sodium bicarbonate (1.7 g, 20.24 mmol, 3.00 equiv) in a solvent mixture of dioxane (10 mL) and water (10 mL). The resulting solution was stirred for 3 h at 70° C., and then it was diluted with 20 mL of H₂O. The resulting solution was extracted with 2×20 mL of dichloromethane, and the combined organic layers were concentrated under vacuum. The residue was applied onto a silica gel column with ethyl acetate/petroleum ether (1:100-1:5) as eluent to yield 1.2 g (78%) of [2-(3-chlorophenyl)pyridin-3-yl]methanol as a white solid.

Step 2:

Into a 50-mL round-bottom flask, was placed a solution of [2-(3-chlorophenyl)pyridin-3-yl]methanol (600 mg, 2.73 mmol, 1.00 equiv) in thionyl chloride (10 mL). The resulting solution was stirred for 1 h at reflux. The resulting mixture was concentrated under vacuum. This resulted in 500 mg (77%) of 3-(chloromethyl)-2-(3-chlorophenyl)pyridine as a white solid.

Step 3:

Into a 50-mL round-bottom flask, was placed a solution of 3-(chloromethyl)-2-(3-chlorophenyl)pyridine (309 mg, 1.30 mmol, 1.00 equiv), 5-hydroxy-2-methoxypyridine-4-carbaldehyde (200 mg, 1.31 mmol, 1.00 equiv), and potassium carbonate (361 mg, 2.61 mmol, 2.00 equiv) in CH₃CN (20 mL). The resulting solution was stirred for 4 h at 70° C., and then it was concentrated under vacuum. The crude product (300 mg) was purified by Prep-HPLC with the following conditions (Prep-HPLC-010): Column, SunFire Prep C18 OBD Column, 5 um, 19*150 mm; mobile phase, water with 0.05% TFA and MeCN (20.0% MeCN up to 60.0% in 10 min, up to 95.0% in 2 min, down to 20.0% in 1 min); Detector, Waters2545 UvDector 254&220 nm. This resulted in 71 mg (9%) of 5-[[2-(3-chlorophenyl)pyridin-3-yl]methoxy]-2-methoxypyridine-4-carbaldehyde; bis(trifluoroacetic acid) as a yellow solid.

¹HNMR (400 MHz, DMSO-d6) δ 10.07 (s, 1H), 8.72 (m, 1H), 8.20 (m, 2H), 7.79 (s, 1H), 7.60 (m, 4H), 6.95 (m, 1H), 5.21 (m, 2H), 3.85 (s, 3H); MS (ESI) m/z 355 [M+H]⁺.

GBT893 Preparation of 5-[[2-(4-chlorophenyl)pyridin-3-yl]methoxy]-2-methoxypyridine-4-carbaldehyde

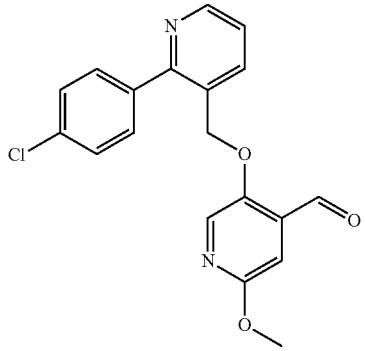 [SMILES: COc1cc(C=O)c(OCc2cccnc2-c2ccc(Cl)cc2)cn1]

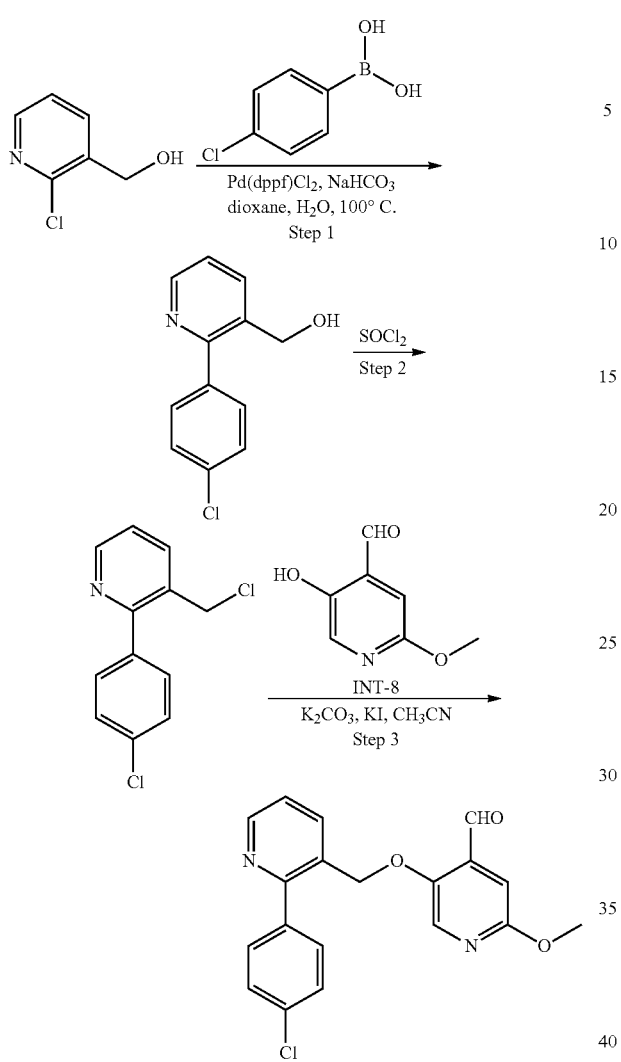

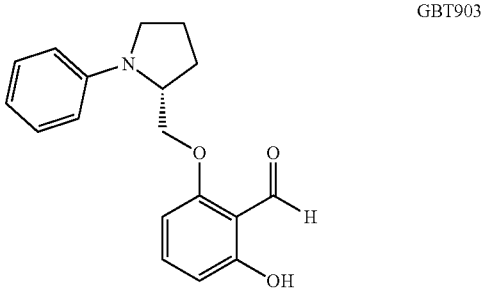

(R)-2-hydroxy-6-((1-phenylpryyolidin-2-yl)methoxy)benzaldehyde

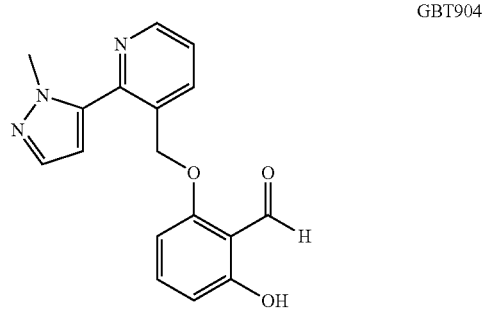

2-hydroxy-6-((2-(1-methyl-1H-pyrazol-5-yl)pyridin-3-yl)methoxy)benzaldehyde

Step 1: Into a 100-mL round-bottom flask, was placed a solution of (4-chlorophenyl)boronic acid (1.6 g, 10.23 mmol, 1.20 equiv), (2-chloropyridin-3-yl)methanol (1 g, 6.97 mmol, 1.00 equiv), Pd(dppf)Cl$_2$ (570 mg, 0.78 mmol, 0.10 equiv), and sodium bicarbonate (1.7 g, 20.24 mmol, 3.00 equiv) in a solvent mixture of dioxane (10 mL) and water (10 mL). The resulting solution was stirred for 4 h at 70° C., and then it was diluted with 100 mL of H$_2$O. The resulting solution was extracted with 2×200 mL of dichloromethane, and the combined organic layers were concentrated under vacuum. The residue was applied onto a silica gel column with ethyl acetate/petroleum ether (1:100-1:5) as eluent to yield 1 g (65%) of [2-(4-chlorophenyl)pyridin-3-yl]methanol as a light yellow oil.

Step 2:
Into a 25-mL round-bottom flask, was placed a solution of [2-(4-chlorophenyl)pyridin-3-yl]methanol (1 g, 4.55 mmol, 1.00 equiv) in thionyl chloride (5 mL). The resulting solution was stirred for 1 h at reflux. The resulting mixture was concentrated under vacuum. This resulted in 1 g (92%) of 3-(chloromethyl)-2-(4-chlorophenyl)pyridine as a white solid.

Step 3:
Into a 50-mL round-bottom flask, was placed a solution of 3-(chloromethyl)-2-(4-chlorophenyl)pyridine (309 mg, 1.30 mmol, 1.00 equiv), 5-hydroxy-2-methoxypyridine-4-carbaldehyde (200 mg, 1.31 mmol, 1.00 equiv), and potassium carbonate (361 mg, 2.61 mmol, 2.00 equiv) in CH$_3$CN (20 mL). The resulting solution was stirred for 4 h at 70° C. and then it was concentrated under vacuum. The crude product (300 mg) was purified by Prep-HPLC with the following conditions (Prep-HPLC-010): Column, SunFire Prep C18 OBD Column, 5 um, 19*150 mm: mobile phase, water with 0.05% TFA and MeCN (20.0% MeCN up to 60.0% in 10 min, up to 95.0% in 2 min, down to 20.0% in 1 min); Detector, Waters2545 UvDector 254&220 nm. This resulted in 148.2 mg (20%) of 5-[[2-(4-chlorophenyl)pyridin-3-yl]methoxy]-2-methoxypyridine-4-carbaldehyde; bis(trifluoroacetic acid) as a yellow solid.

$^1$HNMR (300 MHz, DMSO-d$_6$) δ 10.05 (s, 1H), 8.69 (m, 1H), 8.16 (m, 2H), 7.64 (m, 2H),

GBT903—Preparation of (R)-2-hydroxy-6-((1-phenylpyrrolidin-2-yl)methoxy)benzaldehyde The compound was prepared from (R)-pyrrolidin-2-ylmethanol and iodobenzene according to scheme 8, reaction steps 3 and 4. $^1$H NMR (400 MHz. Chloroform-d) δ 11.96 (d, J=0.4 Hz, 1H), 10.37 (s, 1H), 7.37 (td, J=8.4, 0.4 Hz, 1H), 7.31-7.18 (m, 2H), 6.77-6.64 (m, 3H), 6.53 (dt, J=8.5, 0.7 Hz, 1H), 6.33 (dd, 1=8.3, 0.8 Hz, 1H), 4.25-4.12 (m, 2H), 3.88-3.78 (m, 1H), 3.53 (dt, J=8.8, 4.4 Hz, 1H), 3.27-3.16 (m, 1H), 2.11 (dqt, J=13.0, 6.4, 2.8 Hz, 4H). MS (M+H)+ found for C$_{18}$H$_{19}$NO$_3$: 298.2.

GBT904—Preparation of 2-hydroxy-6-((2-(1-methyl-1H-pyrazol-5-yl)pyridin-3-yl)methoxy)benzaldehyde The compound was prepared from (2-chloropyridin-3-yl) methanol and 1-methyl-5-(4,4,5,5-tetramethyl-1,3,2-dioxaborolan-2-yl)-1H-pyrazole according to scheme 9, reaction steps 1, 2 and 4. In step 4, 2-hydroxy-6-(methoxymethoxy) benzaldehyde was used; the MOM ether protecting group fell off after the reaction to give the final product. $^1$H NMR (400 MHz, Chloroform-d) δ 11.94 (s, 1H), 10.36 (s, 1H), 8.75 (dd, J=4.8, 1.7 Hz, 1H), 7.98 (d, J=8.0 Hz, 1H), 7.54 (d, J=1.9 Hz, 1H), 7.41 (dd, J=8.0, 4.0 Hz, 1H), 7.38 (t, J=8.0 Hz, 1H), 6.58 (dt, J=8.5, 0.7 Hz, 1H), 6.39 (d, J=1.9 Hz, 1H), 6.28 (dd, J=8.3, 0.8 Hz, 1H), 5.12 (s, 2H), 3.95 (s, 3H). MS (M+H) found for $C_{17}H_{15}N_3O_3$: 310.3.

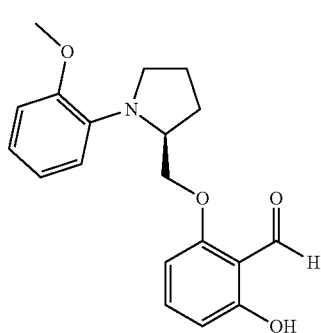

GBT907 and GBT908

(S)-2-hydroxy-6-((1-(2-methoxyphenyl)pyrrolidin-2-yl)methoxy)benzaldehyde

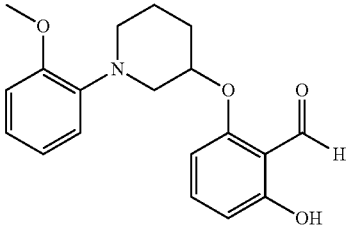

2-hydroxy-6-((1-(2-methoxyphenyl)piperidin-3-yl)oxy)benzaldehyde

GBT907 and GBT908—Preparation of (S)-2-hydroxy-6-((1-(2-methoxyphenyl)pyrrolidin-2-yl)methoxy)benzaldehyde (GBT907) and 2-hydroxy-6-((1-(2-methoxyphenyl)piperidin-3-yl)oxy)benzaldehyde (GBT908)

The reaction of (S)-pyrrolidin-2-ylmethanol with 2-iodoanisole, and subsequent Mitsunobu reaction, according to scheme 8, gave a mixture of GBT907 and GBT908 in 3:2 ratio, which were separated by reverse-phase prep HPLC.

GBT907—(S)-2-hydroxy-6-((1-(2-methoxyphenyl)pyrrolidin-2-yl)methoxy)benzaldehyde $^1$H NMR (400 MHz, Chloroform-d) δ 11.96 (d, J=0.4 Hz, 1H), 10.37 (d, J=0.6 Hz, 1H), 7.39 (td, J=8.4, 0.4 Hz, 1H), 7.04-6.87 (m, 3H), 6.84 (dd, J=8.0, 1.4 Hz, 1H), 6.52 (ddt, J=13.7, 8.4, 0.7 Hz, 2H), 4.66 (tt, J=8.2, 3.9 Hz, 1H), 3.80 (s, 3H), 3.67-3.58 (m, 1H), 3.29 (dt, J=9.9, 4.3 Hz, 1H), 2.85 (dd, J=11.3, 8.3 Hz, 1H), 2.82-2.74 (m, 1H), 2.20 (dd, J=12.4, 4.9 Hz, 1H), 2.00 (dp, J=13.0, 4.6 Hz, 1H), 1.94-1.79 (m, 1H), 1.72 (dddd, J=13.0, 10.7, 9.0, 4.3 Hz, 1H). MS (M+H)+ found for $C_{19}H_{21}NO_4$: 328.3).

GBT908—2-hydroxy-6-((1-(2-methoxyphenyl)piperidin-3-yl)oxy)benzaldehyde (40 mg, $^1$H NMR (400 MHz, Chloroform-d) δ 11.91 (s, 1H), 10.09 (d, J=0.6 Hz, 1H), 7.32 (d, J=8.4 Hz, 1H), 6.93-6.80 (m, 4H), 6.46 (dt, J=8.5, 0.7 Hz, 1H), 6.23 (dd, J=8.4, 0.8 Hz, 1H), 4.49 (tt, J=7.2, 4.7 Hz, 1H), 4.06 (dd, J=9.3, 4.4 Hz, 1H), 3.88-3.78 (m, 1H), 3.80 (s, 3H), 3.63 (ddd, J 9.1, 7.3, 6.3 Hz, 1H), 3.21-3.11 (m, 1H), 2.35-2.22 (m, 1H), 2.09-1.86 (m, 3H), MS (M+H)+ found for $C_{19}H_{21}NO_4$: 328.3).

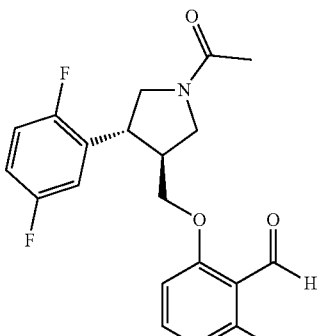

GBT912

2-(((3S,4R)-1-acetyl-4-(2,5-difluorophenyl)pyrrolidin-3-yl)methoxy)-6-hydroxybenzaldehyde

GBT912—2-(((3S,4R)-1-acetyl-4-(2,5-difluorophenyl)pyrrolidin-3-yl)methoxy)-6-hydroxybenzaldehyde The compound was prepared from -(2,5-difluorophenyl)-4-(hydroxymethyl)pyrrolidin-1-yl)ethan-1-one and 2,6-dihydroxybenzaldehyde (INT-7) using general method A (Mitsunobu conditions). $^1$H NMR (400 MHz, Chloroform-d) δ 11.90 (s, 1H), 9.88 (s, 1H), 7.37 (dd, J=8.4, 6.4 Hz, 1H), 7.01 (m, 3H), 6.53 (t, J=8.6 Hz, 1H), 6.27 (dd, J=8.3, 0.8 Hz, 1H), 4.02 (m, 4H), 3.55 (m, 3H), 2.96 (m, 1H), 2.11 (s, 3H). MS (M+1H)+ found for $C_{20}H_{19}F_2NO_4$: 376.3.

Preparation of -(2,5-difluorophenyl)-4-(hydroxymethyl)pyrrolidin-1-yl)ethan-1-one

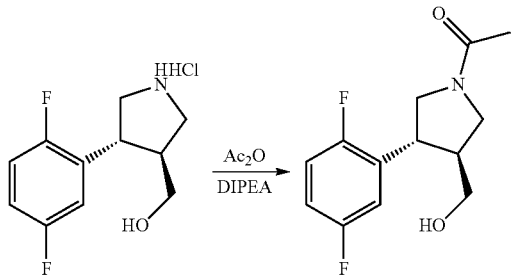

To a solution of ((3S,4R)-4-(2,5-difluorophenyl)pyrrolidin-3-yl)methanol hydrochloride (200 mg, 0.8 mmol) in DCM (2 mL) at 0° C. was added DIPEA (0.3 mL, 1.68 mmol) and Ac$_2$O (90 mg, 0.84 mmol), after stirred for 30 min, the solution was diluted with DCM, organic layer was washed with Sat. NaHCO$_3$, brine, dried over MgSO$_4$ and was concentrated to give 1-((3R,4S)-3-(2,5-difluorophenyl)-4-(hydroxymethyl)pyrrolidin-1-yl)ethan-1-one as crude product (175 mg).

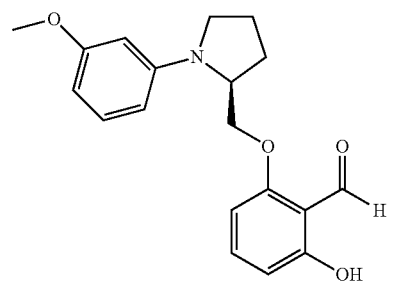

(S)-2-hydroxy-6-((1-(3-methoxyphenyl)pyrrolidin-2-yl)methoxy)benzaldehyde and

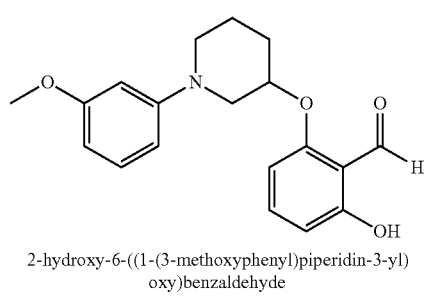

2-hydroxy-6-((1-(3-methoxyphenyl)piperidin-3-yl)oxy)benzaldehyde

GBT913 and GBT914—Preparation of (S)-2-hydroxy-6-((1-(3-methoxyphenyl)pyrrolidin-2-yl)methoxy)benzaldehyde (GBT913) and 2-hydroxy-6-((1-(3-methoxyphenyl)piperidin-3-yl)oxy)benzaldehyde (GBT914)

The reaction of (S)-pyrrolidin-2-ylmethanol with 3-iodoanisole, and subsequent Mitsunobu reaction, according to scheme 8, gave a mixture of GBT913 and GBT914 in 5:4 ratio, which were separated by reverse-phase prep HPLC.

GBT913—(S)-2-hydroxy-6-((1-(3-methoxyphenyl)pyrrolidin-2-yl)methoxy)benzaldehyde $^1$H NMR (400 MHz, Chloroform-d) δ 11.95 (s, 1H), 10.37 (t, J=0.5 Hz, 1H), 7.42-7.31 (m, 1H), 7.16 (t, J=8.2 Hz, 1H), 6.53 (dq, J=8.4, 0.6 Hz, 1H), 6.36-6.24 (m, 3H), 6.23 (t, J=2.4 Hz, 1H), 4.23-4.12 (m, 2H), 3.79 (s, 4H), 3.50 (ddd, J=9.0, 5.6, 3.5 Hz, 1H), 3.27-3.16 (m, 1H), 2.17-1.98 (m, 4H). MS (M+H)+ found for $C_{19}H_{21}NO_4$: 328.3

GBT914—2-hydroxy-6-((1-(3-methoxyphenyl)piperidin-3-yl)oxy)benzaldehyde $^1$H NMR (400 MHz, Chloroform-d) δ 11.94 (d, J=0.4 Hz, 1H), 10.25 (d, J=0.6 Hz, 1H), 7.39 (td, J=8.4, 0.4 Hz, 1H), 7.19-7.08 (m, 1H), 6.51 (dt, J=8.5, 0.7 Hz, 2H), 6.48-6.37 (m, 3H), 4.58 (m, 1H), 3.78 (m, 1H), 3.77 (s, 3H), 3.74-3.64 (m, 1H), 3.39 (d, J=5.6 Hz, 1H), 3.17 (dd, J=12.4, 7.6 Hz, 1H), 3.11-3.01 (m, 1H), 2.14 (s, 1H), 2.02-1.92 (m, 1H), 1.86-1.74 (m, 1H). MS (M+H)+ found for $C_{19}H_{21}NO_4$: 328.4).

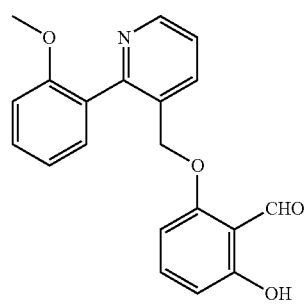

GBT916—2-hydroxy-6-((2-(2-methoxyphenyl)pyridin-3-yl)methoxy)benzaldehyde

The compound was prepared from (2-chloropyridin-3-yl)methanol and (2-methoxyphenyl)boronic acid according to scheme 9, reaction steps 1, 2 and 4. In step 4, alkylation with 2,6-dihydroxybenzaldehyde, the product of TFA salt was obtained after HPLC purification. $^1$HNMR (300 MHz, DMSO, ppm): 11.71 (s, 1H), 9.99 (s, 1H), 8.65 (m, 1H), 8.13 (d, J=7.5 Hz, 1H), 7.50 (m, 3H), 7.31 (m, 1H), 7.04 (m, 2H), 6.47 (m, 1H) 6.38 (m, d, J=8.4 Hz, 1H), 5.00 (s, 2H), 3.73 (s, 3H); MS (ES, m/z): 336 [M+1]+.

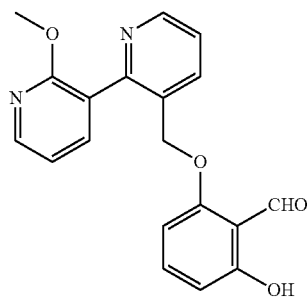

GBT917—2-hydroxy-6-((2'-methoxy-[2,3'-bipyridin]-3-yl)methoxy)benzaldehyde

The compound was prepared from (2-chloropyridin-3-yl)methanol and (2-methoxypyridin-3-yl)boronic acid according to scheme 9, reaction steps 1, 2 and 4. In step 4, alkylation with 2,6-dihydroxybenzaldehyde, the product TFA salt was obtained after HPLC purification.

$^1$HNMR (300 MHz, CDCl3, ppm): 11.91 (s, 1H), 10.24 (s, 1H), 8.71 (t, 1H), 8.69 (m, 1H), 7.93 (d, 1H), 7.75 (d, 1H), 7.40 (m, 1H), 7.39 (m, 1H), 7.08 (m, 1H), 6.53 (d, 1H), 6.50 (d, 1H), 5.07 (s, 2H), 3.94 (s, 31-1H) MS (ES, m/z): 337 [M+1]+

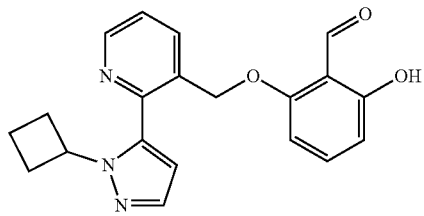

GBT930—2-((2-(1-cyclobutyl-1H-pyrazol-5-yl)pyridin-3-yl)methoxy)-6-hydroxybenzaldehyde The compound was prepared by Mitsunobu reaction (scheme 9, step 3) of (2-(1-cyclobutyl-1H-pyrazol-5-yl)pyridin-3-yl)methanol (A) with 2,6-dihydroxybenzaldehyde (INT3). The product was obtained as pale yellow solid. $^1$HNMR (300 MHz, CDCl3, ppm): 11.95 (s, 1H), 10.35 (s, 1H), 8.75 (m, 1H), 7.97 (d, J=7.2 Hz, 1H), 7.62 (m, 1H), 7.45 (m, 1H), 7.36 (m, 1H), 6.56 (d, J=8.4 Hz, 1H), 6.38 (m, 1H), 6.23 (d, J=8.4 Hz, 1H), 5.07 (s, 2H), 4.85 (m, 1H), 2.75 (m, 2H), 2.27 (m, 2H), 1.25 (m, 2H); (ES, m/z): 350 [M+1]$^+$

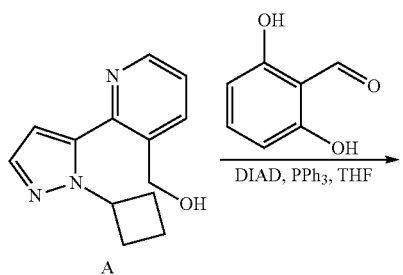

Preparation of Intermediate A

Intermediate A was prepared from pyrazole in three steps according scheme below.

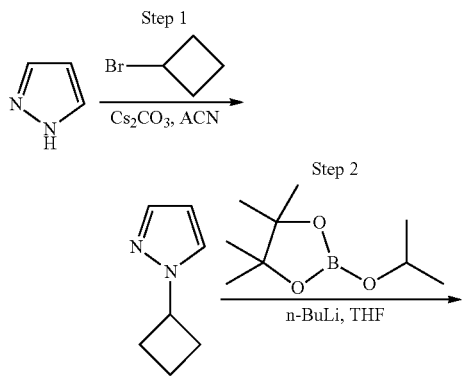

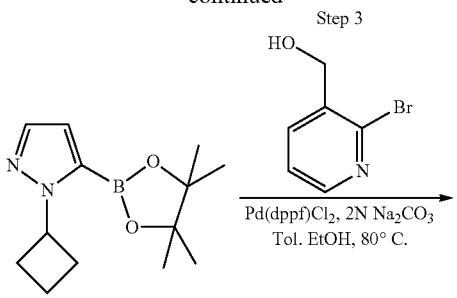

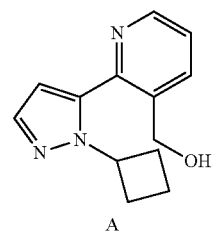

Step 1: Into a 500-mL round-bottom flask, was placed a solution of 1H-pyrazole (10 g, 146.89 mmol, 1.00 equiv), Cs$_2$CO$_3$ (95.9 g, 294.33 mmol, 2.00 equiv), and bromocyclobutane (29.7 g, 220.00 mmol, 1.50 equiv) in CH$_3$CN (150 mL). The resulting solution was stirred overnight at 80° C., and then it was concentrated under vacuum. The residue was applied onto a silica gel column with ethyl acetate/petroleum ether (1:400-1:200) as eluent to yield 8 g (45%) of 1-cyclobutyl-1H-pyrazole as a colorless liquid.

Step 2: Into a 250-mL round-bottom flask, was placed a solution of 1-cyclobutyl-1H-pyrazole (6.5 g, 53.21 mmol, 1.00 equiv) in tetrahydrofuran (100 ml). This was followed by the addition of BuLi (2.5 M, 22.7 mL, 1.10 equiv) dropwise with stirring at −30° C. The mixture was stirred for 30 min at the same temperature. To this was added 4,4,5,5-tetramethyl-2-(propan-2-yloxy)-1,3,2-dioxaborolane (14.9 g, 80.08 mmol, 1.50 equiv) dropwise with stirring at −78° C. The resulting solution was stirred for 3 h at −78° C., and then it was quenched by the addition of 30 mL of water. The resulting solution was extracted with 2×200 mL of dichloromethane. The combined organic layers were concentrated under vacuum. The residue was applied onto a silica gel column with ethyl acetate/petroleum ether (1:200-1:30) as eluent to furnish 6.2 g (47%) of 1-cyclobutyl-5-(tetramethyl-1,3,2-dioxaborolan-2-yl)-1H-pyrazole as a colorless oil.

Step 3: Into a 100-mL round-bottom flask, was placed a solution of 1-cyclobutyl-5-(tetramethyl-1,3,2-dioxaborolan-2-yl)-1H-pyrazole (791 mg, 3.19 mmol, 2.00 equiv), (2-bromopyridin-3-yl)methanol (500 mg, 2.66 mmol, 1.00 equiv), Pd(dppf)Cl$_2$ (217 mg, 0.30 mmol, 0.10 equiv), and sodium carbonate (670 mg, 6.32 mmol, 3.0) equiv) in a solvent mixture of dioxane (10 mL) and water (10 mL). The resulting solution was stirred for 2 h at 80° C. The resulting solution was extracted with 3×20 mL of dichloromethane. The combined organic layers were concentrated under vacuum. The residue was applied onto a silica gel column with ethyl acetate/petroleum ether (1:3-1:1) as eluent to provide 200 mg (33%) of [2-(1-cyclobutyl-1H-pyrazol-5-yl)pyridin-3-yl]methanol as a yellow oil.

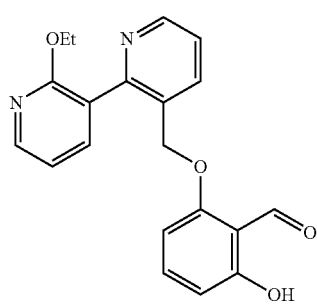

GBT934—2-((2'-ethoxy-[2,3'-bipyridin]-3-yl)
methoxy)-6-hydroxybenzaldehyde

The compound was prepared from (2-chloropyridin-3-yl) methanol and ((2-ethoxypyridin-3-yl)boronic acid according to scheme 9, reaction steps 1, 2 and 4. In step 4, alkylation with 2,6-dihydroxybenzaldehyde (INT3), the product TFA salt as white solid was obtained after HPLC purification. $^1$HNMR (400 MHz, CDCl$_3$, ppm): 11.91 (br s, 1H), 10.29 (s, 1H), 8.97 (s, 2H), 8.97 (br s, 1H), 8.46 (d, J=8.0 Hz, 1H), 8.40 (d, J=4.8 Hz, 1H), 7.87 (s, 1H), 7.81 (d, J=6.8 Hz, 1H), 7.53 (t, J=4.4 Hz, 1H), 7.12 (t, J=6.0 Hz, 1H), 6.59 (d, J=8.4 Hz, 1H), 6.14 (d, J=8.4 Hz, 1H), 5.17 (s, 2H), 4.46 (q, J=6.8 Hz, 2H), 1.32 (t, J=6.8 Hz, 3H); MS (ES, m/z:) 351.1 [M+1]$^+$

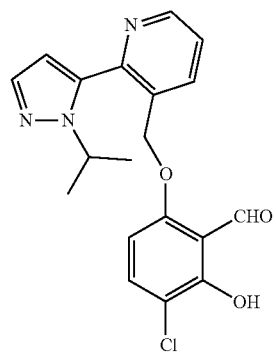

GBT948—3-chloro-2-hydroxy-6-((2-(1-isopropyl-1H-pyrazol-5-yl)pyridin-3-yl)methoxy)benzaldehyde The compound was prepared using general reaction step 4 of scheme 9, by O-alkylation of 3-chloro-6-hydroxy-2-(methoxymethoxy)benzaldehyde (B) with 3-(chloromethyl)-2-(1-isopropyl-1H-pyrazol-5-yl)pyridine (A) and subsequent deprotection of the MOM ether by treating with aqueous 6N HCl in THF. $^1$HNMR (400 MHz, CDCl$_3$, ppm): 12.49 (s, 1H), 10.34 (s, 1H), 8.80 (dd, J=3.6 Hz, 1H), 8.00 (dd, J=5.7 Hz, 1H), 7.63 (d, J=1.2 Hz, 1H), 7.47 (m, 2H), 6.36 (m, 2H), 5.11 (d, J=10.8 Hz, 2H), 4.70 (m, 1H), 4.61 (m, 1H), 1.53 (d, J=4.5 Hz, 6H); MS (ES, m/z): 372[M+1]$^-$

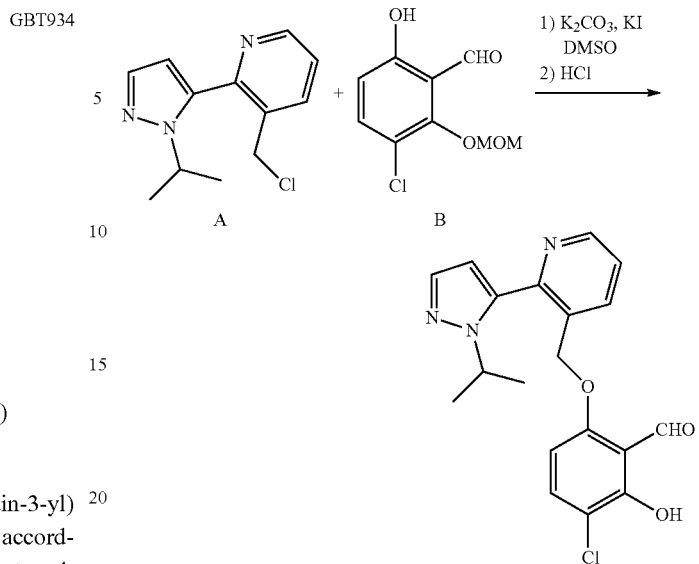

The MOM-protected phenol aldehyde intermediate B was prepared according to the following synthetic scheme:

Step 1: Into a 2000-mL round-bottom flask, was placed a solution of 4-chlorobenzene-1,3-diol (50.0 g, 345.89 mmol, 1.00 equiv) and potassium carbonate (95 g, 687.36 mmol, 2.00 equiv) in acetone (1000 mL). This was followed by the addition of MOMBr (40 g, 320.10 mmol, 0.90 equiv) dropwise with stirring. The resulting solution was stirred for 60 h at room temperature. The solids were filtered out. The resulting mixture was concentrated under vacuum. The residue was applied onto a silica gel column with ethyl acetate/petroleum ether (1:10-1:2) as eluent to furnish 49 g (75%) of 4-chloro-3-(methoxymethoxy)phenol as a colorless oil.

Step 2: Into a 1000-mL round-bottom flask, was placed a solution of 4-chloro-3-(methoxymethoxy)phenol (49.0 g, 259.80 mmol, 1.00 equiv) and potassium carbonate (57.4 g, 415.31 mmol, 1.60 equiv) in acetone (500 mL). This was followed by the addition of BnBr (55 g, 321.58 mmol, 1.20 equiv) dropwise with stirring in 40 min. The resulting solution was stirred overnight at room temperature. The solids were filtered out. The resulting mixture was concentrated under vacuum. The residue was applied onto a silica gel column with ethyl acetate/petroleum ether (1:99-1:10-1:2) as eluent to furnish 40.0 g (55%) of 4-(benzyloxy)-1-chloro-2-(methoxymethoxy)benzene as a colorless oil.

Step 3: Into a 500-mL three neck round-bottom flask, was placed a solution of bis(propan-2-yl)amine (29.7 g, 293.51 mmol, 5.00 equiv) in tetrahydrofuran (70 mL). This was followed by the addition of BuLi (100 mL, 3.00 equiv) dropwise with stirring at −78° C. The mixture was stirred for 10 min at −78° C., then stirred for 10 min at 0° C. To this was added a solution of 4-(benzyloxy)-1-chloro-2-(methoxymethoxy)benzene (23.3 g, 83.59 mmol, 1.00 equiv) in tetrahydrofuran (70 mL) dropwise with stirring at −78° C. The mixture was stirred for 1 h at −40° C. To the mixture was added N,N-dimethylformamide (18.3 g, 250.38 mmol, 3.00 equiv) dropwise with stirring at −78° C. The resulting solution was stirred for 30 min at −78° C. The reaction was then quenched by the addition of 50 mL of NH$_4$Cl (aq). The resulting solution was diluted with 50 mL of water. The resulting solution was extracted with 3×100 mL, of ethyl acetate and the organic layers combined and dried over sodium sulfate and concentrated under vacuum. The residue was applied onto a silica gel column with ethyl acetate/petroleum ether (1:5) as eluent. This resulted in 8.8 g (34%) of 6-(benzyloxy)-3-chloro-2-(methoxymethoxy) benzaldehyde as a yellow solid.

Step 4: Into a 500-mL round-bottom flask, was placed a solution of 6-(benzyloxy)-3-chloro-2-(methoxymethoxy) benzaldehyde (8.8 g, 28.69 mmol, 1.00 equiv) in ethyl acetate (100 mL). Rh/C (1.0 g) was added to the reaction. The resulting solution was stirred for 20 h at room temperature under 1 atm of hydrogen gas. The solids were filtered out. The resulting mixture was concentrated under vacuum. The residue was applied onto a silica gel column with ethyl acetate/petroleum ether (1:2) as eluent. This resulted in 5.2 g (84%) of 3-chloro-6-hydroxy-2-(methoxymethoxy)benzaldehyde as a light yellow solid.

GBT954-4-hydroxy-2-((2-(1-isopropyl-1H-pyrazol-5-yl)pyridin-3-yl)methoxy)benzaldehyde The compound was prepared by Mitsunobu reaction (scheme 9, step 3) of 2-hydroxy-4-(methoxymethoxy)benzaldehyde (A) with (2-(1-isopropyl-1H-pyrazol-5-yl)pyridin-3-yl)methanol (B) and subsequent deprotection of the MOM ether by treating with aqueous 6N HCl in THE according the scheme below. $^1$HNMR (400 MHz, DMSO, ppm): 10.70 (s, 1H), 10.09 (s, 1H), 8.75 (m, 1H), 8.22 (d, J=8 Hz, 1H), 7.59 (m, 3H), 6.52 (m, 3H), 5.16 (s, 2H), 4.65 (m, 1H), 1.37 (m, 6H): (ES, m/z): 338 [M+1]$^+$

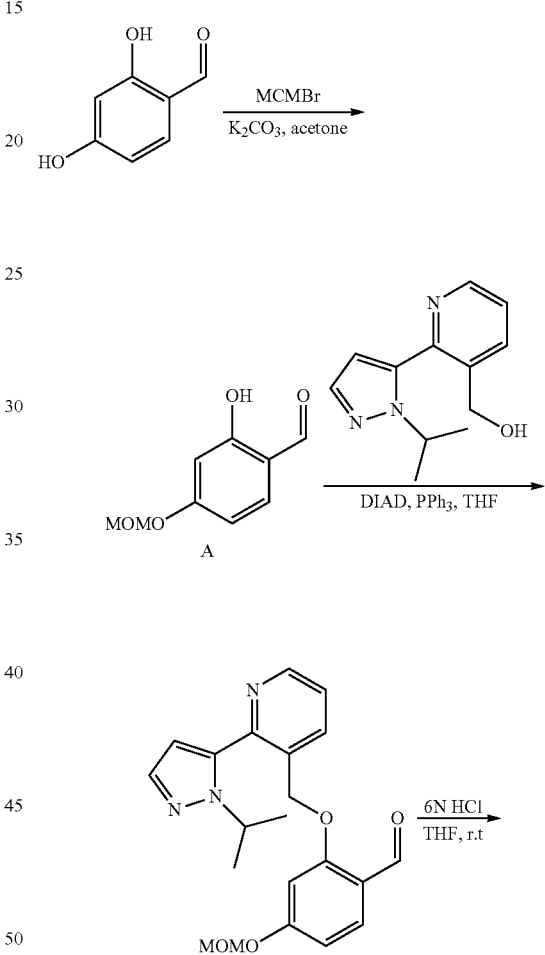

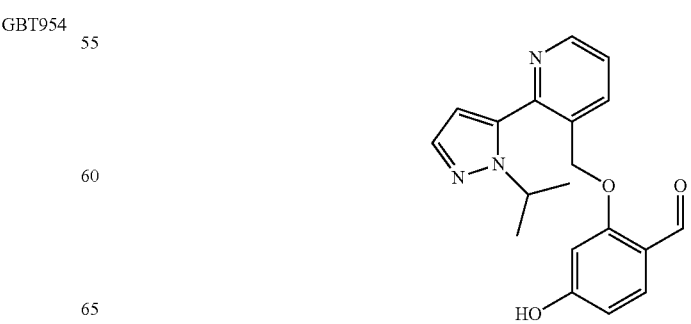

Preparation of Intermediate 2-hydroxy-4-(methoxymethoxy)benzaldehyde

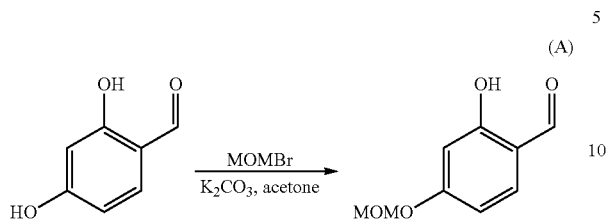

(A)

Into a 100-mL round-bottom flask, was placed a solution of 2,4-dihydroxybenzaldehyde (3 g, 21.72 mmol, 1.00 equiv), MOMBr (3.2 g, 25.60 mmol, 1.20 equiv), and potassium carbonate (3.9 g, 28.22 mmol, 1.30 equiv) in acetone (20 mL). The resulting solution was stirred overnight at room temperature. The resulting solution was diluted with 30 mL of H₂O. The resulting solution was extracted with 3×20 mL of dichloromethane and the organic layers combined and concentrated under vacuum. The residue was applied onto a silica gel column with ethyl acetate/petroleum ether (1:50-1:30) as eluent to furnish 2.6 g (66%) of 2-hydroxy-4-(methoxymethoxy)benzaldehyde as a white solid.

GBT967

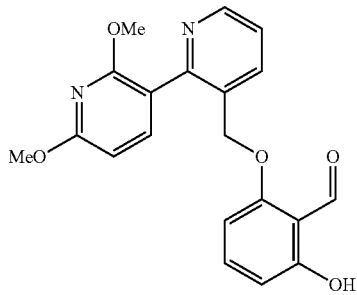

GHT967-2-((2',6'-dimethoxy-[2,3'-bipyridin]-3-yl)methoxy)-6-hydroxybenzaldehyde

The compound was prepared from (2-chloropyridin-3-yl)methanol and 2,6-dimethoxy-3-(4,4,5,5-tetramethyl-1,3,2-dioxaborolan-2-yl)pyridine according to scheme 9, reaction steps 1, 2 and 4. In step 4, alkylation with 2,6-dihydroxybenzaldehyde, the product of TFA salt as white solid was obtained after HPLC purification. ¹HNMR (400 MHz, DMSO, ppm): 10.04 (s, 1H), 8.65 (m, 1H), 8.14 (d, J=7.6 Hz, 1H), 7.73 (d, J=8 Hz, 1H), 7.51 (m, 2H), 6.50 (m, 3H), 5.16 (m, 2H), 3.91 (s, 1H), 3.86 (s, 1H); (ES, m/z): 367 [M+1]⁺

GBT000985

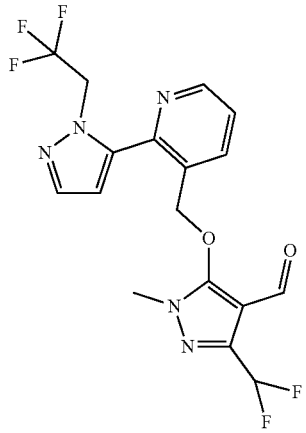

GBT985—3-(difluoromethyl)-1-methyl-5-((2-(1-(2,2,2-trifluoroethyl)-1H-pyrazol-5-yl)pyridin-3-yl)methoxy)-1H-pyrazole-4-carbaldehyde

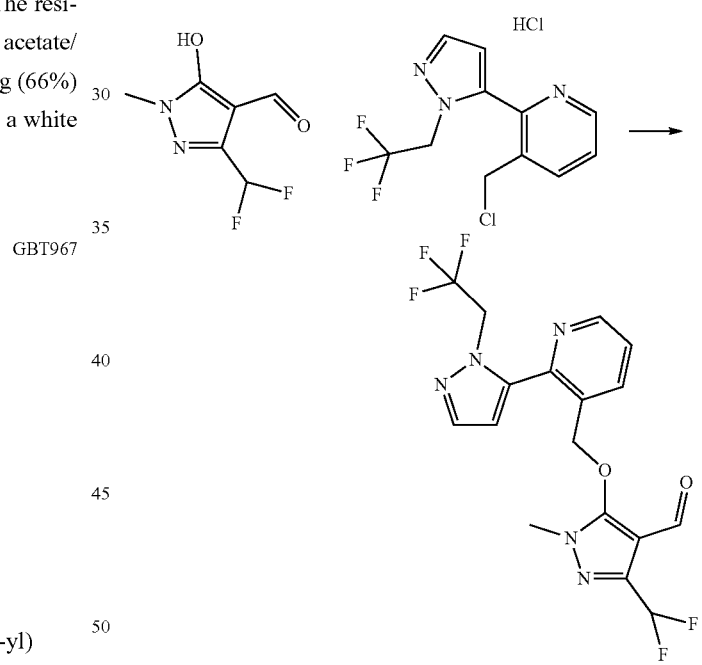

3-(Difluoromethyl)-5-hydroxy-1-methyl-1H-pyrazole-4-carbaldehyde (100 mg, 0.568 mmol) was dissolved in DMF (2.8 ml). 3-(chloromethyl)-2-(1-(2,2,2-trifluoroethyl)-1H-pyrazol-5-yl)pyridine hydrochloride (0.195 g, 0.625 mmol) and potassium carbonate (0.235 g, 1.7 mmol) were then added and the mixture was stirred in a 60° C. heat block for 16 h. The reaction mixture was cooled and water (50 ml) and ethyl acetate (100 ml) were added. The phases were separated and the aqueous phase was extracted with ethyl acetate (2×50 ml). The combined organic phases were washed with water (20 ml) and a saturated aqueous sodium chloride solution (20 ml). After drying over sodium sulfate and evaporation, the residue was purified by silica gel chromatography (5-50% ethyl acetate/hexanes) to give 86 mg (36%) of 3-(difluoromethyl)-1-methyl-5-((2-(1-(2,2,2-trifluoroethyl)-1H-pyrazol-5-yl)pyridin-3-yl)methoxy)-1H-pyrazole-4-carbaldehyde as an off-white solid. $^1$H NMR (400 (MHz, CDCl$_3$) δ 9.97 (s, 1H), 8.75 (d, J=3.64 Hz, 1H), 8.08 (d, J=7.31 Hz, 1H), 7.68 (d, J=1.69 Hz, 1H), 7.44 (dd, J=4.66, 7.83 Hz, 1H), 6.65 (t, J=53.67 Hz, 1H), 6.61 (d, J=1.78 Hz, 1H), 5.64 (s, 2H), 5.24 (q, J=8.60 Hz, 2H), 3.54 (s, 3H). MS (ESI) m/z 416 [M+H]$^+$.

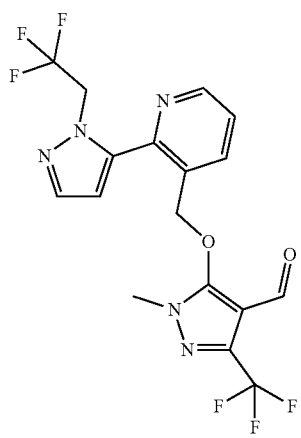

GBT986

GBT986—1-methyl-5-((2-(1-(2,2,2-trifluoroethyl)-1H-pyrazol-5-yl)pyridin-3-yl)methoxy)-3-(trifluoromethyl)-1H-pyrazole-4-carbaldehyde

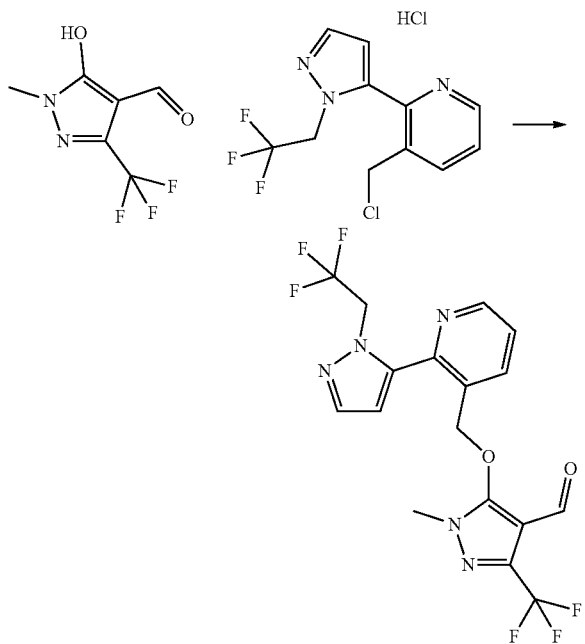

5-Hydroxy-1-methyl-3-(trifluoromethyl)-1H-pyrazole-4-carbaldehyde (100 mg, 0.515 mmol) was dissolved in DMF (2.5 ml). 3-(chloromethyl)-2-(1-(2,2,2-trifluoroethyl)-1H-pyrazol-5-yl)pyridine hydrochloride (0.177 g, 0.567 mmol) and potassium carbonate (0.213 g, 1.545 mmol) were then added and the mixture was stirred in a 60° C. heat block for 16 h. The reaction mixture was cooled and water (50 ml) and ethyl acetate (100 ml) were added. The phases were separated and the aqueous phase was extracted with ethyl acetate (2×50 ml). The combined organic phases were washed with water (20 ml) and a saturated aqueous sodium chloride solution (20 ml). After drying over sodium sulfate and evaporation, the residue was purified by silica gel chromatography (5-50% ethyl acetate/hexanes) to give 86 mg (36%) of 1-methyl-5-((2-(1-(2,2,2-trifluoroethyl)-1H-pyrazol-5-yl)pyridin-3-yl)methoxy)-3-(trifluoromethyl)-1H-pyrazole-4-carbaldehyde as an off-white solid. $^1$H NMR (400 MHz, CDCl$_3$) δ 9.87 (s, 1H), 8.75 (d, J=4.33 Hz, 1H), 8.08 (d, J=7.73 Hz, 1H), 7.68 (d, J=1.74 Hz, 1H), 7.45 (dd, J=4.64, 7.84 Hz, 1H), 6.59 (d, J=1.70 Hz, 1H), 5.63 (s, 2H), 5.24 (q, J=8.60 Hz, 2H), 3.57 (s, 3H). MS (ESI) m/z 434 [M+H]$^+$.

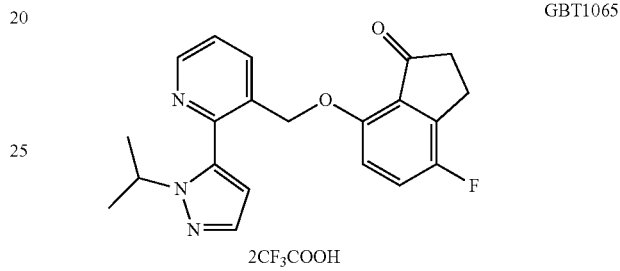

GBT1065

GBT1065—4-fluoro-7-((2-(1-isopropyl-1H-pyrazol-5-yl)pyridin-3-yl)methoxy)-2,3-dihydro-1H-inden-1-one bis(2,2,2-trifluoroacetate)

The compound was prepared by Mitsunobu reaction of 4-fluoro-7-hydroxy-2,3-dihydro-1H-inden-1-one with [2-[1-(propan-2-yl)-1H-pyrazol-5-yl]pyridin-3-yl]methanol according to scheme 9, reaction step 3. The product TFA salt as white solid was obtained after HPLC purification. $^1$HNMR (300 MHz, DMSO, ppm): 8.72 (m, 1H), 8.23 (m, 1H), 7.56 (m, 1H), 7.51 (d, J=1.8 Hz, 1H), 7.43 (m, 1H), 6.93 (m, 1H), 6.58 (d, J=1.8 Hz, 1H), 5.08 (s, 2H), 4.63 (m, 1H), 3.03 (m, 2H), 2.61 (m, 2H), 1.33 (d, J=6.6 Hz, 6H); MS (ES, m/z): 366[M+1]$^+$

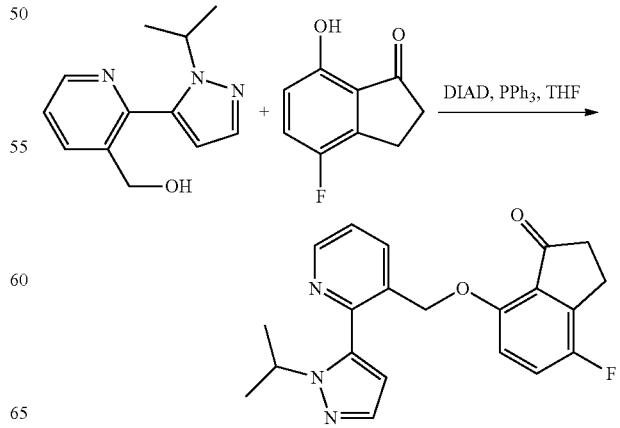

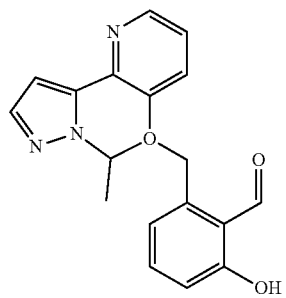

GBT1133—2-(((2-(1-isopropyl-1H-pyrazol-5-yl)pyridin-3-yl)oxy)methyl)benzaldehyde The compound was prepared from ethyl 2-(bromomethyl)benzonitrile in 2 steps according to reaction scheme below.

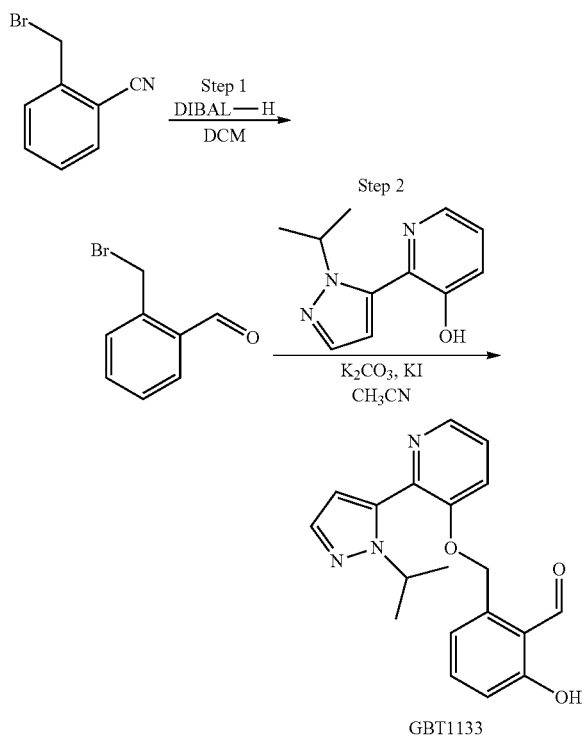

Step 1:
Into a 100-mL round-bottom flask, was placed a solution of 2-(bromomethyl)benzonitrile (1.0 g, 5.10 mmol, 1.00 equiv) in dichloromethane (40 mL). This was followed by the addition of DIBAL-H (5.5 mL, 1.10 equiv) at 0° C. The resulting solution was stirred for 3.5 h at 0° C. The reaction was then quenched by the addition of 10 mL of 5% HBr at 0° C. The resulting solution was extracted with 3×30 mL of dichloromethane and the combined organic layers were dried over anhydrous sodium sulfate. The residue was applied onto a silica gel column with ethyl acetate/petroleum ether (1:10) as eluent. This resulted in 500 mg (49%) of 2-(bromomethyl)benzaldehyde as a green oil.

Step 2:
Into a 50-mL round-bottom flask, was placed a solution of 2-(bromomethyl)benzaldehyde (150 mg, 0.75 mmol, 1.00 equiv) in CH$_3$CN (25 mL). 2-[1-(Propan-2-yl)-1H-pyrazol-5-yl]pyridin-3-ol (150 mg, 0.74 mmol, 1.00 equiv), potassium carbonate (210 mg, 1.52 mmol, 2.00 equiv), and KI (40 mg, 0.30 equiv) were added to the reaction. The resulting solution was heated to reflux for 6 h, and then it was cooled to rt. The resulting solution was diluted with 20 mL of H$_2$O, and then it was extracted with 3×20 mL of ethyl acetate. The combined organic layers were washed with 1×30 mL of brine and concentrated under vacuum. The crude product (200 mg) was purified by Prep-HPLC with the following conditions (Prep-HPLC-010): Column, SunFire Prep C18 OBD Column, 5 um, 19*150 mm; mobile phase, water with 0.05% TFA and MeCN (38.0% MeCN up to 55.0% in 8 min); Detector, nm. This provided 98.6 mg (41%) of 2-[([2-[1-(propan-2-yl)-1H-pyrazol-5-yl]pyridin-3-yl]oxy)methyl]benzaldehyde as a light yellow solid; $^1$HNMR (300 MHz, CDCl$_3$, ppm): 10.01 (s, 1H), 8.43 (m, 1H), 7.88 (m, 1H), 7.86 (m, 1H), 7.61-7.79 (m, 6H), 6.61 (d, J=2.1 Hz, 1H), 5.60 (s, 2H), 4.69-4.78 (m, 1H), 1.46 (d, J=6.6 Hz, 6H); (ES, m/z): 322 [M+1]$^+$ GBT1197

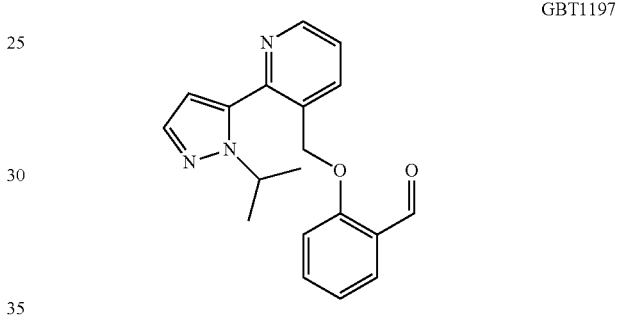

GBT1197—2-((2-(1-isopropyl-1H-pyrazol-5-yl)pyridin-3-yl)methoxy)benzaldehyde

The compound was prepared by O-alkylation of 2-hydroxybenzaldehyde with 3-(chloromethyl)-2-(1-isopropyl-1H-pyrazol-5-yl)pyridine (INT-4). The product of TFA salt as white solid was obtained after HPLC purification. $^1$HNMR (300 MHz, CDCl$_3$, ppm): 10.49 (s, 1H), 8.78 (m, 1H), 8.16 (m, 1H), 7.88 (m, 1H), 7.69 (d, J=6.0 Hz, 1H), 7.54 (m, 2H), 7.13 (m, 1H), 6.90 (d, J=8.4 Hz, 1H), 6.41 (d, J=1.8 Hz, 1H), 5.11 (s, 2H), 4.62 (m, 1H); (ES, m/z): 322[M+1]$^+$

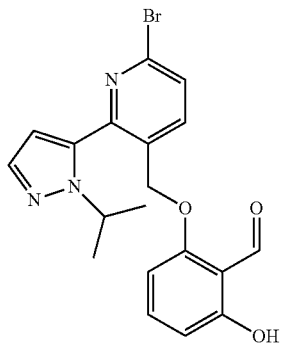

GBT1252

GBT1252-2-((6-bromo-2-(1-isopropyl-1H-pyrazol-5-yl)pyridin-3-yl)methoxy)-6-hydroxybenzaldehyde The compound was prepared by Mitsunobu reaction of (6-bromo-2-(1-isopropyl-1H-pyrazol-5-yl)pyridin-3-yl) methanol (intermediate A) and 2,6-dihydroxybenzaldehyde (INT-3) according to scheme 9, reaction step 3. The product as white solid was obtained after flash column purification. $^1$HNMR (300 MHz, DMSO, ppm): 11.70 (s, 1H), 11.20 (s, 1H), 8.17 (d, J=8.1 Hz, 1H), 7.81 (d, J=8.1 Hz, 1H), 7.57 (s, 1H), 7.50 (t, J=8.4 Hz, 1H), 6.60 (s, 1H), 6.55 (dd, J=8.4 Hz, 3.6 Hz, 1H), 5.19 (s, 2H), 4.65-4.55 (m, 1H), 1.38 (d, J=6.6 Hz, 6H); (ES, m/z:) 418.1 [M+1]$^+$

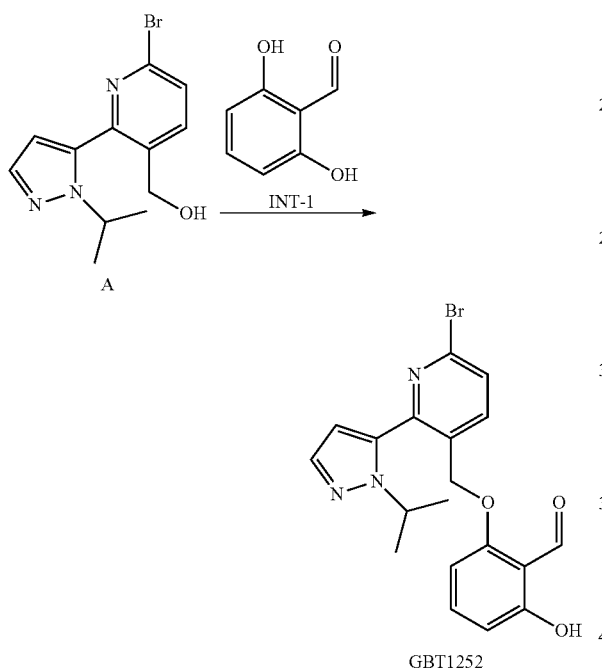

Preparation of Intermediate A

Intermediate A was prepared from 2,6-dichloropyridine-3-carboxylic acid in five steps according to the synthetic scheme below.

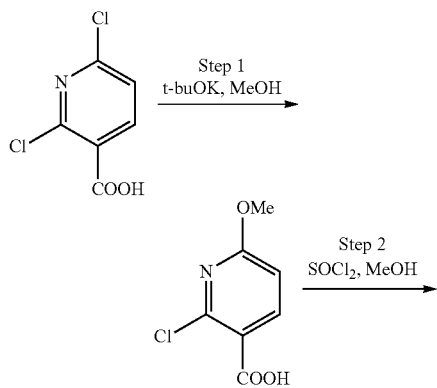

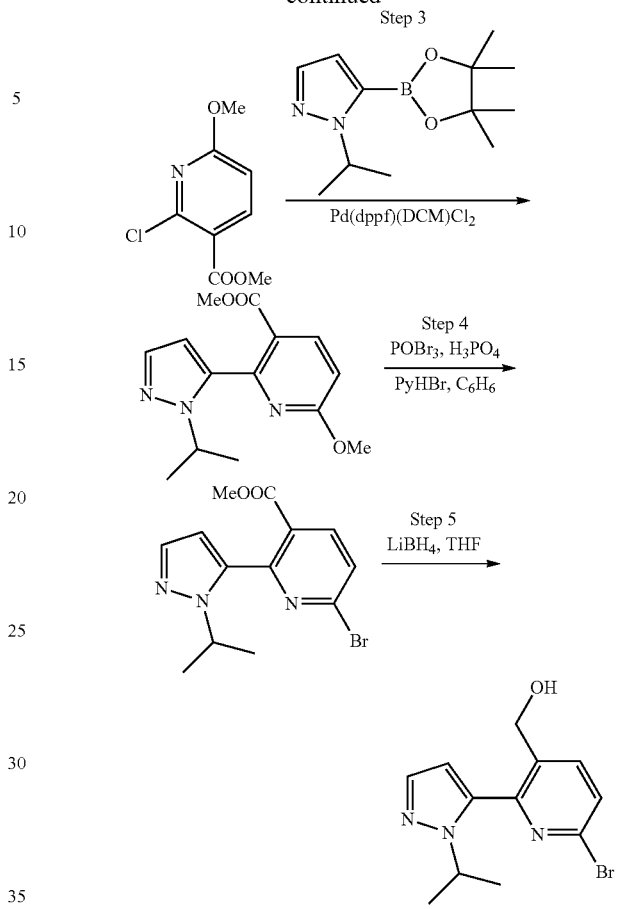

Step 1: Into a 500-mL round-bottom flask, was placed a solution of 2,6-dichloropyridine-3-carboxylic acid (25 g, 130.21 mmol, 1.00 equiv) in methanol (350 mL). This was followed by the addition of t-BuOK (43.8 g, 390.34 mmol, 3.00 equiv), in portions at 0° C. The resulting solution was heated to reflux for 3 days. The resulting mixture was concentrated under vacuum, and then it was diluted with 400 mL of water. The pH value of the solution was adjusted to 1 with hydrogen chloride aq. The solids were collected by filtration. The solid was dried in an oven under reduced pressure. This provided 20.5 g (84%) of 2-chloro-6-methoxypyridine-3-carboxylic acid as a white solid.

Step 2: Into a 100-mL round-bottom flask, was placed a solution of 2-chloro-6-methoxypyridine-3-carboxylic acid (11.3 g, 60.24 mmol, 1.00 equiv) in methanol (50 mL). This was followed by the addition of SOCl$_2$ (26 mL, 5.00 equiv) dropwise with stirring at 0 OC. The resulting solution was stirred for 1 h at room temperature and for an additional 2 h at reflux. The resulting solution was diluted with 100 mL of water. The pH value of the solution was adjusted to 10 with 2M sodium carbonate aq. The resulting solution was extracted with 3×80 mL of ethyl acetate and the organic layers combined. The resulting mixture was washed with 1×150 mL of water and 1×100 mL of brine, dried over anhydrous sodium sulfate and concentrated under vacuum. The residue was applied onto a silica gel column with ethyl acetate/petroleum ether (1:10) as eluent to furnish 7.8 g (64%) of methyl 2-chloro-6-methoxypyridine-3-carboxylate as a white solid.

Step 3: Into a 100-mL round-bottom flask, which was purged and maintained with an inert atmosphere of nitrogen, was placed methyl 2-chloro-6-methoxypyridine-3-carboxylate (3.29 g, 16.32 mmol, 1.00 equiv), 1-(propan-2-yl)-5-(tetramethyl-1,3,2-dioxaborolan-2-yl)-1H-pyrazole (4.63 g, 19.61 mmol, 1.20 equiv), toluene (45 mL), ethanol (15 mL), sodium carbonate (2M in H$_2$O) (15 mL). This was followed by the addition of Pd(dppf)(DCM)Cl$_2$ (665 mg, 0.05 equiv). The resulting solution was stirred for 20 h at 90° C. The reaction was then quenched by the addition of 20 mL of water and 100 mL of ethyl acetate. The resulting mixture was washed with 2×50 mL of water and 1×50 mL of brine. The mixture was dried over anhydrous sodium sulfate. The residue was applied onto a silica gel column with ethyl acetate/petroleum ether (1:25-1:15) as eluent to furnish 3.83 g (85%) of methyl 6-methoxy-2-[1-(propan-2-yl)-1H-pyrazol-5-yl]pyridine-3-carboxylate as a light yellow oil.

Step 4: Into a 250-mL round-bottom flask, was placed methyl 6-methoxy-2-[1-(propan-2-yl)-1H-pyrazol-5-yl]pyridine-3-carboxylate (3.6 g, 13.08 mmol, 1.00 equiv), C$_6$H$_6$ (60 mL), H$_3$PO$_4$(85%) (150 mg, 1.53 mmol, 0.10 equiv), PyHBr (208 mg, 1.30 mmol, 0.10 equiv), POBr$_3$ (11.5 g, 40.11 mmol, 3.00 equiv). The resulting solution was heated to reflux for 40 h. The reaction mixture was cooled to 0° C. with an ice bath. The pH value of the solution was adjusted to 10 with potassium carbonate sat. The resulting solution was extracted with 3×80 mL of ethyl acetate and the organic layers combined. The resulting mixture was washed with 2×50 mL, of water and 1×50 mL of brine. The mixture was dried over anhydrous sodium sulfate and concentrated under vacuum. The residue was applied onto a silica gel column with ethyl acetate/petroleum ether (1:10-1:8) as eluent. This provided 2.62 g (62%) of methyl 6-bromo-2-[1-(propan-2-yl)-1H-pyrazol-5-yl]pyridine-3-carboxylate as a yellow oil.

Step 5: Into a 50-mL round-bottom flask, was placed methyl 6-bromo-2-[1-(propan-2-yl)-1H-pyrazol-5-yl]pyridine-3-carboxylate (2.62 g, 8.08 mmol, 1.00 equiv), tetrahydrofuran (30 mL). This was followed by the addition of LiBH$_4$ (350 mg, 16.07 mmol, 2.00 equiv) at 0° C. The resulting solution was stirred for 30 min at 0° C. and for an additional 1 h at room temperature. The reaction mixture was cooled to 0° C. with an ice bath. The reaction was then quenched by the addition of 20 mL of water. The resulting solution was extracted with 3×60 mL of ethyl acetate and the organic layers combined. The resulting mixture was washed with 2×50 mL of water and 1×50 mL of brine. The mixture was dried over anhydrous sodium sulfate and concentrated under vacuum. The residue was applied onto a silica gel column with ethyl acetate/petroleum ether (1:8-1:5) as eluent to furnish 1.97 g quenched by the addition of 100 mL of sodium hydroxide (aq). The pH value of the solution was adjusted to 12 with sodium hydroxide (aq). The resulting solution was extracted with 3×60 mL of ethyl acetate. The combined organic layers were washed with 1×60 mL of water and 1×60 mL of brine, dried over anhydrous sodium sulfate and concentrated under vacuum. The residue was applied onto a silica gel column with ethyl acetate/petroleum ether (1:1-1:0) as eluent to yield 2.08 g (75%) of 4-(dimethylamino)-2,6-dimethoxybenzaldehyde (3) as a white solid.

Step 3: Into a 50-mL round-bottom flask, was placed a solution of 4-(dimethylamino)-2,6-dimethoxybenzaldehyde (3) (630 mg, 3.01 mmol, 1.00 equiv) in dichloromethane (25 mL). AlCl$_3$ (6 g, 45.11 mmol, 12.50 equiv) was added to the reaction. The resulting solution was heated to reflux for 24 h. The pH value of the solution was adjusted to 8-9 with sodium bicarbonate (aq). The resulting solution was extracted with 3×80 mL of ethyl acetate. The combined organic layers were washed with 1×60 mL of water and 1×60 mL of brine, dried over anhydrous sodium sulfate and concentrated under vacuum. The residue was applied onto a silica gel column with ethyl acetate/petroleum ether (1:4) as eluent to furnish 383 mg (70%) of 4-(dimethylamino)-2,6-dihydroxybenzaldehyde (4) as a light yellow solid.

Step 4: Into a 25-mL round-bottom flask, was placed a solution of [2-[1-(propan-2-yl)-1H-pyrazol-5-yl]pyridin-3-yl]methanol (5) (132 mg, 0.61 mmol, 1.00 equiv), 4-(dimethylamino)-2,6-dihydroxybenzaldehyde (4) (110 mg, 0.61 mmol, 1.00 equiv), PPh$_3$ (207.3 mg, 0.79 mmol, 1.30 equiv) in tetrahydrofuran (10 mL). DIAD (160 mg, 0.79 mmol, 1.30 equiv) was added to the reaction dropwise at 0° C. The resulting solution was stirred for 10 min at 0° C. and for an additional 2 h at room temperature. The reaction was then quenched with 10 mL of water. The resulting solution was extracted with 3×40 ml, of ethyl acetate. The combined organic layers were washed with 3×20 mL of water and 1×20 mL of brine, dried over anhydrous sodium sulfate and concentrated under vacuum. The crude product was purified by Prep-HPLC with the following conditions (Prep-HPLC-010): Column, SunFire Prep C18 OBD Column, 5 um, 19*150 mm; mobile phase, water with 0.05% TFA and MeCN (30.0% MeCN up to 60.0% in 10 min. up to 95.0% in 4 min. down to 30.0% in 2 min); Detector, Waters2545 UvDector 254&220 nm. This resulted in 60 mg (26%) of 4-(dimethylamino)-2-hydroxy-6-([2-[1-(propan-2-yl)-1H-pyrazol-5-yl]pyridin-3-yl]methoxy)benzaldehyde (GBT933) as a light yellow solid.

(82%) of [6-bromo-2-[1-(propan-2-yl)-1H-pyrazol-5-yl]pyridin-3-yl]methanol as a light yellow solid.

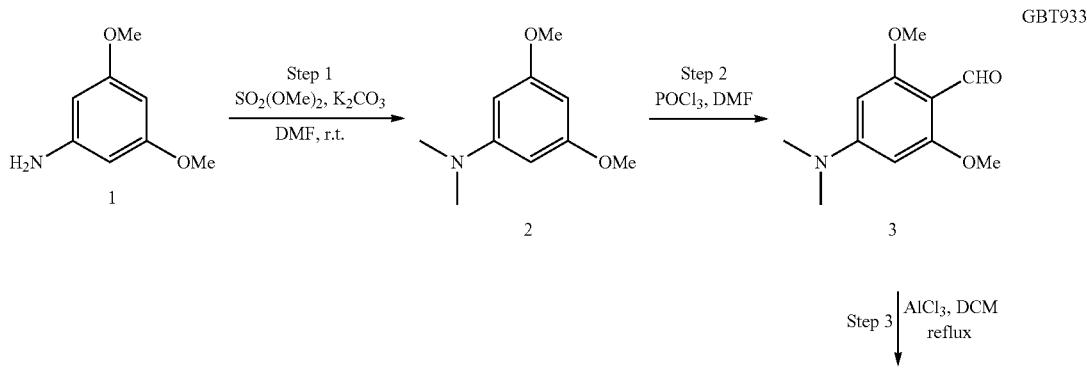

-continued

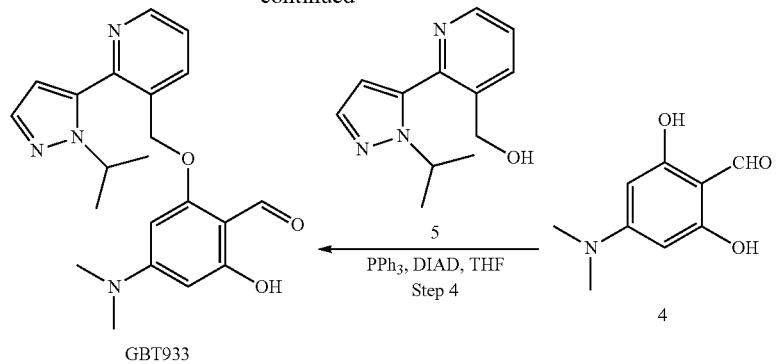

GBT933—4-(dimethylamino)-2-hydroxy-6-((2-(1-isopropyl-H-pyrazol-5-yl)pyridin-3-yl)methoxy)benzaldehyde Step 1: Into a 250-mL round-bottom flask, was placed a solution of 3,5-dimethoxyaniline (1) (4.6 g, 30.03 mmol, 1.00 equiv) and potassium carbonate (14.6 g, 105.64 mmol, 4.00 equiv) in N,N-dimethylformamide (80 mL). This was followed by the addition of $SO_2(OMe)_2$ (8.4 g, 66.67 mmol, 2.00 equiv) dropwise with stirring at 0° C. The mixture was stirred for 2 h at 0° C. The resulting solution was stirred overnight at room temperature, and then it was quenched by the addition of 100 mL of water. The resulting solution was extracted with 2×80 mL of ethyl acetate. The combined organic layers were washed with 1×50 mL of water and 1×50 mL of brine, dried over anhydrous sodium sulfate. The residue was applied onto a silica gel column with PE:EA (30:1-10:1) as eluent to furnish 2.8 g (51%) of 3,5-dimethoxy-N,N-dimethylaniline (2) as a white solid.

Step 2: Into a 50-mL round-bottom flask, was placed a solution of 3,5-dimethoxy-N,N-dimethylaniline (2) (2.4 g, 13.24 mmol, 1.00 equiv) in N,N-dimethylformamide (25 mL). This was followed by the addition of $POCl_3$ (2.57 g, 16.76 mmol, 1.30 equiv) dropwise with stirring at 0° C. The resulting solution was stirred for 15 min at 0° C., and then it was $^1$HNMR (400 MHz, $CDCl_3$, ppm): 12.45 (br s, 1H), 9.87 (s, 1H), 8.70 (d, J=4.0 Hz, 1H), 7.96 (d, J=7.2 Hz, 1H), 7.58 (s, 1H), 7.42-7.39 (m, 1H), 6.32 (s, 1H), 5.68 (s, 1H), 5.43 (s, 1H), 4.94 (s, 2H), 4.58-4.51 (m, 1H), 2.96 (s, 6H), 1.40 (d, J=6.8 Hz, 1H); MS (ES, m/z:) 381.2 [M−2$CF_3$COOH+1]$^+$

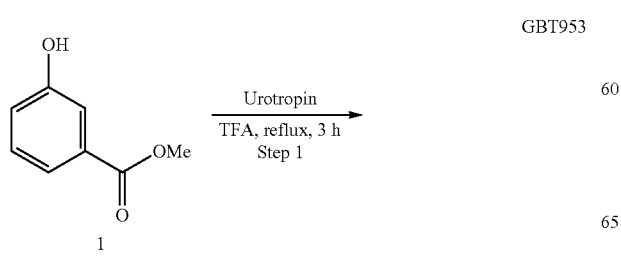

-continued

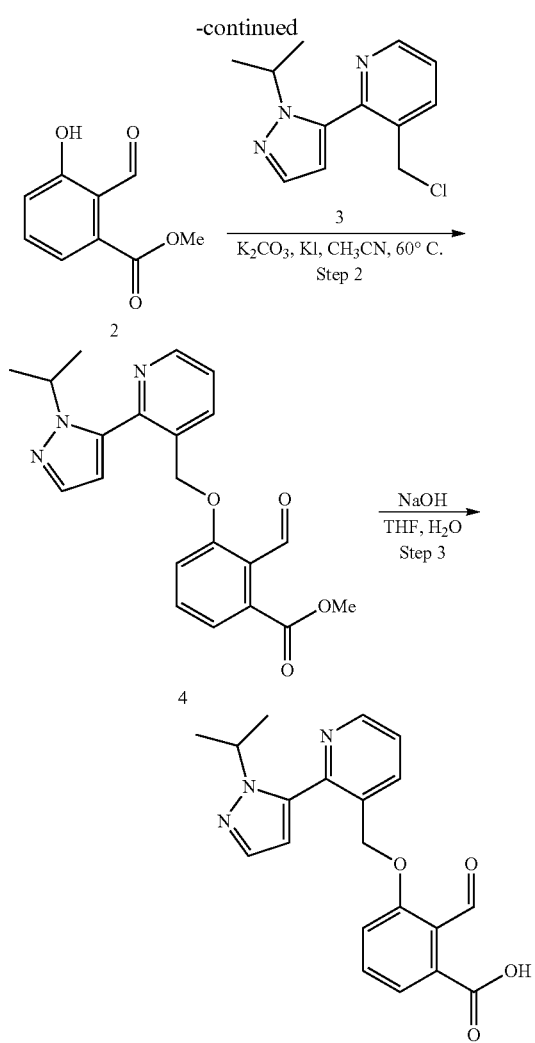

GBT953—(S)-2-hydroxy-6-((2-(1-isopropyl-1H-pyrazol-5-yl)pyridin-3-yl)methoxy)benzaldehyde Step 1: Into a 250-mL round-bottom flask, was placed a solution of methyl 3-hydroxybenzoate (3 g, 19.72 mmol, 1.00 equiv) in trifluoroacetic acid (100 mL). Urotropin (5.5 g, 39.29 mmol, 2.00 equiv) was added to the reaction. The resulting solution was heated to reflux for 2 hr. The resulting mixture was concentrated under vacuum. The residue was applied onto a silica gel column with ethyl acetate/petroleum ether (1:5) as eluent to furnish 0.5 g (14%) of methyl 2-formyl-3-hydroxybenzoate as a yellow solid.

Step 2: Into a 100-mL round-bottom flask, was placed a solution of methyl 2-formyl-3-hydroxybenzoate (400 mg, 2.22 mmol, 1.00 equiv) in CH3CN (30 mL). 3-(Chloromethyl)-2-[1-(propan-2-yl)-1H-pyrazol-5-yl]pyridine (523 mg, 2.22 mmol, 1.00 equiv), potassium carbonate (927 mg, 6.71 mmol, 3.00 equiv), and KI (40 mg, 0.24 mmol, 0.10 equiv) were added to the reaction. The resulting solution was stirred for 2 h at 60° C., and then it was diluted with 200 ml of EA. The resulting mixture was washed with 2×100 mL of brine, and then it was concentrated under vacuum. This provided 500 mg (59%) of methyl 2-formyl-3-([2-[1-(propan-2-yl)-1H-pyrazol-5-yl]pyridin-3-yl]methoxy)benzoate as a yellow oil.

Step 3: Into a 100-mL round-bottom flask, was placed a solution of methyl 2-formyl-3-([2-[1-(propan-2-yl)-1H-pyrazol-5-yl]pyridin-3-yl]methoxy)benzoate (100 mg, 0.26 mmol, 1.00 equiv) in tetrahydrofuran (10 mL). This was followed by the addition of a solution of sodium hydroxide (22 mg, 0.55 mmol, 2.00 equiv) in water (3 mL) dropwise with stirring at 0° C. The resulting solution was stirred for 3 h at room temperature. The pH value of the solution was adjusted to 6 with hydrogen chloride (3 mol/L). The resulting solution was extracted with 2×100 mL of ethyl acetate and the organic layers combined and concentrated under vacuum. The crude product (100 mg) was purified by Prep-HPLC with the following conditions (Prep-HPLC-010): Column, SunFire Prep C18 OBD Column, 5 um, 19*150 mm; mobile phase, water with 0.05% TFA and MeCN (30% MeCN up to 60o/o in 10 min, up to 95% in 3 min, down to 30% in 2 min); Detector, Waters2545 UvDector 254&220 nm. This resulted in 30 mg (19%) of 2-formyl-3-([2-[1-(propan-2-yl)-1H-pyrazol-5-yl]pyridin-3-yl] methoxy)benzoic acid: bis(trifluoroacetic acid) as a white solid. $^1$HNMR (300 MHz, DMSO, ppm): 8.75 (dd, J=4.8 Hz, 1H), 8.15 (m, 2H), 7.59 (m, 3H), 7.40 (d, J=7.8 Hz, 1H), 7.33 (d, J=8.1 Hz, 1H), 6.66 ((d, J=7.8 Hz, 1H), 6.60 (s, 1H), 5.18 (m, 2H), 4.70 (m, 1H), 1.35 (m, 6H); MS (ES, m/z):366 [M+1]+

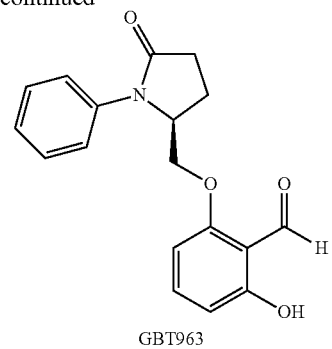

GBT963

GBT963—(S)-2-hydroxy-6-((5-oxo-1-phenylpyrrolidin-2-yl)methoxy)benzaldehyde

Step 1: To a suspension of (S)-5-(hydroxymethyl)pyrrolidin-2-one (230 mg, 2 mmol) and iodobenzene (0.49 g, 2.4 mmol) in Dioxane (4 mL) was added CuI (0.08 g, 0.4 mmol), N,N-dimethylethylenediamine (0.05 mL, 0.4 mmol), K$_2$CO$_3$ (0.55 g, 4 mmol). After heating at 100° C. for 24 h, the mixture was cooled and was diluted with EtOAc, insoluble material was filtered off, the filtrate was concentrated and purified by column (Hexanes/EtOAc=100:0 to 0:100) to give (S)-5-(hydroxymethyl)-1-phenylpyrrolidin-2-one (280 mg).

Step 2: To a solution of (S)-5-(hydroxymethyl)-1-phenylpyrrolidin-2-one (100 mg, 0.52 mmol) and 2,6-dihydroxybenzaldehyde (0.09 g, 0.65 mmol) in THF (5 mL) at 0° C. was added PPh$_3$ (polymer supported, 650 mg, 0.78 mmol) and DIAD (0.16 mL, 0.78 mmol). After stirred for 1 h, it was diluted with AcCN, the insoluble material was filtered off and the filtrate was concentrated and purified by preparative HPLC to give (S)-2-hydroxy-6-((5-oxo-1-phenylpyrrolidin-2-yl)methoxy)benzaldehyde (86 mg). $^1$H NMR (400 MHz, Chloroform-d) δ 11.91 (d, J=0.4 Hz, 1H), 9.93 (d, J=0.6 Hz, 1H), 7.50-7.18 (m, 6H), 6.53 (dt, J=8.5, 0.7 Hz, 1H), 6.21 (dd, J=8.3, 0.8 Hz, 1H), 4.70-4.59 (m, 1H), 4.15-4.01 (m, 2H), 2.82-2.58 (m, 2H), 2.50 (ddt, J=13.1, 9.9, 8.3 Hz, 1H), 2.16 (dddd, J=13.6, 9.5, 5.1, 3.9 Hz, 1H). MS found for C$_{18}$H$_{17}$NO$_4$: 312.3.

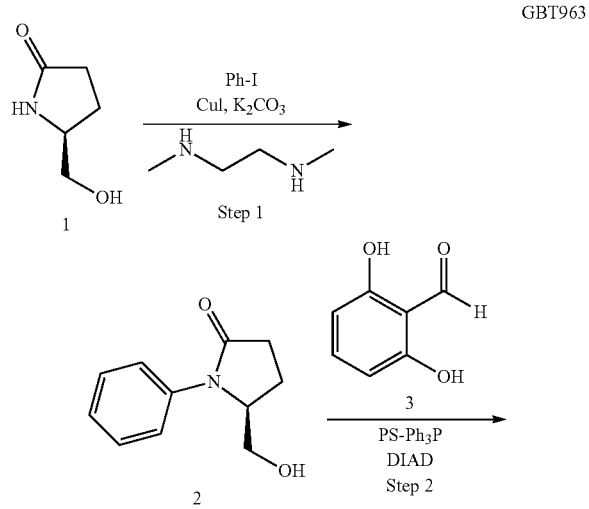

GBT963

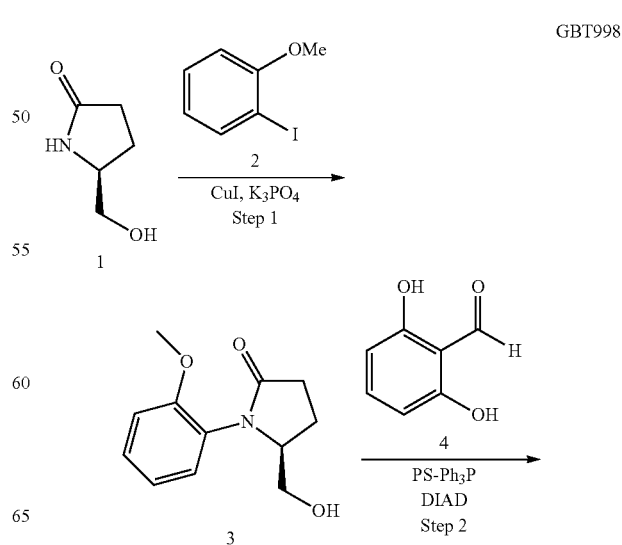

GBT998

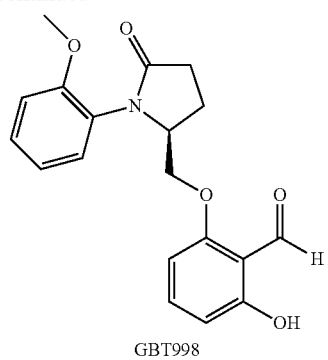

GBT998

GBT998—(S)-2-hydroxy-6-((5-oxo-1-phenylpyrroli-din-2-yl)methoxy)benzaldehyde Step 1: To a suspension of (S)-5-(hydroxymethyl)pyrrolidin-2-one (230 mg, 2 mmol) and 1-iodo-2-methoxybenzene (0.56 g, 2.4 mmol) in Dioxane (4 mL) was added CuI (0.08 g, 0.4 mmol), N,N-dimethylethylenediamine (0.05 mL, 0.4 mmol), $K_3PO_4$ (0.85 g, 4 mmol). After heating at 100° C. for 24 h, the mixture was cooled and was diluted with EtOAc, insoluble material was filtered off, the filtrate was concentrated and purified by column (Hexanes/EtOAc=100:0 to 0:100) to give (S)-5-(hydroxymethyl)-1-(2-methoxyphenyl)pyrrolidin-2-one (110 mg).

Step 2: To a solution of (S)-5-(hydroxymethyl)-1-phenylpyrrolidin-2-one (115 mg, 0.54 mmol) and 2,6-dihydroxybenzaldehyde (0.10 g, 0.70 mmol) in THF (4 mL) at 0 CC was added $PPh_3$ (polymer supported, 675 mg, 0.81 mmol) and DIAD (0.16 mL, 0.81 mmol). After stirred for 1 h, it was diluted with AcCN, the insoluble material was filtered off and the filtrate was concentrated and purified by column (100% EtOAc) to give (S)-2-hydroxy-6-((1-(2-methoxyphenyl)-5-oxopyrrolidin-2-yl)methoxy)benzaldehyde (53 mg). $^1$H NMR (400 MHz, Chloroform-d) δ 11.92 (s, 1H), 9.68 (t, J=0.5 Hz, 1H), 7.38-7.30 (m, 1H), 7.30-7.22 (m, 1H), 7.14 (dd, J=7.7, 1.7 Hz, 1H), 6.99-6.89 (m, 2H), 6.50 (dq, J=8.5, 0.6 Hz, 1H), 6.25-6.18 (m, 1H), 4.55 (dtd, J=9.0, 5.1, 4.0 Hz, 1H), 4.10-3.94 (m, 2H), 3.73 (s, 3H), 2.75-2.55 (m, 2H), 2.48 (dddd, J=13.0, 9.6, 8.4, 7.3 Hz, 1H), 2.16-2.02 (m, 1H). MS found for $C_{19}H_{19}NO_5$: 342.3.

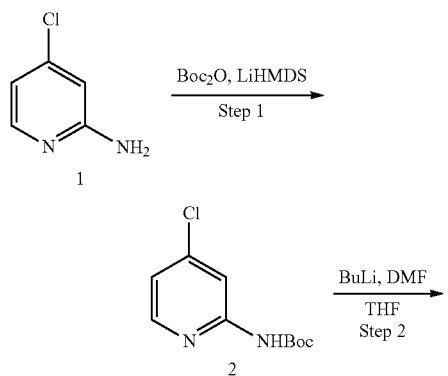

GBT1004

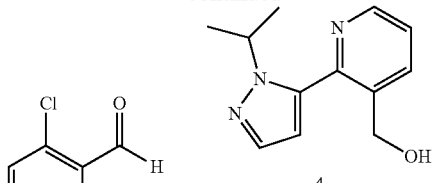

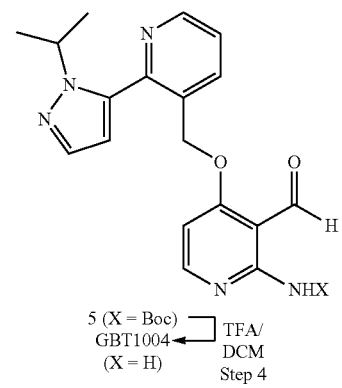

GBT1004—2-amino-4-((2-(1-isopropyl-1H-pyrazol-5-yl)pyridin-3-yl)methoxy) nicotinaldehyde Step 1: Into a 250-mL round-bottom flask, was placed a solution of 4-chloropyridin-2-amine (10 g, 77.78 mmol, 1.00 equiv) in tetrahydrofuran (150 mL). This was followed by the addition of LiHMDS(1 M) (156 mL) dropwise with stirring at 0° C. The mixture was stirred for 20 min at 0° C. To this was added $Boc_2O$ (17.02 g, 77.98 mmol, 1.00 equiv). The resulting solution was stirred for 1 h at 0° C. The reaction was then quenched by the addition of 100 mL of $NH_4Cl$. The resulting solution was extracted with 2×200 mL of ethyl acetate and the organic layers combined. The resulting mixture was washed with 1×150 mL of brine. The resulting mixture was concentrated under vacuum, washed with 2×20 mL of EA/hexane (3:7). This resulted in 12.5 g (70%) of tert-butyl N-(4-chloropyridin-2-yl)carbamate as a white solid.

Step 2: Into a 100-mL three neck round-bottom flask, was placed a solution of tert-butyl N-(4-chloropyridin-2-yl)carbamate (2 g, 8.75 mmol, 1.00 equiv) in tetrahydrofuran (50 mL). This was followed by the addition of BuLi (2.5M) (7.0 mL, 2.00 equiv) dropwise with stirring at −78° C. in 20 min. The mixture was stirred for 0.5 h at −78° C. To this was added N,N-dimethylformamide (2.0 mL, 3.00 equiv) dropwise with stirring at −78° C. in 5 min. The resulting solution was stirred for 1 h at −78° C. The reaction was then quenched by the addition of 3 mL of hydrogen chloride (12M). The resulting mixture was concentrated under vacuum. The resulting solution was diluted with 50 ml, of ethyl acetate. The resulting mixture was washed with 1×40 mL of 5% sodium bicarbonate and 1×30 mL of brine. The resulting mixture was concentrated under vacuum. The residue was applied onto a silica gel column with EA:PE (1:4). This resulted in 1.46 g (65%) of tert-butyl N-(4-chloro-3-formylpyridin-2-yl)carbamate as a yellow solid.

Step 3: Into a 100-mL round-bottom flask, was placed a solution of [2-[1-(propan-2-yl)-1H-pyrazol-5-yl]pyridin-3- yl]methanol (500 mg, 2.30 mmol, 1.20 equiv) in N,N-dimethylformamide (50 mL). This was followed by the addition of sodium hydride (190 mg, 7.92 mmol, 2.50 equiv) at 0° C. The mixture was stirred for 20 min at 0° C. To this was added tert-butyl N-(4-chloro-3-formylpyridin-2-yl)carbamate (500 mg, 1.95 mmol, 1.00 equiv). The resulting solution was stirred overnight at room temperature, and then it was quenched by the addition of S0 mL of water. The resulting solution was extracted with 8×20 mL of ethyl acetate and the organic layers combined and concentrated under vacuum. This resulted in 506 mg (59%) of tert-butyl N-[3-formyl-4-([2-[1-(propan-2-yl)-1H-pyrazol-5-yl]pyridin-3-yl]methoxy)pyridin-2-yl]carbamate as a yellow oil.

Step 4: Into a 100-mL round-bottom flask, was placed a solution of trifluoroacetic acid (10 mL) in dichloromethane (60 mL), tert-butyl N-[3-formyl-4-([2-[1-(propan-2-yl)-1H-pyrazol-5-yl]pyridin-3-yl]methoxy)pyridin-2-yl]carbamate (500 mg, 1.14 mmol, 1.00 equiv). The resulting solution was stirred overnight at room temperature. The resulting mixture was concentrated under vacuum. The crude product (500 mg) was purified by Prep-HPLC with the following conditions (Prep-HPLC-010): Column, SunFire Prep C18 OBD Column, 5 um, 19*150 mm; mobile phase, water with 0.05% TFA and MeCN (5.0% MeCN up to 26.0% in 10 min, up to 95.0% in 2 min, down to 5.0% in 2 min); Detector, Waters2545 UvDector 254&220 nm. This resulted in 122.9 mg (32%) of 2-amino-4-([2-[1-(propan-2-yl)-1H-pyrazol-5-yl]pyridin-3-yl]methoxy)pyridine-3-carbaldehyde as a yellow solid. $^1$HNMR (300 MHz, DMSO, ppm): 10.12 (s, 1H), 8.79 (m, 1H), 8.24 (m, 2H), 7.59 (m, 2H), 6.76 (d, J=5.1 Hz, 1H), 6.55 (d, J=1.2 Hz, 1H), 5.43 (m, 2H), 4.67 (m, 1H), 1.36 (m, 6H): MS (ES, m/z): 338 [M+1-3CF$_3$COOH]$^+$

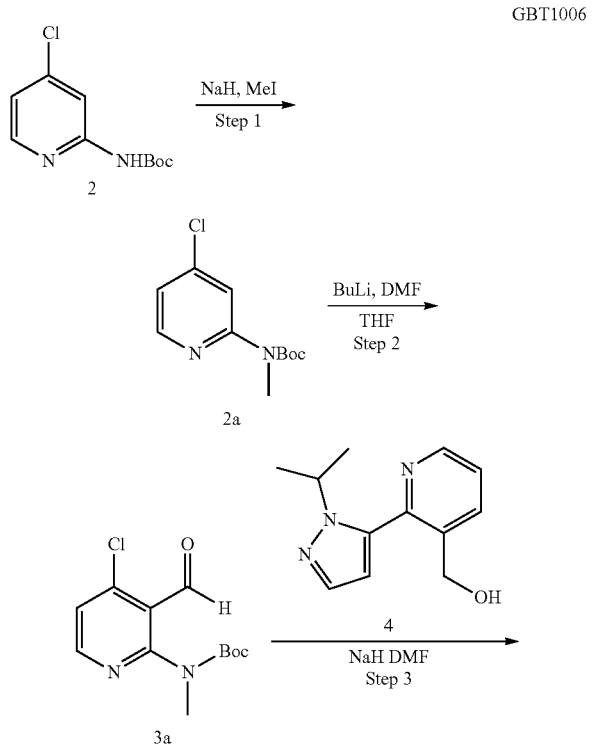

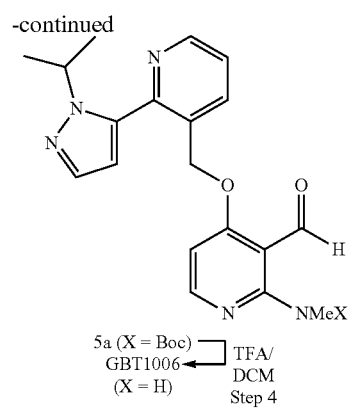

GBT1006—4-((2-(i-isopropyl-1H-pyrazol-5-yl)pyridin-3-yl)methoxy)-2-(methylamino)nicotinaldehyde Step 1: Into a 100-mL round-bottom flask, was placed a solution of tert-butyl N-(4-chloropyridin-2-yl)carbamate (3.0 g, 13.12 mmol, 1.00 equiv) in tetrahydrofuran (50 mL). This was followed by the addition of sodium hydride (631 mg, 26.29 mmol, 1.20 equiv) at 0° C. The mixture was stirred for 20 min at 0° C. To this was added iodomethane (2.24 g, 15.78 mmol, 1.20 equiv) dropwise with stirring. The resulting solution was stirred for 6 h at room temperature. The reaction was then quenched by the addition of 30 mL of water. The resulting solution was extracted with 3×30 mL, of ethyl acetate and the organic layers combined and concentrated under vacuum. This resulted in 3.01 g (95%) of tert-butyl N-(4-chloropyridin-2-yl)-N-methylcarbamate as a yellow oil.

Step 2: Into a 100-mL three neck round-bottom flask, was placed a solution of tert-butyl N-(4-chloropyridin-2-yl)-N-methylcarbamate (1.5 g, 6.18 mmol, 1.00 equiv) in tetrahydrofuran (50 mL). This was followed by the addition of BuLi (2.5M) (3.0 mL, 1.20 equiv) dropwise with stirring at –78° C. The mixture was stirred for 30 mins at –78° C. To this was added N,N-dimethylformamide (1.5 mL, 3.00 equiv) dropwise with stirring at –78° C. The resulting solution was stirred for 1 h at –78° C. The reaction was then quenched by the addition of 2.5 mL of hydrogen chloride (12M). The resulting mixture was concentrated under vacuum. The residue was dissolved in 40 mL of EA. The resulting mixture was washed with 1×30 mL of 5% sodium bicarbonate and 1×20 mL of brine. The resulting mixture was concentrated under vacuum. The residue was applied onto a silica gel column with EA:PE (1:4). This resulted in 0.97 g (92%) of 4-chloro-2-(methylamino)pyridine-3-carbaldehyde as a yellow solid.

Steps 3 &4: Into a 100-mL round-bottom flask, was placed a solution of [2-[1-(propan-2-yl)-1H-pyrazol-5-yl]pyridin-3-yl]methanol (1.15 g, 5.29 mmol, 1.00 equiv) in N,N-dimethylformamide (40 mL). This was followed by the addition of sodium hydride (530 mg, 13.25 mmol, 2.50 equiv, 60%) at 0° C. The mixture was stirred for 15 min at 0° C. To this was added 4-chloro-2-(methylamino)pyridine-3-carbaldehyde (900 mg, 5.28 mmol, 1.00 equiv). The resulting solution was stirred overnight at room temperature. The reaction was then quenched by the addition of 30 mL of water. The resulting solution was extracted with 5×30 mL of ethyl acetate and the organic layers combined and concentrated under vacuum. The crude product (300 mg) was purified by Prep-HPLC with the following conditions (Prep-HPLC-020): Column, SunFire Prep C18 OBD Column, 5 um, 19*100 mm; mobile phase, water with 0.1% TFA and MeCN (3.0% MeCN up to 20.0% in 5 min, up to 95.0% in 2 min, down to 3.0% in 1 min): Detector, waters2489 254&220 nm. This resulted in 107.1 mg (6%) of 2-(methylamino)-4-([2-[1-(propan-2-yl)-1H-pyrazol-5-yl]pyridin-3-yl]methoxy)pyridine-3-carbaldehyde as a yellow solid. $^1$HNMR (400 MHz, DMSO, ppm): 8.72 (m, 1H), 8.17 (s, 1H), 7.91 (m, 1H), 7.52 (m, 3H), 6.56 (s, 1H), 6.26 (d, J=4.2 Hz, 1H), 6.15 (d, J=3.3 Hz, 1H), 5.43 (m, 1H), 5.12 (m, 1H), 4.60 (m, 1H), 2.87 (d, J=3.3 Hz, 1H), 1.46 (d, J=5.1 Hz, 1H), 1.35 (d, J=5.1 Hz, 1H); (ES, m/z):352.1 $[M+1]^+$

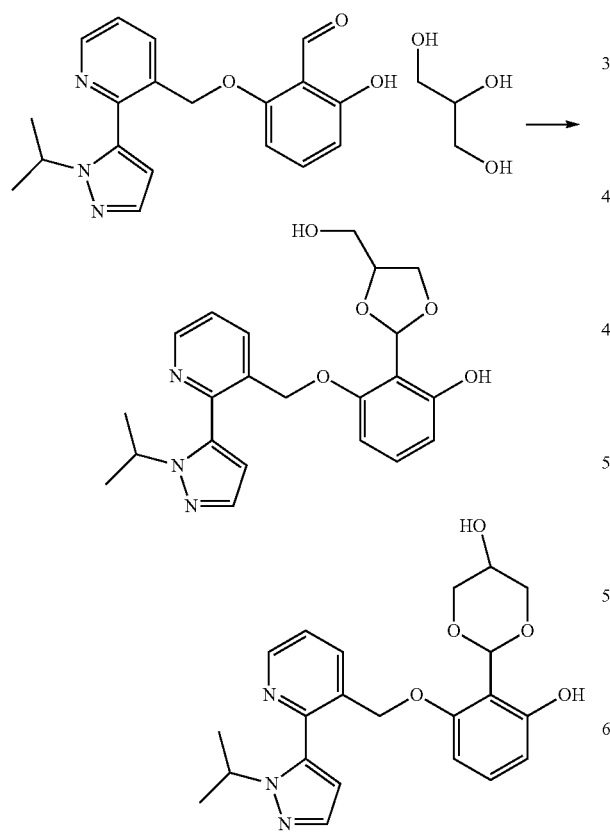

GBT1007—2-(4-(hydroxymethyl)-1,3-dioxolan-2-yl)-3-((2-(1-isopropyl-1H-pyrazol-5-yl)pyridin-3-yl)methoxy)phenol 2-Hydroxy-6-((2-(1-isopropyl-1H-pyrazol-5-yl)pyridin-3-yl)methoxy)benzaldehyde (0.4 g, 1.19 mmol) was dissolved in a solution of propane-1,2,3-triol (5.8 ml, 79 mmol) and DMF (5 ml). Amberlyst 15 resin (80 mg) and 3 Å molecular sieves (1 g) were added and the mixture was stirred in a heat block at 70° C. for 18 h. After cooling the mixture was filtered and taken up in ethyl acetate (200 ml) and water (100 ml). The phases were separated and the aqueous phase was extracted with ethyl acetate (2×50 ml). The combined organic phases were washed with water (50 ml) and a saturated aqueous sodium chloride solution (50 ml), and dried over sodium sulfate. After evaporation, the residue was purified by silica gel chromatography (0-90% ethyl acetate/dichloromethane) to give 0.118 g (24%) of 2-(4-(hydroxymethyl)-1,3-dioxolan-2-yl)-3-((2-(1-isopropyl-1H-pyrazol-5-yl)pyridin-3-yl)methoxy)phenol as an off-white solid after lyophilization from acetonitrile/water. $^1$H NMR (400 MHz, CDCl$_3$) δ 8.74-8.67 (m, 1H), 8.53 (s, 0.6H), 8.18-8.12 (m, 0.4H), 7.97 (d, J=7.90 Hz, 1H), 7.62-7.55 (m, 1H), 7.44-7.34 (m, 1H), 7.17-7.07 (m, 1H), 6.55 (d, J=8.47 Hz, 1H), 6.42-6.36 (m, 1H), 6.31-6.23 (m, 1.6H), 5.95-5.89 (m, 0.4H), 4.98 (s, 2H), 4.71-4.58 (m, 1H), 4.40-4.28 (m, 1.5H), 4.24-4.17 (m, 0.6H), 4.10-4.01 (m, 1H), 3.99-3.92 (m, 0.6H), 3.73-3.65 (m, 0.6H), 3.56 (dd, J=10.09, 20.18 Hz, 1H), 1.51-1.43 (m, 6H). MS (ESI) m/z 412 $[M+H]^+$.

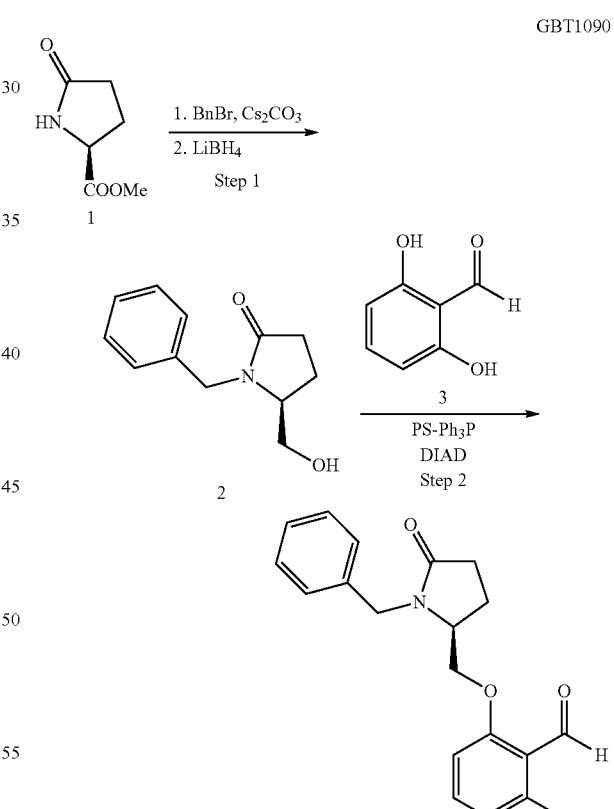

GBT1090—(S)-2-((1-benzyl-5-oxopyrrolidin-2-yl)methoxy)-6-hydroxybenzaldehyde

Step 1: To a solution of (S)-methyl 5-oxopyrrolidine-2-carboxylate (700 mg, 4.89 mmol) in DMF (5 mL) was added Cs$_2$CO$_3$ (1.97 g, 5.99 mmol) and BnBr (0.59 mL, 4.99 mmol). After heated at 60° C. for 15 h, it was diluted with EtOAc, organic layer was washed with water, brine, dried and concentrated to give crude product which was purified by column (Hexanes/EtOAc=40:60) to give methyl (S)-1-benzyl-5-oxopyrrolidine-2-carboxylate (240 mg). To a solution of methyl (S)-1-benzyl-5-oxopyrrolidine-2-carboxylate (240 mg, 1.0 mmol) in THF (2 mL) was added LiBH4 (1M in THF, 1 mL, 1 mmol) at room temperature. After stirred at room temperature for 1 h, the solution was quenched with Sat. NH4Cl, aqueous layer was extracted with EtOAc, EtOAc layer was combined, dried and concentrated to give crude product, which was purified by column (100% EtOAc) to give (S)-1-benzyl-5-(hydroxymethyl)pyrrolidin-2-one (170 mg).

Step 2: To a solution of (S)-1-benzyl-5-(hydroxymethyl)pyrrolidin-2-one (170 mg, 0.83 mmol) and 2,6-dihydroxybenzaldehyde (0.15 g, 1.08 mmol) in THF (6 mL) was added PPh3 (polymer supported, 1.0 g, 1.25 mmol) and DIAD (0.24 mL, 1.25 mmol) at 0° C. Then it was warmed up to room temperature and stirred for 1 h, AcCN was added to dilute the mixture, the insoluble material was filtered off, the filtrate was concentrated and was purified by preparative HPLC to give (S)-2-((1-benzyl-5-oxopyrrolidin-2-yl)methoxy)-6-hydroxybenzaldehyde (95 mg). $^1$H NMR (400 MHz, Chloroform-d) δ 11.93 (t, J=0.4 Hz, 1H), 10.17 (t, J=0.5 Hz, 1H), 7.39-7.29 (m, 1H), 7.29-7.18 (m, 5H), 6.54 (dt, J=8.5, 0.7 Hz, 1H), 6.17 (dd, J=8.3, 0.9 Hz, 1H), 4.85 (d, J=15.2 Hz, 1H), 4.28 (d, J=15.2 Hz, 1H), 3.99 (d, J=4.0 Hz, 2H), 3.92 (td, J=7.8, 7.2, 3.6 Hz, 1H), 2.68-2.45 (m, 2H), 2.33-2.19 (m, 1H), 2.10-1.96 (m, 1H). MS (M+H) found for $C_{19}H_{19}NO_4$: 326.4.

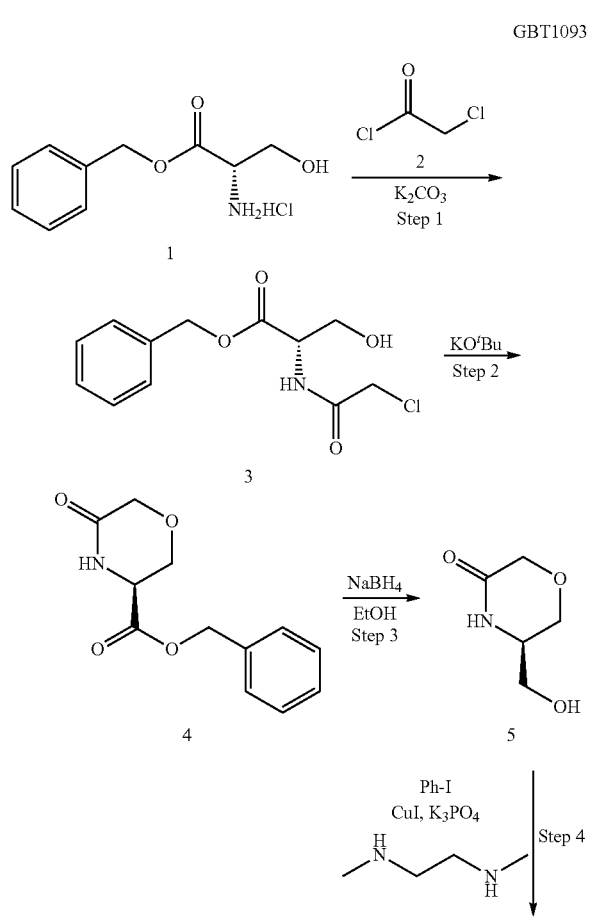

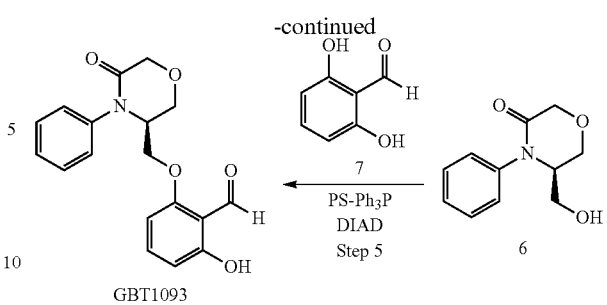

GBT1093—(S)-2-hydroxy-6-((5-oxo-4-phenylmorpholin-3-yl)methoxy)benzaldehyde

Step 1: To a solution of (S)-benzyl 2-amino-3-hydroxypropanoate hydrochloride (5 g, 21.58 mmol) in THF-water (1/1, 80 mL) was added $K_2CO_3$ (8.95 g, 64.74 mmol) and chloroacetyl chloride (2.92 mL, 36.69 mmol). After stirred for 1 h, it was diluted with EtOAc, organic layer was washed with water, brine, dried and concentrated to give benzyl (2-chloroacetyl)-L-serinate (5 g).

Step 2: A solution of (S)-benzyl 2-(2-chloroacetamido)-3-hydroxypropanoate (2.55 g, 9.39 mmol) in iPrOH (20 mL) was added to KOtBu (3.16 g, 28.17 mmol) in iPrOH (15 mL) at room temperature. After stirred at room temperature for 1 h, the mixture was quenched with 6N HCl (10 mL) at 0° C., extracted with EtOAc, organic layers were combined, washed with brine, dried and concentrated to give isopropyl (2-chloroacetyl)-L-serinate as crude product.

Step 3: To a solution of (S)-benzyl 5-oxomorpholine-3-carboxylate in EtOH (7 mL) was added NaBH4 (150 mg) at 0° C., after stirred at room temperature for 3 h, it was quenched with NH4Cl (220 mg in 0.6 mL water), and the insoluble material was filtered off, the filtrate was concentrated and was purified by column (DCM/MeOH=100:0 to 80:20) to give (R)-5-(hydroxymethyl)morpholin-3-one (100 mg).

Step 4: To a suspension of (R)-5-(hydroxymethyl)morpholin-3-one (100 mg, 2 mmol) and 3-iodopyridine (0.57 g, 2.8 mmol) in Dioxane (4 mL) was added CuI (0.08 g, 0.4 mmol), N,N-dimethylethylenediamine (0.05 mL, 0.4 mmol), $K_3PO_4$ (0.85 g, 4 mmol). After heating at 100° C. for 24 h, the mixture was cooled and was diluted with EtOAc, insoluble material was filtered off, the filtrate was concentrated and purified by column (Hexanes/EtOAc=100:0 to 0:100) to give (S)-5-(hydroxymethyl)-1-(pyridin-3-yl)pyrrolidin-2-one (55 mg).

Step 5: To a solution of (S)-5-(hydroxymethyl)-1-(pyridin-3-yl)pyrrolidin-2-one (55 mg, 0.29 mmol) and 2,6-dihydroxybenzaldehyde (0.05 g, 0.38 mmol) in THF (2 mL) was added PPh3 (polymer supported, 367 mg, 0.44 mmol) and DIAD (0.09 mL, 0.44 mmol) at 0° C. Then it was warmed up to room temperature and stirred for 1 h, AcCN was added to dilute the mixture, the insoluble material was filtered off, the filtrate was concentrated and was purified by preparative HPLC to give (S)-2-hydroxy-6-((5-oxo-4-phenylmorpholin-3-yl)methoxy)benzaldehyde (29 mg). $^1$H NMR (400 MHz, Chloroform-d) δ 11.88 (d, J=0.4 Hz, 1H), 9.94 (d, J=0.6 Hz, 1H), 7.53-7.40 (m, 2H), 7.40-7.30 (m, 2H), 7.26 (s, 2H), 6.53 (dt, J=8.5, 0.7 Hz, 1H), 6.20 (dd, J=8.3, 0.8 Hz, 1H), 4.47 (dd, J=16.9, 0.9 Hz, 1H), 4.40-4.25 (m, 3H), 4.25-4.16 (m, 1H), 4.15-4.07 (m, 2H). MS (M+H) found for $C_{18}H_{17}NO_5$: 328.3.

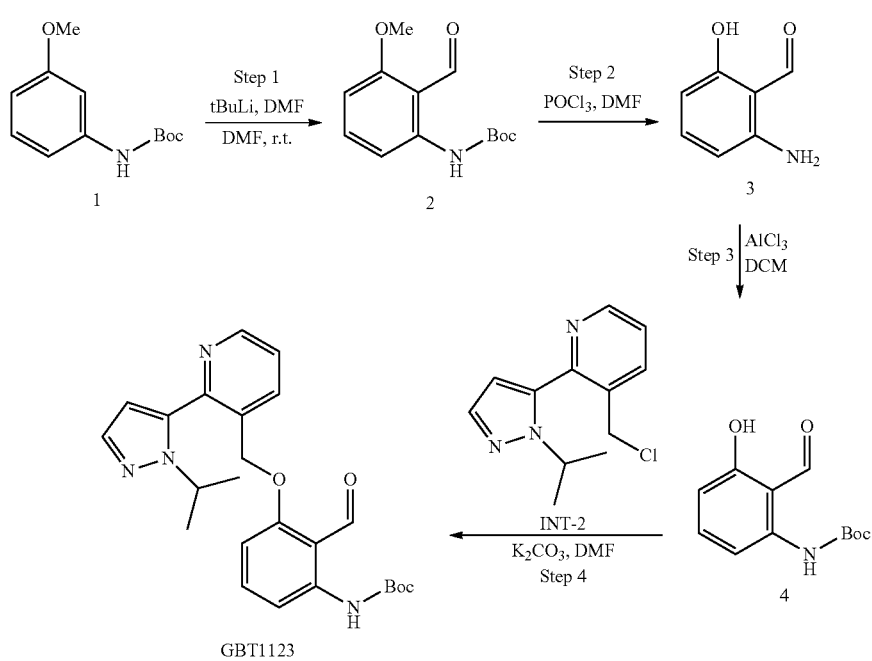

GBT1123—tert-butyl (2-formyl-3-((2-(1-isopropyl-1H-pyrazol-5-yl)pyridin-3-yl)methoxy)phenyl)carbamate Step 1: tert-Butyl(3-methoxyphenyl)carbamate (0.517 g, 2.3 mmol) was dissolved in dry diethyl ether (12 ml) and cooled to −40° C. in a solvent bath. t-Butyl lithium (4.1 ml of a 1.7 M pentane solution, 6.95 mmol) was added dropwise, the reaction was allowed to warm to −20° C. and stirred for 2 h more. The reaction was cooled to −78° C., DMF (0.54 ml, 6.95 mmol) was added, and the reaction was allowed to gradually warm to 25° C. over 16 h. The reaction mixture was cooled in an ice bath and ammonium chloride solution (10 ml) was added. The reaction was extracted with ethyl acetate (3×80 ml), the combined organic phases were washed with a saturated aqueous sodium chloride solution (50 ml) and dried over sodium sulfate. After evaporation, the residue was purified by silica gel chromatography (0-30% ethyl acetate/hexanes) to give 0.46 g (79%) of tert-butyl (2-formyl-3-methoxyphenyl)carbamate as a lightly-colored solid. MS (EST) m/z 252 [M+H]$^+$.

Step 2: tert-Butyl (2-formyl-3-methoxyphenyl)carbamate (0.38 g, 1.5 mmol) was dissolved in dichloromethane (10 ml) and added dropwise to a solution of aluminum chloride (1 g, 7.56 mmol) in dichloromethane (15 ml) while stirring in an ice bath. The yellowish solution was then stirred in a heat block at 50° C. After 4 h, ice and water were added and the mixture stirred for 15 m. The reaction mixture was extracted with dichloromethane (3×50 ml), the combined organic phases were washed with water (30 ml) and a saturated aqueous sodium chloride solution (30 ml), and dried over sodium sulfate. After evaporation the crude residue was carried directly into the next step. MS (ESI) m/z 138 [M+H]$^+$.

Step 3: 2-Amino-6-hydroxybenzaldehyde (0.207 g, 1.5 mmol) was dissolved in THF (4 ml). Di-tert-butyldicarbonate (0.726 g, 3.3 mmol) and 4-dimethylaminopyridine (37 mg, 0.3 mmol) were added and the reaction was stirred for 18 h. The solution was evaporated and the residue was purified by silica gel chromatography (0-40% ethyl acetate/hexanes) to give 50 mg (14%) of tert-butyl (2-formyl-3-hydroxyphenyl)carbamate. MS (ESI) m/z 238 [M+H]$^+$.

Step 4: tert-Butyl (2-formyl-3-hydroxyphenyl)carbamate (50 mg, 0.21 mmol) and 3-(chloromethyl)-2-(1-isopropyl-1H-pyrazol-5-yl)pyridin-1-ium chloride (57 mg, 0.21 mmol) were dissolved in DMF (3 ml). The solution was purged with Ar gas. Potassium carbonate (116 mg 0.84 mmol) was added and the reaction mixture was stirred in a 60° C. heat block for 18 h. The reaction was cooled and water (50 ml) and ethyl acetate (50 ml) were added. The phases were separated and the aqueous phase was extracted with ethyl acetate (2×50 ml). The combined organic phases were washed with a saturated aqueous sodium chloride solution and dried over sodium sulfate. After evaporation the residue was purified by silica gel chromatography (5-50% ethyl acetate/hexanes) to give 5 mg (5%) of tert-butyl (2-formyl-3-((2-(1-isopropyl-1H-pyrazol-5-yl)pyridin-3-yl)methoxy)phenyl)carbamate as a white solid after lyophilization from acetonitrile/water. $^1$H NMR (400 MHz, CDCl$_3$) δ 10.51 (s, 1H), 8.74 (d, J=4.81 Hz, 1H), 8.06 (d, J=7.84 Hz, 1H), 7.60 (s, 1H), 7.48 (t, J=8.22 Hz, 1H), 7.44-7.39 (m, 1H), 6.91-6.81 (m, 2H), 6.36 (s, 1H), 5.10 (s, 2H), 4.64 (d, J=6.51 Hz, 1H), 1.47 (d, J=4.57 Hz, 6H), 1.41 (s, 9H). MS (ESI) m/z 437 [M+H]$^+$.

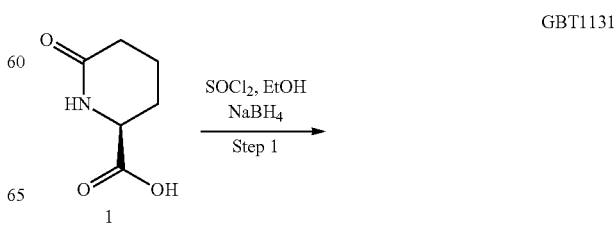

-continued

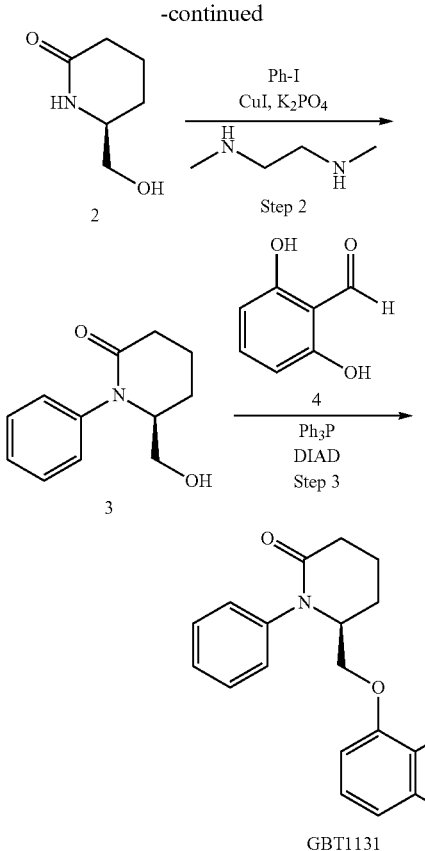

GBT1131

Step 3: To a solution of (S)-6-(hydroxymethyl)-1-phenylpiperidin-2-one (85 mg, 0.44 mmol) and 2,6-dihydroxybenzaldehyde (0.08 g, 0.57 mmol) in THF (5 mL) was added PPh3 (polymer supported, 550 mg, 0.66 mmol) and DIAD (0.13 mL, 0.66 mmol) at 0° C. After warmed to room temperature and further stirred for 2 h, it was diluted with AcCN, the insoluble material was filtered off and the filtrate was concentrated and subjected to preparative HPLC to give (S)-2-hydroxy-6-((6-oxo-1-phenylpiperidin-2-yl)methoxy) benzaldehyde (31 mg). $^1$H NMR (400 MHz, Chloroform-d) δ 11.90 (d, J=0.4 Hz, 1H), 10.08 (d, J=0.6 Hz, 1H), 7.44-7.36 (m, 2H), 7.36-7.27 (m, 2H), 7.22-7.14 (m, 2H), 6.60-6.43 (m, 1H), 6.11 (dd, J=8.3, 0.8 Hz, 1H), 4.25 (qd, J=5.7, 4.2 Hz, 1H), 4.04-3.81 (m, 2H), 2.77-2.53 (m, 2H), 2.29-1.87 (m, 4H). MS (M+H) found for $C_{19}H_9NO_4$: 326.5.

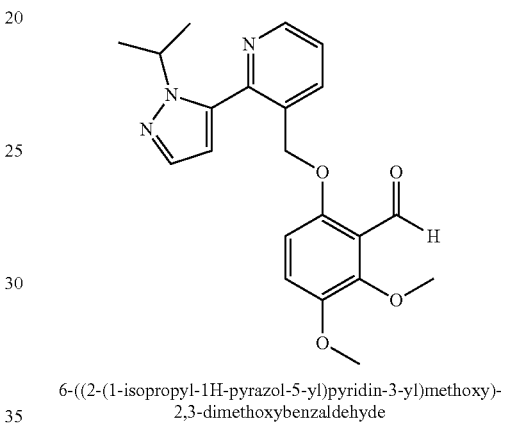

6-((2-(1-isopropyl-1H-pyrazol-5-yl)pyridin-3-yl)methoxy)-2,3-dimethoxybenzaldehyde GBT1131—(S)-2-hydroxy-6-((6-oxo-1-phenylpiperidin-2-yl)methoxy)benzaldehyde Step 1: To a suspension of (S)-6-oxopiperidine-2-carboxylic acid (1.0 g, 6.99 mmol) in EtOH (4 mL) at 0° C. was added $SOCl_2$ (0.61 mL, 8.39 mmol). After stirred at room temperature for 3 h, it was concentrated to remove all solvents, dried under high vacuum to give corresponding ethyl ester. The ester was dissolved in EtOH (15 mL) and was added $NaBH_4$ (300 mg) at 0° C., the mixture was warmed up to room temperature and stirred for additional 15 h. The mixture was quenched with Sat. NH4Cl, filtered off the insolubles and the filtrate was concentrated to give crude product, which was purified by column (DCM/MeOH=90:10) to give (S)-6-(hydroxymethyl)piperidin-2-one (450 mg) as white solid.

Step 2: To a suspension of (S)-6-(hydroxymethyl)piperidin-2-one (150 mg, 1.16 mmol) and iodobenzene (0.35 g, 1.74 mmol) in Dioxane (2 mL) was added CuI (0.09 g, 0.46 mmol). N,N-dimethylethylenediamine (0.04 mL, 0.35 mmol), $K_3PO_4$ (0.49 g, 2.32 mmol). After heating at 100° C. for 24 h, the mixture was cooled and was diluted with EtOAc, organic layer was washed with brine, dried ($Na_2SO_4$) and concentrated to give crude product, which was purified by column (Hexanes/EtOAc=100:0 to 0:100) to give (S)-6-(hydroxymethyl)-1-phenylpiperidin-2-one (85 mg).

GBT1717—6-((2-(1-isopropyl-1H-pyrazol-5-yl) pyridin-3-yl)methoxy)-2,3-dimethoxybenzaldehyde The compound was prepared by O-alkylation of 6-hydroxy-2,3-dimethoxybenzaldehyde (A) and 3-(chloromethyl)-2-[1-(propan-2-yl)-1H-pyrazol-5-yl]pyridine hydrochloride salt (INT-2) according to scheme 9, reaction step 4. The product as white solid was obtained after flash column purification. $^1$H NMR (400 MHz, Chloroform-d) δ 10.49 (t, J=0.4 Hz, 1H), 8.69 (dd, J=4.8, 1.7 Hz, 1H), 8.29 (ddd, J=8.0, 1.7, 0.9 Hz, 1H), 7.61 (dd, J=1.9, 0.5 Hz, 1H), 7.44 (dd, J=7.9, 4.8 Hz, 1H), 7.03 (d, J=9.0 Hz, 1H), 6.52 (d, J=7.9 Hz, 1H), 6.36 (dd, J=1.9, 0.4 Hz, 11H), 4.98 (s, 21H), 4.59 (hept, J=6.7 Hz, 1H), 3.95 (d, J=0.4 Hz, 3H), 3.84 (s, 3H), 1.46 (d, J=6.6 Hz, 6H). MS (M+H) found for $C_{21}H_{23}N_3O_4$. 382.5.

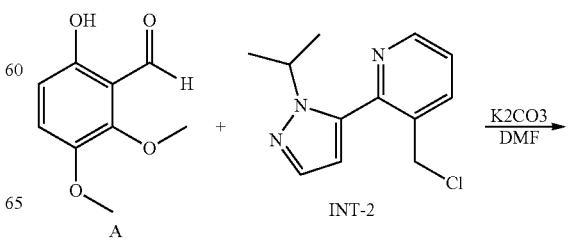

-continued

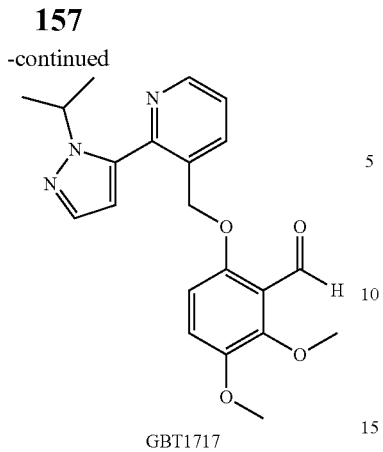

GBT1717

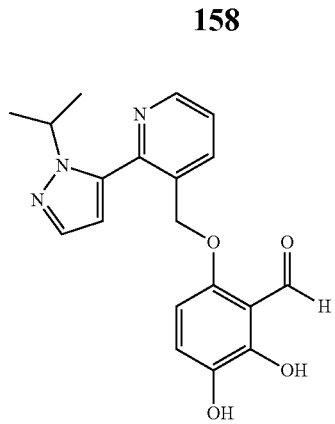

GBT001659

Preparation of Intermediate A 2,3-dihydroxy-6-((2-(1-isopropyl-1H-pyrazol-5-yl)pyridin-3-yl)methoxy)benzaldehyde GBT1659—2,3-dihydroxy-6-((2-(1-isopropyl-1H-pyrazol-5-yl)pyridin-3-yl)methoxy)benzaldehyde

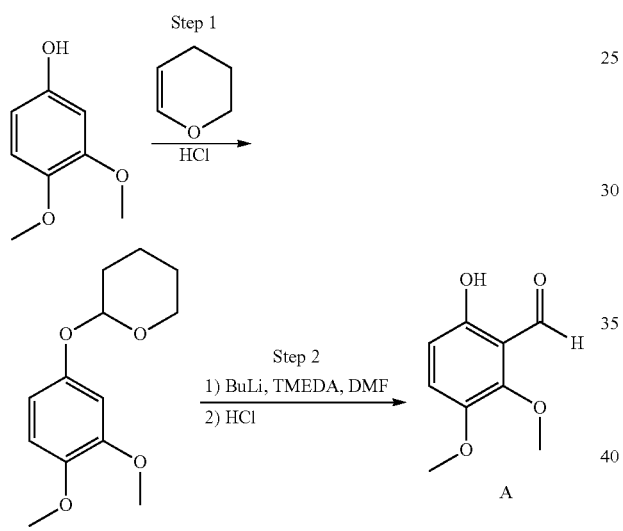

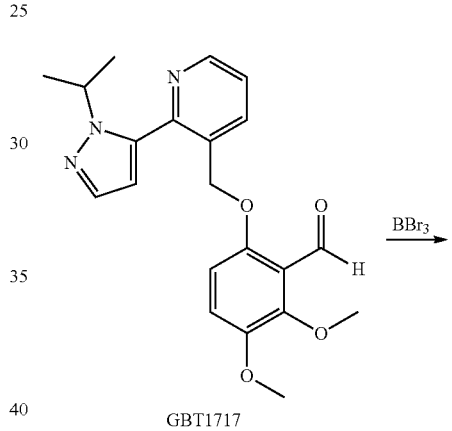

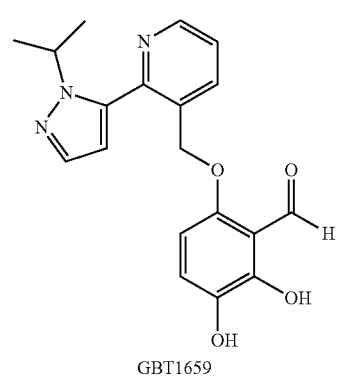

GBT1659

Step 1: To a suspension of 3,4-dimethoxyphenol (2.0 g, 12.97 mmol) in dihydropyran (2 mL, 21.87 mmol) at ambient temperature was added 1 drop of Conc. HCl. After stirred for 1 h, the solution was diluted with EtOAc, organic layer was washed with Sat. NaHCO3, brine, dried and concentrated to give crude product, which was purified by column (Hexanes/EtOAc=65:35) to give 2-(3,4-dimethoxyphenoxy)tetrahydro-2H-pyran (2.9 g).

Step 2: To a solution of 2-(3,4-dimethoxyphenoxy)tetrahydro-2H-pyran (1.0 g, 4.2 mmol) in THF (6 mL) at 0° C. was added TMEDA (0.72 mL, 4.83 mmol) and BuLi (2.5 M, 2.02 mL, 5.05 mmol). After stirred for 1.5 h at 0° C., it was added DMF (1.3 mL). After stirred for 1 h, the mixture was added 6N HCl (4 mL), and was stirred for 1 h at ambient temperature, additional 12N HCl (2 mL) was added to drive the reaction to completion. The solution was diluted with EtOAc and water, organic layer was separated and washed with brine, dried and concentrated to give crude product, which was purified by column chromatography to give 6-hydroxy-2,3-dimethoxybenzaldehyde (490 ing).

To a solution of 6-((2-(1-isopropyl-1H-pyrazol-5-yl)pyridin-3-yl)methoxy)-2,3-dimethoxybenzaldehyde (24 mg, 0.05 mmol) was added BBr₃ (1 M, 0.5 mL), after stirred at ambient temperature for 30 min, the mixture was concentrated and the crude product was purified by preparative HPLC to give 2,3-dihydroxy-6-((2-(1-isopropyl-1H-pyrazol-5-yl)pyridin-3-yl)methoxy)benzaldehyde (10 mg). $^1$H NMR (400 MHz, Chloroform-d) δ 12.01 (s, 1H), 10.32 (d, J=0.5 Hz, 1H), 8.74 (dd, J=4.8, 1.7 Hz, 1H), 8.00-7.92 (m, 1H), 7.60 (dd, J=1.9, 0.6 Hz, 1H), 7.41 (dd, J=7.9, 4.8 Hz, 1H), 7.03 (d, J=8.8 Hz, 1H), 6.34 (d, J=1.9 Hz, 1H), 6.19 (d, J=8.8 Hz, 1H), 5.29 (s, 1H), 5.02 (s, 2H), 4.64 (hept, J=6.6 Hz, 1H), 1.47 (d, J=6.6 Hz, 6H). MS (M+H) found for $C_{19}H_{19}N_3O_4$: 354.4.

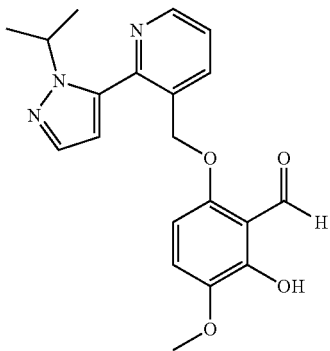

2-hydroxy-6-((2-(1-isopropyl-1H-pyrazol-5-yl)pyridin-3-yl)methoxy)-3-methoxybenzaldehyde GBT1718—2-hydroxy-6-((2-(1-isopropyl-1H-pyrazol-5-yl)pyridin-3-yl)methoxy)-3-methoxybenzaldehyde

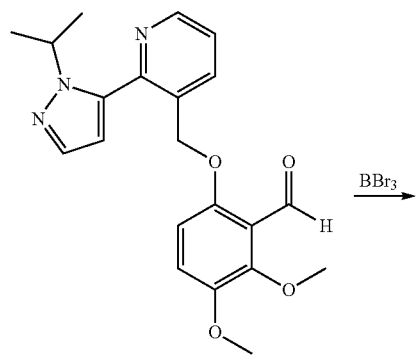

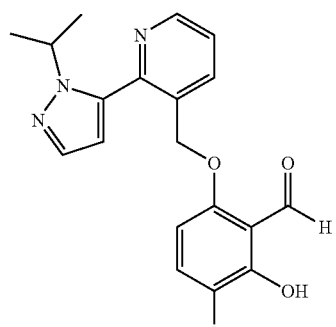

To a solution of 6-((2-(1-isopropyl-1H-pyrazol-5-yl)pyridin-3-yl)methoxy)-2,3-dimethoxybenzaldehyde (50.00 mg; 0.13 mmol) in DCM (0.8 mL) at ambient temperature was added boron tribromide (0.13 ml; 1.00 mol/i). After stirred for 5 min, the red mixture was concentrated and the crude product was purified by preparative HPLC to give 2-hydroxy-6-((2-(1-isopropyl-1H-pyrazol-5-yl)pyridin-3-yl)methoxy)-3-methoxybenzaldehyde (15 mg). $^1$H NMR (400 MHz, Chloroform-d) δ 12.15 (d, J=0.6 Hz, 1H), 10.35 (s, 1H), 8.74 (dd, J=4.8, 1.7 Hz, 1H), 7.97 (ddd, J=7.9, 1.6, 0.7 Hz, 1H), 7.60 (dd, J=1.8, 0.5 Hz, 1H), 7.41 (dd, J=7.9, 4.8 Hz, 1H), 6.98-6.94 (m, 1H), 6.34 (d, J=1.9 Hz, 1H), 6.18 (d, J=8.9 Hz, 1H), 5.02 (s, 2H), 4.72-4.57 (m, 1H), 3.84 (s, 3H), 1.47 (d, J=6.6 Hz, 6H). MS (M+H) found for $C_{20}H_{21}N_3O_4$: 368.4.

GBT001723

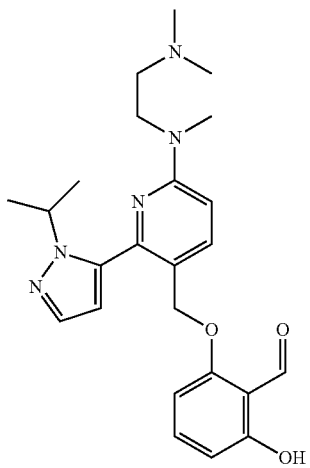

GBT001723—2-((6-((2-(dimethylamino)ethyl)(methyl)amino)-2-(1-isopropyl-1H-pyrazol-5-yl)pyridin-3-yl)methoxy)-6-hydroxybenzaldehyde The compound was prepared by Mitsunobu coupling of (6-((2-(dimethylamino)ethyl)(methyl)amino)-2-(1-isopropyl-1H-pyrazol-5-yl)pyridin-3-yl)methanol (A) with 2,6-dihydroxybenzaldehyde (INT-3) according to scheme 9, reaction step 3. The product as green oil was obtained after flash column purification. $^1$HNMR (400 MHz, CDCl$_3$, ppm): 11.87 (br s, 1H), 10.21 (s, 1H), 7.54 (d, J=8.8 Hz, 1H), 7.44 (s, 1H), 7.26 (t, J=8.4 Hz, 1H), 6.50 (d, J=8.8 Hz, 1H), 6.41 (d, J=8.4 Hz, 1H), 6.20 (d, J=8.4 Hz, 1H), 6.18 (s, 1H), 4.82 (s, 2H), 4.90-4.60 (m, 1H), 3.61 (t, J=11.2 Hz, 2H), 3.03 (s, 3H), 2.43 (t, J=11.2 Hz, 2H), 2.20 (s, 6H), 1.39 (d, J=6.8 Hz, 6H); MS(ES, m/z:) 438.4 [M+1]$^+$

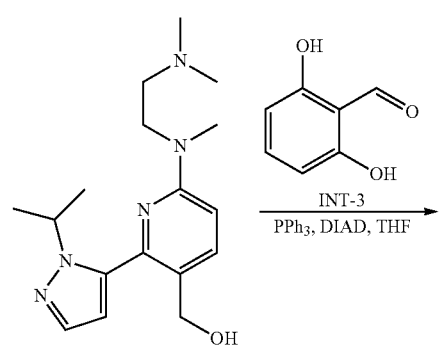

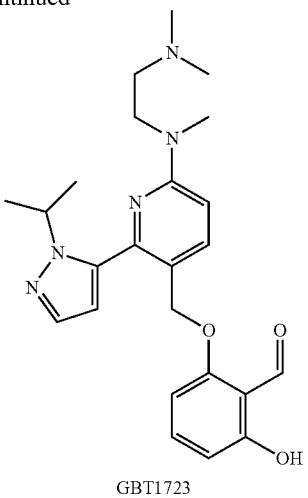

GBT1723

Intermediate A was prepared followed the scheme below:

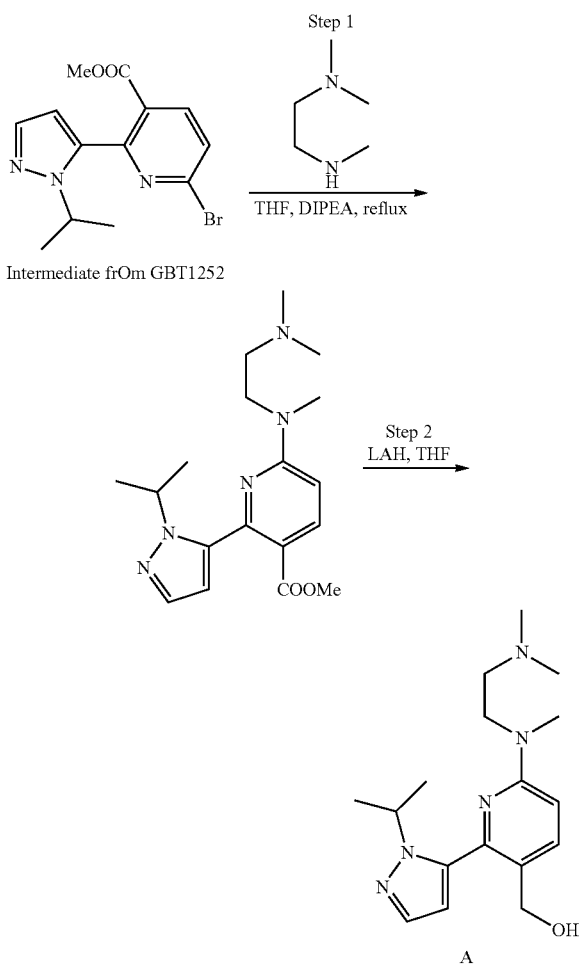

Step 1: Into a 25-mL round-bottom flask, was placed a solution of methyl 6-bromo-2-[1-(propan-2-yl)-1H-pyrazol-5-yl]pyridine-3-carboxylate (1.3 g, 4.01 mmol, 1.00 equiv) in tetrahydrofuran (15 mL). DIPEA (1.55 g, 3.00 equiv) and [2-(dimethylamino)ethyl](methyl)amine (2.4 g, 23.49 mmol, 5.00 equiv) were added to the reaction mixture. The resulting solution was heated to reflux for 24 hr, and then it was quenched with 30 mL of water. The resulting solution was extracted with 3×50 mL of ethyl acetate. The combined organic layers were washed with 1×80 mL of water and 1×80 mL of brine, dried over anhydrous sodium sulfate and concentrated under vacuum. The residue was applied onto a silica gel column with dichloromethane/methanol (30:1-15:1) as eluent to furnish 1.22 g (88%) of methyl 6-[[2-(dimethylamino)ethyl](methyl)amino]-2-[1-(propan-2-yl)-1H-pyrazol-5-yl]pyridine-3-carboxylate as a light yellow oil.

Step 2. Into a 100-mL round-bottom flask, was placed a solution of methyl 6-[[2-(dimethylamino)ethyl](methyl)amino]-2-[1-(propan-2-yl)-1H-pyrazol-5-yl]pyridine-3-carboxylate (1.2 g, 3.47 mmol, 1.00 equiv) in tetrahydrofuran (20 mL). This was followed by the addition of LAH (330 mg, 8.70 mmol, 2.50 equiv), in portions at 0° C. The resulting solution was stirred for 4 h at room temperature. The reaction was quenched by the addition of 0.5 mL water, 0.5 mL 2.5M sodium hydroxide (aq.). The resulting solution was diluted with 50 mL of ethyl acetate. The solids were filtered out and washed with THF for 3 times. The resulting mixture was concentrated under vacuum. This resulted in 1.1 g (100%) of (6-[[2-(dimethylamino)ethyl](methyl)amino]-2-[1-(propan-2-yl)-1H-pyrazol-5-yl]pyridin-3-yl)methanol as a colorless oil.

From the foregoing it will be appreciated that, although specific embodiments of the invention have been described herein for purposes of illustration, various modifications may be made without deviating from the spirit and scope of the invention.

Throughout the description of this invention, reference is made to various patent applications and publications, each of which are herein incorporated by reference in their entirety.

As used herein, Table 1 includes compounds described below or tautomers or pharmaceutically acceptable salts thereof:

2-(imidazo[1,2-a]pyridin-8-ylmethoxy)-5-methoxybenzaldehyde,
2-(imidazo[1,2-a]pyridin-2-ylmethoxy)-5-methoxybenzaldehyde,
2-(imidazo[1,5-a]pyridin-8-ylmethoxy)-5-methoxybenzaldehyde,
5-methoxy-2-(quinolin-5-ylmethoxy)benzaldehyde,
5-methoxy-2-((1-methyl-1H-indazol-4-yl)methoxy)benzaldehyde,
5-methoxy-2-((8-methylimidazo[1,2-a]pyridin-2-yl)methoxy)benzaldehyde,
2-((1H-indazol-4-yl)methoxy)-5-methoxybenzaldehyde,
5-methoxy-2-(pyridin-3-ylmethoxy)benzaldehyde,
2-((2-(1-isopropyl-1H-pyrazol-5-yl)pyridin-3-yl)methoxy)-5-methoxy)benzaldehyde,
2-hydroxy-6-((2-(1-isopropyl-1H-pyrazol-5-yl)pyridin-3-ylmethoxy)benzaldehyde,
2-((3-(2H-tetrazol-5-yl)benzyl)oxy)-6-hydroxybenzaldehyde,
2-((4-(2H-tetrazol-5-yl)benzyl)oxy)-6-hydroxybenzaldehyde,
methyl 4-((2-formylphenoxy)methyl)benzoate,
4-((2-formylphenoxy)methyl)benzoic acid,
methyl 3-((2-formylphenoxy)methyl)benzoate,
2-bromo-3-((2-(1-isopropyl-1H-pyrazol-5-yl)pyridin-3-yl)methoxy)benzaldehyde,
2-hydroxy-6-((2-(1-(2,2,2-trifluoroethyl)-1H-pyrazol-5-yl)pyridin-3-yl)methoxy)benzaldehyde, 2-hydroxy-6-((2-(1-(3,3,3-trifluoropropyl)-1H-pyrazol-5-yl)pyridin-3-yl)methoxy)benzaldehyde,
2-fluoro-6-((2-(1-(2,2,2-trifluoroethyl)-1H-pyrazol-5-yl)pyridin-3-yl)methoxy)benzaldehyde,
2-fluoro-6-((2-(1-(3,3,3-trifluoropropyl)-1H-pyrazol-5-yl)pyridin-3-yl)methoxy)benzaldehyde,
2-fluoro-6-((2-(1-isopropyl-1H-pyrazol-5-yl)pyridin-3-yl)methoxy)benzaldehyde, and
1-(2-formyl-3-hydroxyphenethyl)piperidine-4-caboxylic acid, or a tautomer or pharmaceutically acceptable salt thereof.

| Compound | Structure | Name |
|---|---|---|
| 1 | 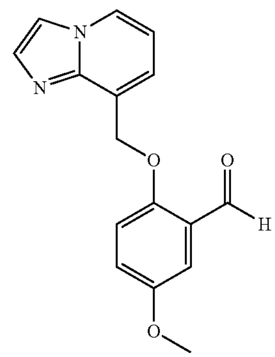 [SMILES: COc1ccc(OCc2cccn3ccnc23)c(C=O)c1] | 2-(imidazo[1,2-a]pyridin-8-ylmethoxy)-5-methoxybenzaldehyde |
| 2 | 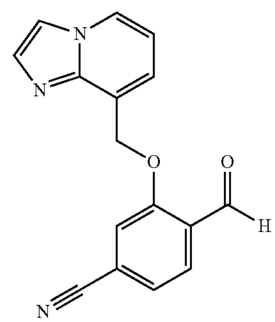 [SMILES: N#Cc1ccc(C=O)c(OCc2cccn3ccnc23)c1] | 4-formyl-3-(imidazo[1,2-a]pyridin-8-ylmethoxy)benzonitrile |
| 3 | 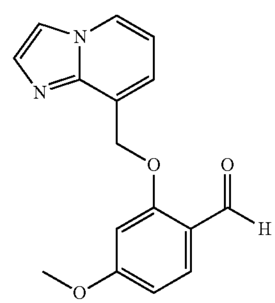 [SMILES: COc1ccc(C=O)c(OCc2cccn3ccnc23)c1] | 2-(imidazo[1,2-a]pyridin-8-ylmethoxy)-4-methoxybenzaldehyde |
| 4 | 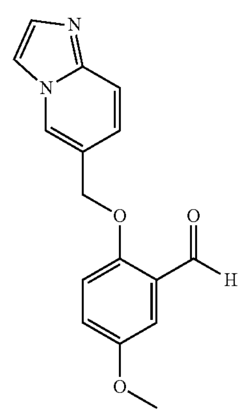 [SMILES: COc1ccc(OCc2ccc3nccn3c2)c(C=O)c1] | 2-(imidazo[1,2-a]pyridin-6-ylmethoxy)-5-methoxybenzaldehyde |

-continued

| Compound | Structure | Name |
|---|---|---|
| 5 | 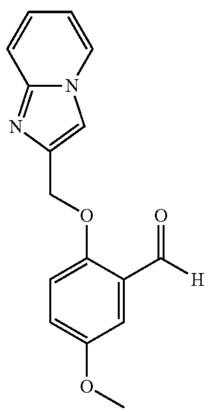 [SMILES: COc1ccc(OCc2cn3ccccc3n2)c(C=O)c1] | 2-(imidazo[1,2-a]pyridin-2-ylmethoxy)-5-methoxybenzaldehyde |
| 6 | 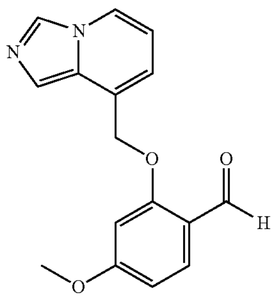 [SMILES: COc1ccc(C=O)c(OCc2cccn3cncc23)c1] | 2-(imidazo[1,5-a]pyridin-8-ylmethoxy)-4-methoxybenzaldehyde |
| 7 | 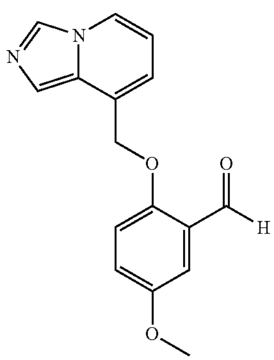 [SMILES: COc1ccc(OCc2cccn3cncc23)c(C=O)c1] | 2-(imidazo[1,5-a]pyridin-8-ylmethoxy)-5-methoxybenzaldehyde |
| 8 | 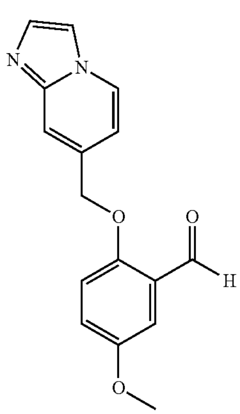 [SMILES: COc1ccc(OCc2ccn3ccnc3c2)c(C=O)c1] | 2-(imidazo[1,2-a]pyridin-7-ylmethoxy)-5-methoxybenzaldehyde |

-continued
| Compound | Structure | Name |
|---|---|---|
| 9 | 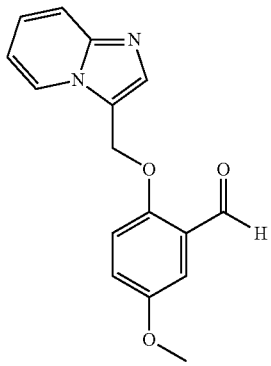 [SMILES: COc1ccc(OCc2cnc3ccccn23)c(C=O)c1] | 2-(imidazo[1,2-a]pyridin-3-ylmethoxy)-5-methoxybenzaldehyde |
| 10 | 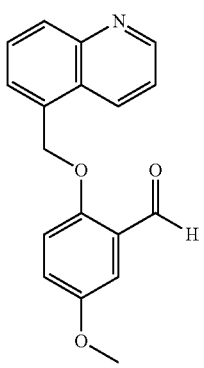 [SMILES: COc1ccc(OCc2cccc3ncccc23)c(C=O)c1] | 5-methoxy-2-(quinolin-5-ylmethoxy)benzaldehyde |
| 11 | 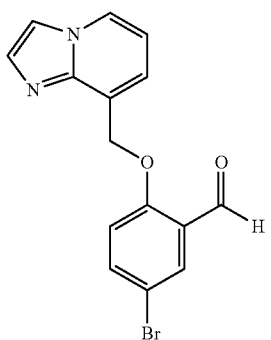 [SMILES: O=Cc1cc(Br)ccc1OCc1cccn2ccnc12] | 5-bromo-2-(imidazo[1,2-a]pyridin-8-ylmethoxy)benzaldehyde |
| 12 | 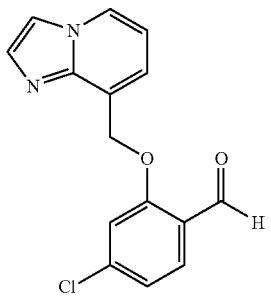 [SMILES: O=Cc1ccc(Cl)cc1OCc1cccn2ccnc12] | 4-chloro-2-(imidazo[1,2-a]pyridin-8-ylmethoxy)benzaldehyde |

-continued

| Compound | Structure | Name |
|---|---|---|
| 13 | 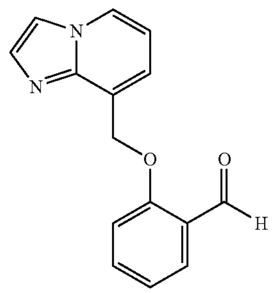 [SMILES: O=Cc1ccccc1OCc1cccn2ccnc12] | 2-(imidazo[1,2-a]pyridin-8-ylmethoxy)benzaldehyde |
| 14 | 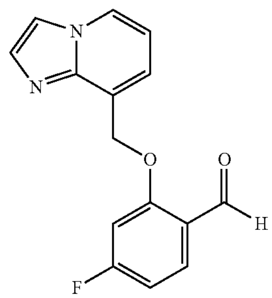 [SMILES: O=Cc1ccc(F)cc1OCc1cccn2ccnc12] | 4-fluoro-2-(imidazo[1,2-a]pyridin-8-ylmethoxy)benzaldehyde |
| 15 | 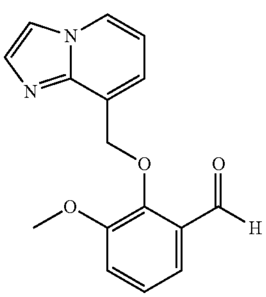 [SMILES: COc1cccc(C=O)c1OCc1cccn2ccnc12] | 2-(imidazo[1,2-a]pyridin-8-ylmethoxy)-3-methoxybenzaldehyde |
| 16 | 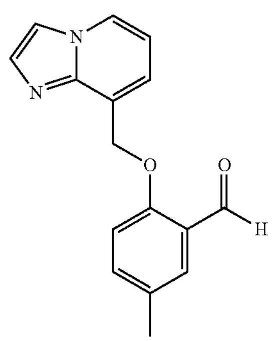 [SMILES: Cc1ccc(OCc2cccn3ccnc23)c(C=O)c1] | 2-(imidazo[1,2-a]pyridin-8-ylmethoxy)-5-methylbenzaldehyde |
| 17 | 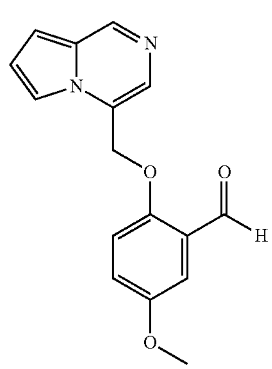 [SMILES: COc1ccc(OCc2cncc3cccn23)c(C=O)c1] | 5-methoxy-2-(pyrrolo[1,2-a]pyrazin-4-ylmethoxy)benzaldehyde |

| Compound | Structure | Name |
|---|---|---|
| 18 | 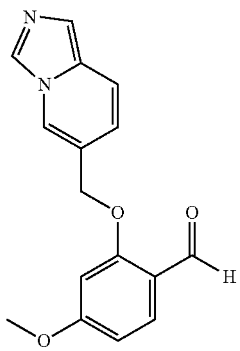 [SMILES: COc1ccc(C=O)c(OCc2ccc3cncn3c2)c1] | 2-(imidazo[1,5-a]pyridin-6-ylmethoxy)-4-methoxybenzaldehyde |
| 19 | 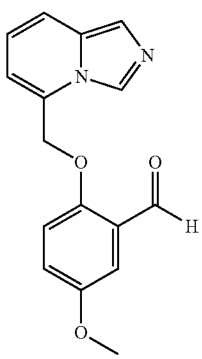 [SMILES: COc1ccc(OCc2cccc3cncn23)c(C=O)c1] | 2-(imidazo[1,5-a]pyridin-5-ylmethoxy)-5-methoxybenzaldehyde |
| 20 | 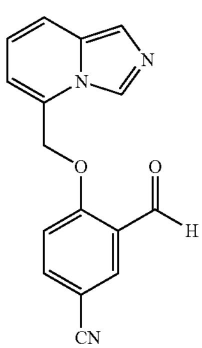 [SMILES: N#Cc1ccc(OCc2cccc3cncn23)c(C=O)c1] | 3-formyl-4-(imidazo[1,5-a]pyridin-5-ylmethoxy)benzonitrile |
| 21 | 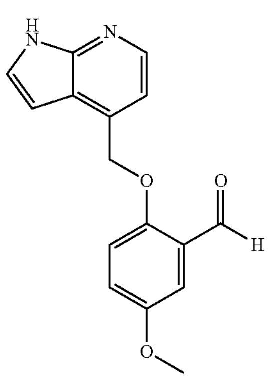 [SMILES: COc1ccc(OCc2ccnc3[nH]ccc23)c(C=O)c1] | 2-((1H-pyrrolo[2,3-b]pyridin-4-yl)methoxy)-5-methoxybenzaldehyde |

-continued
| Compound | Structure | Name |
|---|---|---|
| 22 | 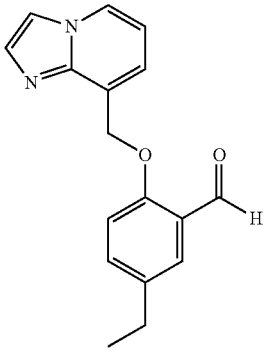 [SMILES: CCc1ccc(OCc2cccn3ccnc23)c(C=O)c1] | 5-ethyl-2-(imidazo[1,2-a]pyridin-8-ylmethoxy)benzaldehyde |
| 23 | 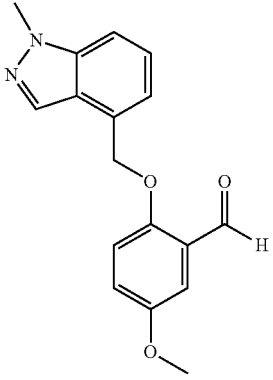 [SMILES: COc1ccc(OCc2cccc3c2cnn3C)c(C=O)c1] | 5-methoxy-2-((1-methyl-1H-indazol-4-yl)methoxy)benzaldehyde |
| 24 | 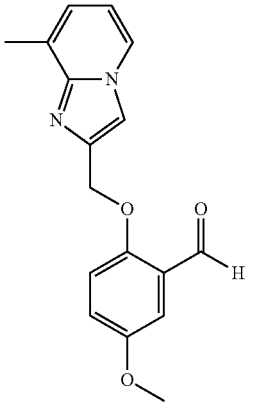 [SMILES: COc1ccc(OCc2cn3cccc(C)c3n2)c(C=O)c1] | 5-methoxy-2-((8-methylimidazo[1,2-a]pyridin-2-yl)methoxy)benzaldehyde |
| 25 | 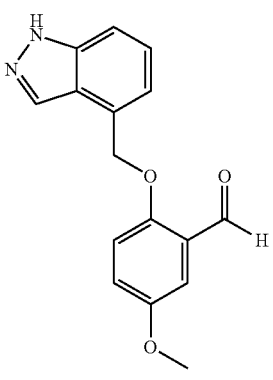 [SMILES: COc1ccc(OCc2cccc3[nH]ncc23)c(C=O)c1] | 2-((1H-indazol-4-yl)methoxy)-5-methoxybenzaldehyde |

| Compound | Structure | Name |
|---|---|---|
| 26 | 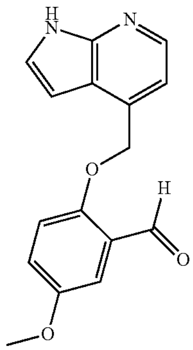 [SMILES: COc1ccc(OCc2ccnc3[nH]ccc23)c(C=O)c1] | 2-((1H-pyrrolo[2,3-b]pyridin-4-yl)methoxy)-5-methoxybenzaldehyde |
| 27 | 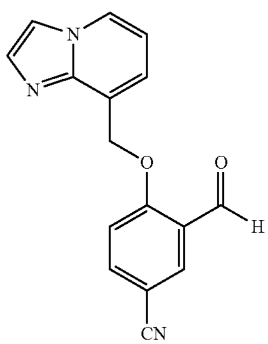 [SMILES: N#Cc1ccc(OCc2cccn3ccnc23)c(C=O)c1] | 3-formyl-4-(imidazo[1,2-a]pyridin-8-ylmethoxy)benzonitrile |
| 28 | 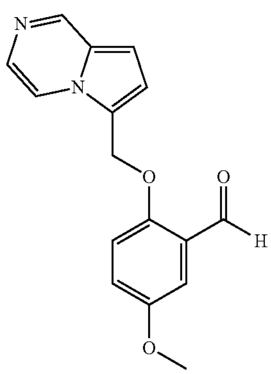 [SMILES: COc1ccc(OCc2ccc3cnccn23)c(C=O)c1] | 5-methoxy-2-(pyrrolo[1,2-a]pyrazin-6-ylmethoxy)benzaldehyde |
| 29 | 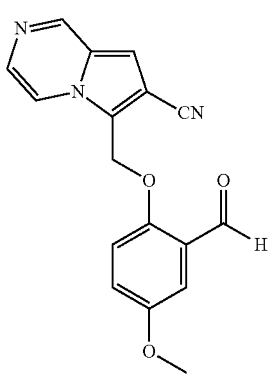 [SMILES: COc1ccc(OCc2c(C#N)cc3cnccn23)c(C=O)c1] | 6-((2-formyl-4-methoxyphenoxy)methyl)pyrrolo[1,2-a]pyrazine-7-carbonitrile |

| Compound | Structure | Name |
|---|---|---|
| 30 | 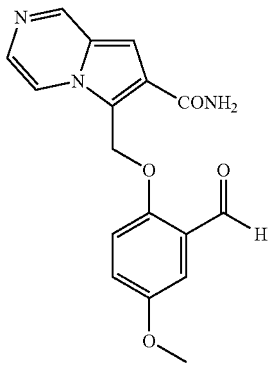 [SMILES: COc1ccc(OCc2c(C(N)=O)cc3cnccn23)c(C=O)c1] | 6-((2-formyl-4-methoxyphenoxy)methyl)pyrrolo[1,2-a]pyrazine-7-carboxamide |
| 31 | 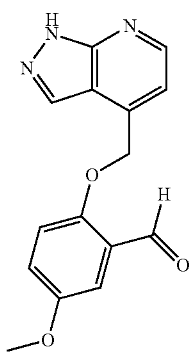 [SMILES: COc1ccc(OCc2ccnc3[nH]ncc23)c(C=O)c1] | 2-((1H-pyrazolo[3,4-b]pyridin-4-yl)methoxy)-5-methoxybenzaldehyde |
| 32 | 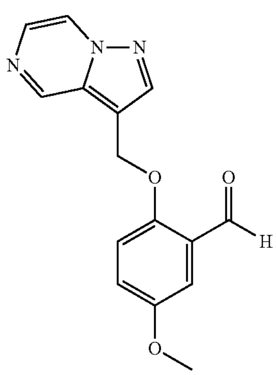 [SMILES: COc1ccc(OCc2cnn3ccncc23)c(C=O)c1] | 5-methoxy-2-(pyrazolo[1,5-a]pyrazin-3-ylmethoxy)benzaldehyde |
| 33 | 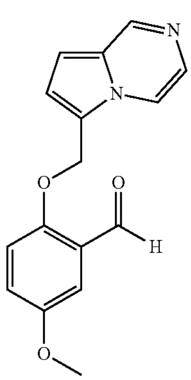 [SMILES: COc1ccc(OCc2ccc3cnccn23)c(C=O)c1] | 5-methoxy-2-(pyrrolo[1,2-a]pyrazin-6-ylmethoxy)benzaldehyde |

-continued
| Compound | Structure | Name |
|---|---|---|
| 34 | 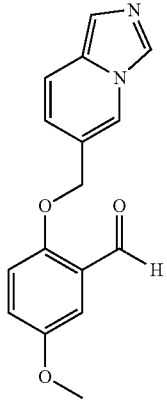 [SMILES: COc1ccc(OCc2ccc3cncn3c2)c(C=O)c1] | 2-(imidazo[1,5-a]pyridin-6-ylmethoxy)-5-methoxybenzaldehyde |
| 35 | 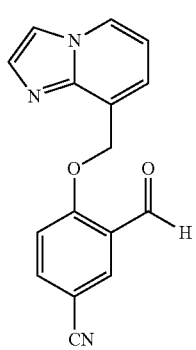 [SMILES: N#Cc1ccc(OCc2cccn3ccnc23)c(C=O)c1] | 3-formyl-4-(imidazo[1,2-a]pyridin-8-ylmethoxy)benzonitrile |
| 36 | 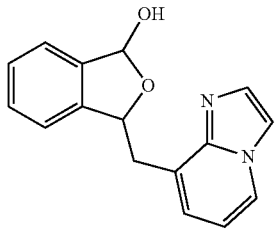 [SMILES: OC1OC(Cc2cccn3ccnc23)c2ccccc21] | 3-(imidazo[1,2-a]pyridin-8-ylmethyl)-1,3-dihydroisobenzofuran-1-ol |
| 37 | 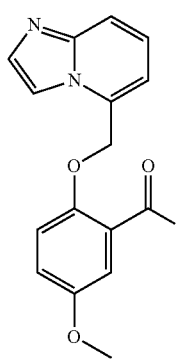 | 2-(imidazo[1,2-a]pyridin-5-ylmethoxy)-5-methoxybenzaldehyde |

-continued
| Compound | Structure | Name |
|---|---|---|
| 38 | 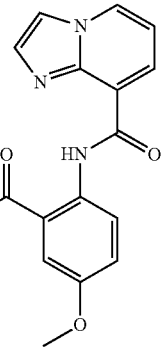 | N-(2-formyl-4-methoxyphenyl)imidazo[1,2-a]pyridine-8-carboxamide |
| 39 | 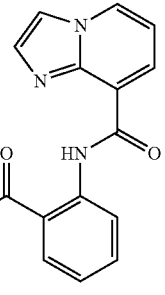 | N-(2-formylphenyl)imidazo[1,2-a]pyridine-8-carboxamide |
| 40 | 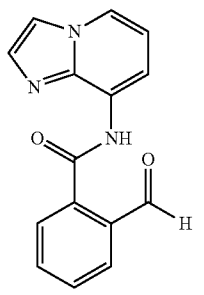 [SMILES: O=Cc1ccccc1C(=O)Nc1cccn2ccnc12] | 2-formyl-N-(imidazo[1,2-a]pyridin-8-yl)benzamide |
| 41 | 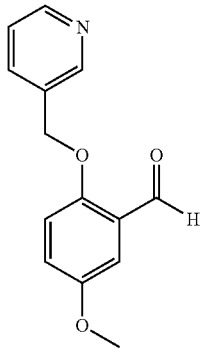 [SMILES: COc1ccc(OCc2cccnc2)c(C=O)c1] | 5-methoxy-2-(pyridin-3-ylmethoxy)benzaldehyde |

-continued

| Compound | Structure | Name |
|---|---|---|
| 42 | 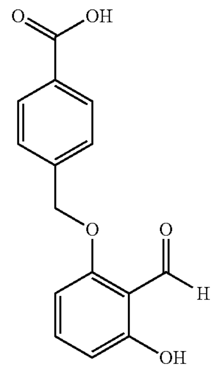 [SMILES: O=Cc1c(O)cccc1OCc1ccc(C(=O)O)cc1] | 4-((2-formyl-3-hydroxyphenoxy)methyl)benzoic acid |
| 43 | 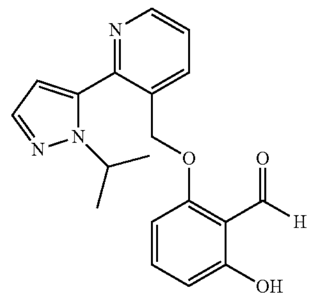 [SMILES: CC(C)n1nccc1-c1ncccc1COc1cccc(O)c1C=O] | 2-hydroxy-6-((2-(1-isopropyl-1H-pyrazol-5-yl)pyridin-3-yl)methoxy)benzaldehyde |
| 44 | 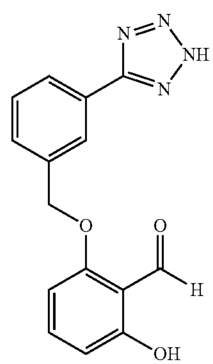 [SMILES: O=Cc1c(O)cccc1OCc1cccc(-c2nn[nH]n2)c1] | 2-((3-(2H-tetrazol-5-yl)benzyl)oxy)-6-hydroxybenzaldehyde |
| 45 | 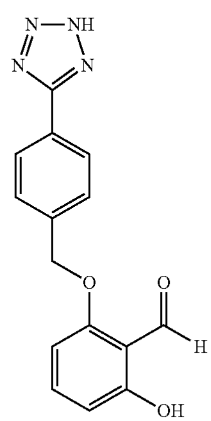 [SMILES: O=Cc1c(O)cccc1OCc1ccc(-c2nn[nH]n2)cc1] | 2-((4-(2H-tetrazol-5-yl)benzyl)oxy)-6-hydroxybenzaldehyde |

-continued

| Compound | Structure | Name |
|---|---|---|
| 46 | 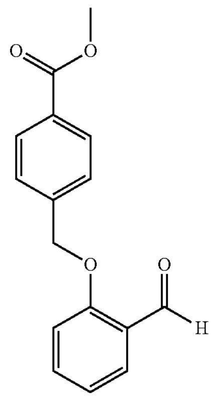 [SMILES: COC(=O)c1ccc(COc2ccccc2C=O)cc1] | methyl 4-((2-formylphenoxy)methyl)benzoate |
| 47 | 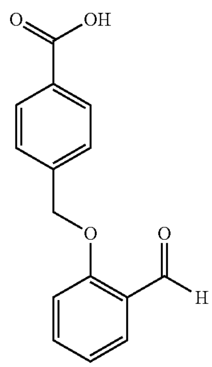 [SMILES: O=Cc1ccccc1OCc1ccc(C(=O)O)cc1] | 4-((2-formylphenoxy)methyl)benzoic acid |
| 48 | 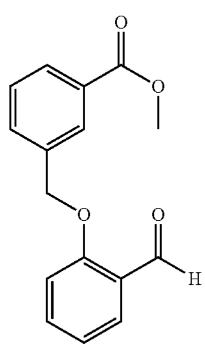 [SMILES: COC(=O)c1cccc(COc2ccccc2C=O)c1] | methyl 3-((2-formylphenoxy)methyl)benzoate |
| 49 | 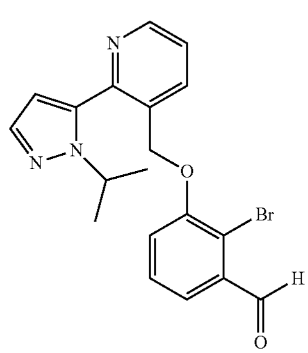 [SMILES: CC(C)n1nccc1-c1ncccc1COc1cccc(C=O)c1Br] | 2-bromo-3-((2-(1-isopropyl-1H-pyrazol-5-yl)pyridin-3-yl)methoxy)benzaldehyde |

-continued

| Compound | Structure | Name |
|---|---|---|
| 50 | 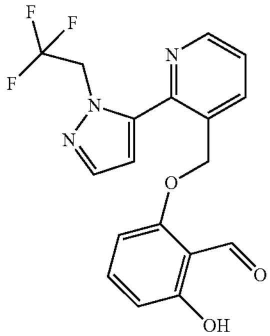 [SMILES: O=Cc1c(O)cccc1OCc1cccnc1-c1ccnn1CC(F)(F)F] | 2-hydroxy-6-((2-(1-(2,2,2-trifluoroethyl)-1H-pyrazol-5-yl)pyridin-3-yl)methoxy)benzaldehyde |
| 51 | 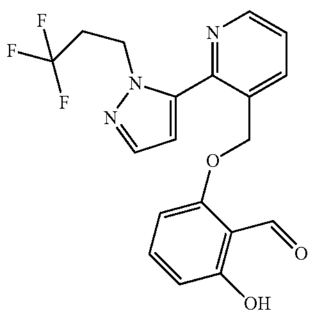 [SMILES: O=Cc1c(O)cccc1OCc1cccnc1-c1ccnn1CCC(F)(F)F] | 2-hydroxy-6-((2-(1-(3,3,3-trifluoropropyl)-1H-pyrazol-5-yl)pyridin-3-yl)methoxy)benzaldehyde |
| 52 | 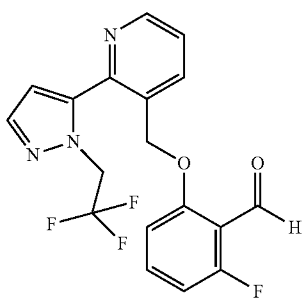 [SMILES: O=Cc1c(F)cccc1OCc1cccnc1-c1ccnn1CC(F)(F)F] | 2-fluoro-6-((2-(1-(2,2,2-trifluoroethyl)-1H-pyrazol-5-yl)pyridin-3-yl)methoxy)benzaldehyde |
| 53 | 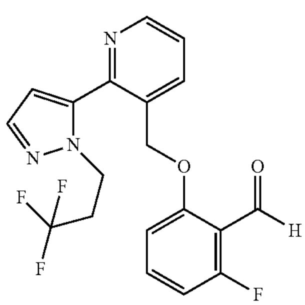 [SMILES: O=Cc1c(F)cccc1OCc1cccnc1-c1ccnn1CCC(F)(F)F] | 2-fluoro-6-((2-(1-(3,3,3-trifluoropropyl)-1H-pyrazol-5-yl)pyridin-3-yl)methoxy)benzaldehyde |
| 54 | 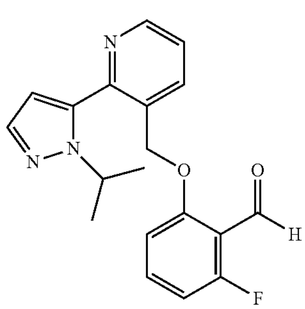 [SMILES: CC(C)n1nccc1-c1ncccc1COc1cccc(F)c1C=O] | 2-fluoro-6-((2-(1-isopropyl-1H-pyrazol-5-yl)pyridin-3-yl)methoxy)benzaldehyde |

-continued

| Compound | Structure | Name |
|---|---|---|
| 55 | 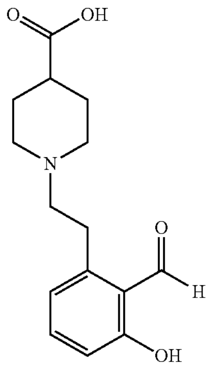 [SMILES: O=Cc1c(O)cccc1CCN1CCC(C(=O)O)CC1] | 1-(2-formyl-3-hydroxyphenethyl)piperidine-4-carboxylic acid |
| 1 | 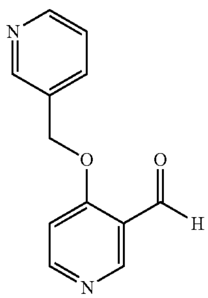 [SMILES: O=Cc1cnccc1OCc1cccnc1] | 4-(pyridin-3-ylmethoxy)nicotinaldehyde |
| 2 | 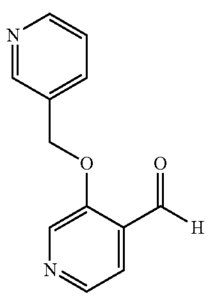 [SMILES: O=Cc1ccncc1OCc1cccnc1] | 3-(pyridin-3-ylmethoxy)isonicotinaldehyde |
| 3 | 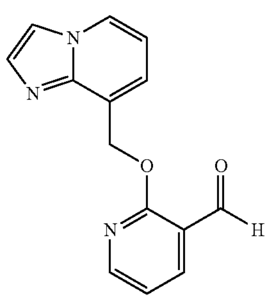 [SMILES: O=Cc1cccnc1OCc1cccn2ccnc12] | 2-(imidazo[1,2-a]pyridin-8-ylmethoxy)nicotinaldehyde |
| 4 | 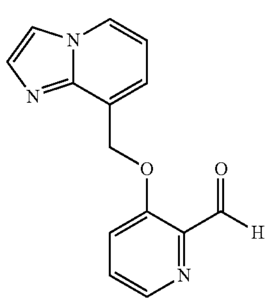 [SMILES: O=Cc1ncccc1OCc1cccn2ccnc12] | 3-(imidazo[1,2-a]pyridin-8-ylmethoxy)picolinaldehyde |

| Compound | Structure | Name |
|---|---|---|
| 5 | 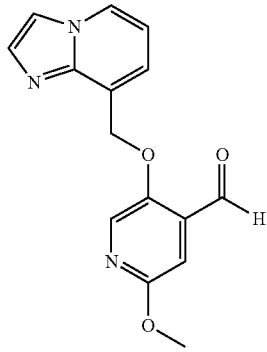 | 5-(imidazo[1,2-a]pyridin-8-ylmethoxy)-2-methoxyisonicotinaldehyde |
| 6 | 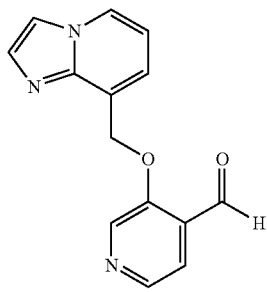 [SMILES: O=Cc1ccncc1OCc1cccn2ccnc12] | 3-(imidazo[1,2-a]pyridin-8-ylmethoxy)isonicotinaldehyde |
| 7 | 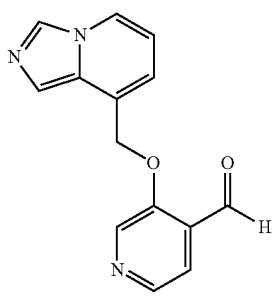 [SMILES: O=Cc1ccncc1OCc1cccn2cncc12] | 3-(imidazo[1,5-a]pyridin-8-ylmethoxy)isonicotinaldehyde |
| 8 | 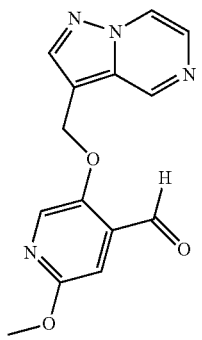 [SMILES: COc1cc(C=O)c(OCc2cnn3ccncc23)cn1] | 2-methoxy-5-(pyrazolo[1,5-a]pyrazin-3-ylmethoxy)isonicotinaldehyde |

| Compound | Structure | Name |
|---|---|---|
| 9 | 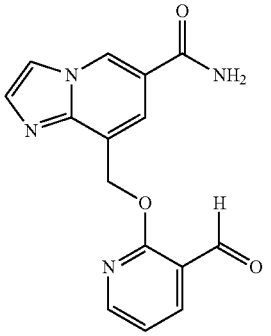 [SMILES: NC(=O)c1cc(COc2ncccc2C=O)c2nccn2c1] | 8-((3-formylpyridin-2-yloxy)methyl)imidazo[1,2-a]pyridin-6-carboxamide |
| 10 | 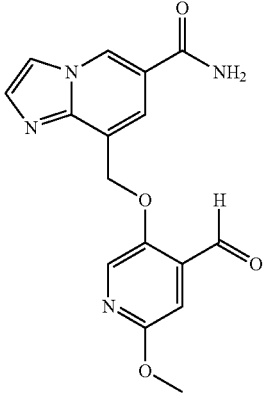 [SMILES: COc1cc(C=O)c(OCc2cc(C(N)=O)cn3ccnc23)cn1] | 8-((4-formyl-6-methoxypyridin-3-yloxy)methyl)imidazo[1,2-a]pyridin-6-carboxamide |
| 11 | 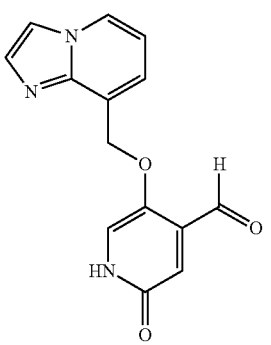 [SMILES: O=Cc1cc(=O)[nH]cc1OCc1cccn2ccnc12] | 5-(imidazo[1,2-a]pyridin-8-ylmethoxy)-2-oxo-1,2-dihydropyridine-4-carbaldehyde |
| 12 | 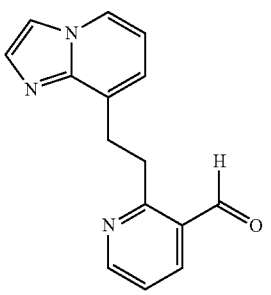 [SMILES: O=Cc1cccnc1CCc1cccn2ccnc12] | 2-(2-(imidazo[1,2-a]pyridin-8-yl)ethyl)nicotinaldehyde |

| Compound | Structure | Name |
|---|---|---|
| 13 | 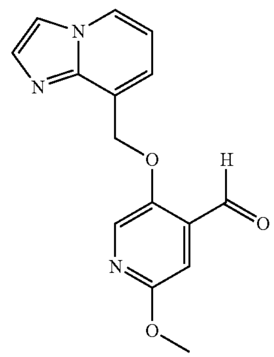 [SMILES: COc1cc(C=O)c(OCc2cccn3ccnc23)cn1] | 5-(2-(imidazo[1,2-a]pyridin-8-yl)ethyl)-2-methoxyisonicotinaldehyde |
| 14 | 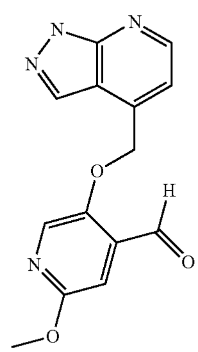 [SMILES: COc1cc(C=O)c(OCc2ccnc3[nH]ncc23)cn1] | 5-((1H-pyrazolo[3,4-b]pyridin-4-yl)methoxy)-2-methoxyisonicotinaldehyde |
| 15 | 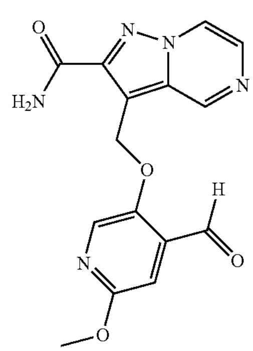 [SMILES: COc1cc(C=O)c(OCc2c(C(N)=O)nn3ccncc23)cn1] | 3-((4-formyl-6-methoxypyridin-3-yloxy)methyl)pyrazolo[1,5-a]pyrazine-2-carboxamide |
| 16 | 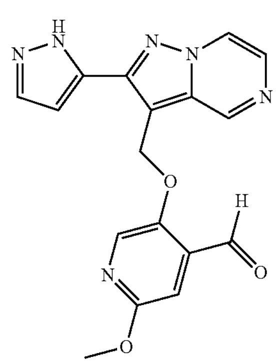 [SMILES: COc1cc(C=O)c(OCc2c(-c3ccn[nH]3)nn3ccncc23)cn1] | 5-((2-(1H-pyrazol-5-yl)pyrazolo[1,5-a]pyrazin-3-yl)methoxy)-2-methoxyisonicotinaldehyde |

-continued

| Compound | Structure | Name |
|---|---|---|
| 17 | 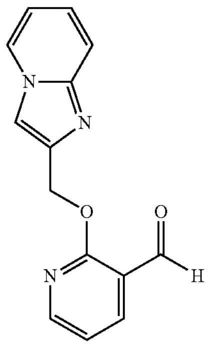 [SMILES: O=Cc1cccnc1OCc1cn2ccccc2n1] | 2-(imidazo[1,2-a]pyridin-2-ylmethoxy)nicotinaldehyde |
| 18 | 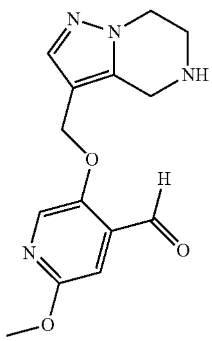 [SMILES: COc1cc(C=O)c(OCc2cnn3c2CNCC3)cn1] | 2-methoxy-5-((4,5,6,7-tetrahydropyrazolo[1,5-a]pyrazin-3-yl)methoxy)isonicotinaldehyde |
| 19 | 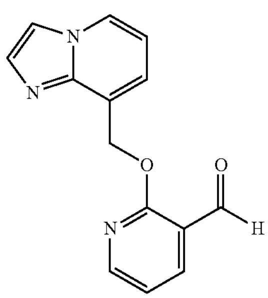 [SMILES: O=Cc1cccnc1OCc1cccn2ccnc12] | 2-(imidazo[1,2-a]pyridin-8-ylmethoxy)nicotinaldehyde |
| 20 | 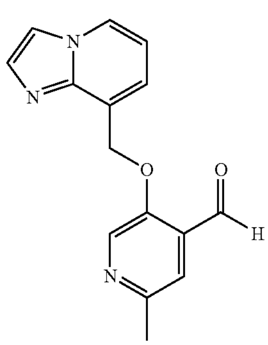 [SMILES: Cc1cc(C=O)c(OCc2cccn3ccnc23)cn1] | 5-(imidazo[1,2-a]pyridin-8-ylmethoxy)-2-methylisonicotinaldehyde |

-continued

| Compound | Structure | Name |
|---|---|---|
| 21 | 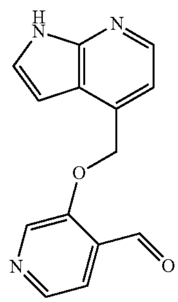 [SMILES: O=Cc1ccncc1OCc1ccnc2[nH]ccc12] | 3-((1H-pyrrolo[2,3-b]pyridin-4-yl)methoxy)isonicotinaldehyde |
| 22 | 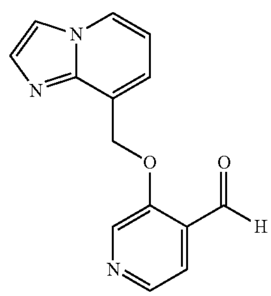 [SMILES: O=Cc1ccncc1OCc1cccn2ccnc12] | 3-(imidazo[1,2-a]pyridin-8-ylmethoxy)isonicotinaldehyde |
| 23 | 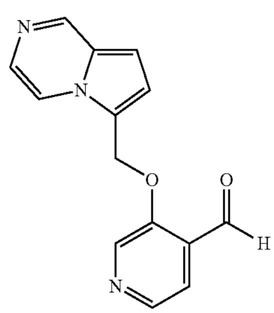 [SMILES: O=Cc1ccncc1OCc1ccc2cnccn12] | 3-(pyrrolo[1,2-a]pyrazin-6-ylmethoxy)isonicotinaldehyde |
| 24 | 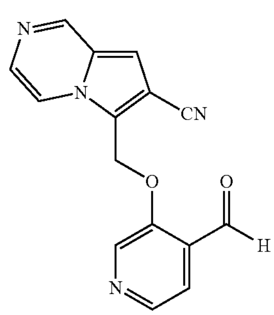 [SMILES: N#Cc1cc2cnccn2c1COc1cnccc1C=O] | 6-((4-formylpyridin-3-yloxy)methyl)pyrrolo[1,2-a]pyrazine-7-carbonitrile |
| 25 | 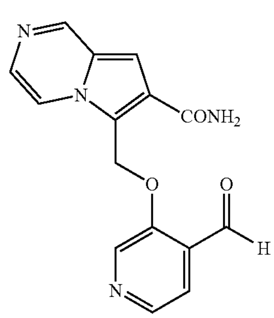 [SMILES: NC(=O)c1cc2cnccn2c1COc1cnccc1C=O] | 6-((4-formylpyridin-3-yloxy)methyl)pyrrolo[1,2-a]pyrazine-7-carboxamide |

-continued

| Compound | Structure | Name |
|---|---|---|
| 26 | 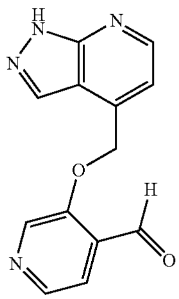 [SMILES: O=Cc1ccncc1OCc1ccnc2[nH]ncc12] | 3-((1H-pyrazolo[3,4-b]pyridin-4-yl)methoxy)isonicotinaldehyde |
| 27 | 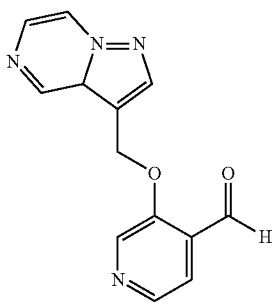 | 3-(pyrazolo[1,5-a]pyrazin-3-ylmethoxy)isonicotinaldehyde |
| 28 | 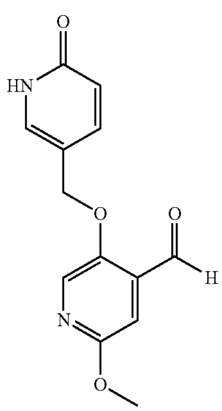 [SMILES: COc1cc(C=O)c(OCc2ccc(=O)[nH]c2)cn1] | 2-methoxy-5-((6-oxo-1,6-dihydropyridin-3-yl)methoxy)isonicotinaldehyde |
| 29 | 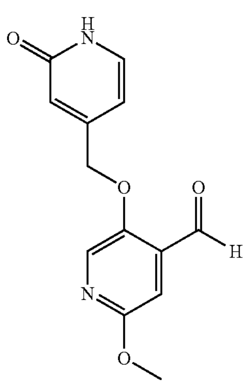 [SMILES: COc1cc(C=O)c(OCc2cc[nH]c(=O)c2)cn1] | 2-methoxy-5-((2-oxo-1,2-dihydropyridin-4-yl)methoxy)isonicotinaldehyde |

| Compound | Structure | Name |
|---|---|---|
| 30 | 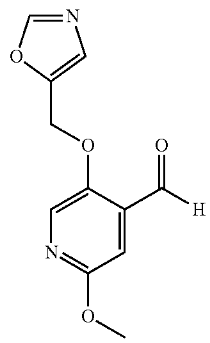 [SMILES: COc1cc(C=O)c(OCc2cnco2)cn1] | 2-methoxy-5-(oxazol-5-ylmethoxy)isonicotinaldehyde |
| 31 | 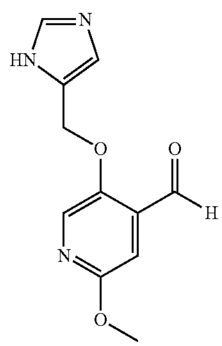 [SMILES: COc1cc(C=O)c(OCc2cnc[nH]2)cn1] | 5-((1H-imidazol-5-yl)methoxy)-2-methoxyisonicotinaldehyde |
| 32 | 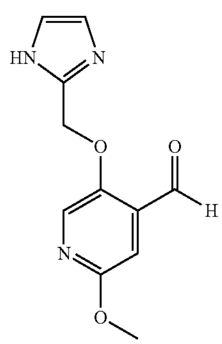 [SMILES: COc1cc(C=O)c(OCc2ncc[nH]2)cn1] | 5-((1H-imidazol-2-yl)methoxy)-2-methoxyisonicotinaldehyde |
| 33 | 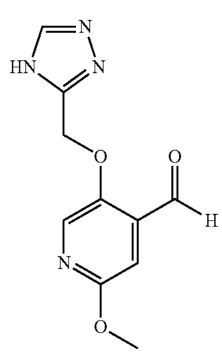 [SMILES: COc1cc(C=O)c(OCc2nnc[nH]2)cn1] | 5-((4H-1,2,4-triazol-3-yl)methoxy)-2-methoxyisonicotinaldehyde |

| Compound | Structure | Name |
|---|---|---|
| 34 | 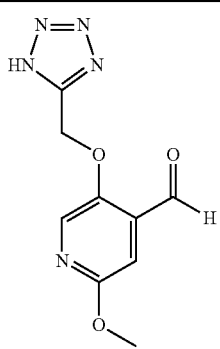 | 5-((1H-tetrazol-5-yl)methoxy)-2-methoxyisonicotinaldehyde |
| 35 | 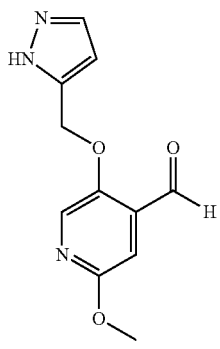 [SMILES: COc1cc(C=O)c(OCc2ccn[nH]2)cn1] | 5-((1H-pyrazol-5-yl)methoxy)-2-methoxyisonicotinaldehyde |
| 36 | 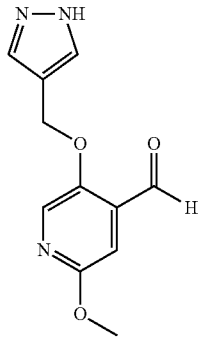 [SMILES: COc1cc(C=O)c(OCc2cn[nH]c2)cn1] | 5-((1H-pyrazol-4-yl)methoxy)-2-methoxyisonicotinaldehyde |
| 37 | 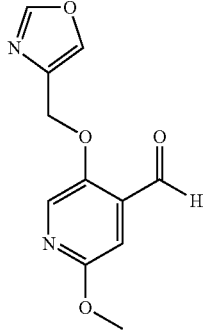 [SMILES: COc1cc(C=O)c(OCc2cocn2)cn1] | 2-methoxy-5-(oxazol-4-yl)methoxy)isonicotinaldehyde |

| Compound | Structure | Name |
|---|---|---|
| 38 | 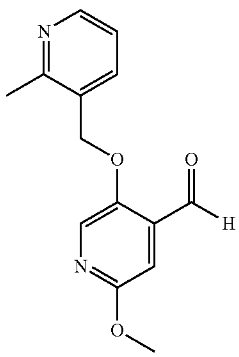 [SMILES: COc1cc(C=O)c(OCc2cccnc2C)cn1] | 2-methoxy-5-((2-methylpyridin-3-yl)methoxy)isonicotinaldehyde |
| 39 | 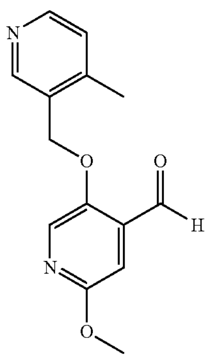 [SMILES: COc1cc(C=O)c(OCc2cnccc2C)cn1] | 2-methoxy-5-((4-methylpyridin-3-yl)methoxy)isonicotinaldehyde |
| 40 | 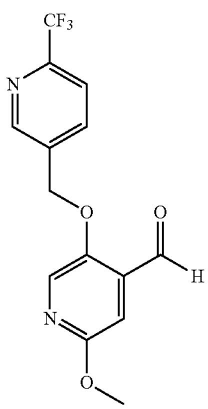 [SMILES: COc1cc(C=O)c(OCc2ccc(C(F)(F)F)nc2)cn1] | 2-methoxy-5-((6-(trifluoromethyl)pyridin-3-yl)methoxy)isonicotinaldehyde |
| 41 | 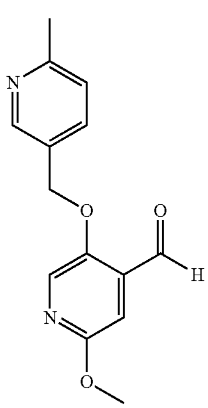 | 2-methoxy-5-((6-methylpyridin-3-yl)methoxy)isonicotinaldehyde |

-continued

| Compound | Structure | Name |
|---|---|---|
| 42 | 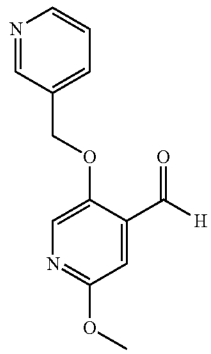 [SMILES: COc1cc(C=O)c(OCc2cccnc2)cn1] | 2-methoxy-5-(pyridin-3-ylmethoxy)isonicotinaldehyde |
| 43 | 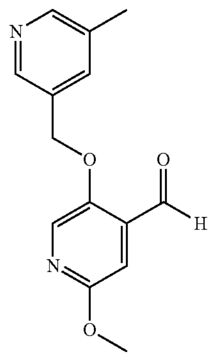 [SMILES: COc1cc(C=O)c(OCc2cncc(C)c2)cn1] | 2-methoxy-5-((5-methylpyridin-3-yl)methoxy)isonicotinaldehyde |
| 44 | 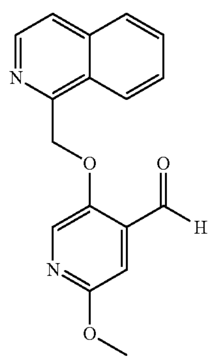 [SMILES: COc1cc(C=O)c(OCc2nccc3ccccc23)cn1] | 5-(isoquinolin-1-ylmethoxy)-2-methoxyisonicotinaldehyde |
| 45 | 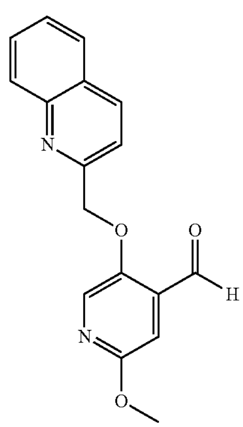 [SMILES: COc1cc(C=O)c(OCc2ccc3ccccc3n2)cn1] | 2-methoxy-5-(quinolin-2-ylmethoxy)isonicotinaldehyde |

-continued

| Compound | Structure | Name |
|---|---|---|
| 46 | 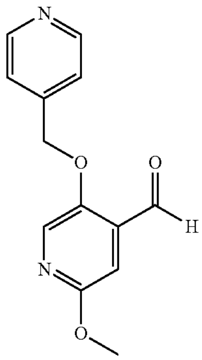 [SMILES: COc1cc(C=O)c(OCc2ccncc2)cn1] | 2-methoxy-5-(pyridin-4-ylmethoxy)isonicotinaldehyde |
| 47 | 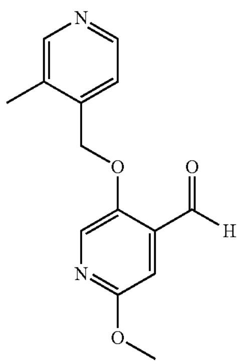 [SMILES: COc1cc(C=O)c(OCc2ccncc2C)cn1] | 2-methoxy-5-((3-methylpyridin-4-yl)methoxy)isonicotinaldehyde |
| 48 | 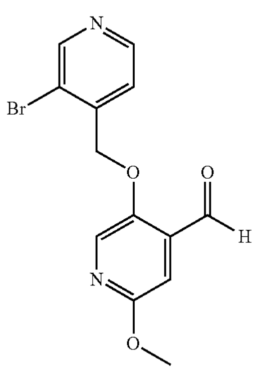 [SMILES: COc1cc(C=O)c(OCc2ccncc2Br)cn1] | 5-((3-bromopyridin-4-yl)methoxy)-2-methoxyisonicotinaldehyde |
| 49 | 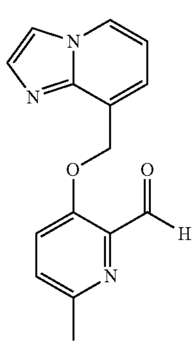 [SMILES: Cc1ccc(OCc2cccn3ccnc23)c(C=O)n1] | 3-(imidazo[1,2-a]pyridin-8-ylmethoxy)-6-methylpicolinaldehyde |

-continued

| Compound | Structure | Name |
|---|---|---|
| 50 | 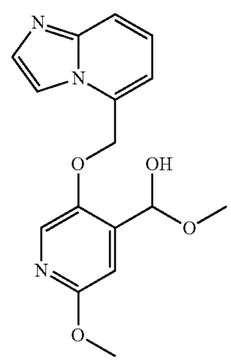 [SMILES: COc1cc(C(O)OC)c(OCc2cccc3nccn23)cn1] | (5-(imidazo[1,2-a]pyridin-5-ylmethoxy)-2-methoxypyridin-4-yl)(methoxy)methanol |
| 51 | 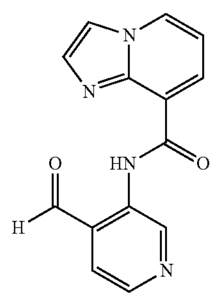 [SMILES: O=Cc1ccncc1NC(=O)c1cccn2ccnc12] | N-(4-formylpyridin-3-yl)imidazo[1,2-a]pyridine-8-carboxamide |
| 52 | 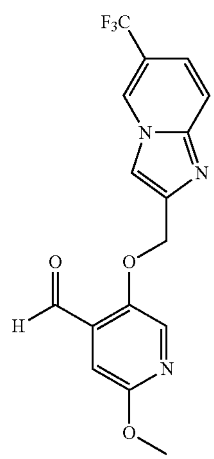 [SMILES: COc1cc(C=O)c(OCc2cn3cc(C(F)(F)F)ccc3n2)cn1] | 2-methoxy-5-((6-(trifluoromethyl)imidazo[1,2-a]pyridin-2-yl)methoxy)isonicotinaldehyde |
| 53 | 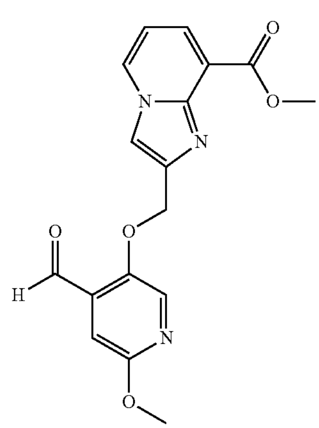 [SMILES: COC(=O)c1cccn2cc(COc3cnc(OC)cc3C=O)nc12] | methyl 2-((4-formyl-6-methoxypyridin-3-yloxy)methyl)imidazo[1,2-a]pyridine-8-carboxylate |

-continued
| Compound | Structure | Name |
|---|---|---|
| 54 | 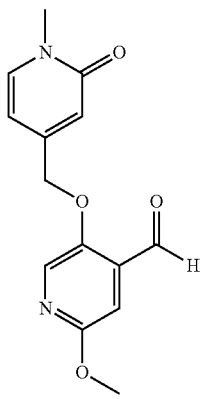 [SMILES: COc1cc(C=O)c(OCc2ccn(C)c(=O)c2)cn1] | 2-methoxy-5-((1-methyl-2-oxo-1,2-dihydropyridin-4-yl)methoxy)isonicotinaldehyde |
| 55 | 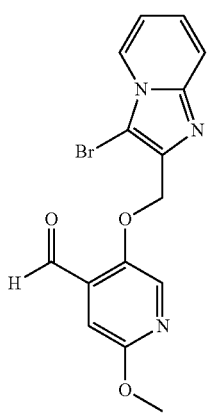 [SMILES: COc1cc(C=O)c(OCc2nc3ccccn3c2Br)cn1] | 5-((3-bromoimidazo[1,2-a]pyridin-2-yl)methoxy)-2-methoxyisonicotinaldehyde |
| 56 | 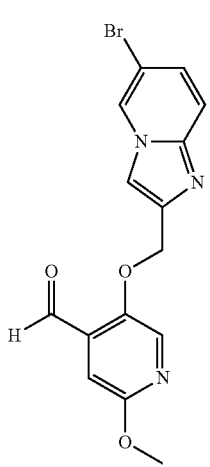 [SMILES: COc1cc(C=O)c(OCc2cn3cc(Br)ccc3n2)cn1] | 5-((6-bromoimidazo[1,2-a]pyridin-2-yl)methoxy)-2-methoxyisonicotinaldehyde |

-continued

| Compound | Structure | Name |
|---|---|---|
| 57 | 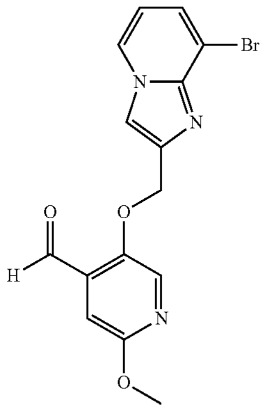 [SMILES: COc1cc(C=O)c(OCc2cn3cccc(Br)c3n2)cn1] | 5-((8-bromoimidazo[1,2-a]pyridin-2-yl)methoxy)-2-methoxyisonicotinaldehyde |
| 58 | 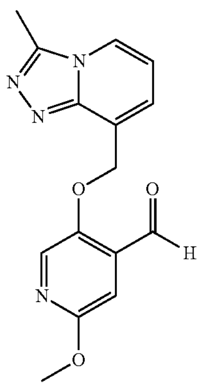 [SMILES: COc1cc(C=O)c(OCc2cccn3c(C)nnc23)cn1] | 2-methoxy-5-((3-methyl-[1,2,4]triazolo[4,3-a]pyridin-8-yl)methoxy)isonicotinaldehyde |
| 59 | 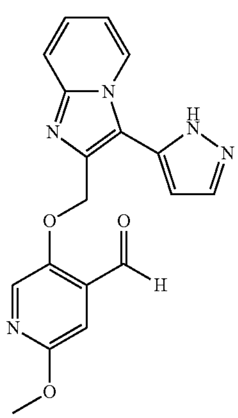 [SMILES: COc1cc(C=O)c(OCc2nc3ccccn3c2-c2ccn[nH]2)cn1] | 5-((3-(1H-pyrazol-5-yl)imidazo[1,2-a]pyridin-2-yl)methoxy)-2-methoxyisonicotinaldehyde |

-continued

| Compound | Structure | Name |
|---|---|---|
| 60 | 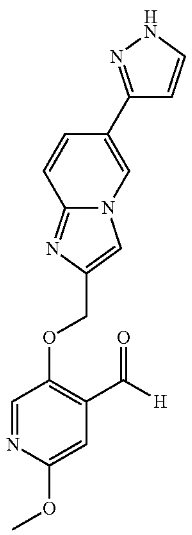 [SMILES: COc1cc(C=O)c(OCc2cn3cc(-c4cc[nH]n4)ccc3n2)cn1] | 5-((6-(1H-pyrazol-3-yl)imidazo[1,2-a]pyridin-2-yl)methoxy)-2-methoxyisonicotinaldehyde |
| 61 | 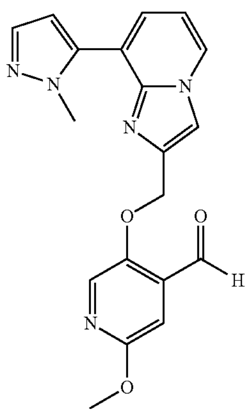 [SMILES: COc1cc(C=O)c(OCc2cn3cccc(-c4ccnn4C)c3n2)cn1] | 2-methoxy-5-((8-(1-methyl-1H-pyrazol-5-yl)imidazo[1,2-a]pyridin-2-yl)methoxy)isonicotinaldehyde |
| 62 | 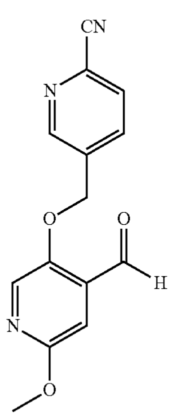 [SMILES: COc1cc(C=O)c(OCc2ccc(C#N)nc2)cn1] | 5-((4-formyl-6-methoxypyridin-3-yloxy)methyl)picolinonitrile |

| Compound | Structure | Name |
|---|---|---|
| 63 | 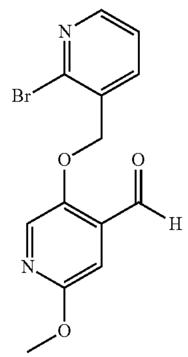 [SMILES: COc1cc(C=O)c(OCc2cccnc2Br)cn1] | 5-((2-bromopyridin-3-yl)methoxy)-2-methoxyisonicotinaldehyde |
| 64 | 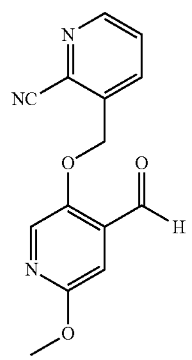 [SMILES: COc1cc(C=O)c(OCc2cccnc2C#N)cn1] | 3-((4-formyl-6-methoxypyridin-3-yloxy)methyl)picolinonitrile |
| 65 | 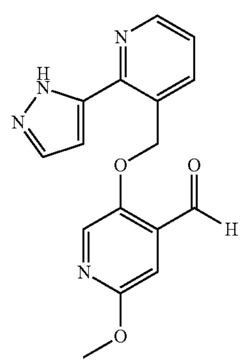 [SMILES: COc1cc(C=O)c(OCc2cccnc2-c2ccn[nH]2)cn1] | 5-((2-(1H-pyrazol-5-yl)pyridin-3-yl)methoxy)-2-methoxyisonicotinaldehyde |
| 66 | 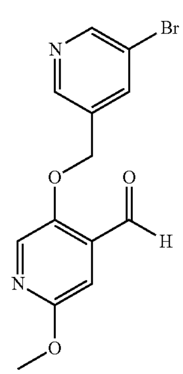 [SMILES: COc1cc(C=O)c(OCc2cncc(Br)c2)cn1] | 5-((5-bromopyridin-3-yl)methoxy)-2-methoxyisonicotinaldehyde |

-continued

| Compound | Structure | Name |
|---|---|---|
| 67 | 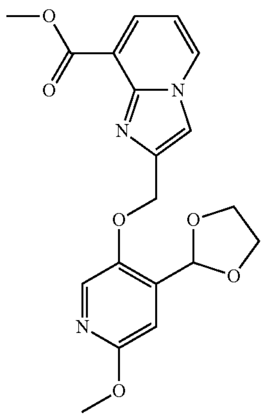 [SMILES: COC(=O)c1cccn2cc(COc3cnc(OC)cc3C3OCCO3)nc12] | methyl 2-((4-(1,3-dioxolan-2-yl)-6-methoxypyridin-3-yloxy)methyl)imidazo[1,2-a]pyridine-8-carboxylate |
| 68 | 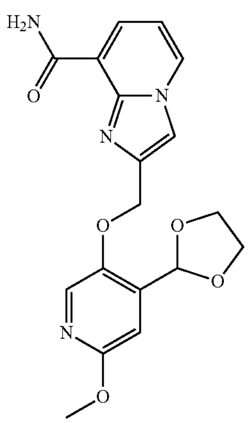 [SMILES: COc1cc(C2OCCO2)c(OCc2cn3cccc(C(N)=O)c3n2)cn1] | 2-((4-(1,3-dioxolan-2-yl)-6-methoxypyridin-3-yloxy)methyl)imidazo[1,2-a]pyridine-8-carboxamide |
| 69 | 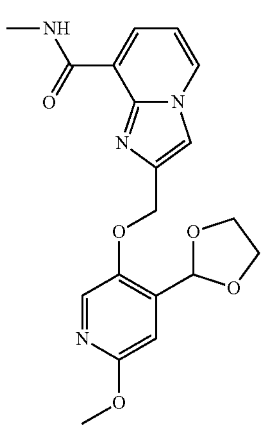 [SMILES: CNC(=O)c1cccn2cc(COc3cnc(OC)cc3C3OCCO3)nc12] | 2-((4-(1,3-dioxolan-2-yl)-6-methoxypyridin-3-yloxy)methyl)-N-methylimidazo[1,2-a]pyridine-8-carboxamide |

-continued

| Compound | Structure | Name |
|---|---|---|
| 70 | 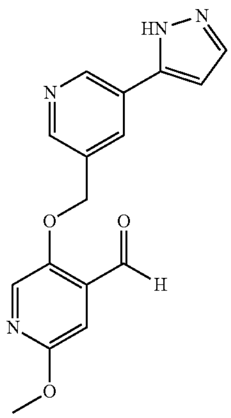 [SMILES: COc1cc(C=O)c(OCc2cncc(-c3ccn[nH]3)c2)cn1] | 5-((5-(1H-pyrazol-5-yl)pyridin-3-yl)methoxy)-2-methoxyisonicotinaldehyde |
| 71 | 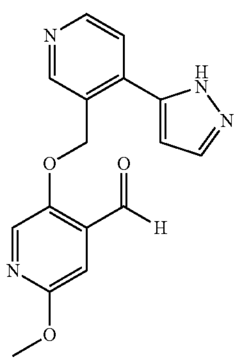 [SMILES: COc1cc(C=O)c(OCc2cnccc2-c2ccn[nH]2)cn1] | 5-((4-(1H-pyrazol-5-yl)pyridin-3-yl)methoxy)-2-methoxyisonicotinaldehyde |
| 72 | 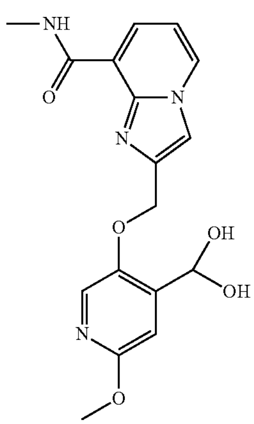 [SMILES: CNC(=O)c1cccn2cc(COc3cnc(OC)cc3C(O)O)nc12] | 2-((4-(dihydroxymethyl)-6-methoxypyridin-3-yloxy)methyl)-N-methylimidazo[1,2-a]pyridine-8-carboxamide |
| 73 | 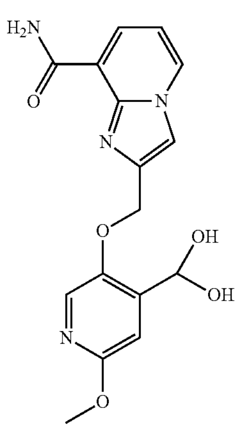 [SMILES: COc1cc(C(O)O)c(OCc2cn3cccc(C(N)=O)c3n2)cn1] | 2-((4-(dihydroxymethyl)-6-methoxypyridin-3-yloxy)methyl)imidazo[1,2-a]pyridine-8-carboxamide |

| Compound | Structure | Name |
|---|---|---|
| 74 | 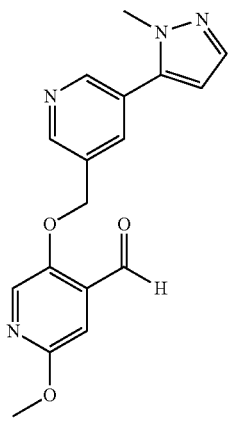 [SMILES: COc1cc(C=O)c(OCc2cncc(-c3ccnn3C)c2)cn1] | 2-methoxy-5-((5-(1-methyl-1H-pyrazol-5-yl)pyridin-3-yl)methoxy)isonicotinaldehyde |
| 75 | 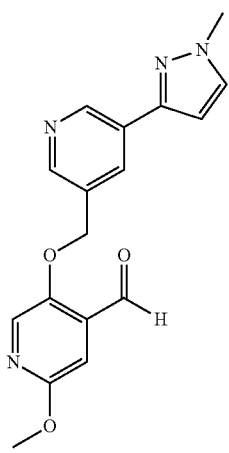 [SMILES: COc1cc(C=O)c(OCc2cncc(-c3ccn(C)n3)c2)cn1] | 2-methoxy-5-((5-(1-methyl-1H-pyrazol-3-yl)pyridin-3-yl)methoxy)isonicotinaldehyde |
| 76 | 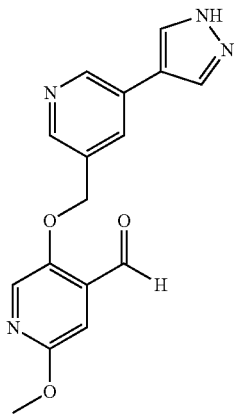 [SMILES: COc1cc(C=O)c(OCc2cncc(-c3cn[nH]c3)c2)cn1] | 5-((5-(1H-pyrazol-4-yl)pyridin-3-yl)methoxy)-2-methoxyisonicotinaldehyde |

-continued

| Compound | Structure | Name |
|---|---|---|
| 77 | 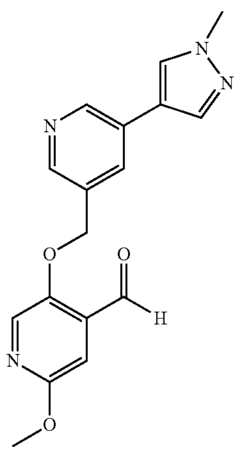 [SMILES: COc1cc(C=O)c(OCc2cncc(-c3cnn(C)c3)c2)cn1] | 2-methoxy-5-((5-(1-methyl-1H-pyrazol-4-yl)pyridin-3-yl)methoxy)isonicotinaldehyde |
| 78 | 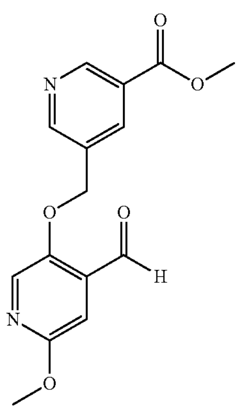 [SMILES: COC(=O)c1cncc(COc2cnc(OC)cc2C=O)c1] | methyl 5-((4-formyl-6-methoxypyridin-3-yloxy)methyl)nicotinate |
| 79 | 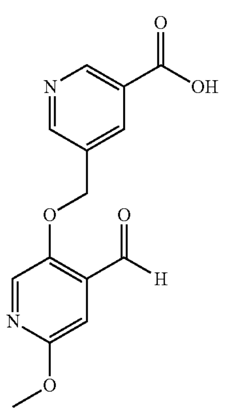 [SMILES: COc1cc(C=O)c(OCc2cncc(C(=O)O)c2)cn1] | 5-((4-formyl-6-methoxypyridin-3-yloxy)methyl)nicotinic acid |

| Compound | Structure | Name |
|---|---|---|
| 80 | 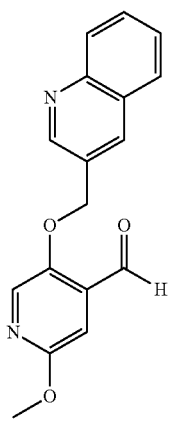 [SMILES: COc1cc(C=O)c(OCc2ccc3ccncc3c2)cn1] | 2-methoxy-5-(quinolin-3-ylmethoxy)isonicotinaldehyde |
| 81 | 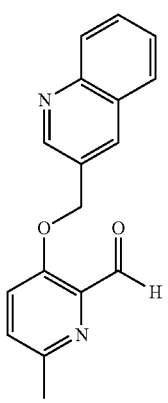 | 6-methyl-3-(quinolin-3-ylmethoxy)picolinaldehyde |
| 82 | 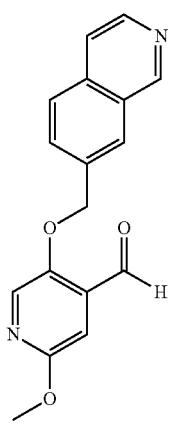 | 5-(isoquinolin-7-ylmethoxy)-2-methoxyisonicotinaldehyde |

| Compound | Structure | Name |
|---|---|---|
| 83 | 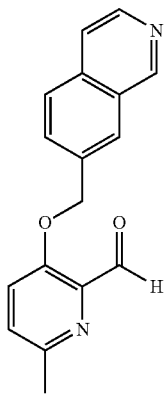 [SMILES: Cc1ccc(OCc2ccc3ccncc3c2)c(C=O)n1] | 3-(isoquinolin-7-ylmethoxy)-6-methylpicolinaldehyde |
| 84 | 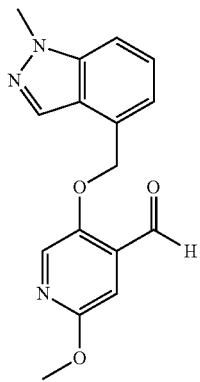 [SMILES: COc1cc(C=O)c(OCc2cccc3c2cnn3C)cn1] | 2-methoxy-5-((1-methyl-1H-indazol-4-yl)methoxy)isonicotinaldehyde |
| 85 | 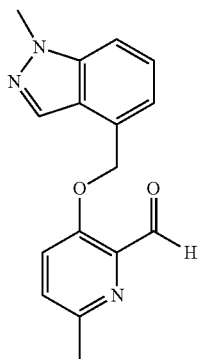 [SMILES: Cc1ccc(OCc2cccc3c2cnn3C)c(C=O)n1] | 6-methyl-3-((1-methyl-1H-indazol-4-yl)methoxy)picolinaldehyde |

| Compound | Structure | Name |
|---|---|---|
| 86 | 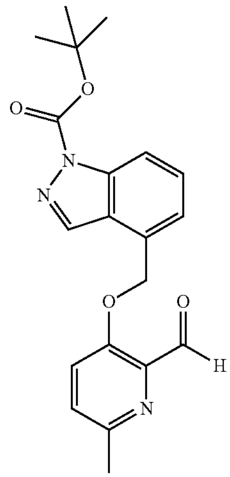 [SMILES: Cc1ccc(OCc2cccc3c2cnn3C(=O)OC(C)(C)C)c(C=O)n1] | tert-butyl 4-((2-formyl-6-methylpyridin-3-yloxy)methyl)-1H-indazole-1-carboxylate |
| 87 | 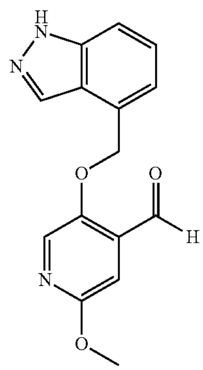 [SMILES: COc1cc(C=O)c(OCc2cccc3[nH]ncc23)cn1] | 5-((1H-indazol-4-yl)methoxy)-2-methoxyisonicotinaldehyde |
| 88 | 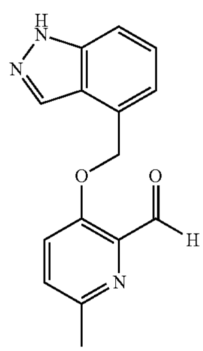 [SMILES: Cc1ccc(OCc2cccc3[nH]ncc23)c(C=O)n1] | 3-((1H-indazol-4-yl)methoxy)-6-methylpicolinaldehyde |
| 89 | 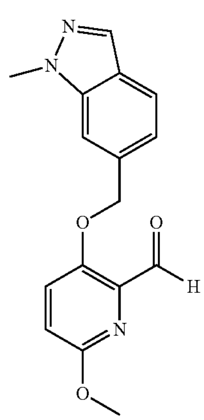 [SMILES: COc1ccc(OCc2ccc3cnn(C)c3c2)c(C=O)n1] | 6-methoxy-3-((1-methyl-1H-indazol-6-yl)methoxy)picolinaldehyde |

-continued

| Compound | Structure | Name |
|---|---|---|
| 90 | 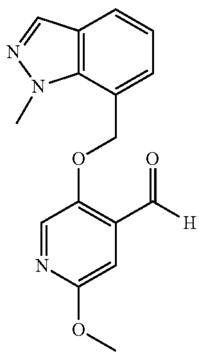 [SMILES: COc1cc(C=O)c(OCc2cccc3cnn(C)c23)cn1] | 2-methoxy-5-((1-methyl-1H-indazol-7-yl)methoxy)isonicotinaldehyde |
| 91 | 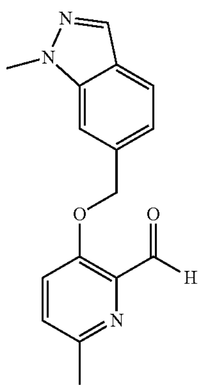 [SMILES: Cc1ccc(OCc2ccc3cnn(C)c3c2)c(C=O)n1] | 6-methyl-3-((1-methyl-1H-indazol-6-yl)methoxy)picolinaldehyde |
| 92 | 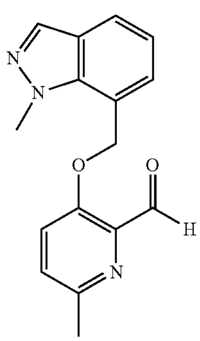 [SMILES: Cc1ccc(OCc2cccc3cnn(C)c23)c(C=O)n1] | 6-methyl-3-((1-methyl-1H-indazol-7-yl)methoxy)picolinaldehyde |
| 93 | 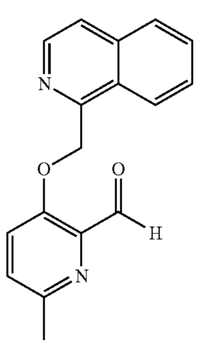 [SMILES: Cc1ccc(OCc2nccc3ccccc23)c(C=O)n1] | 3-(isoquinolin-1-ylmethoxy)-6-methylpicolinaldehyde |

| Compound | Structure | Name |
|---|---|---|
| 94 | 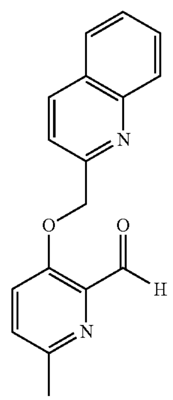 | 6-methyl-3-(quinolin-2-ylmethoxy)picolinaldehyde |
| 95 | 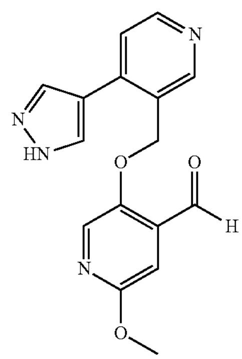 [SMILES: COc1cc(C=O)c(OCc2cnccc2-c2cn[nH]c2)cn1] | 5-((4-((1H-pyrazol-4-yl)pyridin-3-yl)methoxy)-2-methoxyisonicotinaldehyde |
| 96 | 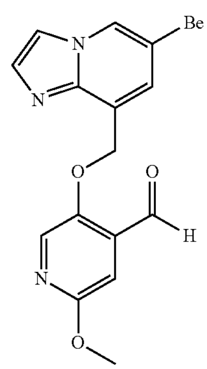 | 5-((6-bromoimidazo[1,2-a]pyridin-8-yl)methoxy)-2-methoxyisonicotinaldehyde |
| 97 | 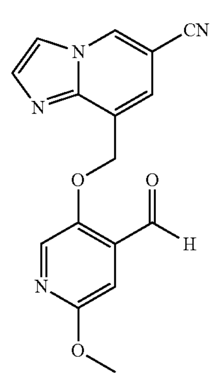 [SMILES: COc1cc(C=O)c(OCc2cc(C#N)cn3ccnc23)cn1] | 8-((4-formyl-6-methoxypyridin-3-yloxy)methyl)imidazo[1,2-a]pyridine-6-carbonitrile |

-continued

| Compound | Structure | Name |
|---|---|---|
| 98 | 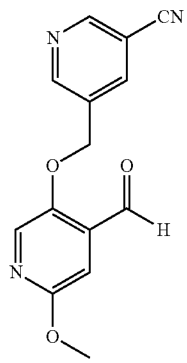 [SMILES: COc1cc(C=O)c(OCc2cncc(C#N)c2)cn1] | 5-((4-formyl-6-methoxypyridin-3-yloxy)methyl)nicotinonitrile |
| 99 | 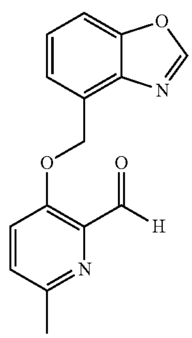 [SMILES: Cc1ccc(OCc2cccc3ocnc23)c(C=O)n1] | 3-(benzo[d]oxazol-4-ylmethoxy)-6-methylpicolinaldehyde |
| 100 | 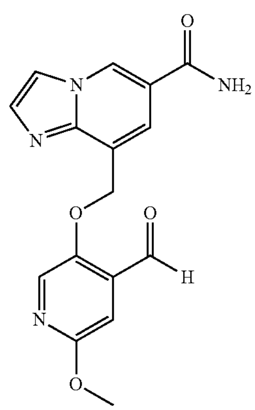 [SMILES: COc1cc(C=O)c(OCc2cc(C(N)=O)cn3ccnc23)cn1] | 8-((4-formyl-6-methoxypyridin-3-yloxy)methyl)imidazo[1,2-a]pyridine-6-carboxamide |
| 101 | 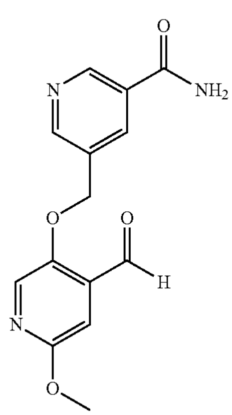 [SMILES: COc1cc(C=O)c(OCc2cncc(C(N)=O)c2)cn1] | 5-((4-formyl-6-methoxypyridin-3-yloxy)methyl)nicotinamide |

-continued

| Compound | Structure | Name |
|---|---|---|
| 102 | 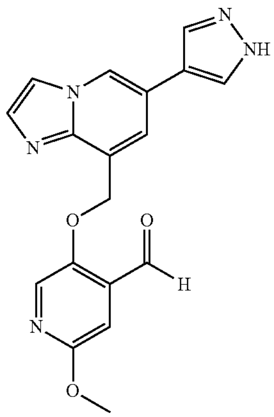 [SMILES: COc1cc(C=O)c(OCc2cc(-c3cn[nH]c3)cn3ccnc23)cn1] | 5-((6-(1H-pyrazol-4-yl)imidazo[1,2-a]pyridin-8-yl)methoxy)-2-methoxyisonicotinaldehyde |
| 103 | 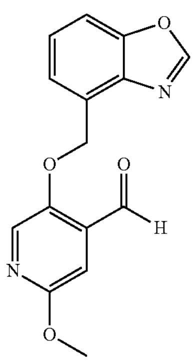 [SMILES: COc1cc(C=O)c(OCc2cccc3ocnc23)cn1] | 5-(benzo[d]oxazol-4-ylmethoxy)-2-methoxyisonicotinaldehyde |
| 104 | 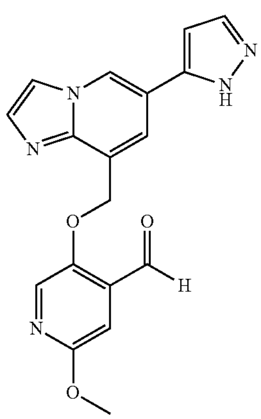 [SMILES: COc1cc(C=O)c(OCc2cc(-c3ccn[nH]3)cn3ccnc23)cn1] | 5-((6-(1H-pyrazol-5-yl)imidazo[1,2-a]pyridin-8-yl)methoxy)-2-methoxyisonicotinaldehyde |
| 105 | 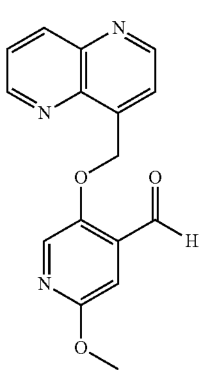 [SMILES: COc1cc(C=O)c(OCc2ccnc3cccnc23)cn1] | 5-(((1,5-naphthyridin-4-yl)methoxy)-2-methoxyisonicotinaldehyde |

| Compound | Structure | Name |
|---|---|---|
| 106 | 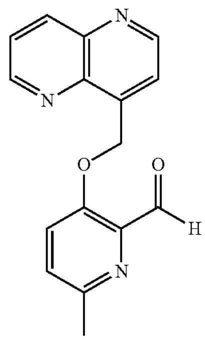 [SMILES: Cc1ccc(OCc2ccnc3cccnc23)c(C=O)n1] | 3-((1,5-naphthyridin-4-yl)methoxy)-6-methylpicolinaldehyde |
| 107 | 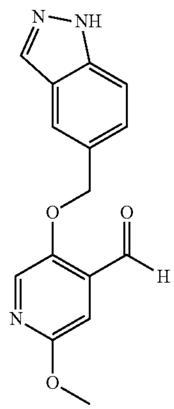 [SMILES: COc1cc(C=O)c(OCc2ccc3[nH]ncc3c2)cn1] | 5-((1H-indazol-5-yl)methoxy)-2-methoxyisonicotinaldehyde |
| 108 | 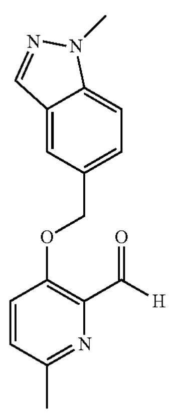 [SMILES: Cc1ccc(OCc2ccc3c(cnn3C)c2)c(C=O)n1] | 6-methyl-3-((1-methyl-1H-indazol-5-yl)methoxy)picolinaldehyde |
| 109 | 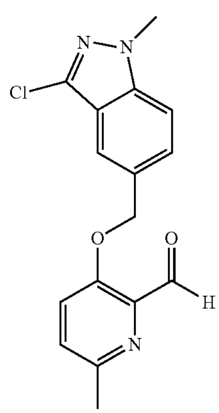 [SMILES: Cc1ccc(OCc2ccc3c(c2)c(Cl)nn3C)c(C=O)n1] | 3-((3-chloro-1-methyl-1H-indazol-5-yl)methoxy)-6-methylpicolinaldehyde |

-continued

| Compound | Structure | Name |
|---|---|---|
| 110 | 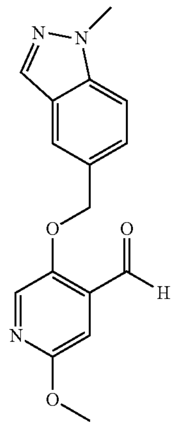 [SMILES: COc1cc(C=O)c(OCc2ccc3c(cnn3C)c2)cn1] | 2-methoxy-5-((1-methyl-1H-indazol-5-yl)methoxy)isonicotinaldehyde |
| 111 | 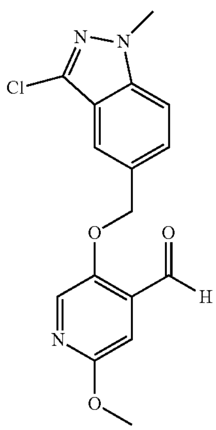 [SMILES: COc1cc(C=O)c(OCc2ccc3c(c2)c(Cl)nn3C)cn1] | 5-((3-chloro-1-methyl-1H-indazol-5-yl)methoxy)-2-methoxyisonicotinaldehyde |
| 112 | 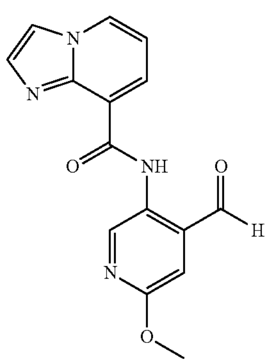 [SMILES: COc1cc(C=O)c(NC(=O)c2cccn3ccnc23)cn1] | N-(4-formyl-6-methoxypyridin-3-yl)imidazo[1,2-a]pyridine-8-carboxamide |
| 113 | 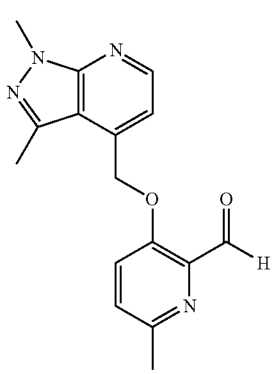 [SMILES: Cc1ccc(OCc2ccnc3c2c(C)nn3C)c(C=O)n1] | 3-((1,3-dimethyl-1H-pyrazolo[3,4-b]pyridin-4-yl)methoxy)-6-methylpicolinaldehyde |

-continued

| Compound | Structure | Name |
|---|---|---|
| 114 | 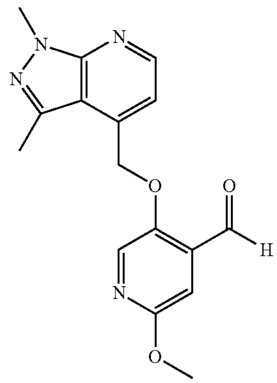 [SMILES: COc1cc(C=O)c(OCc2ccnc3c2c(C)nn3C)cn1] | 5-((1,3-dimethyl-1H-pyrazolo[3,4-b]pyridin-4-yl)methoxy)-2-methoxyisonicotinaldehyde |
| 115 | 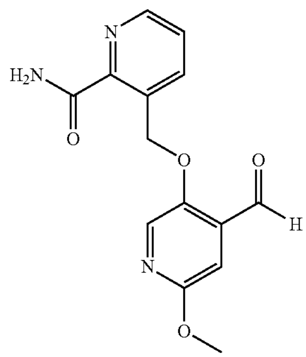 [SMILES: COc1cc(C=O)c(OCc2cccnc2C(N)=O)cn1] | 3-((4-formyl-6-methoxypyridin-3-yloxy)methyl)picolinamide |
| 116 | 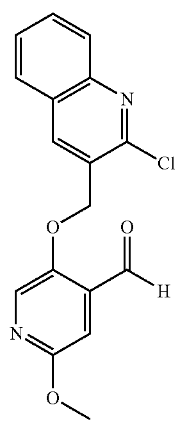 [SMILES: COc1cc(C=O)c(OCc2cc3ccccc3nc2Cl)cn1] | 5-((2-chloroquinolin-3-yl)methoxy)-2-methoxyisonicotinaldehyde |
| 117 | 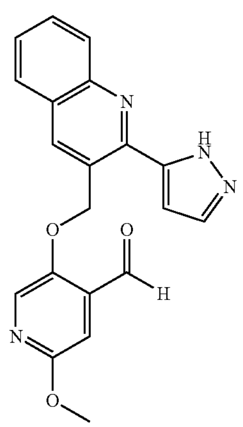 [SMILES: COc1cc(C=O)c(OCc2cc3ccccc3nc2-c2ccn[nH]2)cn1] | 5-((2-(1H-pyrazol-5-yl)quinolin-3-yl)methoxy)-2-methoxyisonicotinaldehyde |

-continued

| Compound | Structure | Name |
|---|---|---|
| 118 | 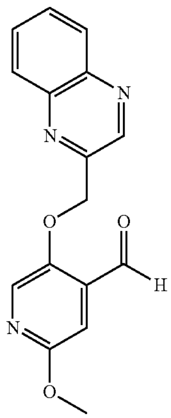 [SMILES: COc1cc(C=O)c(OCc2cnc3ccccc3n2)cn1] | 2-methoxy-5-(quinoxalin-2-ylmethoxy)isonicotinaldehyde |
| 119 | 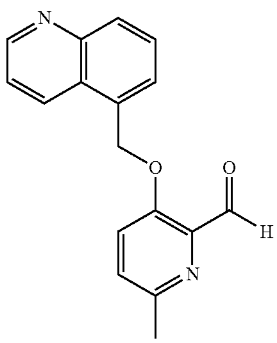 [SMILES: Cc1ccc(OCc2cccc3ncccc23)c(C=O)n1] | 6-methyl-3-(quinolin-5-ylmethoxy)picolinaldehyde |
| 120 | 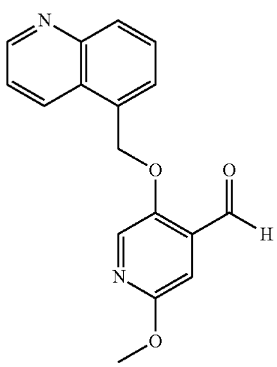 [SMILES: COc1cc(C=O)c(OCc2cccc3ncccc23)cn1] | 2-methoxy-5-(quinolin-5-ylmethoxy)isonicotinaldehyde |
| 121 | 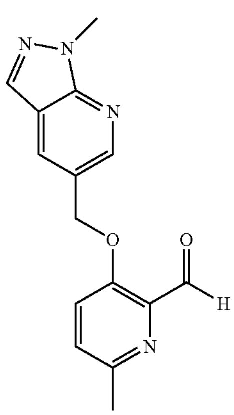 [SMILES: Cc1ccc(OCc2cnc3c(cnn3C)c2)c(C=O)n1] | 6-methyl-3-((1-methyl-1H-pyrazolo[3,4-b]pyridin-5-yl)methoxy)picolinaldehyde |

-continued
| Compound | Structure | Name |
|---|---|---|
| 122 | 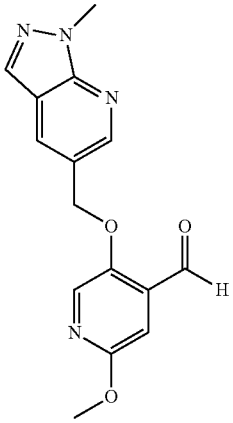 [SMILES: COc1cc(C=O)c(OCc2cnc3c(cnn3C)c2)cn1] | 2-methoxy-5-((1-methyl-1H-pyrazolo[3,4-b]pyridin-5-yl)methoxy)isonicotinaldehyde |
| 123 | 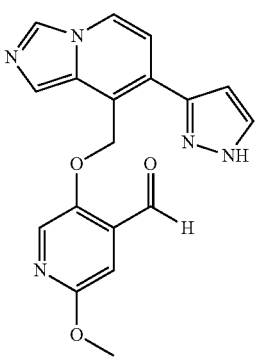 [SMILES: COc1cc(C=O)c(OCc2c(-c3cc[nH]n3)ccn3cncc23)cn1] | 5-((7-(1H-pyrazol-3-yl)imidazo[1,5-a]pyridin-8-yl)methoxy)-2-methoxyisonicotinaldehyde |
| 124 | 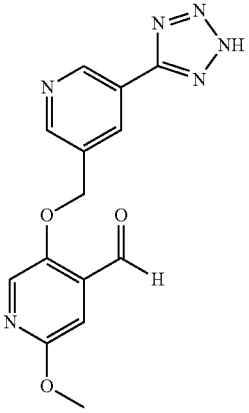 [SMILES: COc1cc(C=O)c(OCc2cncc(-c3nn[nH]n3)c2)cn1] | 5-((5-(2H-tetrazol-5-yl)pyridin-3-yl)methoxy)-2-methoxyisonicotinaldehyde |
| 125 | 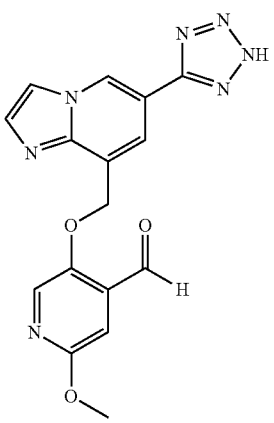 [SMILES: COc1cc(C=O)c(OCc2cc(-c3nn[nH]n3)cn3ccnc23)cn1] | 5-((6-(2H-tetrazol-5-yl)imidazo[1,2-a]pyridin-8-yl)methoxy)-2-methoxyisonicotinaldehyde |

-continued
| Compound | Structure | Name |
|---|---|---|
| 126 | 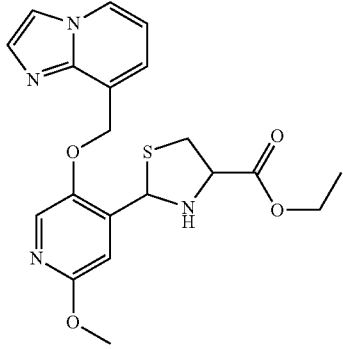 [SMILES: CCOC(=O)C1CSC(c2cc(OC)ncc2OCc2cccn3ccnc23)N1] | ethyl 2-(5-(imidazo[1,2-a]pyridin-8-ylmethoxy)-2-methoxypyridin-4-yl)thiazolidine-4-carboxylate |
| 127 | 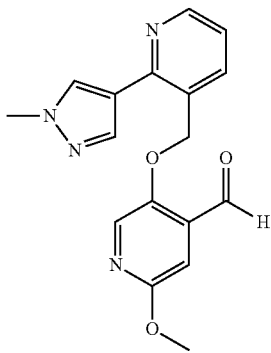 [SMILES: COc1cc(C=O)c(OCc2cccnc2-c2cnn(C)c2)cn1] | 2-methoxy-5-((2-(1-methyl-1H-pyrazol-4-yl)pyridin-3-yl)methoxy)isonicotinaldehyde |
| 128 | 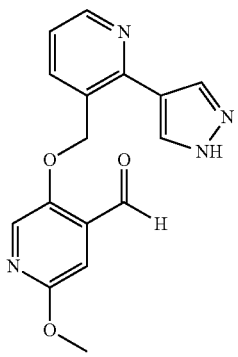 [SMILES: COc1cc(C=O)c(OCc2cccnc2-c2cn[nH]c2)cn1] | 5-((2-(1H-pyrazol-4-yl)pyridin-3-yl)methoxy)-2-methoxyisonicotinaldehyde |
| 129 | 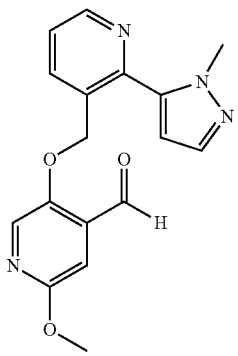 [SMILES: COc1cc(C=O)c(OCc2cccnc2-c2ccnn2C)cn1] | 2-methoxy-5-((2-(1-methyl-1H-pyrazol-5-yl)pyridin-3-yl)methoxy)isonicotinaldehyde |

-continued

| Compound | Structure | Name |
|---|---|---|
| 130 | 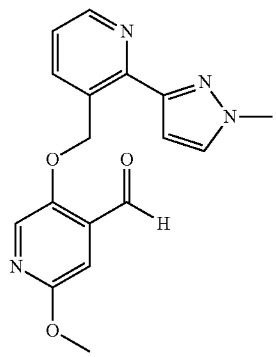 [SMILES: COc1cc(C=O)c(OCc2cccnc2-c2ccn(C)n2)cn1] | 2-methoxy-5-((2-(1-methyl-1H-pyrazol-3-yl)pyridin-3-yl)methoxy)isonicotinaldehyde |
| 131 | 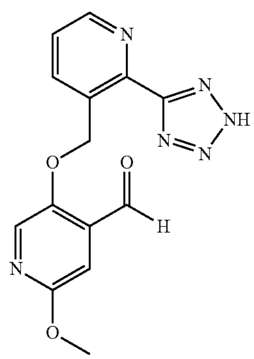 [SMILES: COc1cc(C=O)c(OCc2cccnc2-c2nn[nH]n2)cn1] | 5-((2-(2H-tetrazol-5-yl)pyridin-3-yl)methoxy)-2-methoxyisonicotinaldehyde |
| 132 | 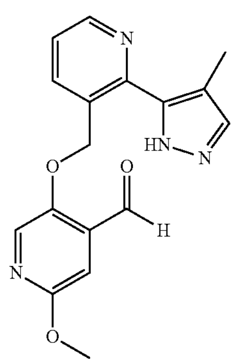 [SMILES: COc1cc(C=O)c(OCc2cccnc2-c2[nH]ncc2C)cn1] | 2-methoxy-5-((2-(4-methyl-1H-pyrazol-5-yl)pyridin-3-yl)methoxy)isonicotinaldehyde |
| 133 | 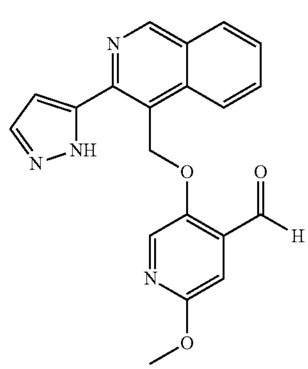 [SMILES: COc1cc(C=O)c(OCc2c(-c3ccn[nH]3)ncc3ccccc23)cn1] | 5-((3-(1H-pyrazol-5-yl)isoquinolin-4-yl)methoxy)-2-methoxyisonicotinaldehyde |

| Compound | Structure | Name |
|---|---|---|
| 134 | 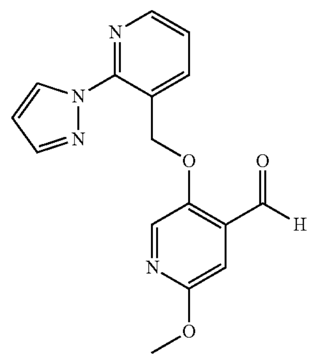 [SMILES: COc1cc(C=O)c(OCc2cccnc2-n2cccn2)cn1] | 5-((2-(1H-pyrazol-1-yl)pyridin-3-yl)methoxy)-2-methoxyisonicotinaldehyde |
| 135 | 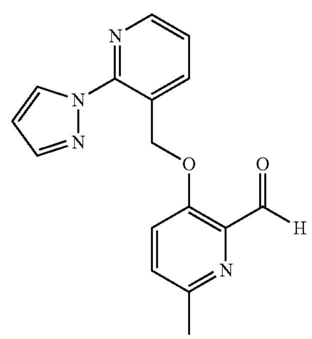 [SMILES: Cc1ccc(OCc2cccnc2-n2cccn2)c(C=O)n1] | 3-((2-(1H-pyrazol-1-yl)pyridin-3-yl)methoxy)-6-methylpicolinaldehyde |
| 136 | 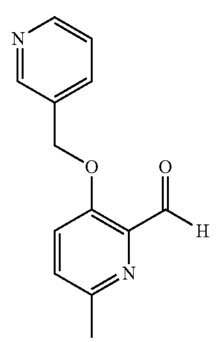 [SMILES: Cc1ccc(OCc2cccnc2)c(C=O)n1] | 6-methyl-3-(pyridin-3-yl)methoxy)picolinaldehyde |
| 137 | 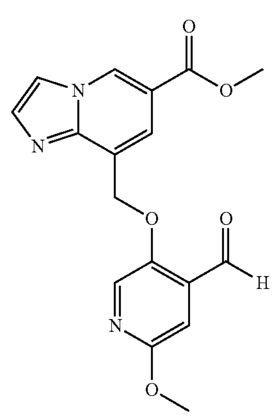 [SMILES: COC(=O)c1cc(COc2cnc(OC)cc2C=O)c2nccn2c1] | methyl 8-(((4-formyl-6-methoxypyridin-3-yl)oxy)methyl)imidazo[1,2-a]pyridine-6-carboxylate |

| Compound | Structure | Name |
|---|---|---|
| 138 | 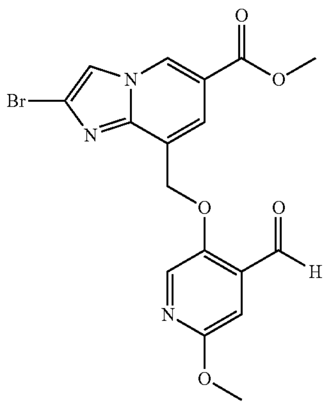 [SMILES: COC(=O)c1cc(COc2cnc(OC)cc2C=O)c2nc(Br)cn2c1] | methyl 2-bromo-8-(((4-formyl-6-methoxypyridin-3-yl)oxy)methyl)imidazo[1,2-a]pyridine-6-carboxylate |
| 139 | 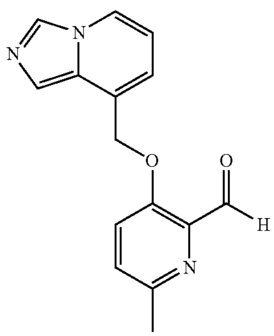 [SMILES: Cc1ccc(OCc2cccn3cncc23)c(C=O)n1] | 3-(imidazo[1,5-a]pyridin-8-ylmethoxy)-6-methylpicolinaldehyde |
| 140 | 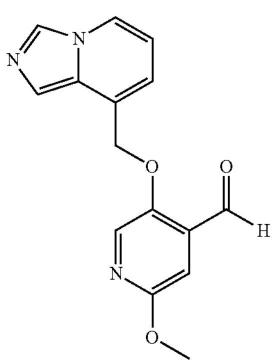 [SMILES: COc1cc(C=O)c(OCc2cccn3cncc23)cn1] | 5-(imidazo[1,5-a]pyridin-8-ylmethoxy)-2-methoxyisonicotinaldehyde |
| 141 | 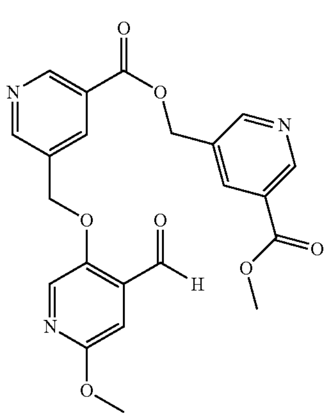 [SMILES: COC(=O)c1cncc(COC(=O)c2cncc(COc3cnc(OC)cc3C=O)c2)c1] | (5-(methoxycarbonyl)pyridin-3-yl)methyl 5-(((4-formyl-6-methoxypyridin-3-yl)oxy)methyl)nicotinate |

| Compound | Structure | Name |
|---|---|---|
| 142 | 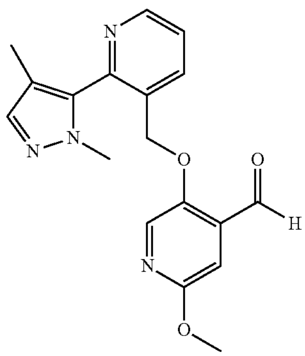 [SMILES: COc1cc(C=O)c(OCc2cccnc2-c2c(C)cnn2C)cn1] | 5-((2-(1,4-dimethyl-1H-pyrazol-5-yl)pyridin-3-yl)methoxy)-2-methoxyisonicotinaldehyde |
| 143 | 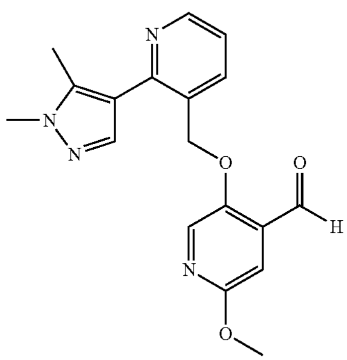 [SMILES: COc1cc(C=O)c(OCc2cccnc2-c2cnn(C)c2C)cn1] | 5-((2-(1,5-dimethyl-1H-pyrazol-4-yl)pyridin-3-yl)methoxy)-2-methoxyisonicotinaldehyde |
| 144 | 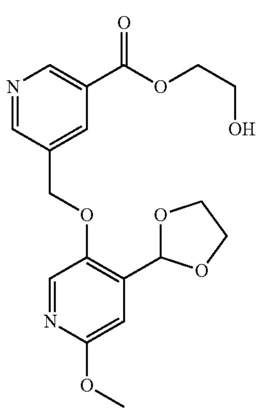 [SMILES: COc1cc(C2OCCO2)c(OCc2cncc(C(=O)OCCO)c2)cn1] | 2-hydroxyethyl 5-(((4-(1,3-dioxolan-2-yl)-6-methoxypyridin-3-yl)oxy)methyl)nicotinate |
| 145 | 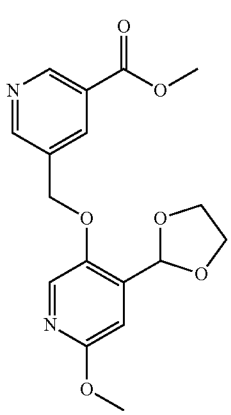 [SMILES: COC(=O)c1cncc(COc2cnc(OC)cc2C2OCCO2)c1] | methyl 5-(((4-(1,3-dioxolan-2-yl)-6-methoxypyridin-3-yl)oxy)methyl)nicotinate |

| Compound | Structure | Name |
|---|---|---|
| 146 | 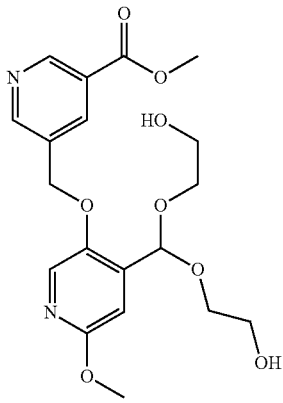 [SMILES: COC(=O)c1cncc(COc2cnc(OC)cc2C(OCCO)OCCO)c1] | methyl 5-(((4-(bis(2-hydroxyethoxy)methyl)-6-methoxypyridin-3-yl)oxy)methyl)nicotinate |
| 147 | 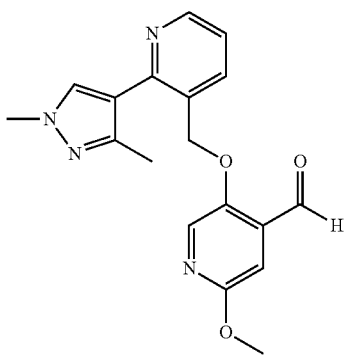 [SMILES: COc1cc(C=O)c(OCc2cccnc2-c2cn(C)nc2C)cn1] | 5-((2-(1,3-dimethyl-1H-pyrazol-4-yl)pyridin-3-yl)methoxy)-2-methoxyisonicotinaldehyde |
| 148 | 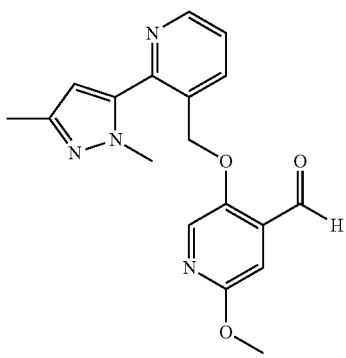 [SMILES: COc1cc(C=O)c(OCc2cccnc2-c2cc(C)nn2C)cn1] | 5-((2-(1,3-dimethyl-1H-pyrazol-5-yl)pyridin-3-yl)methoxy)-2-methoxyisonicotinaldehyde |
| 149 | 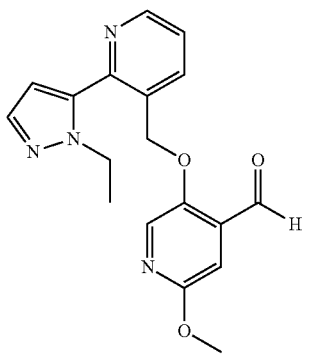 [SMILES: CCn1nccc1-c1ncccc1COc1cnc(OC)cc1C=O] | 5-((2-(1-ethyl-1H-pyrazol-5-yl)pyridin-3-yl)methoxy)-2-methoxyisonicotinaldehyde |

-continued

| Compound | Structure | Name |
|---|---|---|
| 150 | 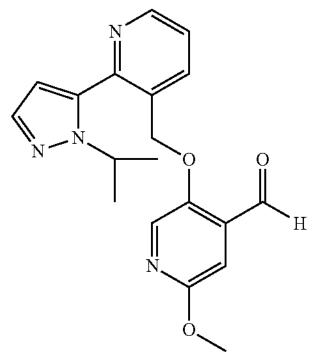 [SMILES: COc1cc(C=O)c(OCc2cccnc2-c2ccnn2C(C)C)cn1] | 5-((2-(1-isopropyl-1H-pyrazol-5-yl)pyridin-3-yl)methoxy)-2-methoxyisonicotinaldehyde |
| 151 | 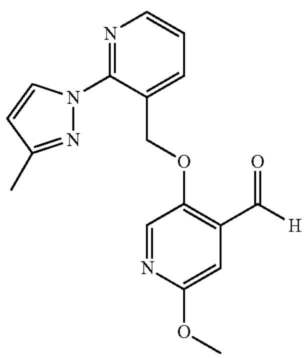 [SMILES: COc1cc(C=O)c(OCc2cccnc2-n2ccc(C)n2)cn1] | 2-methoxy-5-((2-(3-methyl-1H-pyrazol-1-yl)pyridin-3-yl)methoxy)isonicotinaldehyde |
| 152 | 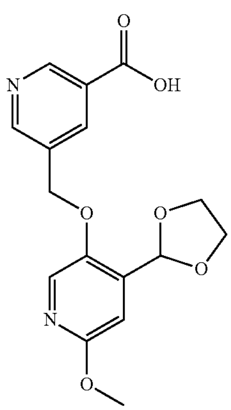 [SMILES: COc1cc(C2OCCO2)c(OCc2cncc(C(=O)O)c2)cn1] | 5-(((4-(1,3-dioxolan-2-yl)-6-methoxypyridin-3-yl)oxy)methyl)nicotinic acid |
| 153 | 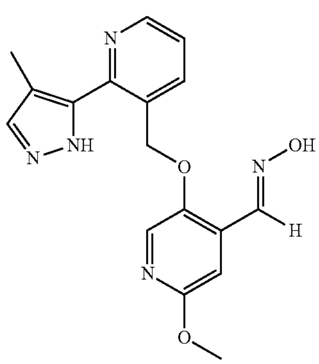 [SMILES: COc1cc(/C=N/O)c(OCc2cccnc2-c2[nH]ncc2C)cn1] | (E)-2-methoxy-5-((2-(4-methyl-1H-pyrazol-5-yl)pyridin-3-yl)methoxy)isonicotinaldehyde oxime |

-continued

| Compound | Structure | Name |
|---|---|---|
| 154 | 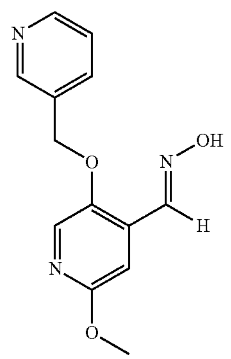 [SMILES: COc1cc(/C=N/O)c(OCc2cccnc2)cn1] | (E)-2-methoxy-5-(pyridin-3-ylmethoxy)isonicotinaldehyde oxime |
| 155 | 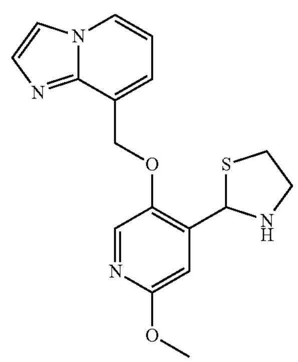 [SMILES: COc1cc(C2NCCS2)c(OCc2cccn3ccnc23)cn1] | 2-(5-(imidazo[1,2-a]pyridin-8-ylmethoxy)-2-methoxypyridin-4-yl)thiazolidine |
| 156 | 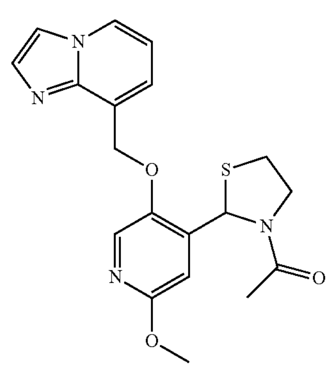 [SMILES: COc1cc(C2SCCN2C(C)=O)c(OCc2cccn3ccnc23)cn1] | 1-(2-(5-(imidazo[1,2-a]pyridin-8-ylmethoxy)-2-methoxypyridin-4-yl)thiazolidin-3-yl)ethanone |
| 157 | 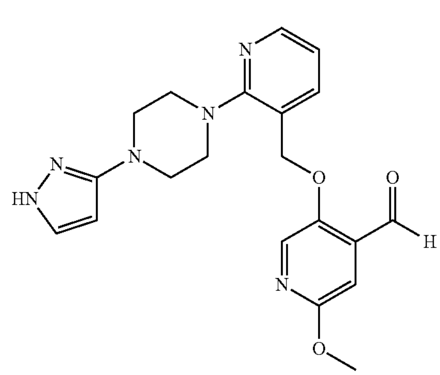 [SMILES: COc1cc(C=O)c(OCc2cccnc2N2CCN(c3cc[nH]n3)CC2)cn1] | 5-((2-(4-(1H-pyrazol-3-yl)piperazin-1-yl)pyridin-3-yl)methoxy)-2-methoxyisonicotinaldehyde |

-continued

| Compound | Structure | Name |
|---|---|---|
| 158 | 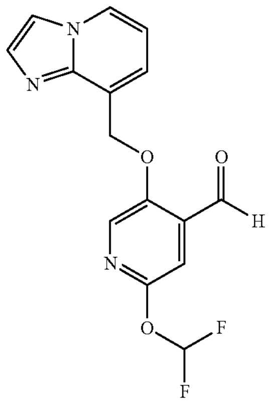 [SMILES: O=Cc1cc(OC(F)F)ncc1OCc1cccn2ccnc12] | 2-(difluoromethoxy)-5-(imidazo[1,2-a]pyridin-8-ylmethoxy)isonicotinaldehyde |
| 159 | 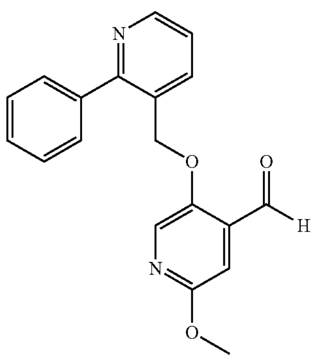 [SMILES: COc1cc(C=O)c(OCc2cccnc2-c2ccccc2)cn1] | 2-methoxy)-5-((2-phenylpyridin-3-yl)methoxy)isonicotinaldehyde |
| 160 | 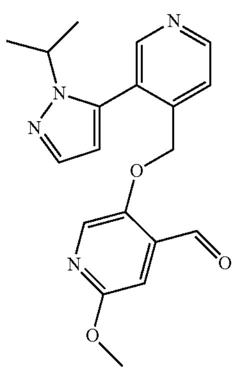 [SMILES: COc1cc(C=O)c(OCc2ccncc2-c2ccnn2C(C)C)cn1] | 5-((3-(1-isopropyl-1H-pyrazol-5-yl)pyridin-4-yl)methoxy)-2-methoxyisonicotinaldehyde |
| 161 | 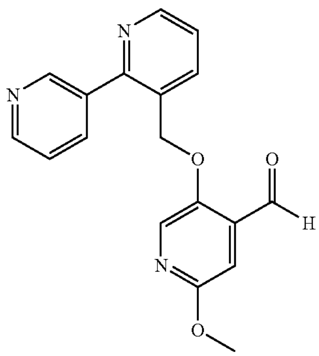 [SMILES: COc1cc(C=O)c(OCc2cccnc2-c2cccnc2)cn1] | 5-([2,3'-bipyridin]-3-ylmethoxy)-2-methoxyisonicotinaldehyde |

-continued

| Compound | Structure | Name |
|---|---|---|
| 162 | 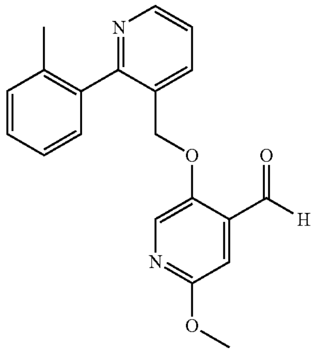 [SMILES: COc1cc(C=O)c(OCc2cccnc2-c2ccccc2C)cn1] | 2-methoxy-5-((2-(o-tolyl)pyridin-3-yl)methoxy)isonicotinaldehyde |
| 163 | 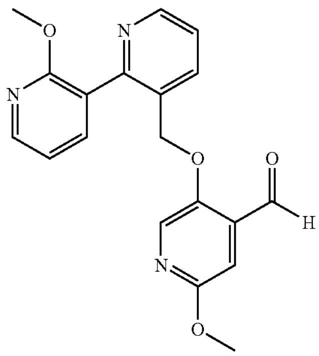 [SMILES: COc1cc(C=O)c(OCc2cccnc2-c2cccnc2OC)cn1] | 2-methoxy-5-((2'-methoxy-[2,3'-bipyridin]-3-yl)methoxy)isonicotinaldehyde |
| 164 | 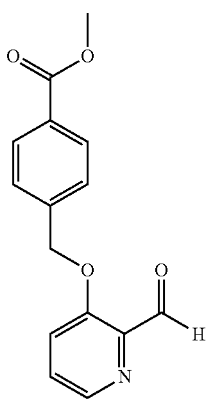 [SMILES: COC(=O)c1ccc(COc2cccnc2C=O)cc1] | methyl 4-(((2-formylpyridin-3-yl)oxy)methyl)benzoate |
| 165 | 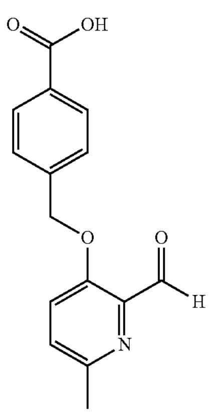 [SMILES: Cc1ccc(OCc2ccc(C(=O)O)cc2)c(C=O)n1] | 4-(((2-formyl-6-methylpyridin-3-yl)oxy)methyl)benzoic acid |

| Compound | Structure | Name |
|---|---|---|
| 166 | 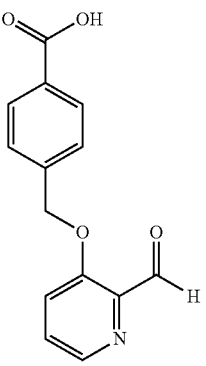 [SMILES: O=Cc1ncccc1OCc1ccc(C(=O)O)cc1] | 4-(((2-formylpyridin-3-yl)oxy)methyl)benzoic acid |
| 167 | 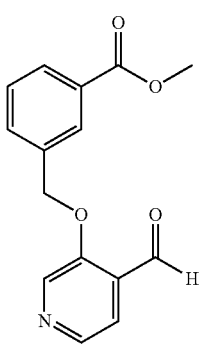 [SMILES: COC(=O)c1cccc(COc2cnccc2C=O)c1] | methyl 3-(((4-formylpyridin-3-yl)oxy)methyl)benzoate |
| 168 | 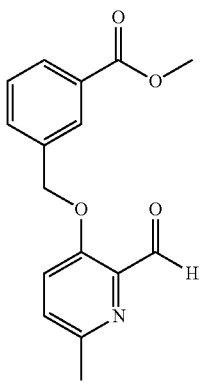 [SMILES: COC(=O)c1cccc(COc2ccc(C)nc2C=O)c1] | methyl 3-(((2-formyl-6-methylpyridin-3-yl)oxy)methyl)benzoate |
| 169 | 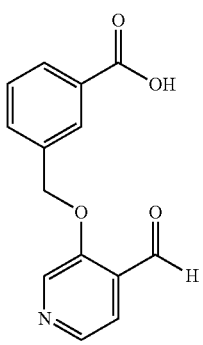 [SMILES: O=Cc1ccncc1OCc1cccc(C(=O)O)c1] | 3-(((4-formylpyridin-3-yl)oxy)methyl)benzoic acid |

-continued

| Compound | Structure | Name |
|---|---|---|
| 170 | 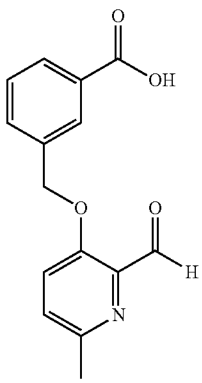 [SMILES: Cc1ccc(OCc2cccc(C(=O)O)c2)c(C=O)n1] | 3-(((2-formyl-6-methylpyridin-3-yl)oxy)methyl)benzoic acid |
| 171 | 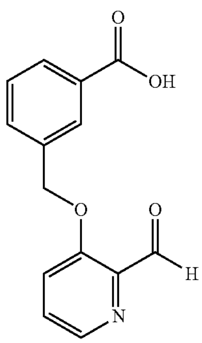 [SMILES: O=Cc1ncccc1OCc1cccc(C(=O)O)c1] | 3-(((2-formylpyridin-3-yl)oxy)methyl)benzoic acid |
| 172 | 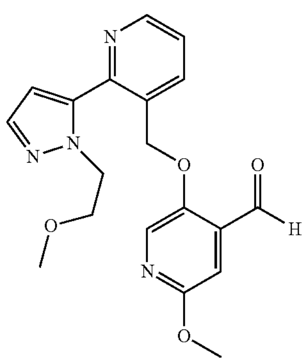 [SMILES: COCCn1nccc1-c1ncccc1COc1cnc(OC)cc1C=O] | 2-methoxy-5-((2-(1-(2-methoxyethyl)-1H-pyrazol-5-yl)pyridin-3-yl)methoxy)isonicotinaldehyde |
| 173 | 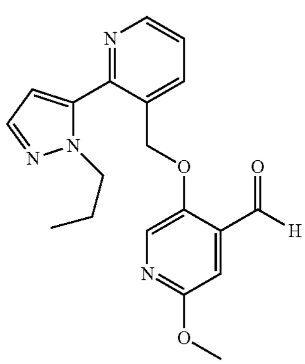 [SMILES: CCCn1nccc1-c1ncccc1COc1cnc(OC)cc1C=O] | 2-methoxy-5-((2-(1-propyl-1H-pyrazol-5-yl)pyridin-3-yl)methoxy)isonicotinaldehyde |

-continued

| Compound | Structure | Name |
|---|---|---|
| 174 | 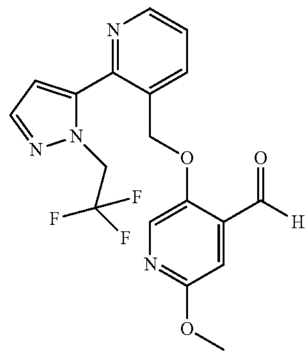 [SMILES: COc1cc(C=O)c(OCc2cccnc2-c2ccnn2CC(F)(F)F)cn1] | 2-methoxy-5-((2-(1-(2,2,2-trifluoroethyl)-1H-pyrazol-5-yl)pyridin-3-yl)methoxy)isonicotinaldehyde |
| 175 | 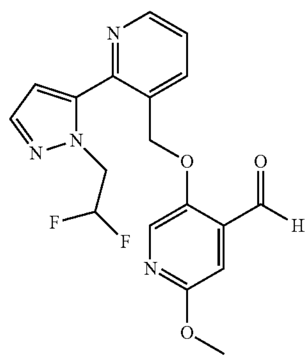 [SMILES: COc1cc(C=O)c(OCc2cccnc2-c2ccnn2CC(F)F)cn1] | 5-((2-(1-(2,2-difluoroethyl)-1H-pyrazol-5-yl)pyridin-3-yl)methoxy)-2-methoxyisonicotinaldehyde |
| 176 | 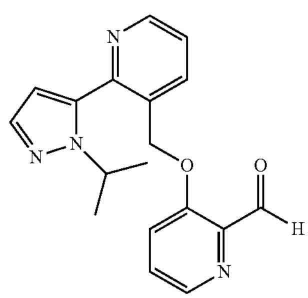 [SMILES: CC(C)n1nccc1-c1ncccc1COc1cccnc1C=O] | 3-((2-(1-isopropyl-1H-pyrazol-5-yl)pyridin-3-yl)methoxy)picolinaldehyde |
| 177 | 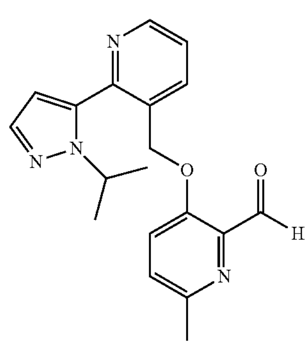 [SMILES: Cc1ccc(OCc2cccnc2-c2ccnn2C(C)C)c(C=O)n1] | 3-((2-(1-isopropyl-1H-pyrazol-5-yl)pyridin-3-yl)methoxy)-6-methylpicolinaldehyde |

-continued

| Compound | Structure | Name |
|---|---|---|
| 178 | 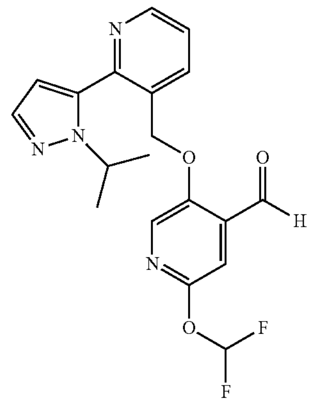 [SMILES: CC(C)n1nccc1-c1ncccc1COc1cnc(OC(F)F)cc1C=O] | 2-(difluoromethoxy)-5-((2-(1-isopropyl-1H-pyrazol-5-yl)pyridin-3-yl)methoxy)isonicotinaldehyde |
| 179 | 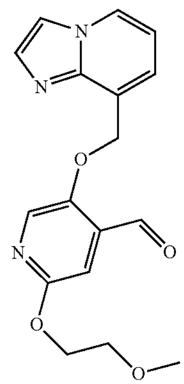 [SMILES: COCCOc1cc(C=O)c(OCc2cccn3ccnc23)cn1] | 5-(imidazo[1,2-a]pyridin-8-ylmethoxy)-2-(2-methoxyethoxy)isonicotinaldehyde |
| 180 | 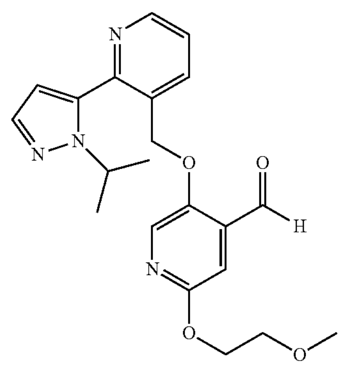 [SMILES: COCCOc1cc(C=O)c(OCc2cccnc2-c2ccnn2C(C)C)cn1] | 5-((2-(1-isopropyl-1H-pyrazol-5-yl)pyridin-3-yl)methoxy)-2-(2-methoxyethoxy)isonicotinaldehyde |
| 181 | 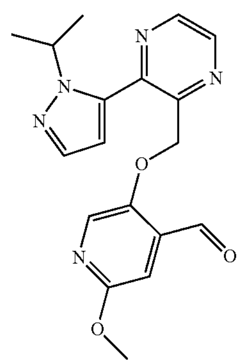 [SMILES: COc1cc(C=O)c(OCc2nccnc2-c2ccnn2C(C)C)cn1] | 5-((3-(1-isopropyl-1H-pyrazol-5-yl)pyrazin-2-yl)methoxy)-2-methoxyisonicotinaldehyde |

-continued

| Compound | Structure | Name |
|---|---|---|
| 182 | 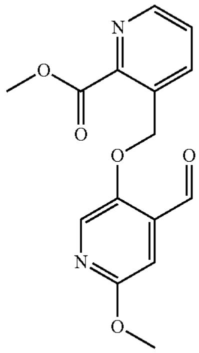 [SMILES: COC(=O)c1ncccc1COc1cnc(OC)cc1C=O] | 3-((4-formyl-6-methoxypyridin-3-yloxy)methyl)picolinate |
| 183 | 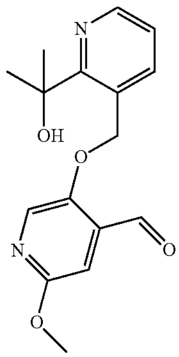 [SMILES: COc1cc(C=O)c(OCc2cccnc2C(C)(C)O)cn1] | 5-((2-(2-hydroxypropan-2-yl)pyridin-3-yl)methoxy)-2-methoxyisonicotinaldehyde |
| 184 | 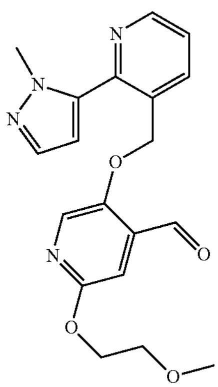 [SMILES: COCCOc1cc(C=O)c(OCc2cccnc2-c2ccnn2C)cn1] | 2-(2-methoxyethoxy)-5-((2-(1-methyl-1H-pyrazol-5-yl)pyridin-3-yl)methoxy)isonicotinaldehyde |
| 185 | 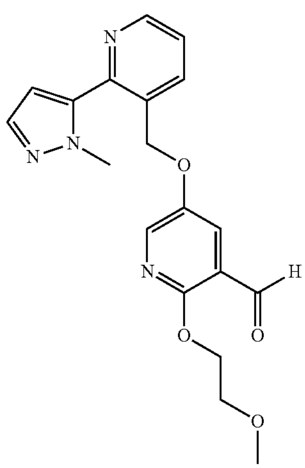 [SMILES: COCCOc1ncc(OCc2cccnc2-c2ccnn2C)cc1C=O] | 2-(2-methoxyethoxy)-5-((2-(1-methyl-1H-pyrazol-5-yl)pyridin-3-yl)methoxy)nicotinaldehyde |

-continued

| Compound | Structure | Name |
|---|---|---|
| 186 | 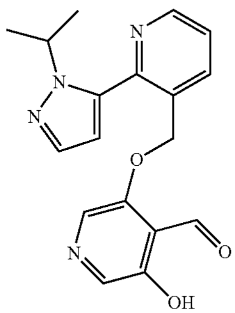 [SMILES: CC(C)n1nccc1-c1ncccc1COc1cncc(O)c1C=O] | 3-hydroxy-5-((2-(1-isopropyl-1H-pyrazol-5-yl)pyridin-3-yl)methoxy)isonicotinaldehyde |
| 187 | 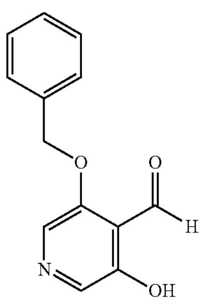 [SMILES: O=Cc1c(O)cncc1OCc1ccccc1] | 3-(benzyloxy)-5-hydroxyisonicotinaldehyde |
| 188 | 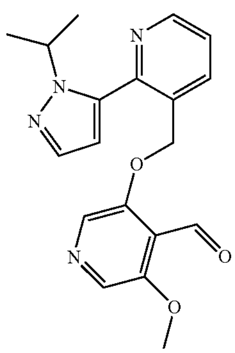 [SMILES: COc1cncc(OCc2cccnc2-c2ccnn2C(C)C)c1C=O] | 3-((2-(1-isopropyl-1H-pyrazol-5-yl)pyridin-3-yl)methoxy)-5-methoxyisonicotinaldehyde |
| 189 | 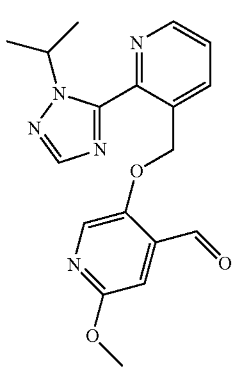 [SMILES: COc1cc(C=O)c(OCc2cccnc2-c2ncnn2C(C)C)cn1] | 5-((2-(2-isopropyl-2H-1,2,4-triazol-3-yl)pyridin-3-yl)methoxy)-2-methoxyisonicotinaldehyde |

-continued

| Compound | Structure | Name |
|---|---|---|
| 190 | 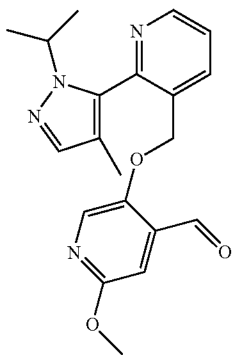 [SMILES: COc1cc(C=O)c(OCc2cccnc2-c2c(C)cnn2C(C)C)cn1] | 5-((2-(1-isopropyl-4-methyl-1H-pyrazol-5-yl)pyridin-3-yl)methoxy)-2-methoxyisonicotinaldehyde |
| 191 | 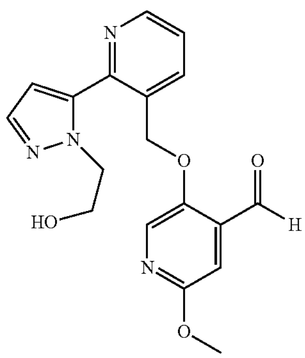 [SMILES: COc1cc(C=O)c(OCc2cccnc2-c2ccnn2CCO)cn1] | 5-((2-(1-(2-hydroxyethyl)-1H-pyrazol-5-yl)pyridin-3-yl)methoxy)-2-methoxyisonicotinaldehyde |
| 192 | 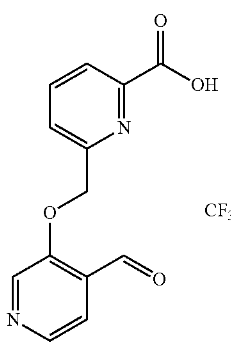 | 2,2,2-trifluoroacetic acid:6-(((4-formylpyridin-3-yl)oxy)methyl)picolinic acid (1:1) |
| 193 | 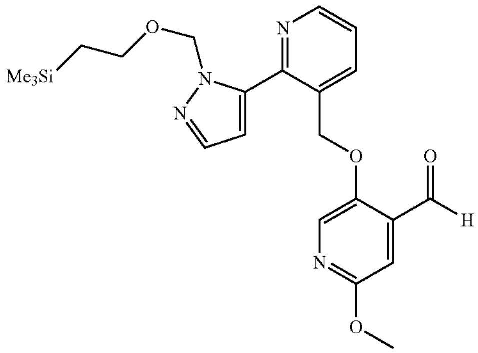 [SMILES: COc1cc(C=O)c(OCc2cccnc2-c2ccnn2COCC[Si](C)(C)C)cn1] | 2-methoxy-5-((2-(1-((2-(trimethylsilyl)ethoxy)methyl)-1H-pyrazol-5-yl)pyridin-3-yl)methoxy)isonicotinaldehyde |

-continued

| Compound | Structure | Name |
|---|---|---|
| 194 | 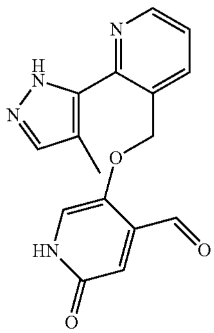 [SMILES: Cc1cn[nH]c1-c1ncccc1COc1c[nH]c(=O)cc1C=O] | 5-((2-(4-methyl-1H-pyrazol-5-yl)pyridin-3-yl)methoxy)-2-oxo-1,2-dihydropyridine-4-carbaldehyde |
| 195 | 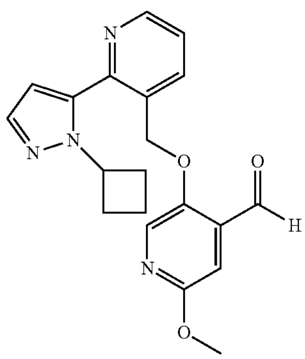 [SMILES: COc1cc(C=O)c(OCc2cccnc2-c2ccnn2C2CCC2)cn1] | 5-((2-(1-cyclobutyl-1H-pyrazol-5-yl)pyridin-3-yl)methoxy)-2-methoxyisonicotinaldehyde |
| 196 | 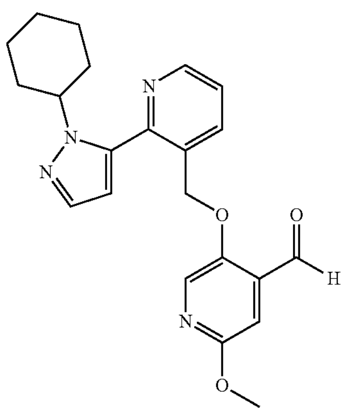 [SMILES: COc1cc(C=O)c(OCc2cccnc2-c2ccnn2C2CCCCC2)cn1] | 5-((2-(1-cyclohexyl-1H-pyrazol-5-yl)pyridin-3-yl)methoxy)-2-methoxyisonicotinaldehyde |
| 197 | 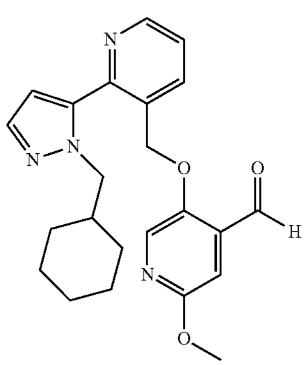 [SMILES: COc1cc(C=O)c(OCc2cccnc2-c2ccnn2CC2CCCCC2)cn1] | 5-((2-(1-(cyclohexylmethyl)-1H-pyrazol-5-yl)pyridin-3-yl)methoxy)-2-methoxyisonicotinaldehyde |

| Compound | Structure | Name |
|---|---|---|
| 198 | 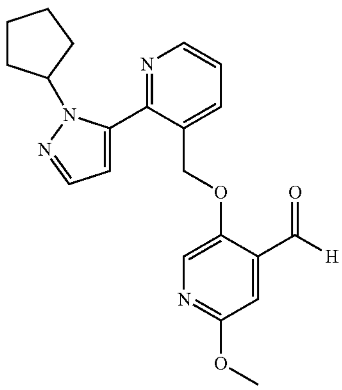 [SMILES: COc1cc(C=O)c(OCc2cccnc2-c2ccnn2C2CCCC2)cn1] | 5-((2-(1-cyclopentyl-1H-pyrazol-5-yl)pyridin-3-yl)methoxy)-2-methoxyisonicotinaldehyde |
| 199 | 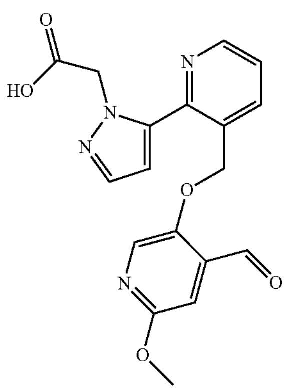 [SMILES: COc1cc(C=O)c(OCc2cccnc2-c2ccnn2CC(=O)O)cn1] | 2-(5-(3-((4-formyl-6-methoxypyridin-3-yloxy)methyl)pyridin-2-yl)-1H-pyrazol-1-yl)acetic acid |
| 200 | 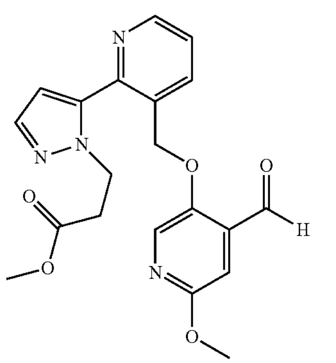 [SMILES: COC(=O)CCn1nccc1-c1ncccc1COc1cnc(OC)cc1C=O] | methyl 3-(5-(3-(((4-formyl-6-methoxypyridin-3-yl)oxy)methyl)pyridin-2-yl)-1H-pyrazol-1-yl)propanoate |
| 201 | 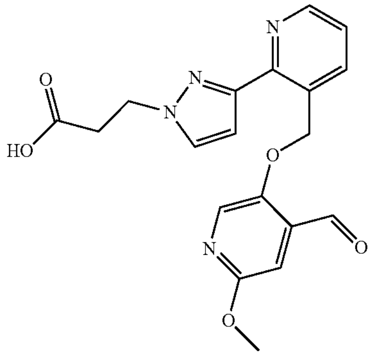 [SMILES: COc1cc(C=O)c(OCc2cccnc2-c2ccn(CCC(=O)O)n2)cn1] | 3-(3-(3-((4-formyl-6-methoxypyridin-3-yloxy)methyl)pyridin-2-yl)-1H-pyrazol-1-yl)propanoic acid |

-continued

| Compound | Structure | Name |
|---|---|---|
| 202 | 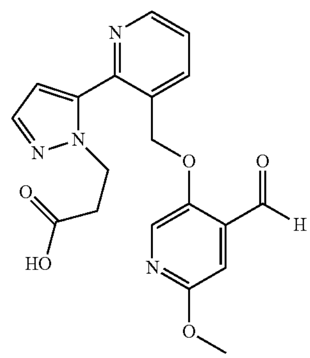 [SMILES: COc1cc(C=O)c(OCc2cccnc2-c2ccnn2CCC(=O)O)cn1] | 3-(5-(3-(((4-formyl-6-methoxypyridin-3-yl)oxy)methyl)pyridin-2-yl)-1H-pyrazol-1-yl)propanoic acid |
| 203 | 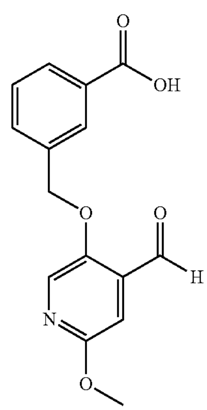 [SMILES: COc1cc(C=O)c(OCc2cccc(C(=O)O)c2)cn1] | 3-(((4-formyl-6-methoxypyridin-3-yl)oxy)methyl)benzoic acid |
| 204 | 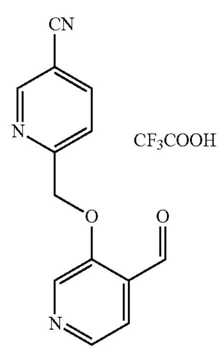 | 6-(((4-formylpyridin-3-yl)oxy)methyl)nicotinonitrile 2,2,2-trifluoroacetate |
| 205 | 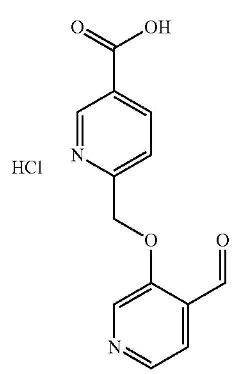 [SMILES: Cl ; O=Cc1ccncc1OCc1ccc(C(=O)O)cn1] | 6-(((4-formylpyridin-3-yl)oxy)methyl)nicotinic acid hydrochloride |

-continued

| Compound | Structure | Name |
|---|---|---|
| 206 | 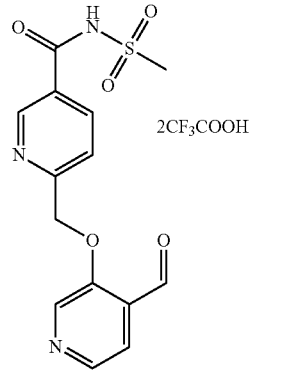 [SMILES: CS(=O)(=O)NC(=O)c1ccc(COc2cnccc2C=O)nc1] | 2,2,2-trifluoroacetic acid:6-(((4-formylpyridin-3-yl)oxy)methyl)-N-(methylsulfonyl)nicotinamide (2:1) |
| 207 | 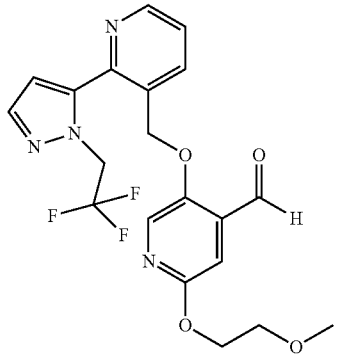 [SMILES: COCCOc1cc(C=O)c(OCc2cccnc2-c2ccnn2CC(F)(F)F)cn1] | 2-(2-methoxyethoxy)-5-((2-(1-(2,2,2-trifluoroethyl)-1H-pyrazol-5-yl)pyridin-3-yl)methoxy)isonicotinaldehyde |
| 208 | 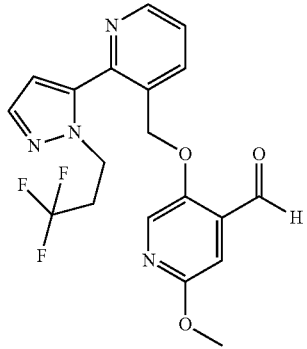 [SMILES: COc1cc(C=O)c(OCc2cccnc2-c2ccnn2CCC(F)(F)F)cn1] | 2-methoxy-5-((2-(1-(3,3,3-trifluoropropyl)-1H-pyrazol-5-yl)pyridin-3-yl)methoxy)isonicotinaldehyde |
| 209 | 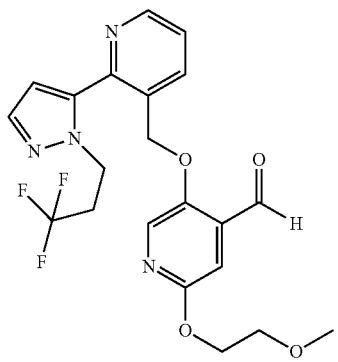 [SMILES: COCCOc1cc(C=O)c(OCc2cccnc2-c2ccnn2CCC(F)(F)F)cn1] | 2-(2-methoxyethoxy)-5-((2-(1-(3,3,3-trifluoropropyl)-1H-pyrazol-5-yl)pyridin-3-yl)methoxy)isonicotinaldehyde |

-continued

| Compound | Structure | Name |
|---|---|---|
| 210 | 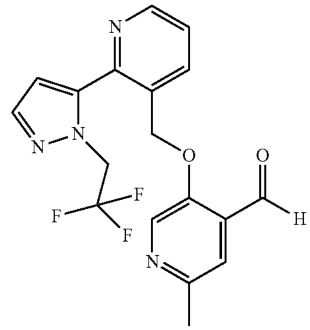 [SMILES: Cc1cc(C=O)c(OCc2cccnc2-c2ccnn2CC(F)(F)F)cn1] | 2-methyl-5-((2-(1-(2,2,2-trifluoroethyl)-1H-pyrazol-5-yl)pyridin-3-yl)methoxy)isonicotinaldehyde |
| 211 | 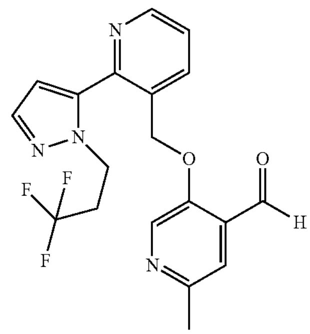 [SMILES: Cc1cc(C=O)c(OCc2cccnc2-c2ccnn2CCC(F)(F)F)cn1] | 2-methyl-5-((2-(1-(3,3,3-trifluoropropyl)-1H-pyrazol-5-yl)pyridin-3-yl)methoxy)isonicotinaldehyde |
| 212 | 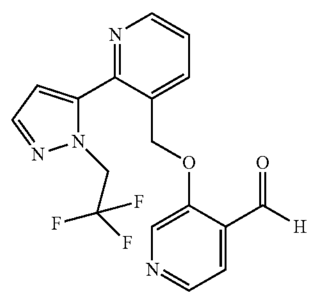 [SMILES: O=Cc1ccncc1OCc1cccnc1-c1ccnn1CC(F)(F)F] | 3-((2-(1-(2,2,2-trifluoroethyl)-1H-pyrazol-5-yl)pyridin-3-yl)methoxy)isonicotinaldehyde |
| 213 | 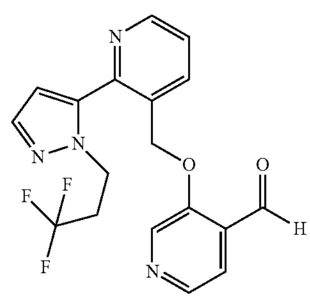 [SMILES: O=Cc1ccncc1OCc1cccnc1-c1ccnn1CCC(F)(F)F] | 3-((2-(1-(3,3,3-trifluoropropyl)-1H-pyrazol-5-yl)pyridin-3-yl)methoxy)isonicotinaldehyde |
| 214 | 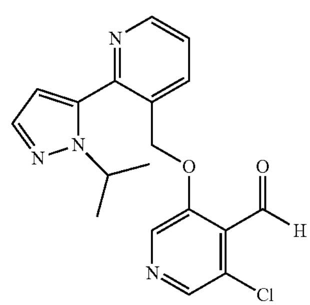 [SMILES: CC(C)n1nccc1-c1ncccc1COc1cncc(Cl)c1C=O] | 3-chloro-5-((2-(1-isopropyl-1H-pyrazol-5-yl)pyridin-3-yl)methoxy)isonicotinaldehyde |

| Compound | Structure | Name |
|---|---|---|
| 215 | 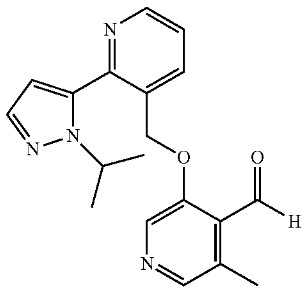 [SMILES: Cc1cncc(OCc2cccnc2-c2ccnn2C(C)C)c1C=O] | 3-((2-(1-isopropyl-1H-pyrazol-5-yl)pyridin-3-yl)methoxy)-5-methylisonicotinaldehyde |
| 216 | 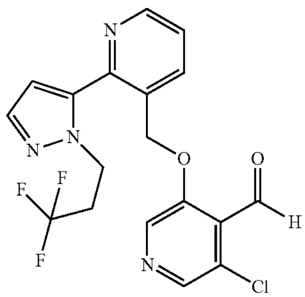 [SMILES: O=Cc1c(Cl)cncc1OCc1cccnc1-c1ccnn1CCC(F)(F)F] | 3-chloro-5-((2-(1-(3,3,3-trifluoropropyl)-1H-pyrazol-5-yl)pyridin-3-yl)methoxy)isonicotinaldehyde |
| 217 | 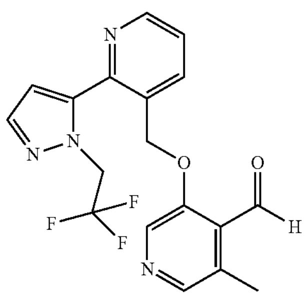 [SMILES: Cc1cncc(OCc2cccnc2-c2ccnn2CC(F)(F)F)c1C=O] | 3-methyl-5-((2-(1-(2,2,2-trifluoroethyl)-1H-pyrazol-5-yl)pyridin-3-yl)methoxy)isonicotinaldehyde |

The compound is selected from 5-hydroxy-2-(2-methoxyethoxy)isonicotinaldehyde (Compound 218), 5-hydroxy-2-(2-methoxyethoxy)nicotinaldehyde (Compound 219), 5-((2-(1-isopropyl-1H-pyrazol-5-yl)pyridin-3-yl)methoxy)-2-oxo-1,2-dihydropyridine-4-carbaldehyde (Compound 220), 5-((2-(4-methyl-1H-pyrazol-5-yl)pyridin-3-yl)methoxy)-2-oxo-1,2-dihydropyridine-4-carbaldehyde (Compound 221), or a tautomer or pharmaceutically acceptable salt thereof.

5-(imidazo[1,2-a]pyridin-8-ylmethoxy)-2-methoxyisonicotinaldehyde,
2-methoxy-5-((5-methylpyridin-3-yl)methoxy)isonicotinaldehyde,
5-(isoquinolin-1-ylmethoxy)-2-methoxyisonicotinaldehyde,
2-methoxy-5-(quinolin-2-yl methoxy)isonicotinaldehyde,
2-methoxy-5-(pyridin-4-ylmethoxy)isonicotinaldehyde,
3-(imidazo[1,2-a]pyridin-8-ylmethoxy)-6-methylpicolinaldehyde,
methyl 2-((4-formyl-6-methoxypyridin-3-yloxy)methyl)imidazo[1,2-a]pyridine-8-carboxylate,
2-methoxy-5-((3-methyl-[1,2,4]triazolo[4,3-a]pyridin-8-yl)methoxy)isonicotinaldehyde,
5-((2-bromopyridin-3-yl)methoxy)-2-methoxy isonicotinaldehyde,
5-((2-(1H-pyrazol-5-yl)pyridin-3-yl)methoxy)-2-methoxyisonicotinaldehyde,
5-((5-bromopyridin-3-yl)methoxy)-2-methoxyisonicotinaldehyde,
2-methoxy-5-((5-(1-methyl-1H-pyrazol-5-yl)pyridin-3-yl)methoxy)isonicotinaldehyde,
5-((4-formyl-6-methoxypyridin-3-yloxy)methyl)nicotinic acid,
2-methoxy-5-(quinolin-3-ylmethoxy)isonicotinaldehyde,
2-methoxy-5-((1-methyl-1H-indazol-4-yl)methoxy)isonicotinaldehyde,
tert-butyl 4-((2-formyl-6-methylpyridin-3-yloxy)methyl)-1H-indazole-1-carboxylate,
6-methyl-3-((1-methyl-1H-indazol-6-yl)methoxy)picolinaldehyde,
6-methyl-3-((1-methyl-1H-indazol-7-yl)methoxy)picolinaldehyde,
3-(isoquinolin-1-ylmethoxy)-6-yl)methyl)picolinaldehyde,
5-(benzo[d]oxazol-4-ylmethoxy)-2-methoxyisonicotinaldehyde,
3-((1,5-naphthyridin-4-yl)methoxy)-6-methylpicolinaldehyde,
6-methyl-3-((1-methyl-1H-indazol-5-yl)methoxy)picolinaldehyde,
6-methyl-3-(quinolin-5-ylmethoxy)picolinaldehyde,
2-methoxy-5-(quinolin-5-ylmethoxy)isonicotinaldehyde,
2-methoxy-5-((2-(1-methyl-1H-pyrazol-5-yl)pyridin-3-yl)methoxy)isonicotinaldehyde,
2-methoxy-5-((2-(1-methyl-1H-pyrazol-3-yl)pyridin-3-yl)methoxy)isonicotinaldehyde, 5-((2-(2H-tetrazol-5-yl)pyridin-3-yl)methoxy)-2-methoxyisonicotinaldehyde,
2-methoxy-5-((2-(4-methyl-1H-pyrazol-5-yl)pyridin-3-yl)methoxy)isonicotinaldehyde,
5-((3-(1H-pyrazol-5-yl)isoquinolin-4-yl)methoxy)-2-methoxyisonicotinaldehyde,
5-((2-(1H-pyrazol-1-yl)pyridin-3-yl)methoxy)-2-methoxyisonicotinaldehyde,
5-(imidazo[1,5-a]pyridin-8-ylmethoxy)-2-methoxyisonicotinaldehyde,
5-((2-(1,5-dimethyl-1H-pyrazol-4-yl)pyridin-3-yl)methoxy)-2-methoxyisonicotinaldehyde,
5-((2-(1-ethyl-1H-pyrazol-5-yl)pyridin-3-yl)methoxy)-2-methoxyisonicotinaldehyde,
5-((2-(1-isopropyl-1H-pyrazol-5-yl)pyridin-3-yl)methoxy)-2-methoxyisonicotinaldehyde,
2-(difluoromethoxy)-5-(imidazo[1,2-a]pyridin-8-ylmethoxy)isonicotinaldehyde,
2-methoxy-5-((2-phenylpyridin-3-yl)methoxy)isonicotinaldehyde,
5-((3-(1-isopropyl-1H-pyrazol-5-yl)pyridin-4-yl)methoxy)-2-methoxyisonicotinaldehyde,
5-([2,3'-bipyridin]-3-ylmethoxy)-2-methoxyisonicotinaldehyde,
2-methoxy-5-((2-(o-tolyl)pyridin-3-yl)methoxy)isonicotinaldehyde,
2-methoxy-5-((2'-methoxy-[2,3'-bipyridin]-3-yl)methoxy)isonicotinaldehyde,
4-(((2-formyl-6-methylpyridin-3-yl)oxy)methyl)benzoic acid,
4-(((2-formylpyridin-3-yl)oxy)methyl)benzoic acid,
methyl 3-(((4-formylpyridin-3-yl)oxy)methyl)benzoate,
methyl 3-(((2-formyl-6-methylpyridin-3-yl)oxy)methyl)benzoate,
3-(((4-formylpyridin-3-yl)oxy)methyl)benzoic acid,
3-(((2-formyl-6-methylpyridin-3-yl)oxymethyl)benzoic acid,
3-(((2-formylpyridin-3-yl)oxy)methyl)benzoic acid,
2-methoxy-5-((2-(1-(2-methoxyethyl)-1H-pyrazol-5-yl)pyridin-3-yl)methoxy)isonicotinaldehyde,
2-methoxy-5-((2-(1-propyl-1H-pyrazol-5-yl)pyridin-3-yl)methoxy)isonicotinaldehyde,
2-methoxy-5-((2-(1-(2,2,2-trifluoroethyl)-1H-pyrazol-5-yl)pyridin-3-yl)methoxy)isonicotinaldehyde,
5-((2-(1-(2,2-difluoroethyl)-1H-pyrazol-5-yl)pyridin-3-yl)methoxy)-2-methoxyisonicotinaldehyde,
3-((2-(1-isopropyl-1H-pyrazol-5-yl)pyridin-3-yl)methoxy)picolinaldehyde,
3-((2-(1-isopropyl-1H-pyrazol-5-yl)pyridin-3-yl)methoxy)-6-methylpicolinaldehyde,
2-(difluoromethoxy)-5-((2-(1-isopropyl-1H-pyrazol-5-yl)pyridin-3-yl)methoxy)isonicotinaldehyde,
5-(imidazo[1,2-a]pyridin-8-ylmethoxy)-2-(2-methoxyethoxy)isonicotinaldehyde,
5-((2-(1-isopropyl-1H-pyrazol-5-yl)pyridin-3-yl)methoxy)-2-(2-methoxyethoxy)isonicotinaldehyde,
5-((3-(1-isopropyl-1H-pyrazol-5-yl)pyrazin-2-yl)methoxy)-2-methoxyisonicotinaldehyde,
3-((4-formyl-6-methoxypyridin-3-yloxy)methyl)picolinate,
5-((2-(2-hydroxypropan-2-yl)pyridin-3-yl)methoxy)-2-methoxyisonicotinaldehyde,
2-(2-methoxyethoxy)-5-((2-(1-methyl-1H-pyrazol-5-yl)pyridin-3-yl)methoxy)isonicotinaldehyde,
2-(2-methoxyethoxy)-5-((2-(1-methyl-1H-pyrazol-5-yl)pyridin-3-yl)methoxy)nicotinaldehyde,
3-hydroxy-5-((2-(1-isopropyl-1H-pyrazol-5-yl)pyridin-3-yl)methoxy)isonicotinaldehyde,
3-(benzyloxy)-5-hydroxyisonicotinaldehyde,
3-((2-(1-isopropyl-1H-pyrazol-5-yl)pyridin-3-yl)methoxy)-5-methoxyisonicotinaldehyde,
5-((2-(2-isopropyl-2H-1,2,4-triazol-3-yl)pyridin-3-yl)methoxy)-2-methoxyisonicotinaldehyde,
5-((2-(1-isopropyl-4-methyl-1H-pyrazol-5-yl)pyridin-3-yl)methoxy)-2-methoxyisonicotinaldehyde,
5-((2-(1-(2-hydroxyethyl)-1H-pyrazol-5-yl)pyridin-3-yl)methoxy)-2-methoxyisonicotinaldehyde,
6-(((4-formylpyridin-3-yl)oxy)methyl)picolinic acid,
2,2,2-trifluoroacetic acid: 6-(((4-formylpyridin-3-yl)oxy)methyl)picolinic acid (1:1),
2-methoxy-5-((2-(1-((2-(trimethylsilyl)ethoxy)methyl)-1H-pyrazol-5-yl)pyridin-3-yl)methoxy)isonicotinaldehyde,
5-((2-(4-methyl-1H-pyrazol-5-yl)pyridin-3-yl)methoxy)-2-oxo-1,2-dihydropyridine-4-carbaldehyde,
5-((2-(1-cyclobutyl-1H-pyrazol-5-yl)pyridin-3-yl)methoxy)-2-methoxyisonicotinaldehyde,
5-((2-(1-cyclohexyl-11H-pyrazol-5-yl)pyridin-3-yl)methoxy)-2-methoxyisonicotinaldehyde,
5-((2-(1-(cyclohexylmethyl)-1H-pyrazol-5-yl)pyridin-3-yl)methoxy)-2-methoxyisonicotinaldehyde,
5-((2-(1-cyclopentyl-1H-pyrazol-5-yl)pyridin-3-yl)methoxy)-2-methoxyisonicotinaldehyde,
2-(5-(3-((4-formyl-6-methoxypyridin-3-yloxy)methyl)pyridin-2-yl)-1H-pyrazol-1-yl)acetic acid,
methyl 3-(5-(3-(((4-formyl-6-methoxypyridin-3-yl)oxy)methyl)pyridin-2-yl)-1H-pyrazol-1-yl)propanoate,
3-(3-(3-((4-formyl-6-methoxypyridin-3-yloxymethyl)pyridin-2-yl)-1H-pyrazol-1-yl)propanoic acid,
3-(5-(3-(((4-formyl-6-methoxypyridin-3-yl)oxy)methyl)pyridin-2-yl)-1H-pyrazol-1-yl)propanoic acid,
3-(((4-formyl-6-methoxypyridin-3-yl)oxy)methyl)benzoic acid,
6-(((4-formylpyridin-3-yl)oxy)methyl)nicotinonitrile 2,2,2-trifluoroacetate,
6-(((4-formylpyridin-3-yl)oxy)methyl)nicotinic acid,
6-(((4-formylpyridin-3-yl)oxy)methyl)nicotinic acid hydrochloride,
6-(((4-formylpyridin-3-yl)oxy)methyl)-N-(methylsulfonyl)nicotinamide,
2,2,2-trifluoroacetic acid: 6-(((4-formylpyridin-3-yl)oxy)methyl)-N-(methylsulfonyl)nicotinamide (2:1),
2-(2-methoxyethoxy)-5-((2-(1-(2,2,2-trifluoroethyl)-1H-pyrazol-5-yl)pyridin-3-yl)methoxy)isonicotinaldehyde,
2-methoxy-5-((2-(1-(3,3,3-trifluoropropyl)-1H-pyrazol-5-yl)pyridin-3-yl)methoxy)isonicotinaldehyde,
2-(2-methoxyethoxy)-5-((2-(1-(3,3,3-trifluoropropyl)-1H-pyrazol-5-yl)pyridin-3-yl)methoxy)isonicotinaldehyde,
2-methyl-5-((2-(1-(2,2,2-trifluoroethyl)-1H-pyrazol-5-yl)pyridin-3-yl)methoxy)isonicotinaldehyde,
2-methyl-5-((2-(1-(3,3,3-trifluoropropyl)-1H-pyrazol-5-yl)pyridin-3-yl)methoxy)isonicotinaldehyde,
3-((2-(1-(2,2,2-trifluoroethyl)-1H-pyrazol-5-yl)pyridin-3-yl)methoxy)isonicotinaldehyde,
3-((2-(1-(3,3,3-trifluoropropyl)-1H-pyrazol-5-yl)pyridin-3-yl)methoxy)isonicotinaldehyde,
3-chloro-5-((2-(1-isopropyl-1H-pyrazol-5-yl)pyridin-3-yl)methoxy)isonicotinaldehyde,
3-((2-(1-isopropyl-1H-pyrazol-5-yl)pyridin-3-yl)methoxy)-5-methylisonicotinaldehyde,
3-chloro-5-((2-(1-(3,3,3-trifluoropropyl)-1H-pyrazol-5-yl)pyridin-3-yl)methoxy)isonicotinaldehyde, and
3-methyl-5-((2-(1-(2,2,2-trifluoroethyl)-1H-pyrazol-5-yl)pyridin-3-yl)methoxy)isonicotinaldehyde,
or a tautomer or pharmaceutically acceptable salt thereof.

What is claimed is:

1. A compound selected from:

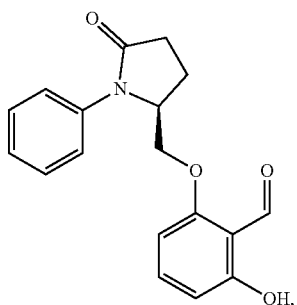

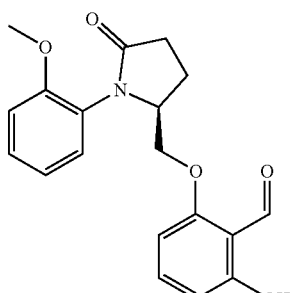

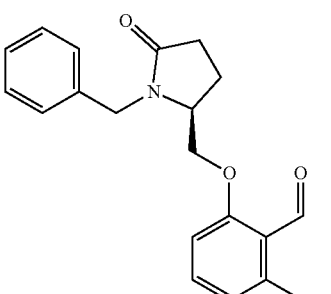

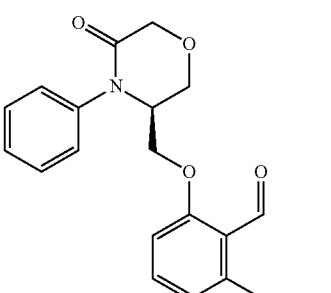

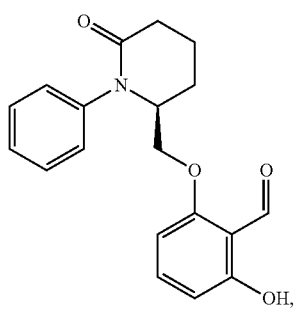

or
a pharmaceutically acceptable salt thereof.

2. The compound of claim 1, wherein the compound is:

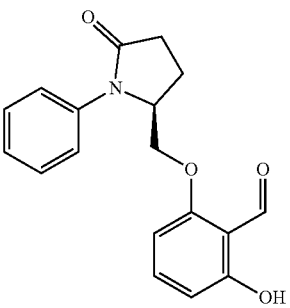 [SMILES: O=Cc1c(O)cccc1OC[C@@H]1CCC(=O)N1c1ccccc1]

or
a pharmaceutically acceptable salt thereof.

3. The compound of claim 1, wherein the compound is:

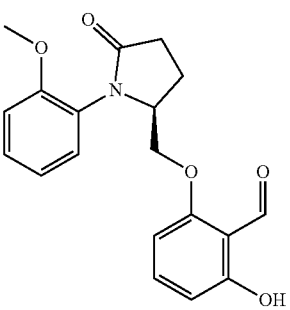 [SMILES: COc1ccccc1N1C(=O)CC[C@H]1COc1cccc(O)c1C=O]

or
a pharmaceutically acceptable salt thereof.

4. The compound of claim 1, wherein the compound is:

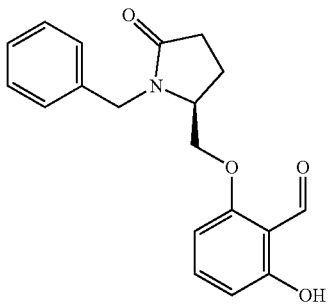 [SMILES: O=Cc1c(O)cccc1OC[C@@H]1CCC(=O)N1Cc1ccccc1]

or
a pharmaceutically acceptable salt thereof.

5. The compound of claim 1, wherein the compound is:

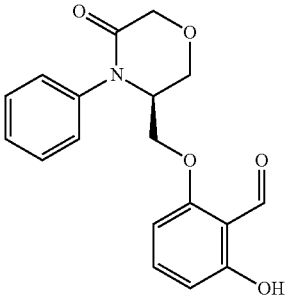 [SMILES: O=Cc1c(O)cccc1OC[C@@H]1COCC(=O)N1c1ccccc1]

or
a pharmaceutically acceptable salt thereof.

6. The compound of claim 1, wherein the compound is:
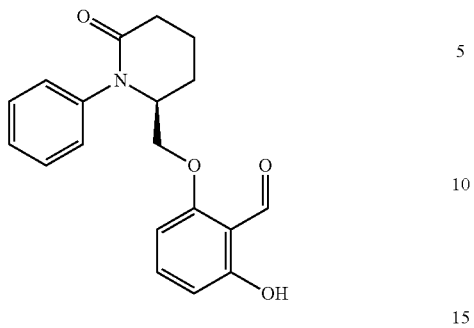
or
a pharmaceutically acceptable salt thereof.
7. A pharmaceutical composition comprising a compound of claim 1, or a pharmaceutically acceptable salt thereof, and a pharmaceutically acceptable excipient.
* * * * *